United States Patent
Baxter, III et al.

(10) Patent No.: US 9,839,428 B2
(45) Date of Patent: Dec. 12, 2017

(54) SURGICAL CUTTING AND STAPLING INSTRUMENTS WITH INDEPENDENT JAW CONTROL FEATURES

(71) Applicant: Ethicon Endo-Surgery, Inc., Cincinnati, OH (US)

(72) Inventors: Chester O. Baxter, III, Loveland, OH (US); Frederick E. Shelton, IV, Hillsboro, OH (US); John R. Dugan, Lebanon, OH (US)

(73) Assignee: Ethicon LLC, Los Frailes Industrial Park Guaynabo, PR (US)

( * ) Notice: Subject to any disclaimer, the term of this patent is extended or adjusted under 35 U.S.C. 154(b) by 877 days.

(21) Appl. No.: 14/138,485

(22) Filed: Dec. 23, 2013

(65) Prior Publication Data

US 2015/0173746 A1    Jun. 25, 2015

(51) Int. Cl.
*A61B 17/068* (2006.01)
*A61B 17/072* (2006.01)
(Continued)

(52) U.S. Cl.
CPC .. *A61B 17/07207* (2013.01); *A61B 17/07292* (2013.01); *A61B 2017/00309* (2013.01); *A61B 2017/00398* (2013.01); *A61B 2017/00473* (2013.01); *A61B 2017/00734* (2013.01); *A61B 2017/07257* (2013.01);
(Continued)

(58) Field of Classification Search
CPC .... A61B 2017/2938; A61B 2017/2944; A61B 2017/07278; A61B 2017/2927
See application file for complete search history.

(56) References Cited

U.S. PATENT DOCUMENTS

| 2,853,074 A | 9/1958 | Olson |
| 3,060,972 A | 10/1962 | Sheldon |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

U.S. Appl. No. 14/138,554, filed Dec. 23, 2013.
(Continued)

*Primary Examiner* — Andrew M Tecco

(57) ABSTRACT

Surgical instruments and end effectors therefor are disclosed. In various implementations, the surgical instrument includes a surgical end effector that comprises a lower jaw and an upper jaw that are supported for movable travel toward and away from each other. The instrument may further include a firing member that is operably supported for selective operable travel within the surgical end effector. The instrument may also include a first jaw closure system that operably interfaces with the lower jaw and is configured to selectively move the lower jaw relative to the upper jaw. A second jaw closure system operably interfaces with the upper jaw and is configured to selectively move the upper jaw relative to the lower jaw. A firing system operably interfaces with the firing member and is configured to apply firing motions to the firing member to move the firing member within the end effector.

20 Claims, 110 Drawing Sheets

(51) Int. Cl.
    *A61B 17/00*  (2006.01)
    *A61B 17/29*  (2006.01)
(52) U.S. Cl.
    CPC .............. *A61B 2017/07278* (2013.01); *A61B 2017/07285* (2013.01); *A61B 2017/2927* (2013.01)

(56) References Cited

U.S. PATENT DOCUMENTS

| | | | |
|---|---|---|---|
| 3,499,591 | A | 3/1970 | Green |
| 3,551,987 | A | 1/1971 | Wilkinson |
| 3,583,393 | A | 6/1971 | Takahashi |
| 3,799,151 | A | 3/1974 | Fukaumi et al. |
| 4,060,089 | A | 11/1977 | Noiles |
| 4,108,211 | A | 8/1978 | Tanaka |
| 4,111,206 | A | 9/1978 | Vishnevsky et al. |
| 4,198,982 | A | 4/1980 | Fortner et al. |
| 4,207,898 | A | 6/1980 | Becht |
| 4,241,861 | A * | 12/1980 | Fleischer ............ A61B 17/072 222/155 |
| 4,429,695 | A | 2/1984 | Green |
| 4,434,796 | A | 3/1984 | Karapetian et al. |
| 4,473,077 | A | 9/1984 | Noiles et al. |
| 4,489,875 | A | 12/1984 | Crawford et al. |
| 4,505,272 | A | 3/1985 | Utyamyshev et al. |
| 4,505,273 | A | 3/1985 | Braun et al. |
| 4,506,671 | A | 3/1985 | Green |
| 4,531,911 | A | 7/1985 | Bedi et al. |
| 4,532,927 | A | 8/1985 | Miksza, Jr. |
| 4,573,468 | A | 3/1986 | Conta et al. |
| 4,605,001 | A | 8/1986 | Rothfuss et al. |
| 4,605,004 | A | 8/1986 | Di Giovanni et al. |
| D286,180 | S | 10/1986 | Korthoff |
| D286,442 | S | 10/1986 | Korthoff et al. |
| 4,619,262 | A | 10/1986 | Taylor |
| 4,655,222 | A | 4/1987 | Florez et al. |
| 4,700,703 | A | 10/1987 | Resnick et al. |
| 4,708,141 | A | 11/1987 | Inoue et al. |
| 4,754,909 | A | 7/1988 | Barker et al. |
| 4,773,420 | A | 9/1988 | Green |
| 4,781,186 | A | 11/1988 | Simpson et al. |
| 4,802,478 | A | 2/1989 | Powell |
| 4,809,695 | A | 3/1989 | Gwathmey et al. |
| 4,844,068 | A | 7/1989 | Arata et al. |
| 4,873,977 | A | 10/1989 | Avant et al. |
| 4,874,122 | A | 10/1989 | Froelich et al. |
| 4,890,613 | A | 1/1990 | Golden et al. |
| 4,893,622 | A | 1/1990 | Green et al. |
| 4,894,051 | A | 1/1990 | Shiber |
| 4,903,697 | A | 2/1990 | Resnick et al. |
| 4,930,674 | A | 6/1990 | Barak |
| 4,932,960 | A | 6/1990 | Green et al. |
| 4,955,898 | A | 9/1990 | Matsutani et al. |
| 4,978,049 | A | 12/1990 | Green |
| 5,042,707 | A | 8/1991 | Taheri |
| 5,071,430 | A | 12/1991 | de Salts et al. |
| 5,074,454 | A | 12/1991 | Peters |
| 5,089,009 | A | 2/1992 | Green |
| D327,323 | S | 6/1992 | Hunt |
| 5,122,156 | A | 6/1992 | Granger et al. |
| 5,139,513 | A | 8/1992 | Segato |
| 5,141,144 | A | 8/1992 | Foslien et al. |
| 5,156,614 | A | 10/1992 | Green et al. |
| 5,158,567 | A | 10/1992 | Green |
| 5,197,649 | A | 3/1993 | Bessler et al. |
| 5,222,975 | A | 6/1993 | Crainich |
| D338,729 | S | 8/1993 | Sprecklemeier et al. |
| 5,236,440 | A | 8/1993 | Hlavacek |
| 5,258,009 | A | 11/1993 | Conners |
| 5,258,012 | A | 11/1993 | Luscombe et al. |
| 5,271,543 | A | 12/1993 | Grant et al. |
| 5,282,329 | A | 2/1994 | Hermes |
| 5,304,204 | A | 4/1994 | Bregen |
| D347,474 | S | 5/1994 | Olson |
| 5,312,023 | A | 5/1994 | Green et al. |
| D348,930 | S | 7/1994 | Olson |
| 5,329,923 | A | 7/1994 | Lundquist |
| 5,332,142 | A | 7/1994 | Robinson et al. |
| 5,333,772 | A | 8/1994 | Rothfuss et al. |
| 5,333,773 | A | 8/1994 | Main et al. |
| 5,342,395 | A | 8/1994 | Jarrett et al. |
| 5,342,396 | A | 8/1994 | Cook |
| 5,350,400 | A | 9/1994 | Esposito et al. |
| 5,352,229 | A | 10/1994 | Goble et al. |
| 5,352,238 | A | 10/1994 | Green et al. |
| 5,358,510 | A | 10/1994 | Luscombe et al. |
| 5,366,479 | A | 11/1994 | McGarry et al. |
| 5,405,072 | A | 4/1995 | Zlock et al. |
| 5,405,073 | A | 4/1995 | Porter |
| D357,981 | S | 5/1995 | Green et al. |
| 5,411,481 | A | 5/1995 | Allen et al. |
| 5,413,272 | A | 5/1995 | Green et al. |
| 5,415,334 | A | 5/1995 | Williamson, IV et al. |
| 5,417,361 | A | 5/1995 | Williamson, IV |
| 5,425,745 | A | 6/1995 | Green et al. |
| 5,439,479 | A | 8/1995 | Shichman et al. |
| 5,452,837 | A | 9/1995 | Williamson, IV et al. |
| 5,454,822 | A | 10/1995 | Schob et al. |
| 5,465,894 | A | 11/1995 | Clark et al. |
| 5,465,895 | A | 11/1995 | Knodel et al. |
| 5,474,223 | A | 12/1995 | Viola et al. |
| 5,478,354 | A | 12/1995 | Tovey et al. |
| 5,480,089 | A | 1/1996 | Blewett |
| 5,482,197 | A | 1/1996 | Green et al. |
| 5,484,095 | A | 1/1996 | Green et al. |
| 5,485,947 | A | 1/1996 | Olson et al. |
| 5,485,952 | A | 1/1996 | Fontayne |
| 5,487,499 | A | 1/1996 | Sorrentino et al. |
| 5,487,500 | A | 1/1996 | Knodel et al. |
| 5,489,058 | A | 2/1996 | Plyley et al. |
| 5,497,933 | A | 3/1996 | DeFonzo et al. |
| 5,503,320 | A | 4/1996 | Webster et al. |
| 5,505,363 | A | 4/1996 | Green et al. |
| 5,507,426 | A | 4/1996 | Young et al. |
| 5,509,596 | A | 4/1996 | Green et al. |
| 5,529,235 | A | 6/1996 | Boiarski et al. |
| 5,533,661 | A | 7/1996 | Main et al. |
| 5,535,934 | A | 7/1996 | Boiarski et al. |
| 5,535,935 | A | 7/1996 | Vidal et al. |
| 5,540,375 | A | 7/1996 | Bolanos et al. |
| 5,542,594 | A | 8/1996 | McKean et al. |
| 5,547,117 | A | 8/1996 | Hamblin et al. |
| 5,549,628 | A | 8/1996 | Cooper et al. |
| 5,549,637 | A | 8/1996 | Crainich |
| 5,551,622 | A | 9/1996 | Yoon |
| 5,553,765 | A | 9/1996 | Knodel et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,564,615 | A | 10/1996 | Bishop et al. |
| 5,571,285 | A | 11/1996 | Chow et al. |
| 5,577,654 | A | 11/1996 | Bishop |
| 5,580,067 | A | 12/1996 | Hamblin et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,609,285 | A | 3/1997 | Grant et al. |
| 5,615,820 | A | 4/1997 | Viola |
| 5,628,446 | A | 5/1997 | Geiste et al. |
| 5,630,539 | A | 5/1997 | Plyley et al. |
| 5,630,540 | A | 5/1997 | Blewett |
| 5,630,541 | A | 5/1997 | Williamson, IV et al. |
| 5,632,432 | A | 5/1997 | Schulze et al. |

(56) References Cited

U.S. PATENT DOCUMENTS

| | | |
|---|---|---|
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze |
| 5,673,840 A | 10/1997 | Schulze et al. |
| 5,673,841 A | 10/1997 | Schulze et al. |
| 5,680,981 A | 10/1997 | Willi et al. |
| 5,680,982 A | 10/1997 | Schulze |
| 5,685,474 A | 11/1997 | Seeker |
| 5,690,269 A | 11/1997 | Bolanos et al. |
| 5,692,668 A | 12/1997 | Schulze et al. |
| 5,693,051 A | 12/1997 | Schulze et al. |
| 5,695,524 A | 12/1997 | 12-09-1997 |
| 5,697,542 A | 12/1997 | Knodel et al. |
| 5,697,543 A | 12/1997 | Burdorff |
| 5,704,534 A | 1/1998 | Huitema et al. |
| 5,706,997 A | 1/1998 | Green et al. |
| 5,711,472 A | 1/1998 | Bryan |
| 5,713,505 A | 2/1998 | Huitema |
| 5,715,987 A | 2/1998 | Kelley et al. |
| 5,718,359 A | 2/1998 | Palmer et al. |
| 5,718,360 A | 2/1998 | Green et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,738,474 A | 4/1998 | Blewett |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Aiesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,860,581 A | 1/1999 | Robertson et al. |
| 5,865,361 A | 2/1999 | Milliman et al. |
| 5,871,135 A | 2/1999 | Williamson, IV et al. |
| 5,878,937 A | 3/1999 | Green et al. |
| 5,894,979 A | 4/1999 | Powell |
| 5,901,895 A | 5/1999 | Heaton et al. |
| 5,911,353 A | 6/1999 | Bolanos et al. |
| 5,915,616 A | 6/1999 | Viola et al. |
| 5,937,951 A | 8/1999 | Izuchukwu et al. |
| 5,941,442 A | 8/1999 | Geiste et al. |
| 5,941,890 A | 8/1999 | Voegele et al. |
| 5,954,259 A | 9/1999 | Viola et al. |
| 5,964,394 A | 10/1999 | Robertson |
| D416,089 S | 11/1999 | Barton et al. |
| 6,010,054 A | 1/2000 | Johnson et al. |
| 6,015,417 A | 1/2000 | Reynolds, Jr. |
| 6,032,849 A | 3/2000 | Mastri et al. |
| 6,033,427 A | 3/2000 | Lee |
| 6,050,472 A | 4/2000 | Shibata |
| 6,053,390 A | 4/2000 | Green et al. |
| 6,079,606 A | 6/2000 | Milliman et al. |
| 6,083,242 A | 7/2000 | Cook |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,131,790 A * | 10/2000 | Piraka ............... A61B 17/072 227/176.1 |
| 6,155,473 A | 12/2000 | Tompkins et al. |
| 6,171,330 B1 | 1/2001 | Benchetrit |
| 6,179,195 B1 | 1/2001 | Adams et al. |
| 6,179,849 B1 | 1/2001 | Yencho et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,241,139 B1 | 6/2001 | Milliman et al. |
| 6,241,140 B1 | 6/2001 | Adams et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,338,737 B1 | 1/2002 | Toledano |
| 6,343,731 B1 | 2/2002 | Adams et al. |
| 6,348,061 B1 | 2/2002 | Whitman |
| 6,387,113 B1 | 5/2002 | Hawkins et al. |
| 6,387,114 B2 | 5/2002 | Adams |
| 6,418,909 B2 | 7/2002 | Rossi et al. |
| RE37,814 E | 8/2002 | Allgeyer |
| 6,439,446 B1 | 8/2002 | Perry et al. |
| 6,443,973 B1 | 9/2002 | Whitman |
| 6,447,518 B1 | 9/2002 | Krause et al. |
| 6,450,391 B1 | 9/2002 | Kayan et al. |
| 6,478,210 B2 | 11/2002 | Adams et al. |
| 6,488,196 B1 | 12/2002 | Fenton, Jr. |
| 6,488,197 B1 | 12/2002 | Whitman |
| 6,491,201 B1 | 12/2002 | Whitman |
| 6,494,896 B1 | 12/2002 | D'Alessio et al. |
| 6,505,768 B2 | 1/2003 | Whitman |
| 6,517,565 B1 | 2/2003 | Whitman et al. |
| 6,517,566 B1 | 2/2003 | Hovland et al. |
| 6,523,043 B1 | 2/2003 | Miranda et al. |
| 6,533,157 B1 | 3/2003 | Whitman |
| 6,578,751 B2 | 6/2003 | Haltwick |
| 6,585,144 B2 | 7/2003 | Adams et al. |
| 6,588,643 B2 | 7/2003 | Bolduc et al. |
| 6,601,749 B2 | 8/2003 | Sullivan et al. |
| 6,602,252 B2 | 8/2003 | Mollenauer |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,631,978 B1 | 10/2003 | Watanabe et al. |
| 6,631,979 B2 | 10/2003 | Lebens et al. |
| 6,638,297 B1 | 10/2003 | Huitema |
| RE38,335 E | 11/2003 | Aust et al. |
| 6,644,532 B2 | 11/2003 | Green et al. |
| 6,663,641 B1 | 12/2003 | Kovac et al. |
| 6,669,073 B2 | 12/2003 | Milliman et al. |
| 6,685,727 B2 | 2/2004 | Fisher et al. |
| 6,695,198 B2 | 2/2004 | Adams et al. |
| 6,695,199 B2 | 2/2004 | Whitman |
| 6,698,643 B2 | 3/2004 | Whitman |
| 6,716,233 B2 | 4/2004 | Whitman |
| 6,722,552 B2 | 4/2004 | Fenton, Jr. |
| 6,755,338 B2 | 6/2004 | Hahnen et al. |
| 6,767,356 B2 | 7/2004 | Kanner et al. |
| 6,769,594 B2 | 8/2004 | Orban, III |
| 6,786,382 B1 | 9/2004 | Hoffman |
| 6,805,273 B2 | 10/2004 | Bilotti et al. |
| 6,817,508 B1 | 11/2004 | Racenet et al. |

(56) References Cited

U.S. PATENT DOCUMENTS

| | | |
|---|---|---|
| 6,817,509 B2 | 11/2004 | Geiste et al. |
| 6,820,791 B2 | 11/2004 | Adams |
| 6,827,246 B2 | 12/2004 | Sullivan et al. |
| 6,830,174 B2 | 12/2004 | Hillstead et al. |
| 6,840,423 B2 | 1/2005 | Adams et al. |
| 6,843,403 B2 | 1/2005 | Whitman |
| RE38,708 E | 3/2005 | Bolanos et al. |
| D502,994 S | 3/2005 | Blake, III |
| 6,863,668 B2 | 3/2005 | Gillespie et al. |
| 6,866,178 B2 | 3/2005 | Adams et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,921,412 B1 | 7/2005 | Black et al. |
| 6,931,628 B2 | 8/2005 | McGeorge, Jr. |
| 6,936,451 B2 | 8/2005 | Ye et al. |
| D509,297 S | 9/2005 | Wells |
| D509,589 S | 9/2005 | Wells |
| 6,945,444 B2 | 9/2005 | Gresham |
| 6,953,138 B1 | 10/2005 | Oworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,097,089 B2 | 8/2006 | Marczyk |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,134,587 B2 | 11/2006 | Schwemberger et al. |
| 7,140,527 B2 | 11/2006 | Ehrenfels et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,156,863 B2 | 1/2007 | Sormenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,296,722 B2 | 11/2007 | Ivanko |
| 7,296,724 B2 | 11/2007 | Green et al. |
| 7,303,106 B2 | 12/2007 | Milliman et al. |
| 7,303,107 B2 | 12/2007 | Millirnan et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,334,718 B2 | 2/2008 | McAlister et al. |
| 7,341,591 B2 | 3/2008 | Grinberg |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,476,237 B2 | 1/2009 | Taniguchi et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hrstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |

(56) References Cited

U.S. PATENT DOCUMENTS

| | | |
|---|---|---|
| 7,546,939 B2 | 6/2009 | Adams et al. |
| 7,546,940 B2 | 6/2009 | Milliman et al. |
| 7,549,563 B2 | 6/2009 | Mather et al. |
| 7,549,564 B2 | 6/2009 | Boudreaux |
| 7,556,185 B2 | 7/2009 | Viola |
| 7,556,186 B2 | 7/2009 | Milliman |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,092 B2 | 1/2010 | Kruszynski et al. |
| 7,641,095 B2 | 1/2010 | Viola |
| 7,644,848 B2 | 1/2010 | Swayze et al. |
| 7,651,017 B2 | 1/2010 | Oiliz et al. |
| 7,651,498 B2 | 1/2010 | Shifrin et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,682,367 B2 | 3/2010 | Shah et al. |
| 7,686,201 B2 | 3/2010 | Csiky |
| 7,694,865 B2 | 4/2010 | Scirica |
| 7,699,204 B2 | 4/2010 | Viola |
| 7,703,653 B2 | 4/2010 | Shah et al. |
| 7,708,180 B2 | 5/2010 | Murray et al. |
| 7,708,181 B2 | 5/2010 | Cole et al. |
| 7,717,312 B2 | 5/2010 | Beetel |
| 7,717,313 B2 | 5/2010 | Criscuolo et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,731,073 B2 | 6/2010 | Wxey et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,823,760 B2 | 11/2010 | Zernlok et al. |
| 7,824,426 B2 | 11/2010 | Racenet et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,850,623 B2 | 12/2010 | Griffin et al. |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,886,951 B2 | 2/2011 | Hessler |
| 7,886,952 B2 | 2/2011 | Scirica et al. |
| 7,887,563 B2 | 2/2011 | Cummins |
| 7,891,531 B1 | 2/2011 | Ward |
| 7,891,532 B2 | 2/2011 | Mastri et al. |
| 7,896,214 B2 | 3/2011 | Farascioni |
| 7,896,215 B2 | 3/2011 | Adams et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,867 B2 | 4/2011 | Dana et al. |
| 7,918,873 B2 | 4/2011 | Cummins |
| 7,922,061 B2 | 4/2011 | Shelton, IV et al. |
| 7,922,063 B2 | 4/2011 | Zernlok et al. |
| 7,922,743 B2 | 4/2011 | Heinrich et al. |
| 7,926,691 B2 | 4/2011 | Viola et al. |
| 7,934,630 B2 | 5/2011 | Shelton, IV et al. |
| 7,934,631 B2 | 5/2011 | Balbierz et al. |

(56) References Cited

U.S. PATENT DOCUMENTS

| | | | |
|---|---|---|---|
| 7,938,307 | B2 | 5/2011 | Bettuchi |
| 7,942,303 | B2 | 5/2011 | Shah |
| 7,950,560 | B2 | 5/2011 | Zernlok et al. |
| 7,950,561 | B2 | 5/2011 | Aranyi |
| 7,954,682 | B2 | 6/2011 | Giordano et al. |
| 7,954,684 | B2 | 6/2011 | Boudreaux |
| 7,954,686 | B2 | 6/2011 | Baxter, III et al. |
| 7,954,687 | B2 | 6/2011 | Zemlok et al. |
| 7,954,688 | B2 | 6/2011 | Argentine et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,839 | B2 | 6/2011 | Flock et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,757 | B2 | 8/2011 | Wheeler et al. |
| 7,993,360 | B2 | 8/2011 | Hacker et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,889 | B2 | 8/2011 | Adams et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,858 | B2 | 9/2011 | Whitman |
| 8,020,742 | B2 | 9/2011 | Marczyk |
| 8,020,743 | B2 | 9/2011 | Shelton, IV |
| 8,025,199 | B2 | 9/2011 | Whitman et al. |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,034,077 | B2 | 10/2011 | Smith et al. |
| 8,038,045 | B2 | 10/2011 | Bettuchi et al. |
| 8,038,046 | B2 | 10/2011 | Smith et al. |
| 8,056,787 | B2 | 11/2011 | Boudreaux et al. |
| 8,056,788 | B2 | 11/2011 | Mastri et al. |
| 8,057,508 | B2 | 11/2011 | Shelton, IV |
| 8,061,576 | B2 | 11/2011 | Cappola |
| 8,066,167 | B2 | 11/2011 | Measamer et al. |
| 8,066,168 | B2 | 11/2011 | Vidal et al. |
| D650,074 | S | 12/2011 | Hunt et al. |
| 8,070,033 | B2 | 12/2011 | Milliman et al. |
| 8,070,035 | B2 | 12/2011 | Holsten et al. |
| 8,083,118 | B2 | 12/2011 | Milliman et al. |
| 8,083,119 | B2 | 12/2011 | Prommersberuer |
| 8,083,120 | B2 | 12/2011 | Shelton, IV et al. |
| 8,087,563 | B2 | 1/2012 | Milliman et al. |
| 8,091,756 | B2 | 1/2012 | Viola |
| 8,096,458 | B2 | 1/2012 | Hessler |
| 8,097,017 | B2 | 1/2012 | Viola |
| 8,100,310 | B2 | 1/2012 | Zemlok |
| 8,109,426 | B2 | 2/2012 | Milliman et al. |
| 8,113,405 | B2 | 2/2012 | Milliman |
| 8,113,410 | B2 | 2/2012 | Hall et al. |
| 8,123,103 | B2 | 2/2012 | Milliman |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,706 | B2 | 3/2012 | Marczyk et al. |
| 8,136,712 | B2 | 3/2012 | Zingman |
| 8,136,713 | B2 | 3/2012 | Hathaway et al. |
| 8,141,762 | B2 | 3/2012 | Beta et al. |
| 8,141,763 | B2 | 3/2012 | Milliman |
| 8,146,790 | B2 | 4/2012 | Milliman |
| 8,152,041 | B2 | 4/2012 | Kostrzewski |
| 8,157,145 | B2 | 4/2012 | Shelton, IV et al. |
| 8,157,148 | B2 | 4/2012 | Scirica |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |
| 8,161,977 | B2 | 4/2012 | Shelton, IV et al. |
| 8,162,197 | B2 | 4/2012 | Mastri et al. |
| 8,167,185 | B2 | 5/2012 | Shelton, IV et al. |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,181,840 | B2 | 5/2012 | Milliman |
| 8,186,555 | B2 | 5/2012 | Shelton, IV et al. |
| 8,186,560 | B2 | 5/2012 | Hess et al. |
| 8,191,752 | B2 | 6/2012 | Scirica |
| 8,196,795 | B2 | 6/2012 | Moore et al. |
| 8,196,796 | B2 | 6/2012 | Shelton, IV et al. |
| 8,201,720 | B2 | 6/2012 | Hessler |
| 8,201,721 | B2 | 6/2012 | Zemlok et al. |
| 8,205,779 | B2 | 6/2012 | Ma |
| 8,205,780 | B2 | 6/2012 | Sorrentino et al. |
| 8,205,781 | B2 | 6/2012 | Baxter, III et al. |
| 8,210,411 | B2 | 7/2012 | Yates et al. |
| 8,210,414 | B2 | 7/2012 | Bettuchi et al. |
| 8,210,415 | B2 | 7/2012 | Ward |
| 8,210,416 | B2 | 7/2012 | Milliman et al. |
| 8,215,531 | B2 | 7/2012 | Shelton, IV et al. |
| 8,215,533 | B2 | 7/2012 | Viola et al. |
| 8,220,688 | B2 | 7/2012 | Laurent et al. |
| 8,220,690 | B2 | 7/2012 | Hess et al. |
| 8,231,040 | B2 | 7/2012 | Zernlok et al. |
| 8,231,041 | B2 | 7/2012 | Marczyk et al. |
| 8,231,042 | B2 | 7/2012 | Hessler et al. |
| 8,231,043 | B2 | 7/2012 | Tarinelli et al. |
| 8,236,010 | B2 | 8/2012 | Ortiz et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,245,901 | B2 | 8/2012 | Stopek |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,257,634 | B2 | 9/2012 | Scirica |
| 8,267,300 | B2 | 9/2012 | Boudreaux |
| 8,272,553 | B2 | 9/2012 | Mastri et al. |
| 8,272,554 | B2 | 9/2012 | Whitman et al. |
| 8,276,801 | B2 | 10/2012 | Zemlok et al. |
| 8,276,802 | B2 | 10/2012 | Kostrzewski |
| 8,281,973 | B2 | 10/2012 | Wenchell et al. |
| 8,281,974 | B2 | 10/2012 | Hessler et al. |
| 8,286,845 | B2 | 10/2012 | Perry et al. |
| 8,292,147 | B2 | 10/2012 | Viola |
| 8,292,150 | B2 | 10/2012 | Bryant |
| 8,292,151 | B2 | 10/2012 | Viola |
| 8,292,152 | B2 | 10/2012 | Milliman et al. |
| 8,292,155 | B2 | 10/2012 | Shelton, IV et al. |
| 8,292,157 | B2 | 10/2012 | Smith et al. |
| 8,292,888 | B2 | 10/2012 | Whitman |
| 8,308,040 | B2 | 11/2012 | Huang et al. |
| 8,308,042 | B2 | 11/2012 | Aranyi |
| 8,308,046 | B2 | 11/2012 | Prommersberg |
| 8,317,070 | B2 | 11/2012 | Hueil et al. |
| 8,317,071 | B1 | 11/2012 | Knodel |
| 8,317,074 | B2 | 11/2012 | Ortiz et al. |
| 8,317,790 | B2 | 11/2012 | Bell et al. |
| 8,322,455 | B2 | 12/2012 | Shelton, IV et al. |
| 8,322,589 | B2 | 12/2012 | Boudreaux |
| 8,322,590 | B2 | 12/2012 | Patel et al. |
| 8,328,061 | B2 | 12/2012 | Kasvikis |
| 8,328,062 | B2 | 12/2012 | Viola |
| 8,328,063 | B2 | 12/2012 | Milliman et al. |
| 8,328,064 | B2 | 12/2012 | Racenet et al. |
| 8,333,313 | B2 | 12/2012 | Boudreaux et al. |
| 8,336,753 | B2 | 12/2012 | Olson et al. |

(56) References Cited

U.S. PATENT DOCUMENTS

| | | |
|---|---|---|
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Beth et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,975 B1 | 2/2013 | Manoux et al. |
| 8,365,976 B2 | 2/2013 | Hess et al. |
| 8,371,491 B2 | 2/2013 | Hulterna et al. |
| 8,371,492 B2 | 2/2013 | Aranyi et al. |
| 8,371,493 B2 | 2/2013 | Aranyi et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,430,292 B2 | 4/2013 | Patel et al. |
| 8,439,246 B1 | 5/2013 | Knodel et al. |
| 8,444,036 B2 | 5/2013 | Shelton, IV |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Null et al. |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,499,992 B2 | 8/2013 | Whitman et al. |
| 8,499,993 B2 | 8/2013 | Shelton, IV et al. |
| 8,512,359 B2 | 8/2013 | Whitman et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Beth et al. |
| 8,540,735 B2 | 9/2013 | Mitelberg et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,574,263 B2 | 11/2013 | Mueller |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,191 B2 | 1/2014 | Meagher |
| 8,636,736 B2 | 1/2014 | Yates et al. |
| 8,636,766 B2 | 1/2014 | Milliman et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,684,250 B2 | 4/2014 | Bettuchi et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,312 B1 | 7/2014 | Knodel et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |

(56) References Cited

U.S. PATENT DOCUMENTS

| | | |
|---|---|---|
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,496 B2 | 8/2014 | Scirica |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,732 B2 | 8/2014 | Harris et al. |
| 8,801,734 B2 | 8/2014 | Shelton, IV et al. |
| 8,801,735 B2 | 8/2014 | Shelton, IV et al. |
| 8,808,294 B2 | 8/2014 | Fox et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,911,471 B2 | 12/2014 | Spivey et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,016,542 B2 | 4/2015 | Shelton, IV et al. |
| 9,017,331 B2 | 4/2015 | Fox |
| 9,027,817 B2 | 5/2015 | Milliman et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,055,944 B2 | 6/2015 | Hodgkinson et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,089,330 B2 | 7/2015 | Widenhouse |
| 9,095,339 B2 | 8/2015 | Moore et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,149,325 B2 | 10/2015 | Worrell et al. |
| 9,168,038 B2 | 10/2015 | Shelton, IV et al. |
| 9,179,911 B2 | 11/2015 | Morgan et al. |
| 9,179,912 B2 | 11/2015 | Yates |
| 9,186,143 B2 | 11/2015 | Timm et al. |
| 9,192,380 B2 | 11/2015 | Racenet et al. |
| 9,192,384 B2 | 11/2015 | Bettuchi |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,751 B2 | 1/2016 | Shelton, IV et al. |
| 9,232,941 B2 | 1/2016 | Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,265,500 B2 | 2/2016 | Sorrentino et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,314,246 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |

(56) References Cited

U.S. PATENT DOCUMENTS

| | | |
|---|---|---|
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,358,005 B2 | 6/2016 | Shelton, IV et al. |
| 9,364,220 B2 | 6/2016 | Williams |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Oiliz Et A |
| 9,408,604 B2 | 8/2016 | Shelton, IV et al. |
| 9,414,838 B2 | 8/2016 | Shelton, IV et al. |
| 9,433,419 B2 | 9/2016 | Gonzalez et al. |
| 9,445,813 B2 | 9/2016 | Shelton, IV et al. |
| 9,451,958 B2 | 9/2016 | Shelton, IV et al. |
| 9,480,476 B2 | 11/2016 | Aldridge et al. |
| 2002/0049472 A1 | 4/2002 | Coleman et al. |
| 2002/0117534 A1 | 8/2002 | Green et al. |
| 2004/0006372 A1 | 1/2004 | Racenet et al. |
| 2004/0044364 A1 | 3/2004 | DeVries et al. |
| 2004/0073222 A1 | 4/2004 | Koseki |
| 2004/0093024 A1 | 5/2004 | Lousararian et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0254608 A1 | 12/2004 | Huitema et al. |
| 2005/0010213 A1 | 1/2005 | Stad et al. |
| 2005/0059997 A1 | 3/2005 | Bauman et al. |
| 2005/0103819 A1 | 5/2005 | Racenet et al. |
| 2005/0145675 A1 | 7/2005 | Hartwick et al. |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0267530 A1 | 12/2005 | Cummins |
| 2005/0274768 A1 | 12/2005 | Cummins et al. |
| 2005/0283188 A1 | 12/2005 | Loshakove et al. |
| 2006/0011699 A1 | 1/2006 | Olson et al. |
| 2006/0025811 A1 | 2/2006 | Shelton, IV |
| 2006/0047307 A1 | 3/2006 | Ortiz et al. |
| 2006/0049229 A1 | 3/2006 | Milkman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100649 A1 | 5/2006 | Hart |
| 2006/0108393 A1 | 5/2006 | Heinrich et al. |
| 2006/0180634 A1 | 8/2006 | Shelton, IV et al. |
| 2006/0201989 A1 | 9/2006 | Ojeda |
| 2006/0212071 A1 | 9/2006 | Ginn et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0034668 A1 | 2/2007 | Holsten et al. |
| 2007/0073341 A1 | 3/2007 | Smith |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106317 A1 | 5/2007 | Shelton, IV et al. |
| 2007/0118175 A1 | 5/2007 | Butler et al. |
| 2007/0170225 A1 | 7/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0260278 A1 | 11/2007 | Wheeler et al. |
| 2008/0015598 A1 | 1/2008 | Prornmersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0065153 A1 | 3/2008 | Allard et al. |
| 2008/0078802 A1 | 4/2008 | Hess et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0078736 A1 | 3/2009 | Van Lee |
| 2009/0090763 A1 | 4/2009 | Zemlok et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0277949 A1 | 11/2009 | Viola et al. |
| 2009/0303907 A1 | 12/2009 | Nalagatla et al. |
| 2010/0012704 A1 | 1/2010 | Tarinai Racenet et al. |
| 2010/0016888 A1 | 1/2010 | Calabrese et al. |
| 2010/0069942 A1 | 3/2010 | Shelton, IV |
| 2010/0072254 A1 | 3/2010 | Aranyi et al. |
| 2010/0089970 A1* | 4/2010 | Smith ............ A61B 17/07207 227/175.1 |

(56) References Cited

U.S. PATENT DOCUMENTS

| | | |
|---|---|---|
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0133316 A1 | 6/2010 | Lizee et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0191262 A1 | 7/2010 | Harris et al. |
| 2010/0193566 A1 | 8/2010 | Schieb et al. |
| 2010/0200637 A1 | 8/2010 | Beetel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0258611 A1 | 10/2010 | Smith et al. |
| 2010/0276471 A1 | 11/2010 | Whitman |
| 2010/0294827 A1 | 11/2010 | Boyden et al. |
| 2010/0320252 A1 | 12/2010 | Viola et al. |
| 2010/0331880 A1 | 12/2010 | Stopek |
| 2011/0006101 A1 | 1/2011 | Hall et al. |
| 2011/0011916 A1 | 1/2011 | Levine |
| 2011/0024477 A1 | 2/2011 | Hall et al. |
| 2011/0024478 A1 | 2/2011 | Shelton, IV |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0046666 A1 | 2/2011 | Sorrentino et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0137340 A1 | 6/2011 | Cummins |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0295295 A1 | 12/2011 | Shelton, IV et al. |
| 2012/0016413 A1 | 1/2012 | Timm et al. |
| 2012/0029272 A1 | 2/2012 | Shelton, IV et al. |
| 2012/0046692 A1 | 2/2012 | Smith et al. |
| 2012/0074200 A1* | 3/2012 | Schmid ............ A61B 17/07207 227/180.1 |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080484 A1* | 4/2012 | Morgan ................. A61B 90/92 227/176.1 |
| 2012/0080498 A1 | 4/2012 | Shelton, IV et al. |
| 2012/0138658 A1 | 6/2012 | Ullrich et al. |
| 2012/0175398 A1 | 7/2012 | Sandborn et al. |
| 2012/0187179 A1 | 7/2012 | Gleiman |
| 2012/0228355 A1 | 9/2012 | Cornbrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241492 A1 | 9/2012 | Shelton, IV et al. |
| 2012/0241493 A1 | 9/2012 | Baxter, III et al. |
| 2012/0248169 A1 | 10/2012 | Widenhouse et al. |
| 2012/0273550 A1 | 11/2012 | Scirica |
| 2012/0283707 A1 | 11/2012 | Giordano et al. |
| 2012/0286021 A1 | 11/2012 | Kostrzewski et al. |
| 2012/0292367 A1 | 11/2012 | Morgan et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0325892 A1 | 12/2012 | Kostrzewski |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0032626 A1 | 2/2013 | Srnith et al. |
| 2013/0037596 A1 | 2/2013 | Bear et al. |
| 2013/0062391 A1 | 3/2013 | Boudreaux et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0098970 A1 | 4/2013 | Racenet et al. |
| 2013/0105548 A1 | 5/2013 | Hodgkinson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0146641 A1 | 6/2013 | Shelton, IV et al. |
| 2013/0146642 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zernlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233905 A1 | 9/2013 | Sorrentino et al. |
| 2013/0233906 A1 | 9/2013 | Hess et al. |
| 2013/0233908 A1 | 9/2013 | Knodel et al. |
| 2013/0256371 A1 | 10/2013 | Shelton, IV et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0261661 A1* | 10/2013 | Piraka .................. A61B 17/072 606/219 |
| 2013/0270322 A1 | 10/2013 | Scheib et al. |
| 2013/0274722 A1 | 10/2013 | Kostrzewski et al. |
| 2013/0277412 A1 | 10/2013 | Gresham et al. |
| 2013/0282052 A1 | 10/2013 | Aranyi et al. |
| 2013/0310873 A1 | 11/2013 | Stopek (nee Prommersberger) et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |

(56) References Cited

U.S. PATENT DOCUMENTS

| | | |
|---|---|---|
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334280 A1* | 12/2013 | Krehel ............. A61B 17/07207 227/176.1 |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0018832 A1 | 1/2014 | Shelton, IV |
| 2014/0025046 A1 | 1/2014 | Williams et al. |
| 2014/0042205 A1 | 2/2014 | Baxter, III et al. |
| 2014/0043580 A1 | 2/2014 | Merchant et al. |
| 2014/0061279 A1 | 3/2014 | Laurent et al. |
| 2014/0061280 A1 | 3/2014 | Ingmarson et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175157 A1 | 6/2014 | Vold et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207166 A1 | 7/2014 | Shelton, IV et al. |
| 2014/0224857 A1 | 8/2014 | Schmid |
| 2014/0236184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hauser et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV et al. |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0173744 A1 | 6/2015 | Shelton, IV et al. |
| 2015/0173745 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |

(56) References Cited

U.S. PATENT DOCUMENTS

| | | |
|---|---|---|
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201923 A1 | 7/2015 | Fan et al. |
| 2015/0201932 A1 | 7/2015 | Swayze et al. |
| 2015/0201935 A1 | 7/2015 | Weisenburgh, II et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | - Hr Terra et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0351854 A1 | 12/2015 | Hegeman et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh et al. |
| 2016/0000440 A1 | 1/2016 | Weisenburgh et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0074038 A1 | 3/2016 | Leinibach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | 06-23-2016 06-23-2016 |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |

(56) References Cited

U.S. PATENT DOCUMENTS

| | | |
|---|---|---|
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |
| 2016/0199059 A1 | 7/2016 | Iv et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, Iv et al. |
| 2016/0199089 A1 | 7/2016 | Hess et al. |
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | 08-04-2016 |
| 2016/0220249 A1 | 8/2016 | Shelton, IV et al. |
| 2016/0220254 A1 | 8/2016 | Baxter et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, Iv et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256160 A1 | 9/2016 | 09-08-2016 09-08-2016 |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | 09-08-2016 09-15-2016 09-15-2016 |
| 2016/0262760 A1 | 9/2016 | Shelton, IV et al. |
| 2016/0270780 A1 | 9/2016 | Hall et al. |
| 2016/0287249 A1 | 10/2016 | Alexander et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101541251 A | 9/2009 |
| CN | 101675898 A | 3/2010 |
| CN | 101683280 A | 3/2010 |
| CN | 101028205 A | 1/2011 |
| CN | 101934098 A | 5/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 202397539 U | 8/2012 |
| CN | 101317782 B | 10/2012 |
| CN | 101507633 B | 2/2013 |
| CN | 101023879 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 | 3/2014 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 9/1988 |
| DE | 9412228 U | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |

(56) References Cited

FOREIGN PATENT DOCUMENTS

| | | |
|---|---|---|
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0050554 B1 | 1/1986 |
| EP | 2005901 A1 | 1/1986 |
| EP | 0033548 B1 | 5/1986 |
| EP | 0077262 131 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0537572 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0923907 A1 | 6/1999 |
| EP | 0959784 B1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0852480 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 2002143078 A | 5/2002 |
| EP | 0862386 B1 | 6/2002 |
| EP | 0949886 B1 | 9/2002 |
| EP | 1238634 A2 | 9/2002 |
| EP | 2002-314298 A | 10/2002 |
| EP | 0853295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 1330201 B1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0891154 B1 | 9/2003 |
| EP | 0813843 B1 | 10/2003 |
| EP | 0873089 B1 | 10/2003 |
| EP | 0856326 61 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1425012 A1 | 6/2004 |
| EP | 0833593 B2 | 7/2004 |
| EP | 1442694 A1 | 8/2004 |
| EP | 0883749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |

(56) References Cited

FOREIGN PATENT DOCUMENTS

| | | |
|---|---|---|
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 61 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1045672 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1080694 A1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1 736105 A1 | 12/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 2030579 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1982657 B1 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |

(56) References Cited

FOREIGN PATENT DOCUMENTS

| | | |
|---|---|---|
| EP | 2110082 A1 | 10/2009 |
| EP | 2110084 A2 | 10/2009 |
| EP | 2111803 A2 | 10/2009 |
| EP | 1 762 190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A1 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 81 | 3/2011 |
| EP | 1884201 B1 | 3/2011 |
| EP | 2292153 A1 | 3/2011 |
| EP | 1769755 B1 | 4/2011 |
| EP | 2090240 61 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 61 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A1 | 2/2012 |
| EP | 2090253 B1 | 3/2012 |
| EP | 2430986 A2 | 3/2012 |
| EP | 2444008 A2 | 4/2012 |
| EP | 1347638 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 81 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777528 A2 | 9/2014 |
| EP | 2777538 A2 | 9/2014 |
| EP | 2446835 B1 | 1/2015 |
| EP | 2923660 A2 | 9/2015 |
| EP | 2371296 B1 | 8/2016 |
| EP | 2116192 B1 | 3/2017 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S47-11908 Y1 | 5/1972 |
| JP | 50-33988 U | 4/1975 |
| JP | S56-112235 A | 9/1981 |
| JP | S58500053 A | 1/1983 |
| JP | S58-501360 A | 8/1983 |
| JP | S59-174920 A | 3/1984 |
| JP | 60-100955 A | 6/1985 |
| JP | 60-212152 A | 10/1985 |
| JP | 61-98249 A | 5/1986 |
| JP | S61502036 A | 9/1986 |
| JP | S62-170011 U | 10/1987 |
| JP | S63-59764 A | 3/1988 |
| JP | S63-147449 A | 6/1988 |
| JP | 63-203149 A | 8/1988 |
| JP | H02-279149 | 11/1990 |

(56) References Cited

FOREIGN PATENT DOCUMENTS

| | | |
|---|---|---|
| JP | 3-12126 A | 1/1991 |
| JP | H04-215747 | 8/1992 |
| JP | H4-131860 U | 12/1992 |
| JP | H05-084252 | 4/1993 |
| JP | H05-123325 | 5/1993 |
| JP | 5-212039 A | 8/1993 |
| JP | 6007357 A | 1/1994 |
| JP | H6-30945 A | 2/1994 |
| JP | H06-54857 A | 3/1994 |
| JP | H06-63054 | 3/1994 |
| JP | H06-26812 U | 4/1994 |
| JP | H6-121798 A | 5/1994 |
| JP | H6-125913 A | 5/1994 |
| JP | H06-197901 A | 7/1994 |
| JP | H06-237937 | 8/1994 |
| JP | H06-327684 A | 11/1994 |
| JP | 7-31623 A | 2/1995 |
| JP | 7051273 A | 2/1995 |
| JP | H07-9622 U | 2/1995 |
| JP | H7-47070 A | 2/1995 |
| JP | 7-124166 A | 5/1995 |
| JP | H7-163574 A | 6/1995 |
| JP | 07-171163 A | 7/1995 |
| JP | 7-255735 A | 10/1995 |
| JP | H7-285089 A | 10/1995 |
| JP | 8-33642 A | 2/1996 |
| JP | 8033641 A | 2/1996 |
| JP | 8-164141 A | 6/1996 |
| JP | H08-182684 A | 7/1996 |
| JP | H08-507708 A | 8/1996 |
| JP | 8229050 A | 9/1996 |
| JP | H8-336540 A | 12/1996 |
| JP | H08-336544 A | 12/1996 |
| JP | H09-501081 A | 2/1997 |
| JP | H09-501577 A | 2/1997 |
| JP | H09-164144 A | 6/1997 |
| JP | H10-113352 A | 5/1998 |
| JP | H10-118090 A | 5/1998 |
| JP | 10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002-204801 A | 7/2002 |
| JP | 2002-528161 A | 9/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 1522264 A1 | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-237881 A | 10/2008 |
| JP | 2008-259860 A | 10/2008 |
| JP | 2008-264535 A | 11/2008 |

(56) References Cited

FOREIGN PATENT DOCUMENTS

| | | |
|---|---|---|
| JP | 2008-283459 A | 11/2008 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-075695 A | 4/2010 |
| JP | 2010-088876 A | 4/2010 |
| JP | 2010-098844 A | 4/2010 |
| JP | 2010-214166 A | 9/2010 |
| JP | 4549018 B2 | 9/2010 |
| JP | 2010-540192 A | 12/2010 |
| JP | 20110003229 A | 1/2011 |
| JP | 4783373 B2 | 7/2011 |
| JP | 2011-524199 A | 9/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93115850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19152 A1 | 6/1996 |
| WO | WO 96118344 A2 | 6/1996 |
| WO | WO 96119151 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10764 A1 | 3/1997 |
| WO | WO 97110763 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 93/17180 A1 | 4/1998 |
| WO | WO 93/22154 A2 | 5/1998 |
| WO | WO 93/30153 A1 | 7/1998 |
| WO | WO 98/27880 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |

(56) References Cited

FOREIGN PATENT DOCUMENTS

| | | |
|---|---|---|
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/41638 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/094746 A1 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/058079 A2 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2008/118728 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A1 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |

(56) References Cited

FOREIGN PATENT DOCUMENTS

| | | |
|---|---|---|
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039237 A1 | 4/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/112912 A2 | 9/2008 |
| WO | WO 2008/124748 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2012/166503 A1 | 12/2012 |
| WO | WO 2013/009699 A2 | 1/2013 |
| WO | WO 2013/016633 A1 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |
| WO | WO 2014/004294 A2 | 1/2014 |
| WO | WO 2012/135705 A1 | 10/2014 |

OTHER PUBLICATIONS

U.S. Appl. No. 14/138,465, filed Dec. 23, 2013.
U.S. Appl. No. 14/138,485, filed Dec. 23, 2013.
U.S. Appl. No. 14/138,475, filed Dec. 23, 2013.
U.S. Appl. No. 14/138,481, filed Dec. 23, 2013.
U.S. Appl. No. 14/138,489, filed Dec. 23, 2013.
U.S. Appl. No. 29/477,488, filed Dec. 23, 2013.
U.S. Appl. No. 14/138,518, filed Dec. 23, 2013.
U.S. Appl. No. 14/138,530, filed Dec. 23, 2013.
U.S. Appl. No. 14/138,507, filed Dec. 23, 2013.
U.S. Appl. No. 14/138,497, filed Dec. 23, 2013.
U.S. Appl. No. 14/138,516, filed Dec. 23, 2013.
U.S. Appl. No. 14/138,474, filed Dec. 23, 2013.
U.S. Appl. No. 14/138,505, filed Dec. 23, 2013.
U.S. Appl. No. 13/803,097, filed Mar. 14, 2013.
U.S. Appl. No. 13/974,205, filed Aug. 23, 2013.
International Search Report for Application No, PCT/US2014/069270, dated Mar. 30, 2015 (5 pages).
International Preliminary Report on Patentability for Application No. PCT/US2014/069270, dated Jun. 28, 2016 (7 pages).
European Search Report for Application No. 14200224.5, dated May 29, 2015 (5 pages).
European Examination Report for Application No. 14200224.5, dated May 4, 2016 (5 pages).
Disclosed Anonymously, "Motor-Driven Surgical Stapler Improvements" Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.75397cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; online] URL: http://electroniodesign.com/Articles/Print.cfm?ArticleID=17465 accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Dun meter Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.

(56) References Cited

OTHER PUBLICATIONS

Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2012), 2 pages.
Covidien Brochure, "Endo GIA™ Ultra Universal Stapler," (2012), 2 pages.
Miyata et al., "Biomolecule-Sensitive Hydrogels,", Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environmental-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 30-12.
Hoffman, "Hydrogels for Biomedical Applications," Advanced Drug Delivery Reviews, 54 (2002) pp. 30-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1936.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology a 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med (2010), 4(7) pp. 514-523.
http//ninpgan.net/publications/51-100/89.pdf; 2004, Ning Pan, On Uniqueness of Fibrous Materials, Design & Nature II. Eds: Colins, M. And Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Sells et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Black in Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http//:www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

* cited by examiner

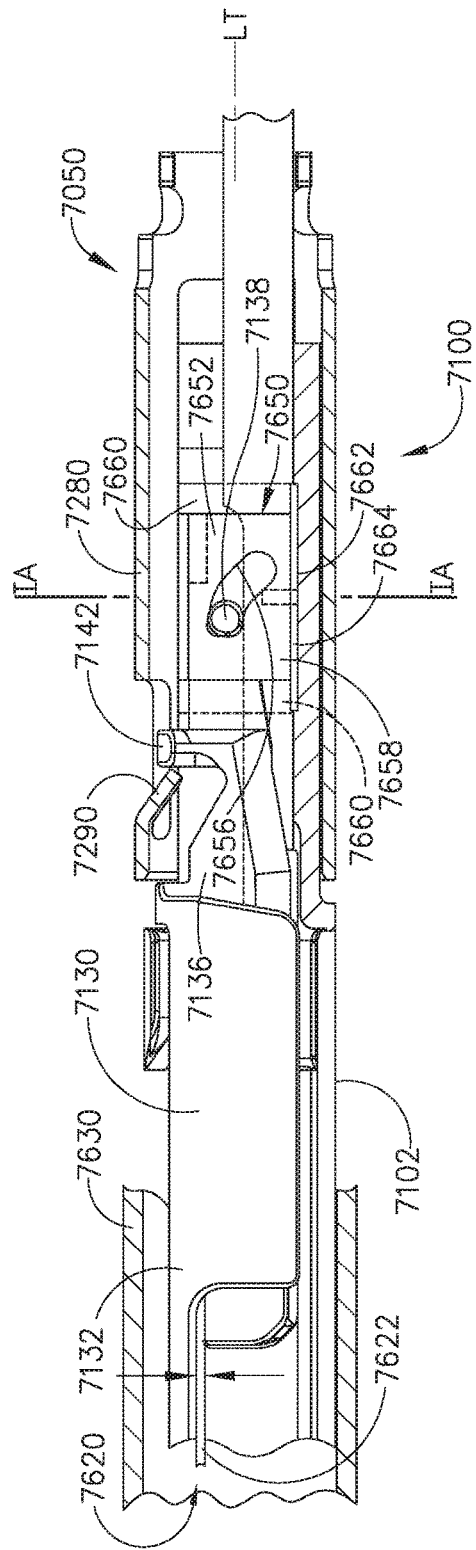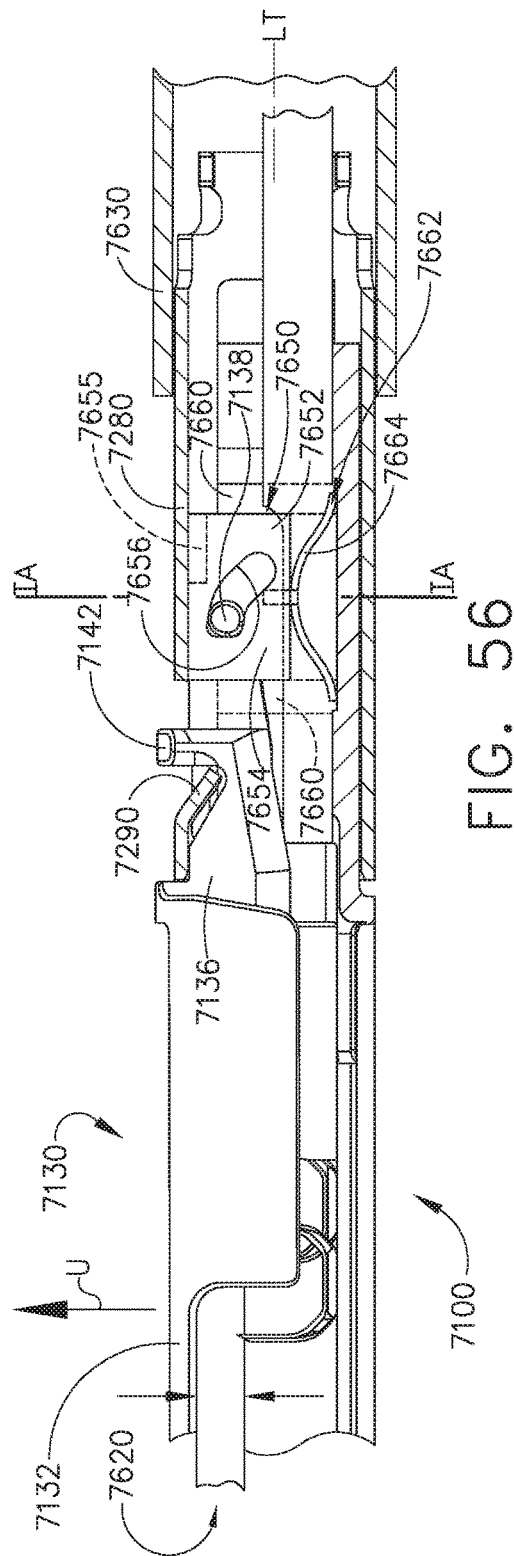

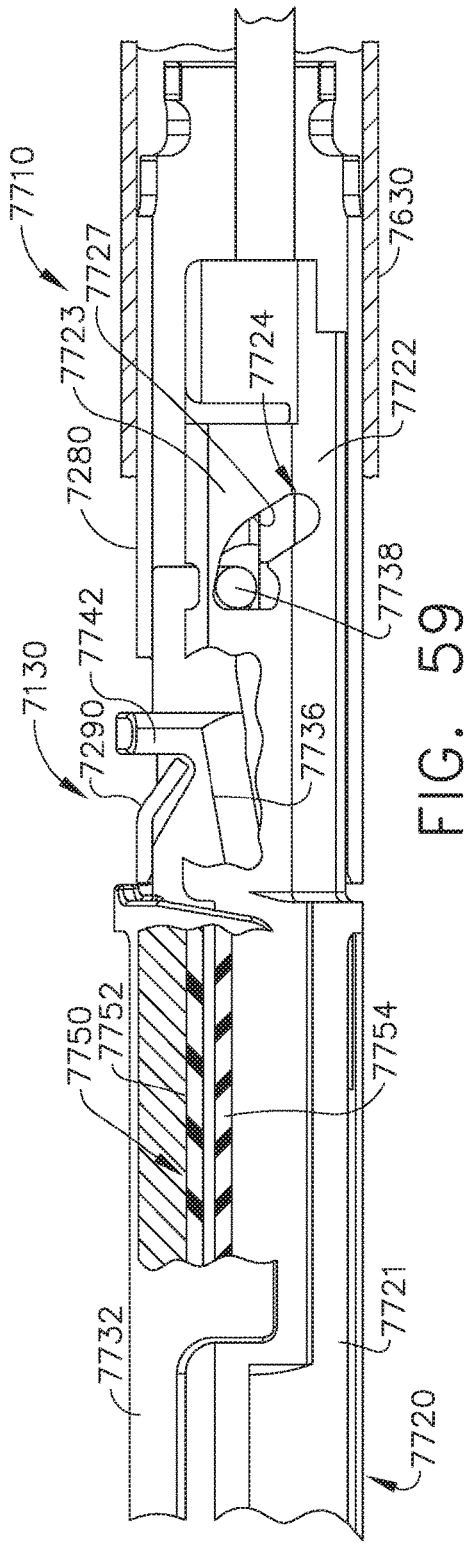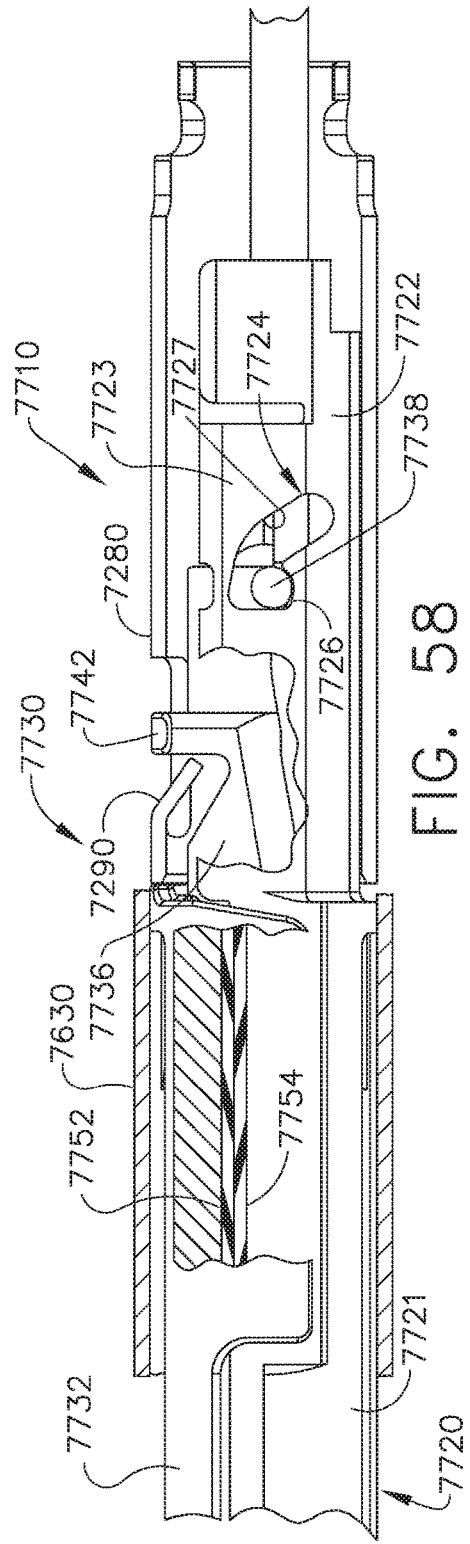

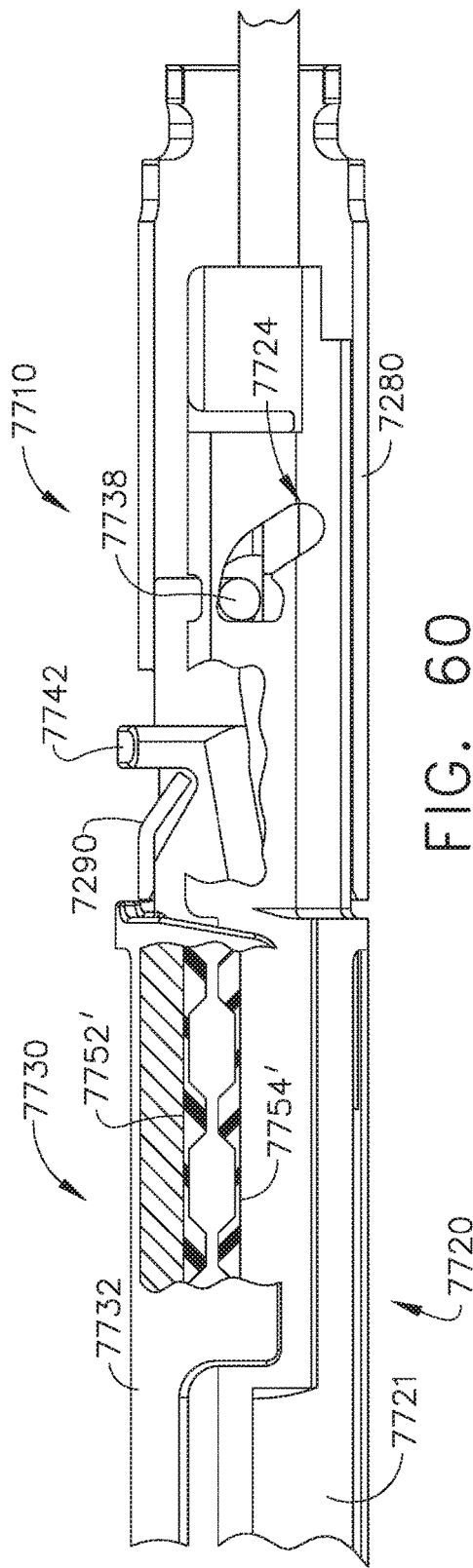
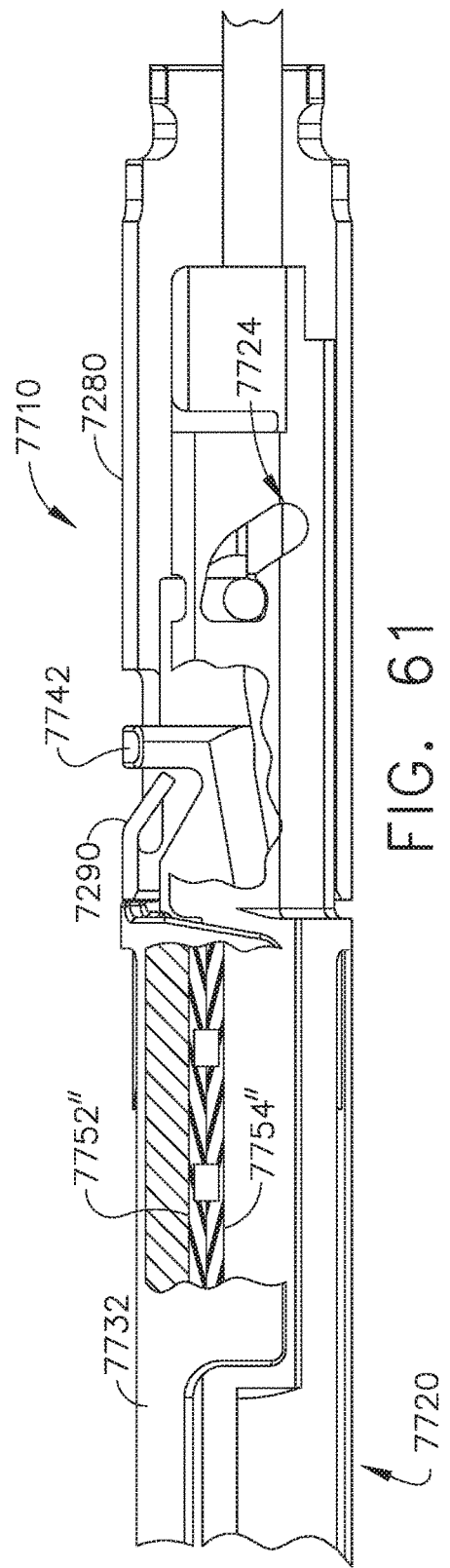

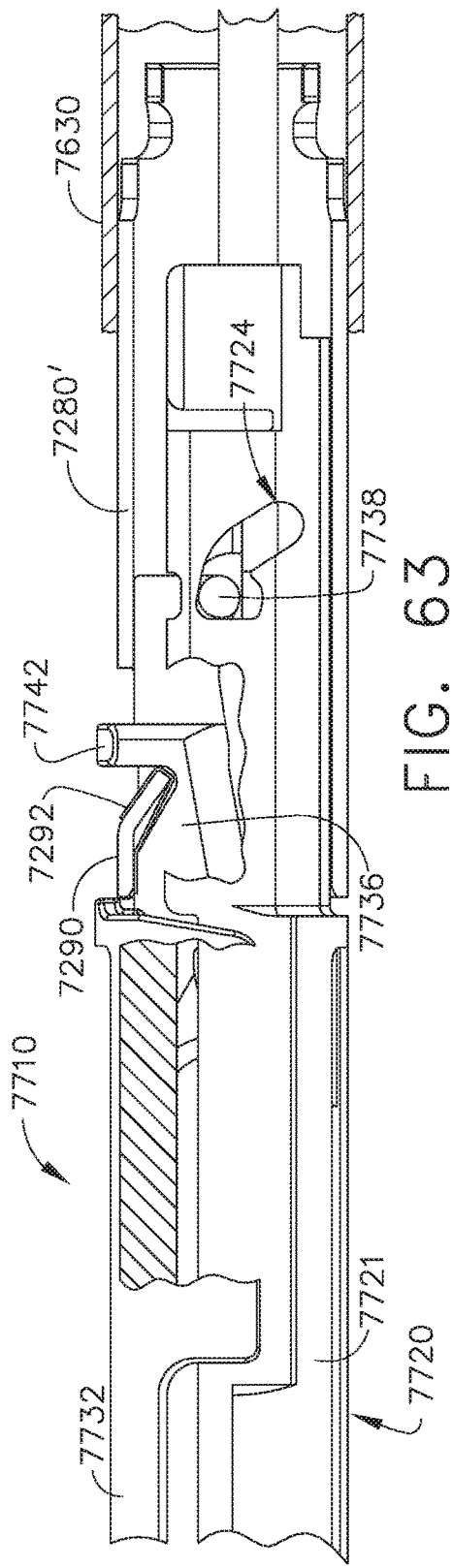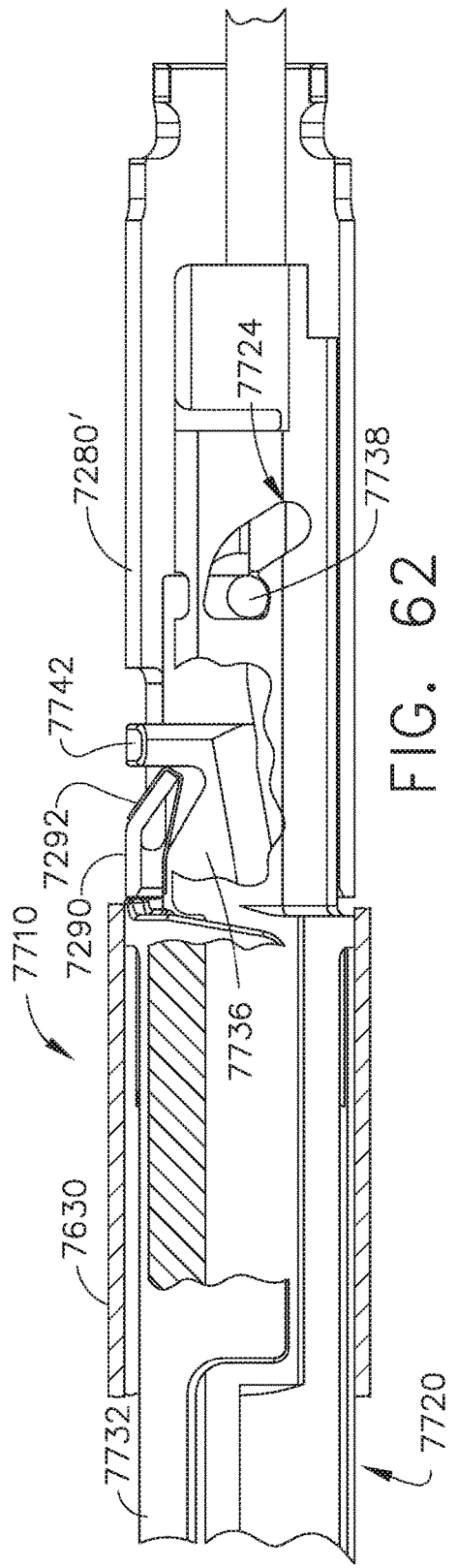

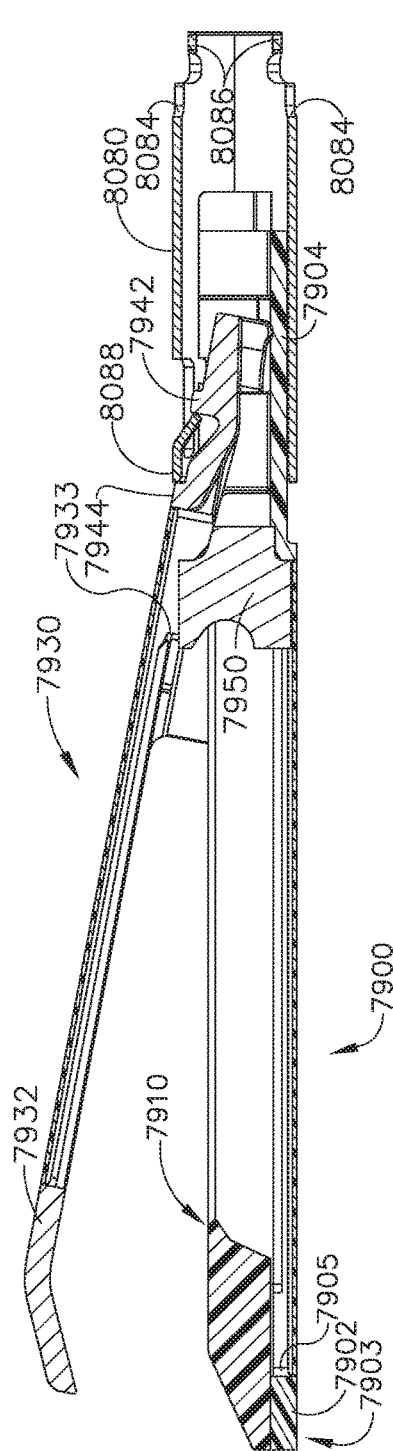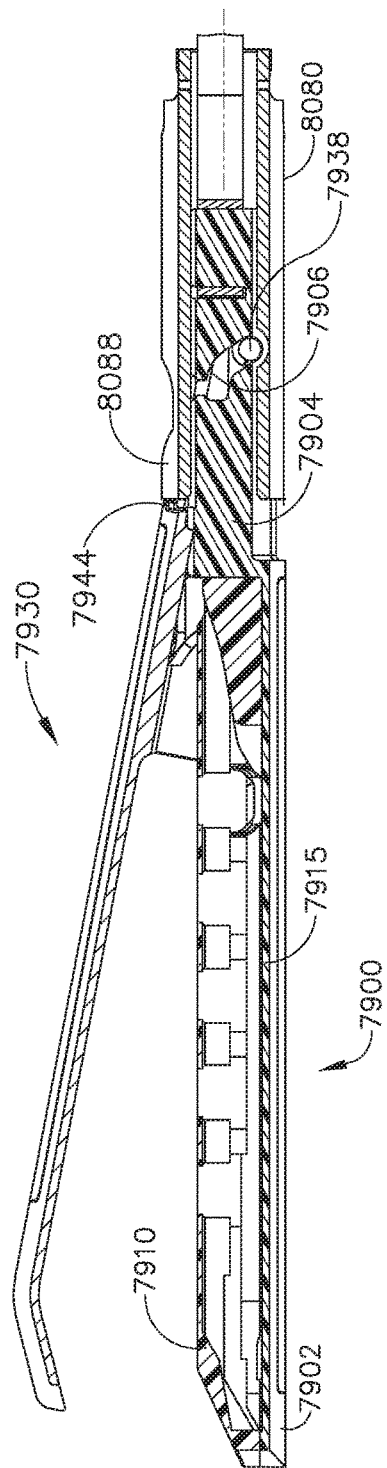

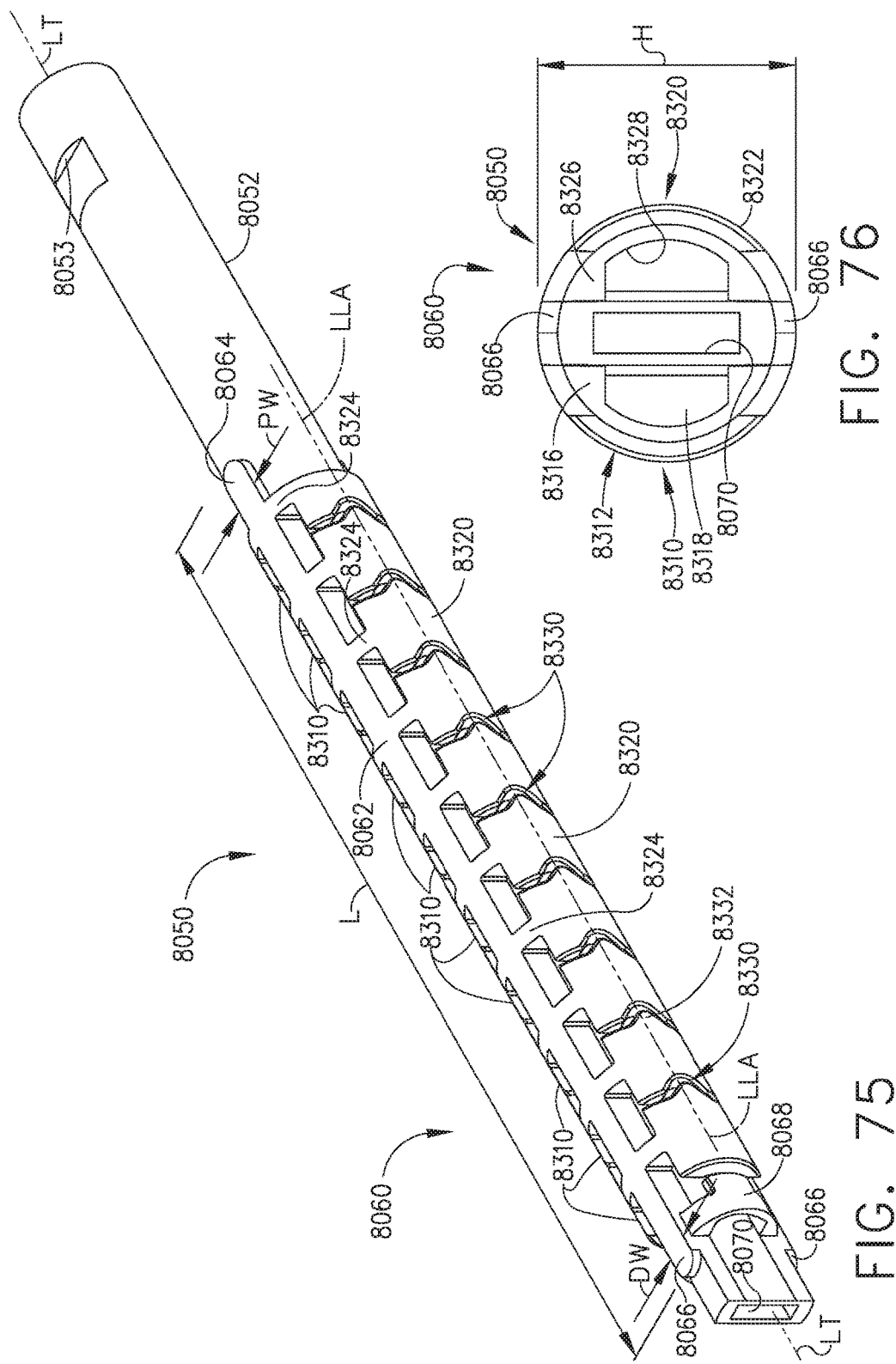

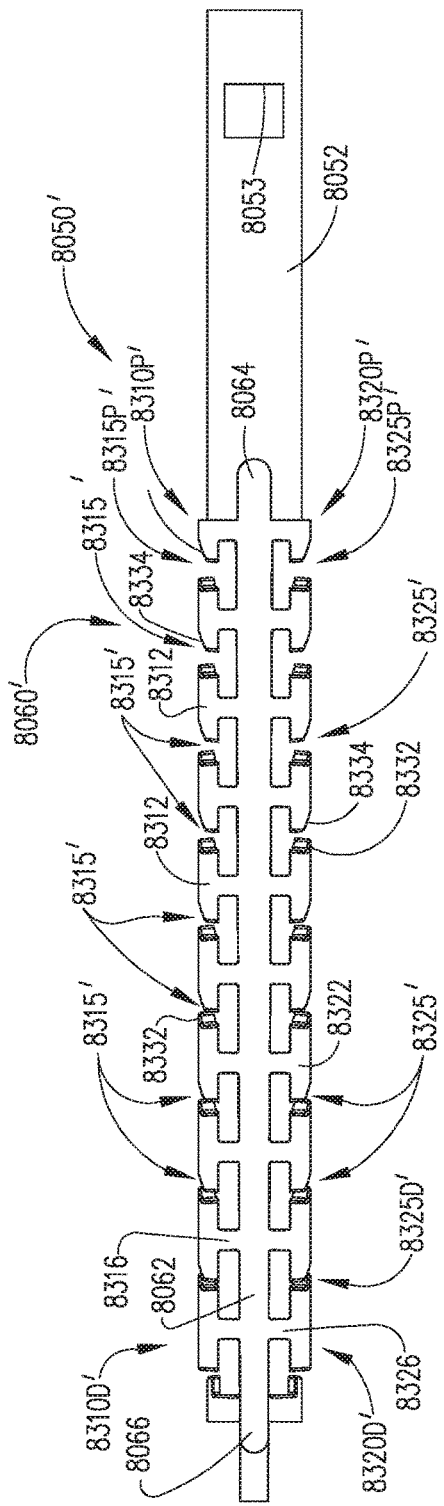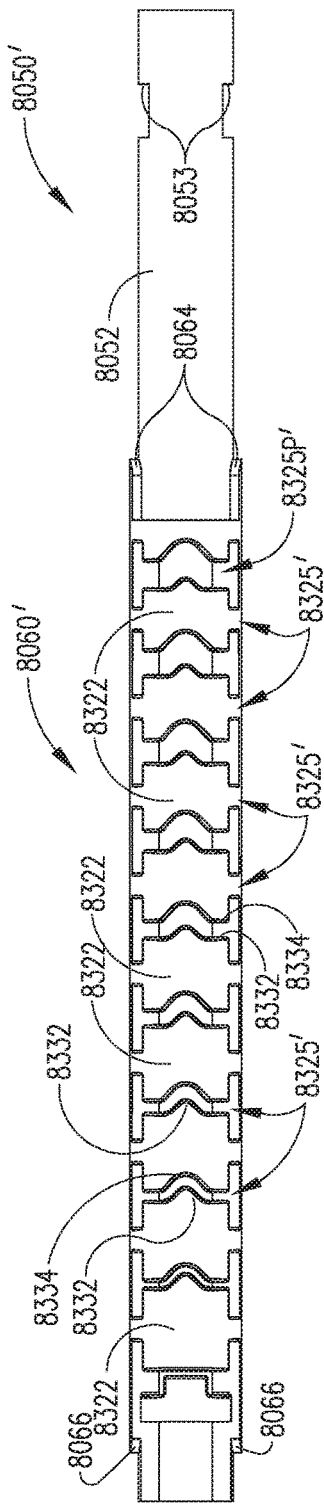
FIG. 80
FIG. 81

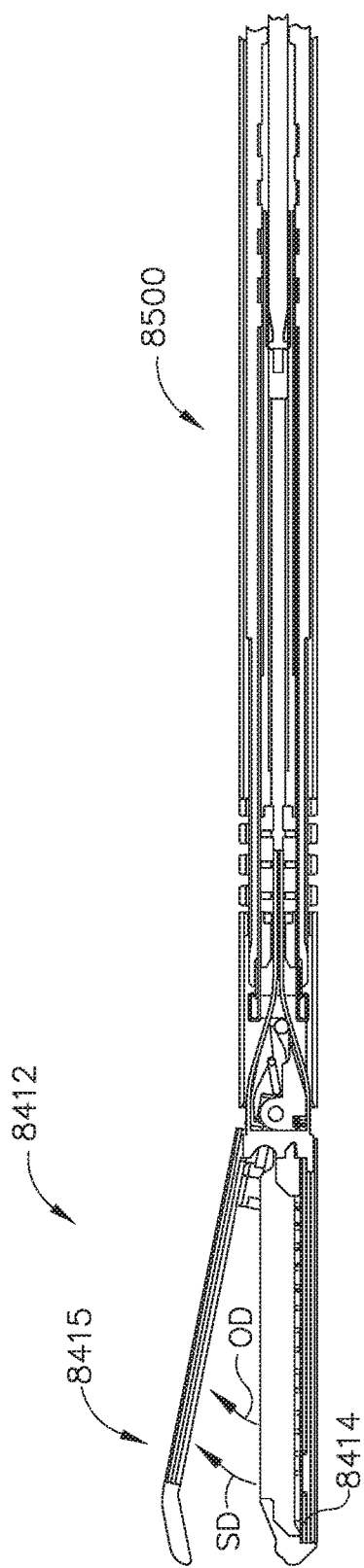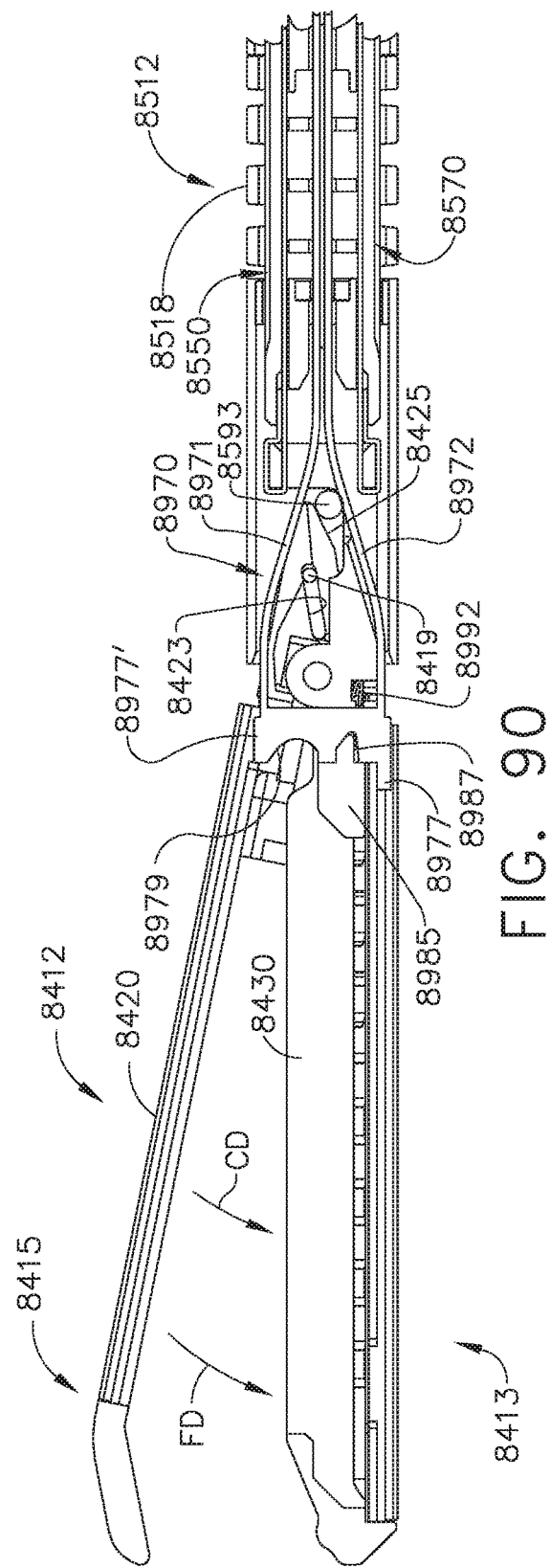

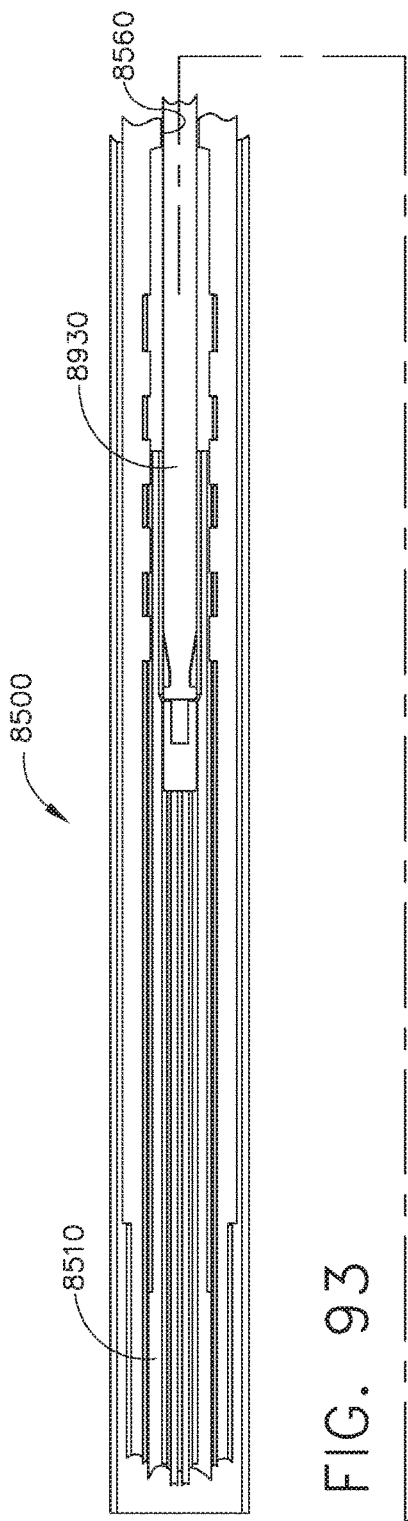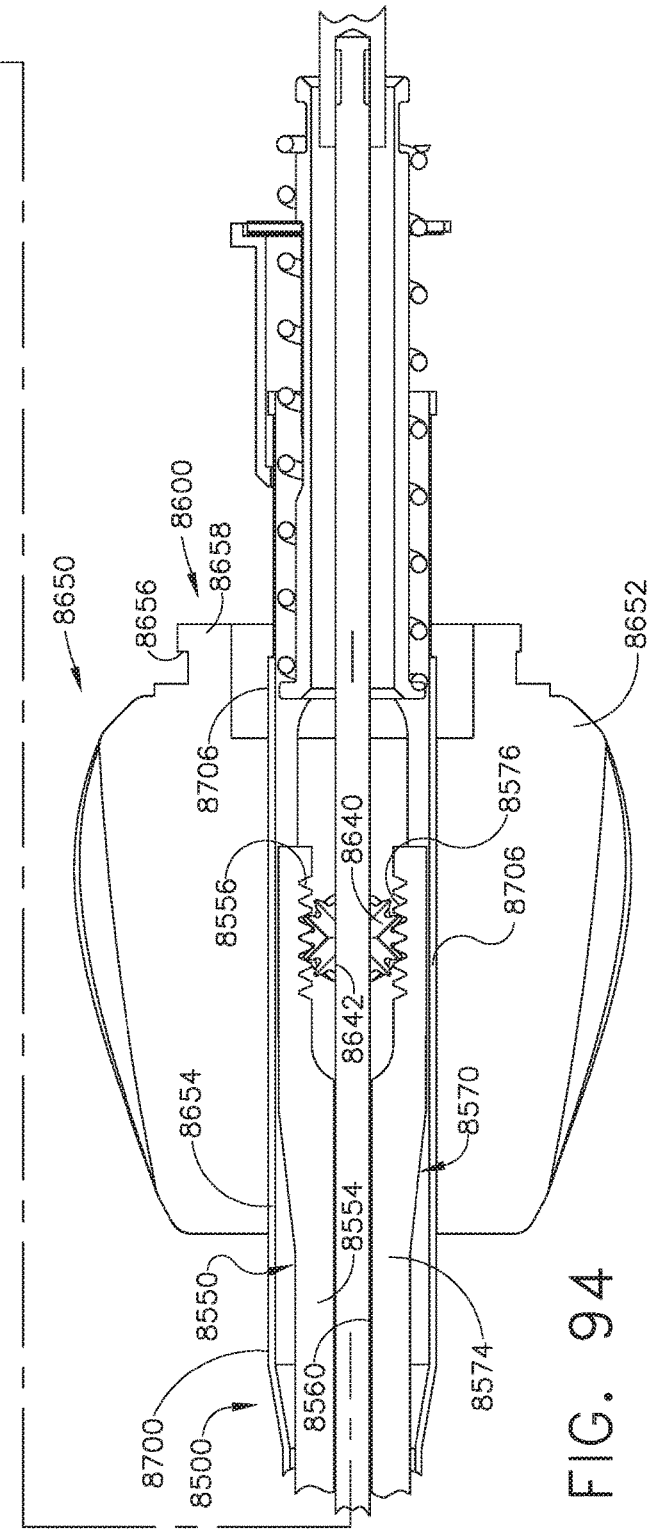

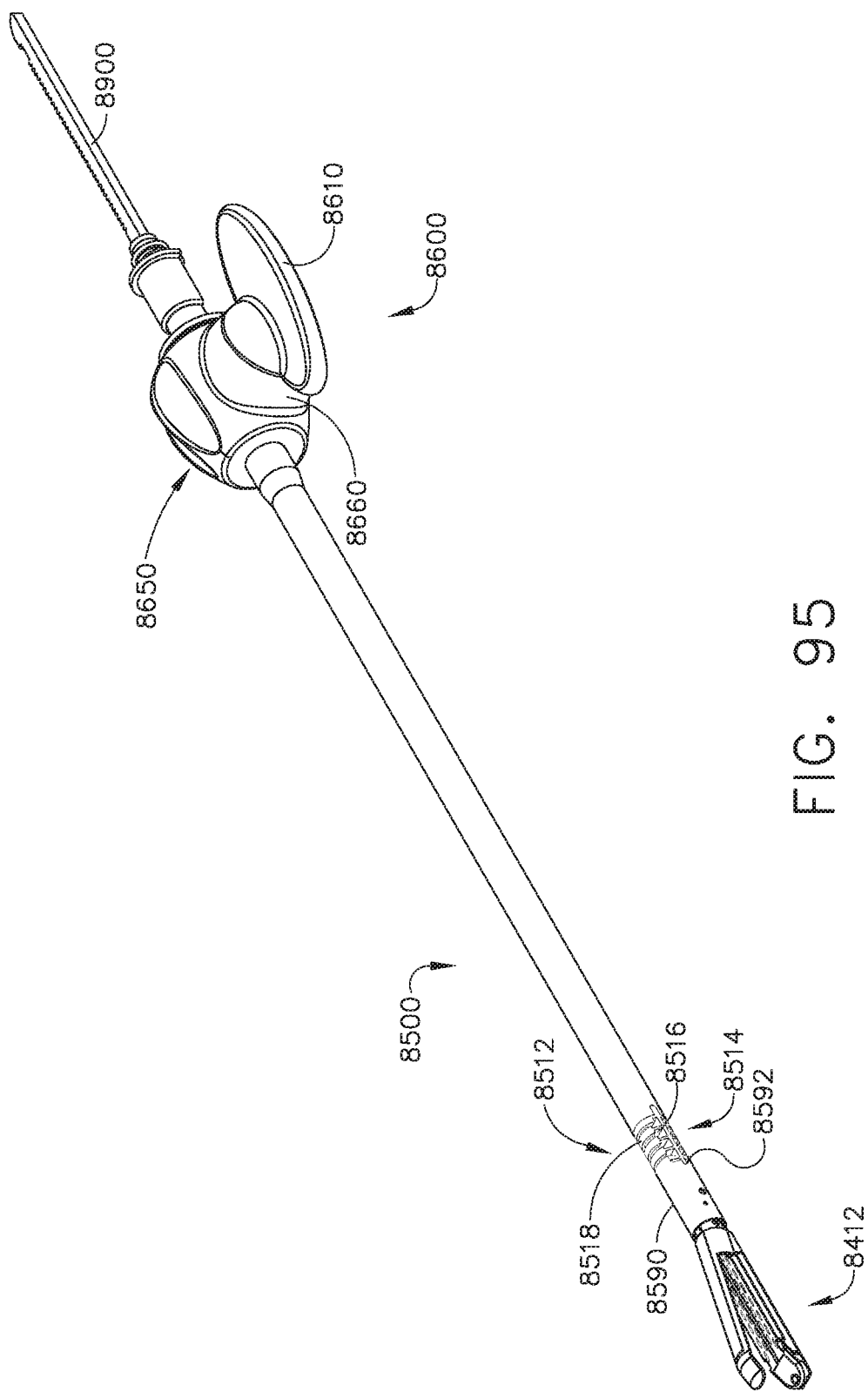

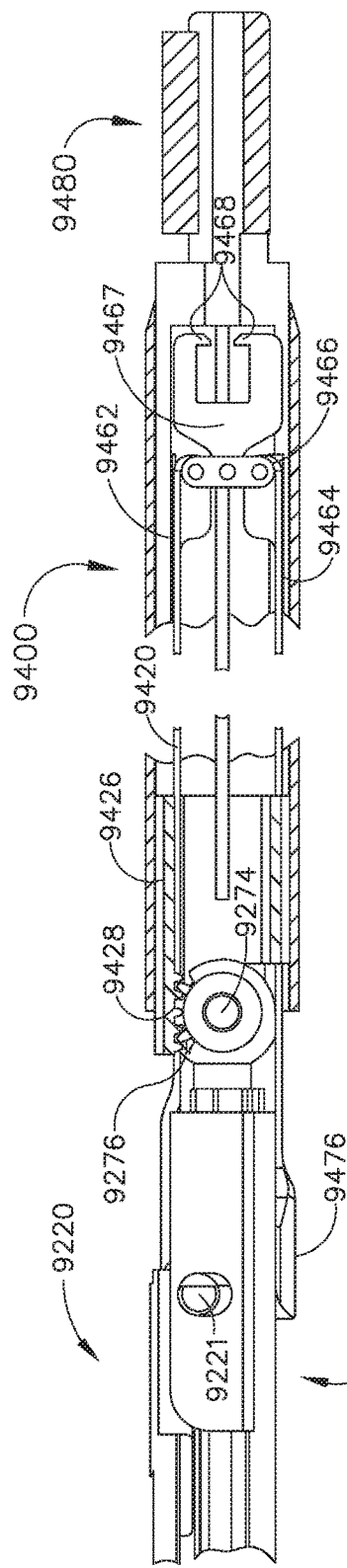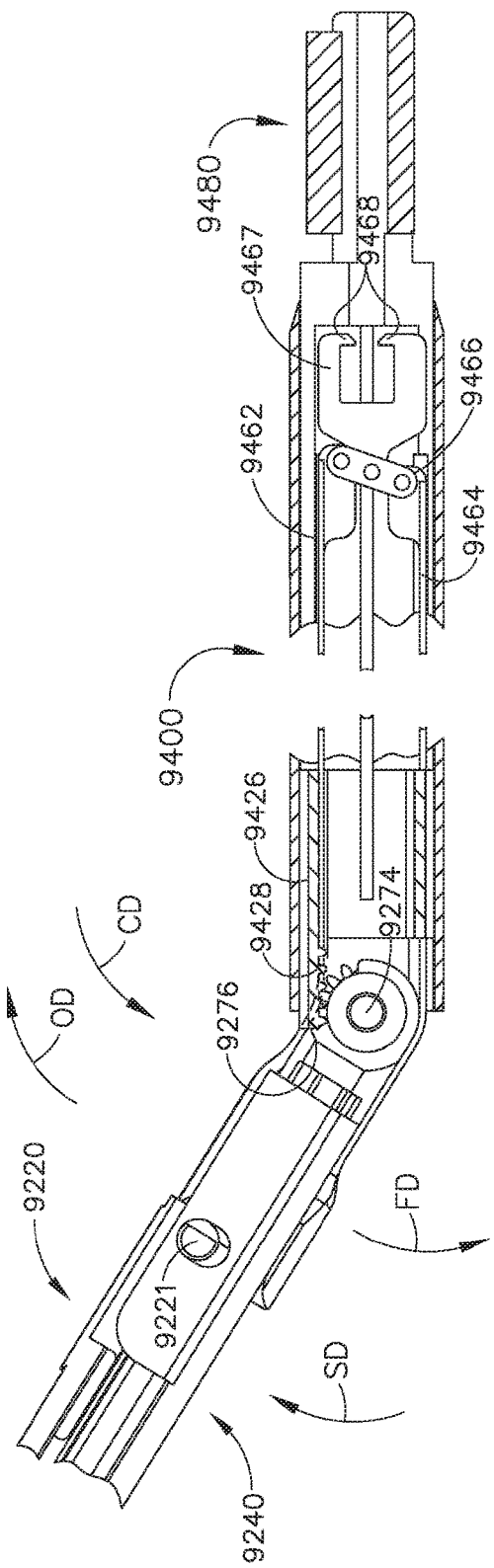

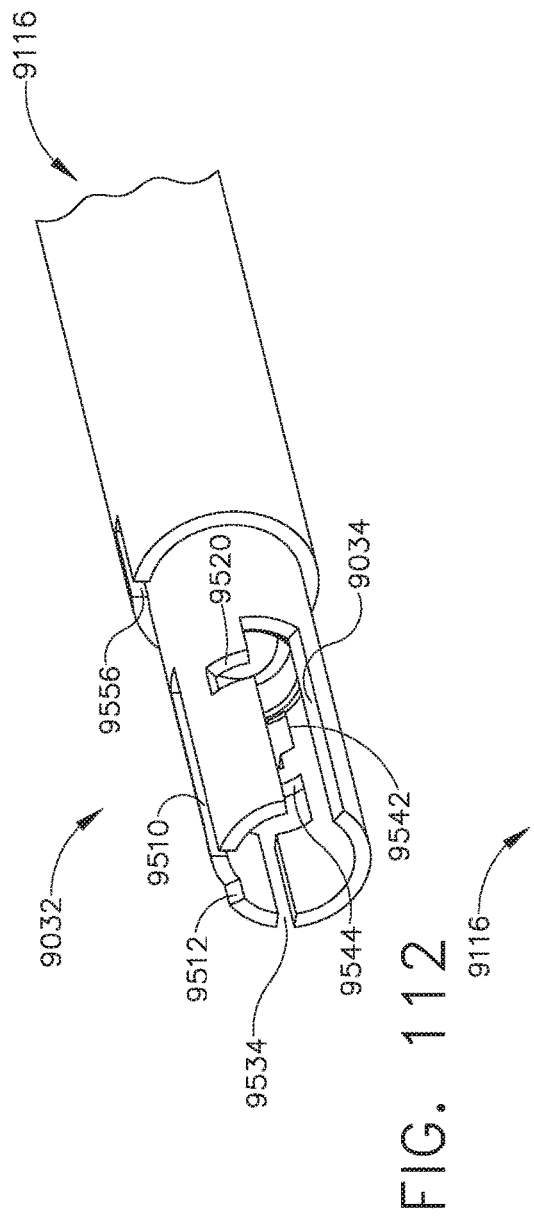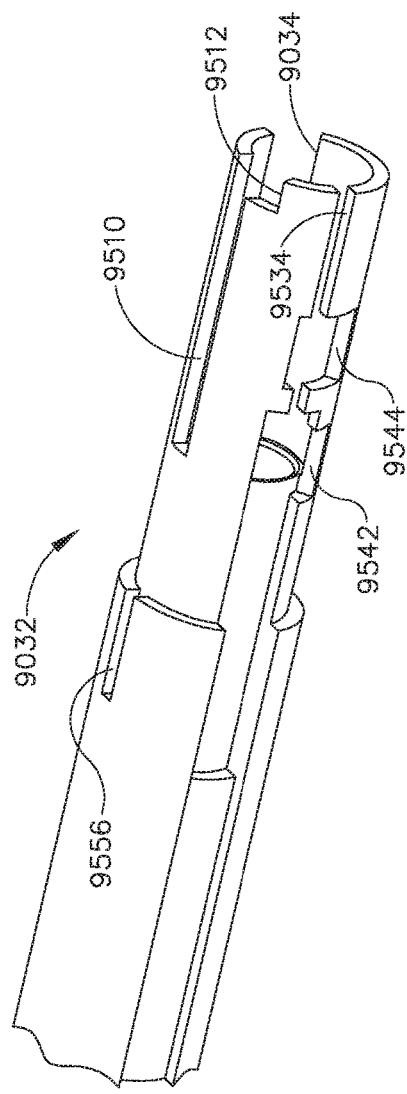

SURGICAL CUTTING AND STAPLING INSTRUMENTS WITH INDEPENDENT JAW CONTROL FEATURES

BACKGROUND

The present invention relates to surgical instruments and, in various embodiments, to surgical cutting and stapling instruments and staple cartridges therefor that are designed to cut and staple tissue.

BRIEF DESCRIPTION OF DRAWINGS

The various features and advantages of this invention and the manner of attaining them will become more apparent and the invention itself will be better understood by reference to the following description of embodiments of the invention taken in conjunction with the accompanying drawings, wherein:

FIG. 55 is a cross-sectional side view of a portion of another surgical instrument inserted through a portion of a trocar port;

FIG. 56 is another cross-sectional side view of the surgical instrument of FIG. 55 after the end effector has passed through the trocar port into the patient;

FIG. 58 is a cross-sectional side view of a portion of another end effector inserted through a portion of a trocar port;

FIG. 59 is another cross-sectional side view of the end effector of FIG. 58 exiting the trocar port;

FIG. 60 is a cross-sectional view of another end effector arrangement;

FIG. 61 is a cross-sectional view of another end effector arrangement;

FIG. 62 is a cross-sectional side view of a portion of another end effector and distal closure tube arrangement wherein a portion of the end effector is inserted through a portion of a trocar port;

FIG. 63 is another cross-sectional side view of the end effector of FIG. 62 exiting the trocar port;

FIG. 71 is a side cross-sectional view of a surgical end effector and distal closure tube segment with the anvil assembly in an open position;

FIG. 72 is another side cross-sectional view of the surgical end effector and distal closure tube segment of FIG. 71;

FIG. 75 is a perspective view of an intermediate portion of an elongated shaft assembly embodiment;

FIG. 76 is an elevational view of the distal end of the intermediate shaft portion of FIG. 75;

FIG. 80 is a plan view of another intermediate shaft portion embodiment;

FIG. 81 is a side elevational view of the intermediate shaft portion of FIG. 80;

FIG. 89 is another side cross-sectional view of an end effector and portion of an elongated shaft assembly with the anvil in an open position and the cutting head in a starting position;

FIG. 90 is an enlarged cross-sectional view of the end effector and portion of the elongated shaft assembly of FIG. 89;

FIG. 93 is a cross-sectional view of a distal portion of an elongated shaft assembly;

FIG. 94 is a cross-sectional view of a proximal portion of the elongated shaft assembly of FIG. 11 along with a portion of an articulation system;

FIG. 95 is a perspective view of an elongated shaft assembly and end effector;

FIG. 104 is another cross-sectional view of the loading unit of FIG. 103 in an unarticulated position;

FIG. 105 is another cross-sectional view of the loading unit of FIGS. 103 and 104 with the carrier and anvil assembly articulated as a unit in a second direction;

FIG. 112 is a perspective view of a proximal attachment portion of the elongated shaft assembly of FIG. 109;

FIG. 113 is another perspective view of the proximal attachment portion of the elongated shaft assembly of FIG. 109;

FIG. 114 is a perspective view of the collar and a firing shaft arrangement;

FIG. 115 is a partial perspective, cross-section view of the loading unit, the coupling assembly, and a proximal end of the elongated shaft assembly of FIG. 109, depicting the loading unit attached to the elongated shaft assembly;

FIG. 116 is a partial elevation, cross-sectional view of the loading unit, the coupling assembly, and the elongated shaft assembly of FIG. 109, depicting the loading unit unattached to the elongated shaft assembly;

FIG. 117 is a partial elevation, cross-sectional view of the loading unit, the coupling assembly and the elongated shaft assembly of FIG. 109, depicting the loading unit attached to the elongated shaft assembly;

FIG. 118 is an elevational view of the coupling assembly and the elongated shaft assembly of FIG. 109 taken along the plane indicated in FIG. 115;

FIG. 119 is a perspective, partial cross-sectional view of the loading unit, the coupling assembly, and the elongated shaft assembly of FIG. 109, depicting the loading unit unattached to the elongated shaft assembly, and further depicting the coupling collar in an initial orientation relative to the elongated shaft assembly;

FIG. 120 is a perspective, partial cross-sectional view of the loading unit, the coupling assembly, and the elongated shaft assembly of FIG. 109, depicting the loading unit unattached to the shaft, and further depicting the coupling collar in the initial orientation relative to the elongated shaft assembly;

FIG. 121 is a perspective, partial cross-sectional view of the loading unit, the coupling assembly, and the elongated shaft assembly of FIG. 109, depicting the loading unit entering the elongated shaft assembly, and further depicting the coupling collar in the initial orientation relative to the elongated shaft assembly;

FIG. 122 is a perspective, partial cross-sectional view of the loading unit, the coupling assembly, and the elongated shaft assembly of FIG. 109, depicting the loading unit entering the elongated shaft assembly, and further depicting the coupling collar in a secondary, rotated orientation relative to the elongated shaft assembly;

FIG. 123 is a perspective, partial cross-sectional view of the loading unit, the coupling assembly, and the elongated shaft assembly of FIG. 109, depicting the loading unit entering the elongated shaft assembly, and further depicting the coupling collar in the secondary, rotated orientation relative to the elongated shaft assembly;

FIG. 124 is a perspective, partial cross-sectional view of the loading unit, the coupling assembly, and the elongated shaft assembly of FIG. 109, depicting the loading unit fully inserted into the elongated shaft assembly, and further depicting the coupling collar in the secondary, rotated orientation relative to the elongated shaft assembly;

Figure 109:
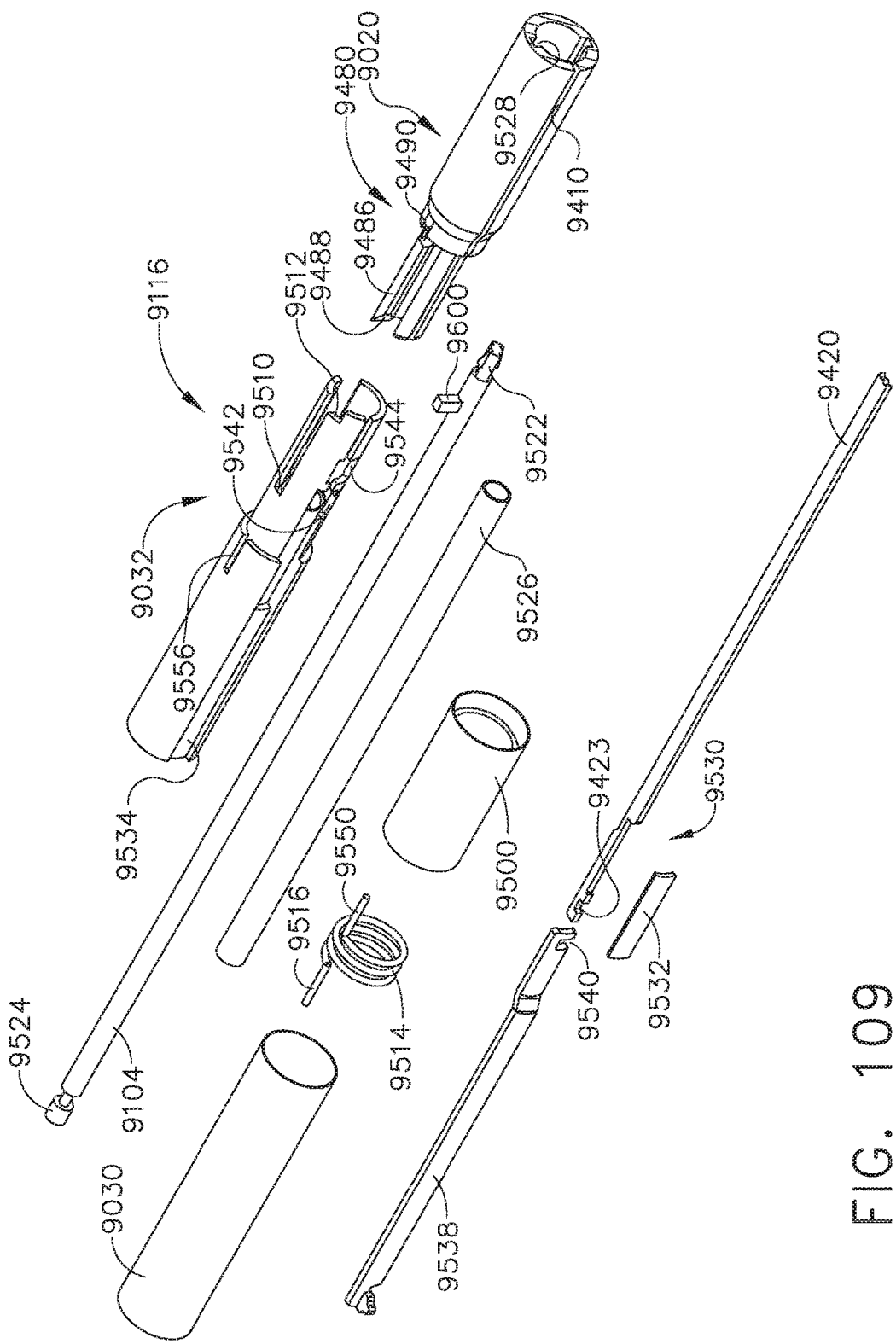
FIG. 109 is another partial exploded perspective view of the shaft assembly, the coupling assembly and the loading unit of FIG. 106.
Figure 125:
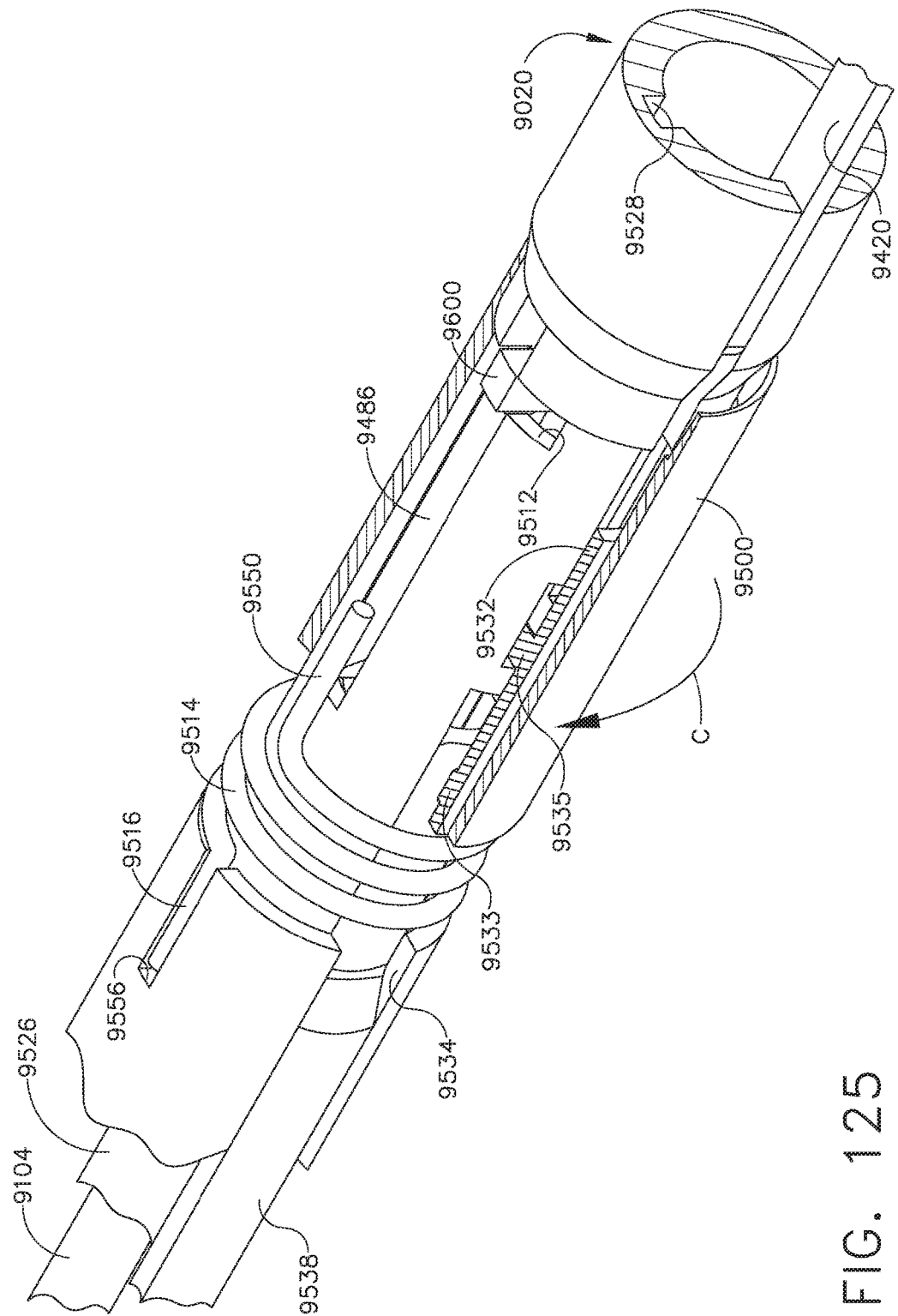
Figure 126:
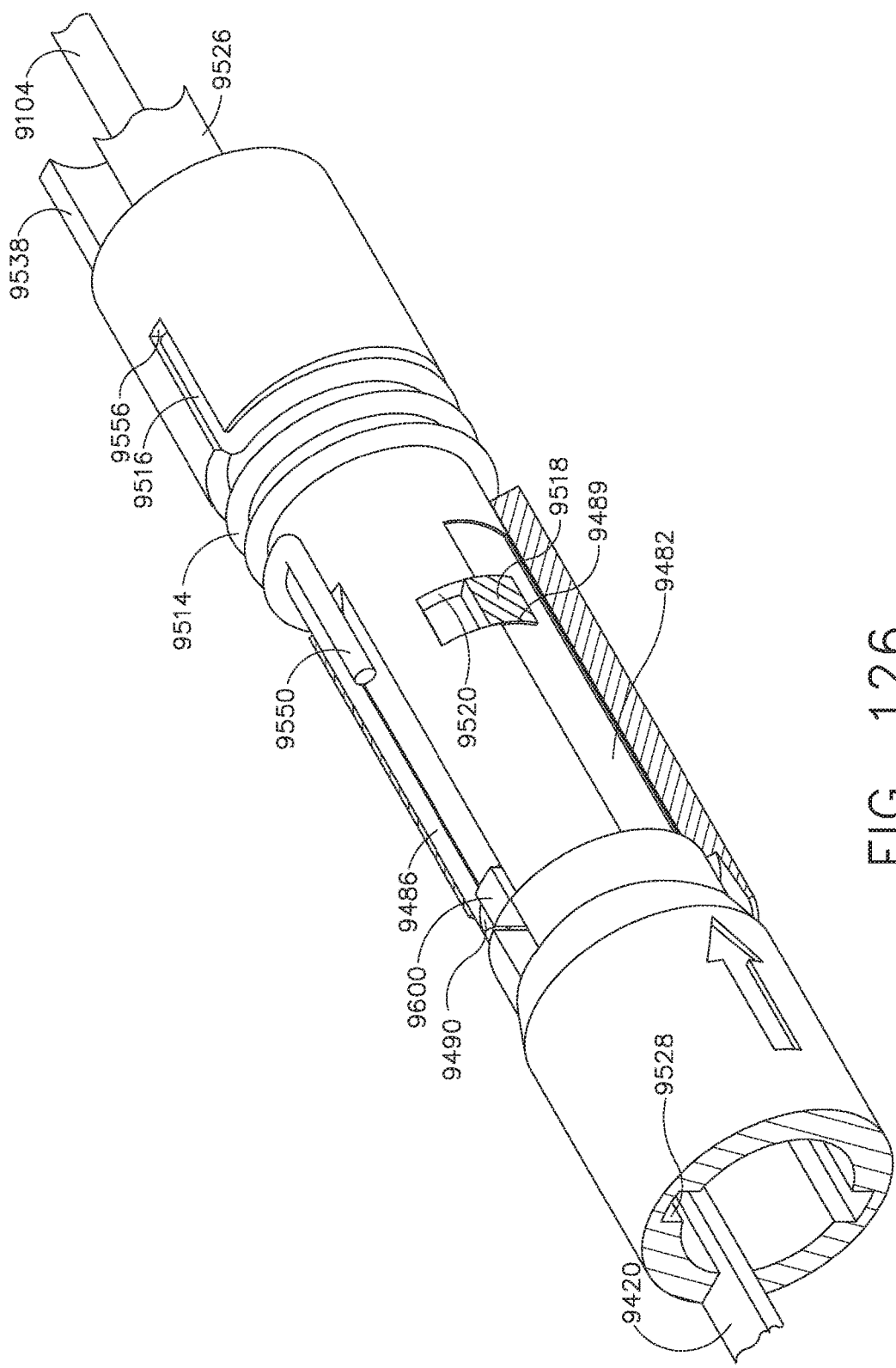

FIG. 125 is a perspective, partial cross-sectional view of the loading unit, the coupling assembly, and the elongated shaft assembly of FIG. 109, depicting the loading unit fully inserted into the elongated shaft assembly, and further depicting the coupling collar in the initial orientation relative to the elongated shaft assembly; and FIG. 126 is a perspective, partial cross-sectional view of the loading unit, the coupling assembly, and the elongated shaft assembly of FIG. 109, depicting the loading unit fully inserted into the elongated shaft assembly, and further depicting the coupling collar in the initial orientation relative to the elongated shaft assembly.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Applicant of the present application also owns the following patent applications that were filed on Dec. 23, 2013 and which are each herein incorporated by reference in their respective entireties:

U.S. patent application Ser. No. 14/138,465, entitled: "Surgical Staples and Staple Cartridges", now U.S. Patent Application Publication No. 2015/0173744;

U.S. patent application Ser. No. 14/138,475, entitled: "Surgical Staples and Staple Cartridges", now U.S. Patent Application Publication No. 2015/0173749;

U.S. patent application Ser. No. 14/138,481, entitled: "Surgical Staples and Methods For Making the Same", now U.S. Patent Application Publication No. 2015/0173750;

U.S. patent application Ser. No. 14/138,489, entitled: "Surgical Staples, Staple Cartridges and Surgical End Effectors", now U.S. Patent Application Publication No. 2015/0173751;

U.S. Design Pat. Application No. 29/477,488, entitled: "Surgical Fastener", now U.S. Pat. No. D775,336;

U.S. patent application Ser. No. 14/138,505, entitled: "Fastener Cartridge Comprising an Extendable Firing Member", now U.S. Pat. No. 9,585,662;

U.S. patent application Ser. No. 14/138,518, entitled: "Fastener Cartridge Comprising a Firing Member Configured to Directly Engage and Eject Fasteners From the Fastener Cartridge", now U.S. Patent Application Publication No. 2015/0173761;

U.S. patent application Ser. No. 14/138,530, entitled: "Fastener Cartridge Comprising a Firing Member Including Fastener Surfaces", now U.S. Pat. No. 9,549,735;

U.S. patent application Ser. No. 14/138,554, entitled: "Surgical Instruments With Articulatable Shaft Arrangements", now U.S. Patent Application Publication No. 2015/0173789;

U.S. patent application Ser. No. 14/138,474, entitled: "Articulatable Surgical Instruments With Separate and Distinct Closing and Firing Systems", now U.S. Patent Application Publication No. 2015/0173745;

U.S. patent application Ser. No. 14/138,497, entitled: "Surgical Cutting and Stapling Instruments With Articulatable End Effectors", now U.S. Patent Application Publication No. 2015/0173755;

U.S. patent application Ser. No. 14/138,516, entitled: "Surgical Cutting and Stapling Methods", now U.S. Patent Application Publication No. 2015/0173756; and U.S. patent application Ser. No. 14/138,507, entitled: "Modular Surgical Instruments", now U.S. Patent Application Publication No. 2015/0173747.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
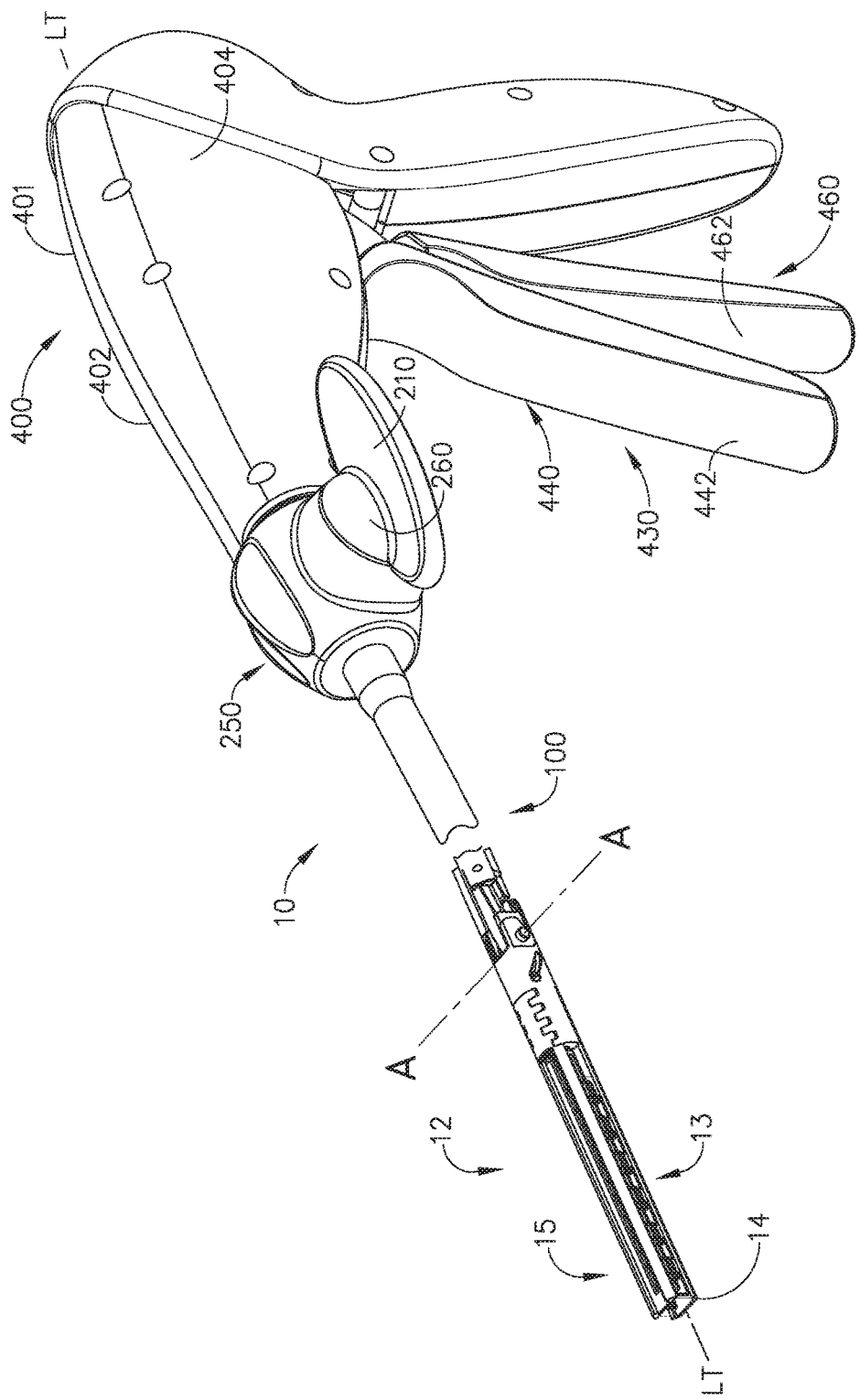
FIG. 1 is a perspective view of one surgical instrument arrangement.

Turning to the Drawings wherein like numerals denote like components throughout the several views, FIG. 1 depicts a surgical instrument 10 that is capable of practicing several unique benefits of the present invention. The surgical instrument 10 is designed to manipulate and/or actuate various forms and sizes of end effectors 12 that are operably attached to an elongated shaft assembly 100 of the surgical instrument. In the depicted embodiment, for example, the end effector 12 comprises a surgical stapling device that has openable and closable jaws 13 and 15. More specifically, the end effector 12 includes an elongated channel 14 that forms a lower jaw 13 of the end effector 12. See FIG. 2. In the illustrated arrangement, the elongated channel 14 is configured to operably support a staple cartridge 30 and also movably supports an anvil assembly 20 that functions as an upper jaw 15 of the end effector 12.

In various implementations, the end effector 12 is configured to be coupled to an elongated shaft assembly 100 that protrudes from a handle assembly or housing 400. See FIG. 1. The end effector 12 (when closed) and the elongated shaft assembly 100 may have similar cross-sectional shapes and be sized to operably pass through a trocar tube or working channel in another form of access instrument. As used herein, the term "operably pass" means that the end effector and at least a portion of the elongated shaft assembly 100 may be inserted through or passed through the channel or tube opening and can be manipulated therein as needed to complete the surgical stapling procedure. In some embodiments, for example, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various implementations, the elongated shaft assembly 100 may have an outer diameter that is substantially the same as the outer diameter of the end effector 12 when the end effector 12 is in a closed position. For example, a 5 mm end effector may be coupled to an elongated shaft assembly 100 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 100 may have a 10 mm (or larger) cross-sectional diameter, but may also be able to actuate a 5 mm or 10 mm end effector. Accordingly, the outer shaft assembly 100 may have an outer diameter that is the same as or is different from the outer diameter of a closed end effector 12 attached thereto.

Figure 2:
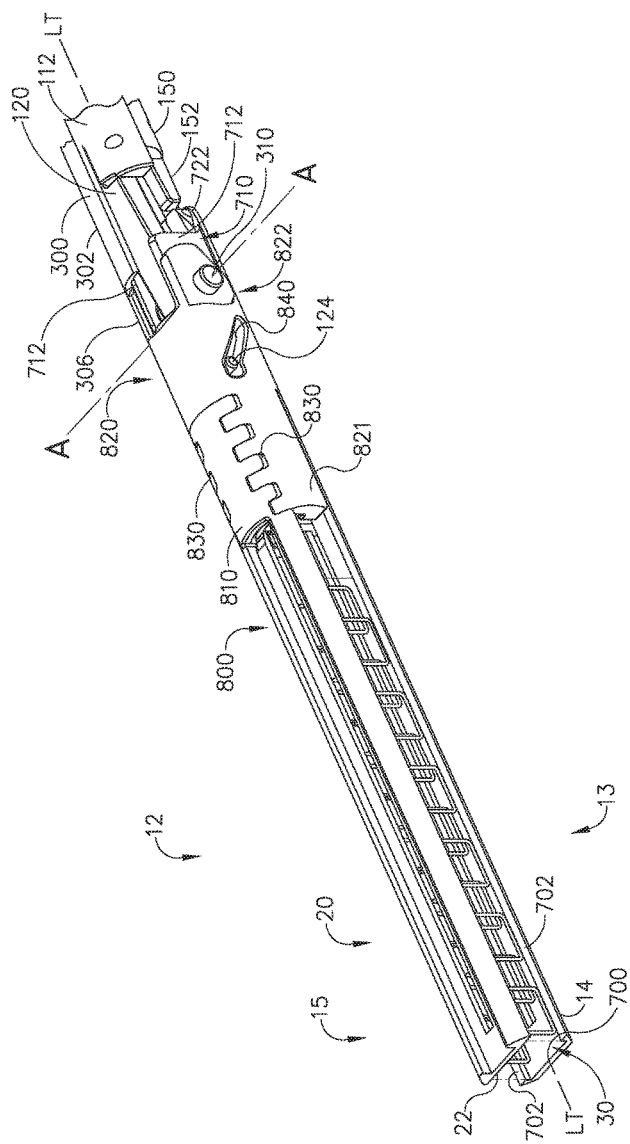
FIG. 2 is an enlarged perspective view of an end effector and a portion of the elongated shaft assembly of the surgical instrument of FIG. 1.
Figure 3:
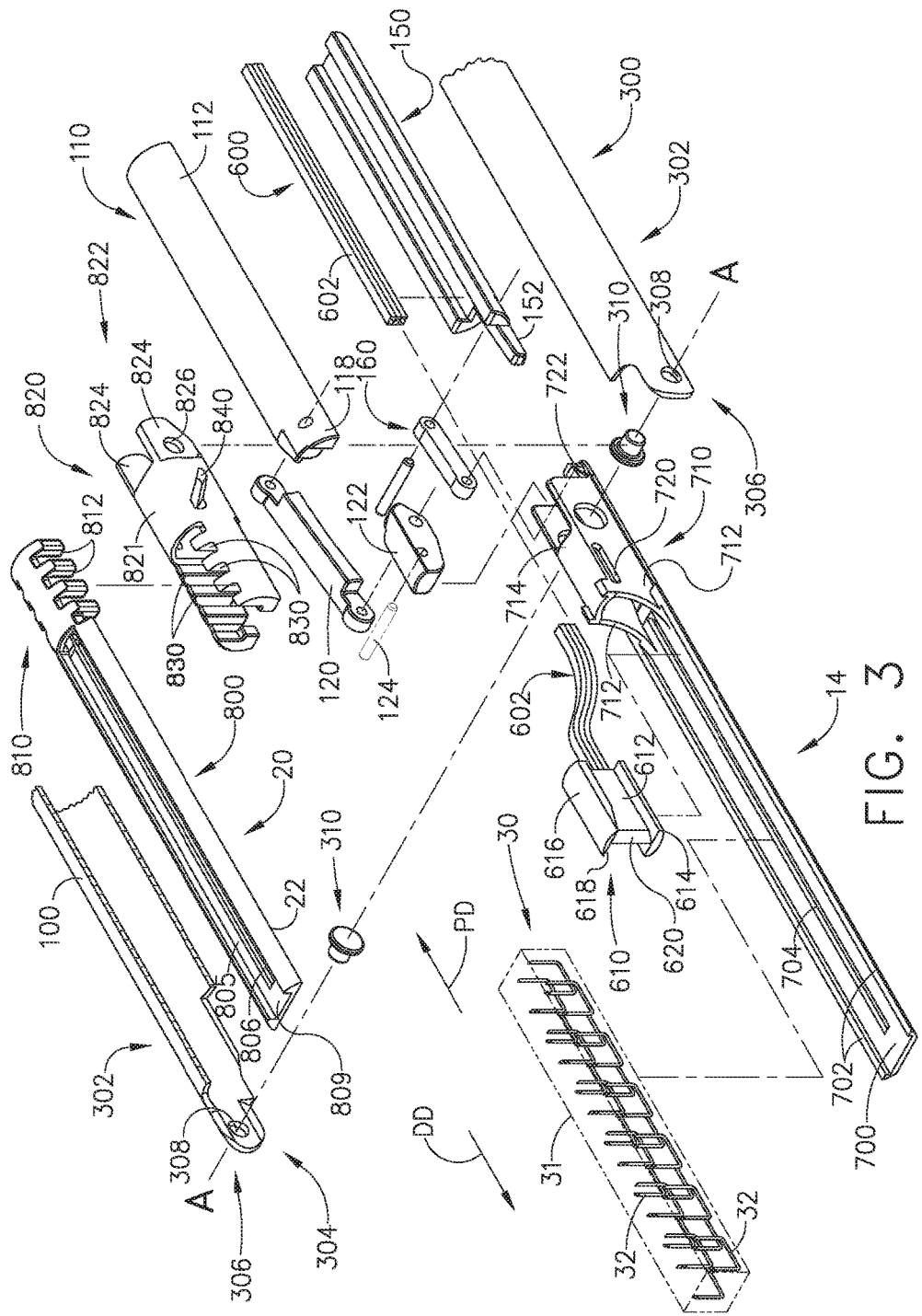
FIG. 3 is an exploded perspective view of the end effector and portion of the elongated shaft assembly of FIGS. 1 and 2.

Referring now to FIGS. 2 and 3, the elongated channel 14 may comprise an elongated trough 700 that is configured to removably support a surgical staple cartridge 30 thereon. In various implementations, for example, the elongated channel 14 may be fabricated from, for example, 300 & 400 Series, 17-4 & 17-7 stainless steel, titanium, etc. and be formed with spaced side walls 702. As will be discussed in further detail below, the anvil assembly 20 may include a distal anvil portion 800 and a proximal anvil mounting tube 820. The distal anvil portion 800 may, for the most part, be substantially coextensive with the portion of the elongated channel 14 that supports the staple cartridge 30. The distal anvil portion 800 may be fabricated from, for example, 300 & 400 Series, 17-4 & 17-7 stainless steel, titanium, etc. and have a staple forming undersurface, generally labeled as 22 that has a plurality of staple forming pockets (not shown) formed therein.

The elongated channel 14 may be configured to support a variety of different surgical staple cartridges that are designed to be "implanted" within the patient. For example, the implantable surgical staple cartridge 30 may comprise any of the various surgical staple cartridge arrangements disclosed in U.S. Patent Application Publication No. 2012-0080484, filed Sep. 30, 2010, entitled SURGICAL STAPLING INSTRUMENT WITH A VARIABLE STAPLE FORMING SYSTEM, now U.S. Pat. No. 9,113,862, the entire disclosure of which is hereby incorporated by reference herein. In at least one implementation for example, the staple cartridge 30 includes a body portion 31 that consists of a compressible hemostat material such as, for example, oxidized regenerated cellulose ("ORC") or a bio-absorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets in the distal anvil portion 800 when the distal anvil portion 800 is driven into forming contact with the staple cartridge 30.

Referring to FIG. 3, the elongated channel 14 may further include a boxed mounting end 710 that includes a pair of spaced side walls 712 and a top wall 714. In at least one implementation, the end effector 12 is configured to be articulated relative to the elongated shaft assembly 100 about an articulation and pivot axis A-A about which the anvil assembly 20 is pivoted relative to the elongated channel 14. The elongated shaft assembly 100 defines a longitudinal tool axis LT-LT. The articulation and pivot axis A-A is transverse to the longitudinal tool axis LT-LT. The elongated shaft assembly 100 comprises a hollow outer shaft 300 and serves to function as the shaft spine of the elongated shaft assembly 100. The proximal end of the elongated shaft assembly 100 may be rotatably supported by the handle assembly 400 so that the clinician may selectively rotate the elongated shaft assembly 100 and the end effector 12 attached thereto about the longitudinal tool axis LT-LT. The distal end 302 of the outer shaft 300 is formed with a clevis arrangement 304 that comprises a pair of spaced attachment tabs 306. Each attachment tab 306 has a mounting hole 308 therein that is adapted to receive a corresponding pivot pin 310 therethrough.

Figure 4:
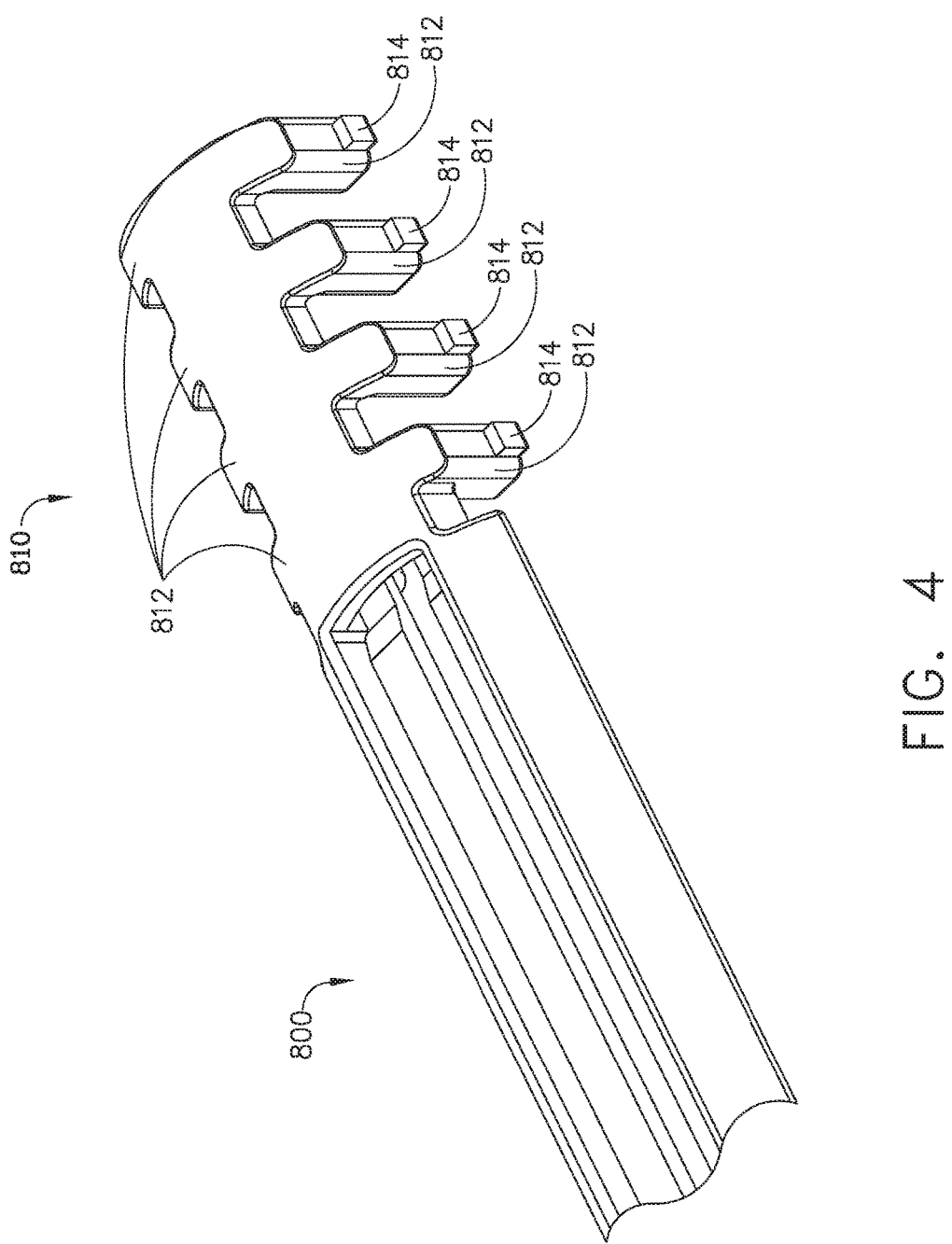
FIG. 4 is a perspective view of a portion of a distal anvil portion of the end effector of FIGS. 2 and 3.
Figure 5:
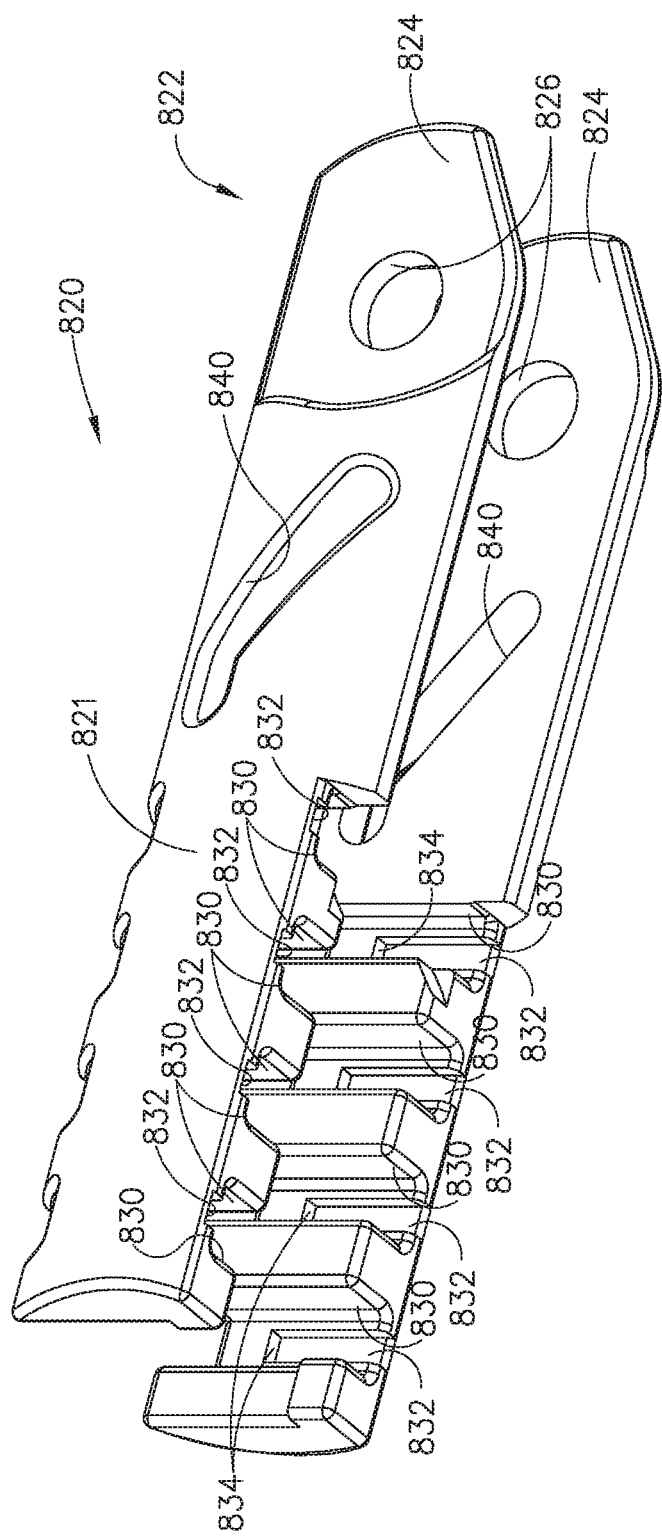
FIG. 5 is a lower perspective view of a proximal anvil mounting tube arrangement of the end effector of FIGS. 2 and 3.
Figure 6:
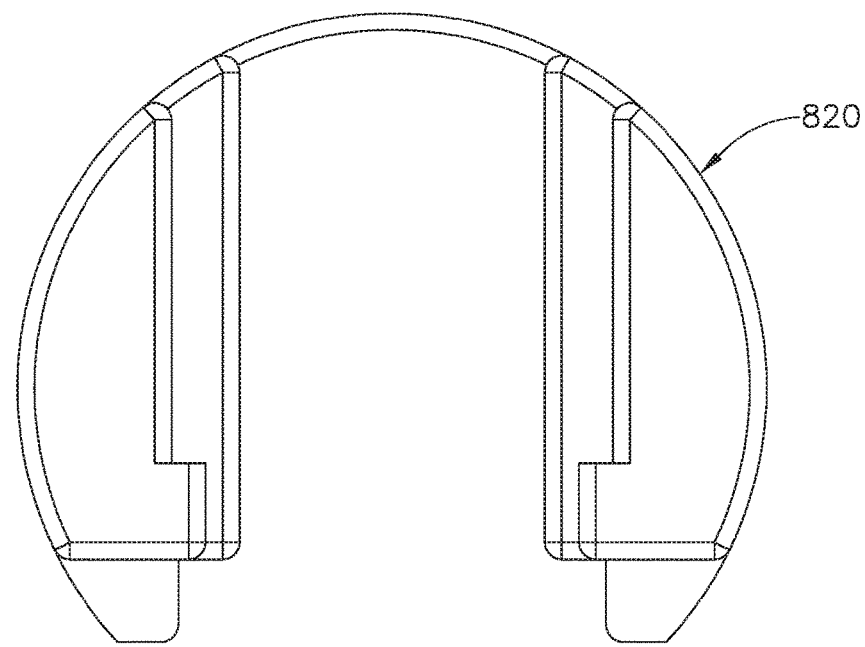
FIG. 6 is an elevational view of the distal end of the proximal anvil mounting tube of FIG. 5.
Figure 7:
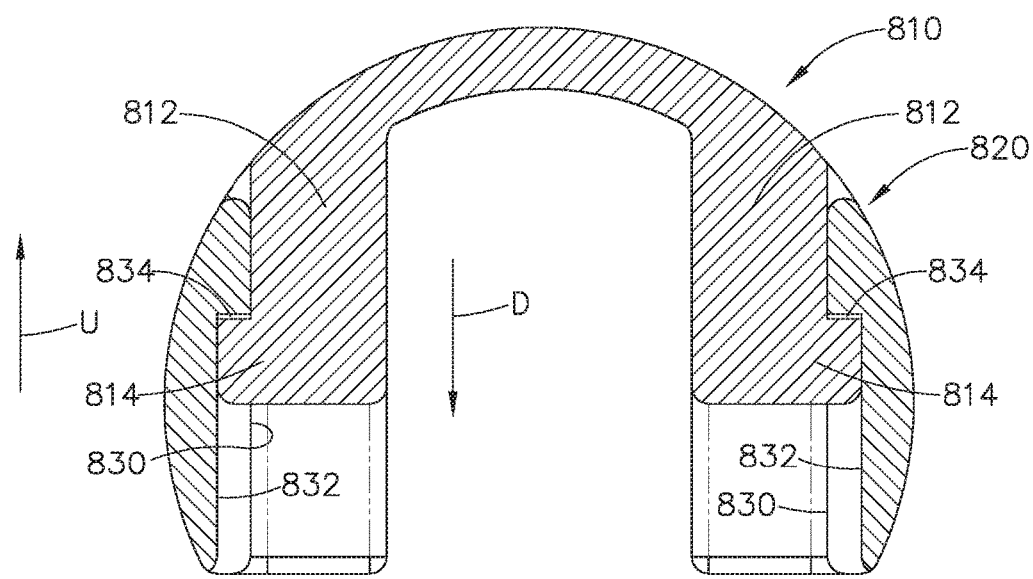
FIG. 7 is an end cross-sectional view of the distal anvil portion and proximal anvil mounting tube assembled together.

In various implementations, the anvil assembly 20 includes a distal anvil portion 800 and a proximal anvil mounting tube 820. As can be seen in FIGS. 2, 3 and 5, the proximal anvil mounting tube 820 includes a body portion 821 that has a proximally extending clevis portion 822 that is formed by two proximally extending anvil attachment tabs 824. Each anvil attachment tab 824 has an anvil mounting hole 826 therethrough that is configured to be pivotally journaled on the pivot pins 310. In various implementations, the distal anvil portion 800 is configured to be coupled to the proximal anvil mounting tube 820 such that the distal anvil portion 800 may "float" relative to the proximal anvil mounting tube 820. Referring to FIG. 5, the body 821 of the proximal anvil mounting tube 820 may be formed with a series of opposed, vertically-extending opened ended grooves 830. Grooves 830 are sized to slidably receive therein corresponding vertically extending attachment lugs 812 formed on a proximal end 810 of the distal anvil portion 800. See FIG. 4. Each attachment lug 812 has a stop lug 814 formed thereon that is sized to be movably received in a stop groove 832 formed in each groove 830 as shown in FIG. 5. Each stop groove 832 has a closed end 834. The proximal end 810 of the distal anvil portion 800 is movably coupled to the proximal anvil mounting tube 820 by aligning the attachment lugs 812 with the open bottom ends of the corresponding grooves 830 and then inserting the proximal end upward into the proximal anvil mounting tube 820. This assembly may be completed before the anvil assembly 20 is pivotally journaled on the pivot pins 310. Once assembled and pivotally coupled to the elongated channel 14, the distal anvil portion 800 will be unable to slidably disengage the proximal anvil mounting tube 820 due to contact with elongated channel 14. The stop lugs 812 will likewise contact the closed ends 834 of the corresponding stop groove 832 to prevent the proximal end 810 of the distal anvil portion 800 from becoming disconnected from the proximal anvil mounting tube 820. See FIG. 7. As can be seen in FIG. 7, the distal anvil portion 820 may move upward (arrow "U") and downward (arrow "D") relative to the proximal anvil mounting tube 820. Such range of vertical travel of the distal anvil portion 800 relative to the proximal anvil mounting portion 820 may be referred to herein as "floating" vertical travel or movement.

Figure 8:
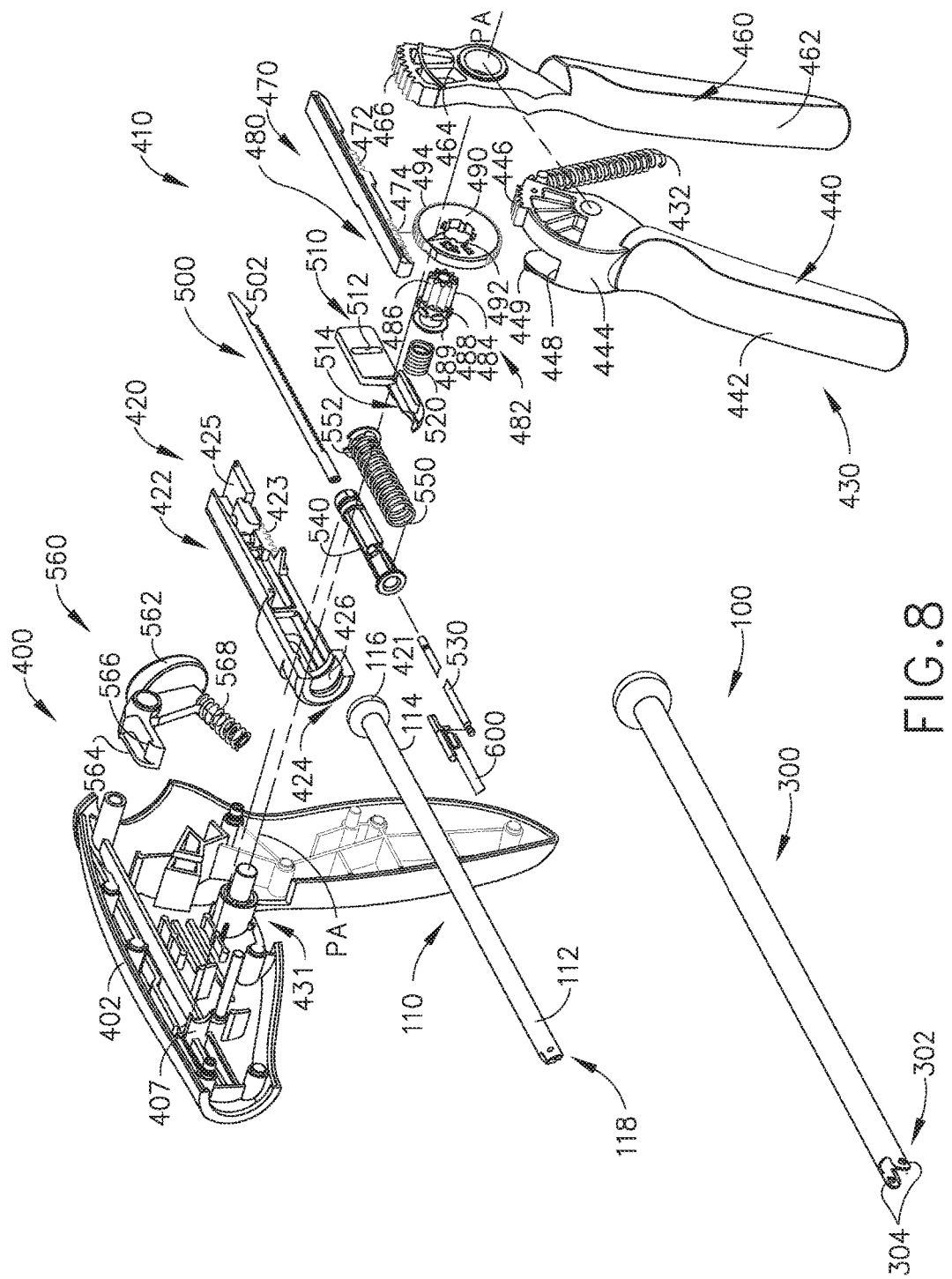
FIG. 8 is an exploded perspective assembly view of a portion of the handle assembly of the surgical instrument of FIG. 1.

Referring now to FIG. 8, initial closure of the anvil assembly 20 relative to the elongated channel assembly 14 and the surgical staple cartridge 30 operably supported therein may be accomplished by a unique and novel closure system, generally designated as 110. The closure system 110 may also be referred to herein as the "second jaw closure system". In one implementation, the closure system 110 includes an anvil closure rod 112 that has a proximal end 114 that has a flanged end 116 that is configured to be rotatably attached to a closure carriage 420 of the closure system that is operably supported within the housing assembly 400. See FIG. 8. The anvil closure rod 112 may also be referred to herein as the "second jaw actuator bar 112." The closure carriage and firing system may be similar in construction and operation to the closure carriage and closure system disclosed in U.S. Patent Application Publication No. US 2012/0074200 A1, entitled SURGICAL INSTRUMENT WITH SELECTIVELY ARTICULATABLE END EFFECTOR, the entire disclosure of which is hereby incorporated by reference herein.

Referring again to FIG. 8, the closure carriage 420 may comprise two carriage segments 422 (only one is illustrated) that are interconnected together by adhesive, snap features, screws, etc. As used herein, the term "snap feature" includes, but is not limited to, for example, a tab that has a protrusion thereon that is configured to retainingly engage a corresponding mating portion of another component. Such features may be designed to releasably engage the mating portion or it may not be designed or intended to be removed. In at least one form, the closure carriage 420 has a distal end 424 that has a groove arrangement 426 that is adapted to receive the flanged end 116 of the anvil closure rod 112. Such arrangement serves to attach the proximal end 114 of the anvil closure rod 112 to the closure carriage 420 while facilitating its selective rotation of the anvil closure rod 112 relative to the closure carriage 420. Therefore, the elongated shaft assembly 100 and the end effector 12 that is operably coupled thereto may be selectively rotated about the longitudinal tool axis LT-LT relative to the housing assembly 400.

Still referring to FIG. 8, in various implementations, the housing assembly 400 comprises a pistol-shaped handle housing that may be fabricated in two or more pieces for assembly purposes. For example, the housing assembly 400 as shown comprises a right hand case member 402 and a left hand case member 404 (FIG. 1) that are molded or otherwise fabricated from a polymer or plastic material and are designed to mate together. Such case members 402 and 404 may be attached together by snap features, pegs and sockets molded or otherwise formed therein and/or by adhesive, screws, etc. When assembled, the housing assembly 400 movably supports the closure carriage 420 for selective axial travel therein in response to actuation motions from a trigger, generally designated as 430. As the present Detailed Description proceeds, however, it will be understood that the various unique and novel aspects and attributes of the various implementations of the present invention may be effectively attained when employed with robotically controlled or otherwise remotely controlled systems. Thus, the term "housing" or "housing assembly" may also encompass a housing or similar portion of a robotic or automated control system that houses or otherwise operably supports at least one drive system that is configured to generate and apply at least one control motion which could be used to actuate various forms of surgical end effectors attached thereto. For example, various implementations of the surgical instruments described herein may be used in connection with those robotic systems and arrangements disclosed in U.S. patent application Ser. No. 13/536,323, entitled ROBOTICALLY-POWERED SURGICAL DEVICE WITH MANUALLY ACTUATABLE REVERSING SYSTEM, filed Jun. 28, 2012, now U.S. Pat. No. 9,408,606, the entire disclosure of which is hereby incorporated by reference herein.

The trigger assembly 430 may, for example, comprise a primary trigger 440 and a secondary trigger 460. The primary and secondary triggers 440 and 460 are pivotally journaled on a pivot pin assembly 431 formed in the housing assembly 400 such that the triggers 440 and 460 may essentially move relative to each other. Such arrangement permits the trigger assembly 430 to pivot relative to the housing assembly 400 about a pivot axis PA-PA. See FIG. 8. The primary trigger 440 has an elongated, grippable primary trigger paddle 442 that protrudes from a primary drive portion 444 that has a firing rack 446 formed thereon. In one embodiment, the secondary trigger 460 has a secondary trigger paddle 462 that protrudes from a secondary drive portion 464 that is pivotally journaled on the pivot pin assembly 431. The primary drive portion 444 has a slot 448 that is adapted to receive the secondary drive portion 464 of the secondary trigger 460 therein as the primary trigger paddle 442 is pivoted towards a pistol grip portion 406 of the housing assembly 400. Such arrangement essentially enables the secondary trigger 460 to "nest" within the primary trigger 440 during actuation. As will be discussed in detail below, the secondary trigger 460 is pivotally actuated by pivoting the primary trigger 440. Thus, in other embodiments, the secondary trigger 460 may lack the secondary trigger paddle 442. In various forms, the trigger assembly 430 may be biased into the unactuated position by a trigger spring (not shown).

As can be seen in FIG. 8, the secondary drive portion 464 of the secondary trigger 460 may have a closure gear segment 466 formed thereon that is configured for meshing engagement with a carriage gear rack 423 formed on the underside of the closure carriage 420. Thus, when the secondary trigger 460 is pivoted toward the pistol grip 406, the closure carriage 420 is driven in the distal direction "DD" which thereby drives the anvil closure rod 112 in the distal direction.

Referring again to FIG. 3, a distal end 118 of the anvil closure rod 112 is configured to be pinned to an anvil closure link 120. The anvil closure link 120 is pivotally pinned to an anvil pin slide 122. An anvil cam pin 124 is mounted to the anvil pin slide 122 an is configured to be received within anvil pin slots 720 provided in each of the lateral side walls 712 of the boxed mounting end 710 of the elongated channel 14 as well as anvil cam slots 840 in the proximal anvil mounting tube 820. Movement of the anvil closure rod 112 in the distal direction "DD" will cause the anvil assembly 20 to move from an open position towards the elongated channel 14 (referred to herein as the "closing direction "CD") and movement of the anvil closure rod 112 in the proximal direction "PD" will cause the anvil assembly 20 to move from a closed position to an open position (referred to herein as the opening direction "OD"). Such opening and closing of the anvil assembly 20 is accomplished by the camming action or movement of the anvil pin 124 in the anvil camming slots 840 in the proximal anvil mounting tube 820. Thus, actuation of the closure system 110, also known as the "second jaw closure system" will result in movement of the anvil assembly 20, also known as the "second jaw 15" relative to the elongated channel 14, also known as the "first jaw 13". Such movement may, for example, comprise pivotal travel of the second jaw (anvil assembly 20) relative to the first jaw (elongated channel 14) about a common pivot axis A-A that is established at their points of attachment to the distal end of the elongated shaft assembly 100.

Figure 9:
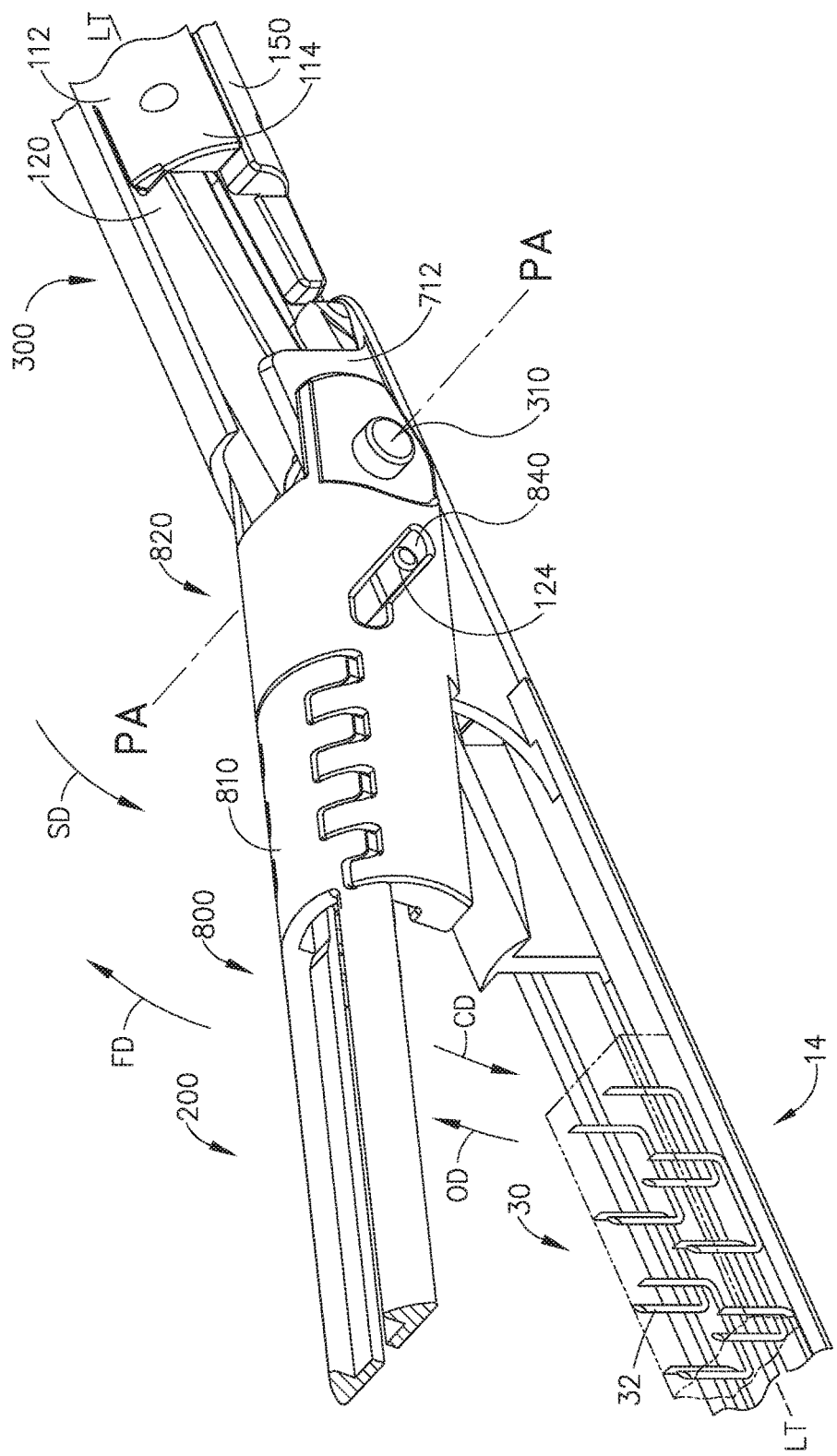
FIG. 9 is another perspective view of the end effector and elongated shaft assembly of FIG. 2 with the anvil assembly in an open position.
Figure 10:
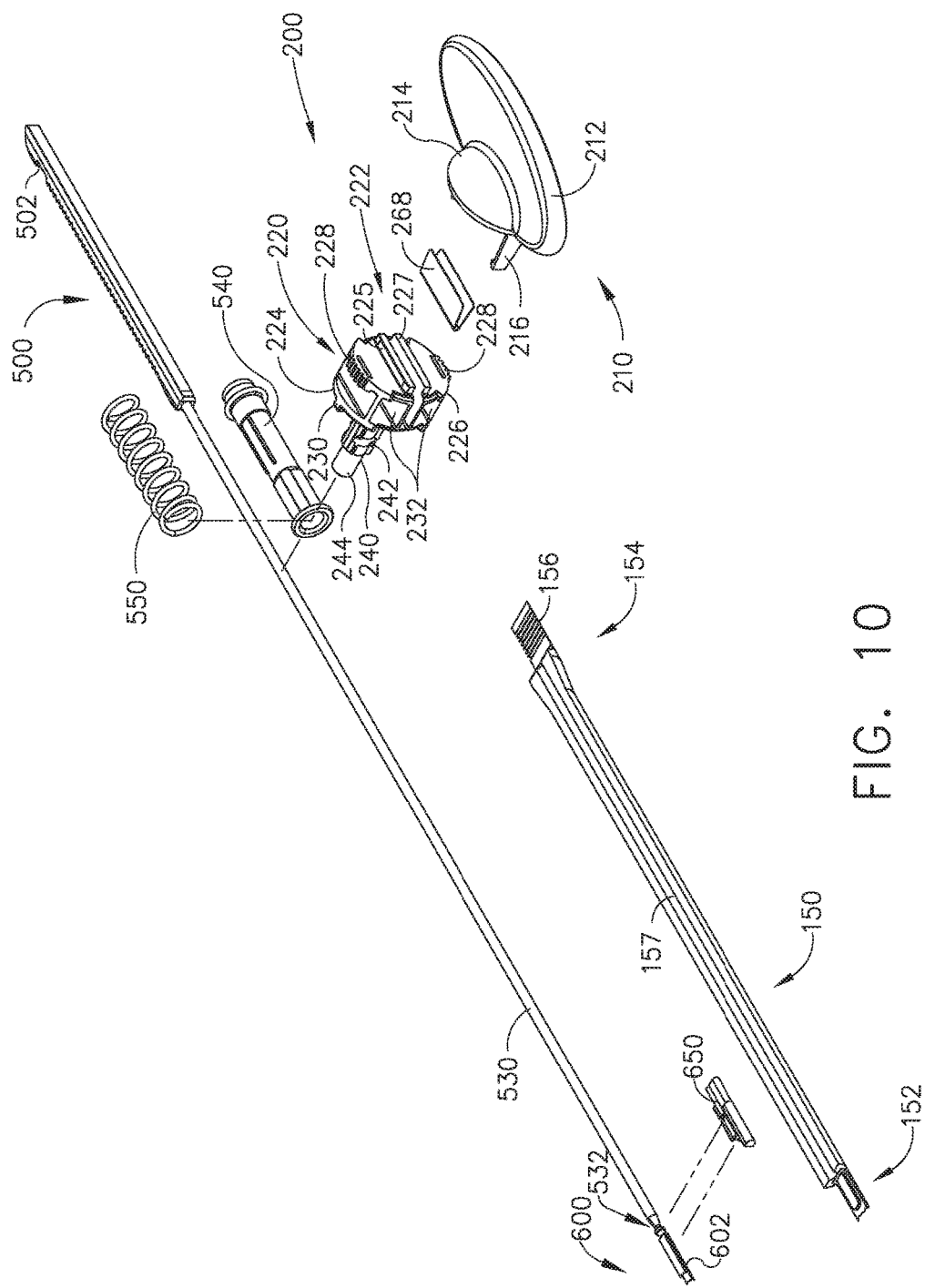
FIG. 10 is a perspective view of portions of the elongated shaft assembly, articulation system and firing system of the surgical instrument of FIG. 1.

In various arrangements, the end effector 12 may be configured to be selectively articulated relative to the longitudinal tool axis LT-LT. Stated another way, however, the first jaw 13 which comprises the elongated channel 14 may be selectively movable relative to the second jaw 15 which comprises the anvil assembly 20. As described above, the elongated channel 14 is pivotally coupled to the distal end 302 of the outer tube 300 by pivot pins 310. Such attachment arrangement permits the elongated channel 14 to articulate or move in a first direction "FD" about the pivot axis A-A which is essentially the same direction that the anvil assembly 20 moves in when the anvil assembly 20 is moved from a closed position to an open position (the anvil opening direction "OD"). See FIG. 9. Such arrangement further facilitates movement or articulation in a second articulation direction "SD" that is essentially the same as the direction that the anvil assembly 20 moves from an open position to a closed position (the anvil closing direction "CD"). To facilitate such movement of the elongated channel 14, a reciprocatable articulation rod 150 is employed. The articulation rod 150 may also be referred to herein as the "first jaw actuator bar 150". More specifically and with reference to FIG. 3, the articulation rod 150 is sized to be movably received with the outer tube 300 and has a distal end 152 that is pivotally pinned to an articulation link 160. The articulation link 160 is pivotally pinned to a proximal attachment lug 722 on the proximal boxed mounting end 710 of the elongated channel 14. As can be seen in FIG. 10, a proximal end 154 of the articulation rod 150 has an articulation rack 156 formed thereon that drivingly interfaces with an articulation control system 200. The articulation control system 200 may also be referred to herein as the "first jaw closure system 200".

Figure 11:
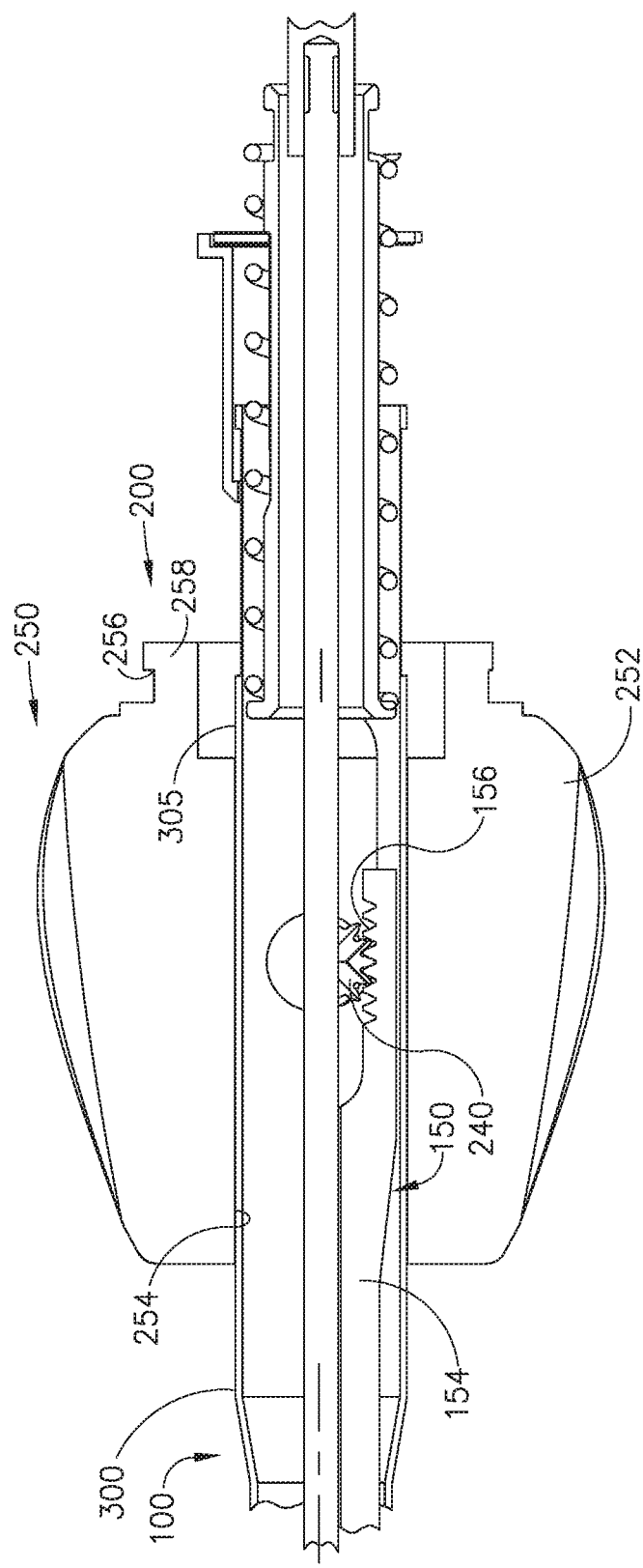
FIG. 11 is a side view of a portion of the articulation system of the surgical instrument of FIG. 1 with portions thereof shown in cross-section.
Figure 12:
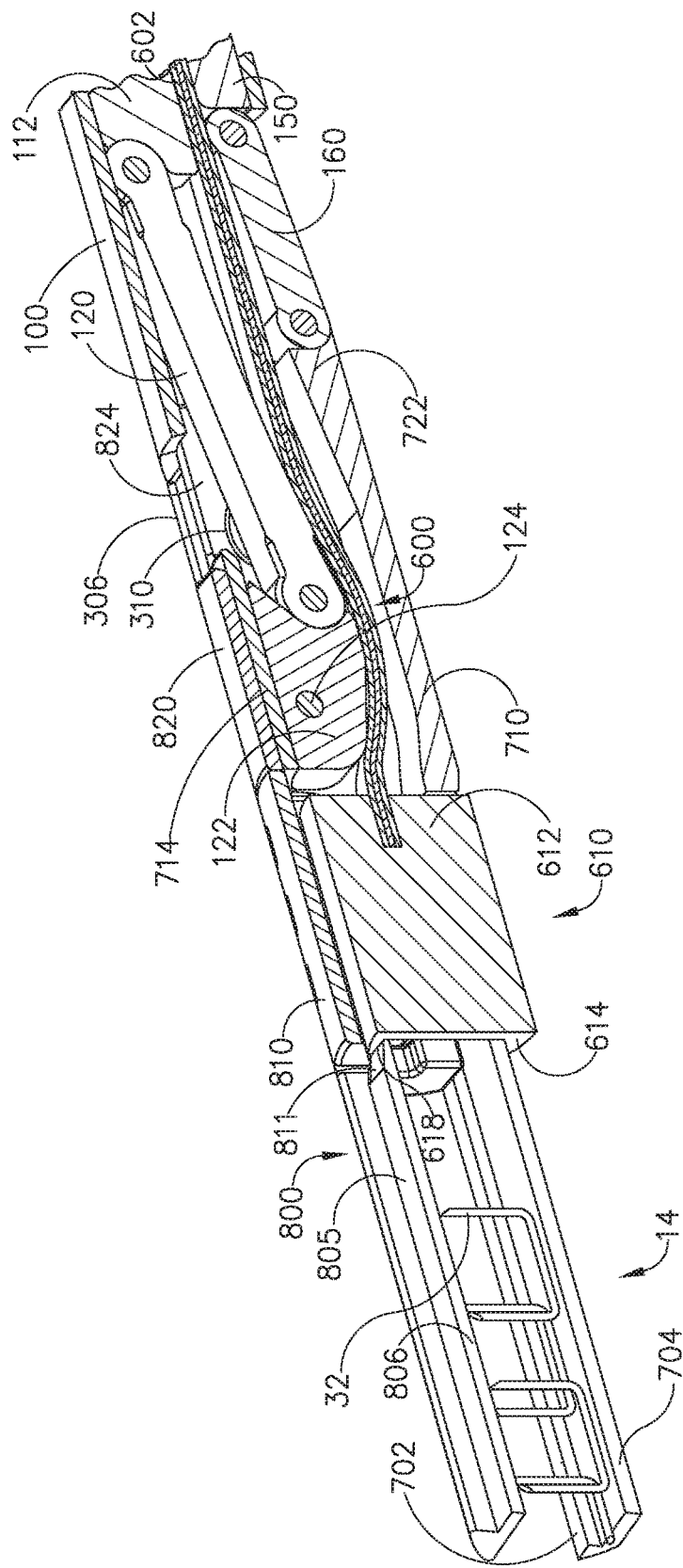
FIG. 12 is a cross-sectional view of the end effector and elongated shaft assembly portion of FIGS. 2 and 9 with the anvil assembly in a closed, but unfired position.

The component parts of one form of articulation control system 200 are illustrated in FIGS. 10 and 11. In one form, the articulation control system 200 may include an actuator 210, an articulation body 220 and a nozzle 250. Rotational movement of the actuator 210 causes corresponding rotation of the articulation body 220 within the nozzle 250. Rotation of the actuator 210 thereby results in the axial travel of the articulation rod 150 within the outer shaft 300 to cause the remote articulation of the end effector 12.

Still referring to FIG. 10, the articulation body 220 has a deck 222 consisting of first and second spaced-apart, semi-circular deck halves, 224, 226. The deck halves are mutually opposed to each other and essentially represent mirror images of each other. The first and second deck halves 224, 226 have protruding from their surfaces mutually opposed first and second detents 225, 227, respectively. Each deck half 224, 226 has a set of deck teeth 228 spaced about 180 degrees from the set of deck teeth on the other deck half. The articulation body 220 has a pair of rotation stops 230 protruding from its surface as well as a pair of finger recesses 232. A drive gear 240 protrudes laterally from the articulation body 220. The drive gear 240 has a flared opening 242 through it, and a lateral pivot 244. Within the flared opening 242 of the drive gear 240, there is a firing rod orifice (not shown) for receiving a firing rod 530 therethrough enabling the application of a firing motion to the end effector 12. The drive gear 240 is configured to intermesh with the articulation rack 156 to effect the desired reciprocating movement of the articulation rod 150.

The nozzle 250 of the articulation control system 200 may include a nozzle body 252. The nozzle body 252 may have an axial bore 254 therethrough that facilitates the passage of the articulation rod 150 and other operative components of the instrument 10 including a the proximal end 306 of the outer shaft 300. See FIG. 11. The nozzle body 252 may also have a frame groove 256 and flange 258 to rotatably fasten the nozzle body 252 to the housing 400. In various forms, a detent housing 260 comprises a portion of the nozzle body 252. See FIG. 1. An annular array of detent teeth (not shown) is formed within the detent housing 260. A detent housing floor is spaced from the detent teeth. The floor may have a pair of ledges which interact within the rotation stops 230 of the articulation body 220 to limit the degree of rotation. When the articulation body 220 is inserted into the detent housing 260, the base of the articulation body 220 is supported on the floor within the detent housing 260, and the deck teeth 228 of the first and second deck halves, 224, 226 are aligned for meshing engagement with the detent teeth of the detent housing 260. A spring member 268 is supported within the articulation body to bias the deck teeth 228 into meshing engagement with the detent teeth.

Referring again to FIG. 10, the actuator 210 may consist of a lever arm 212, a cap 214 and a pair of retaining fingers 216. The lever arm 212 is mounted on the top of the cap 214. The pair of retaining fingers 216 protrudes laterally from the underside of the cap 214. Each of the retaining fingers 216 has a retaining clip. The retaining fingers 216 are received within the finger recesses 232 of the articulation body 220. First and second detents, 225, 227, on the deck halves of the articulation body are inserted into a slot depression within the underside of the circular cap 214. Advantageously, each of the three significant components of the articulation control system, namely the actuator, articulation body and nozzle, may be injection molded components. Such components, for example, may be fabricated from a glass fiber-reinforced amorphous polyamide, sold commercially under the trade name Grivory GV-4H by EMS-American Grilon 150.

Figure 13:
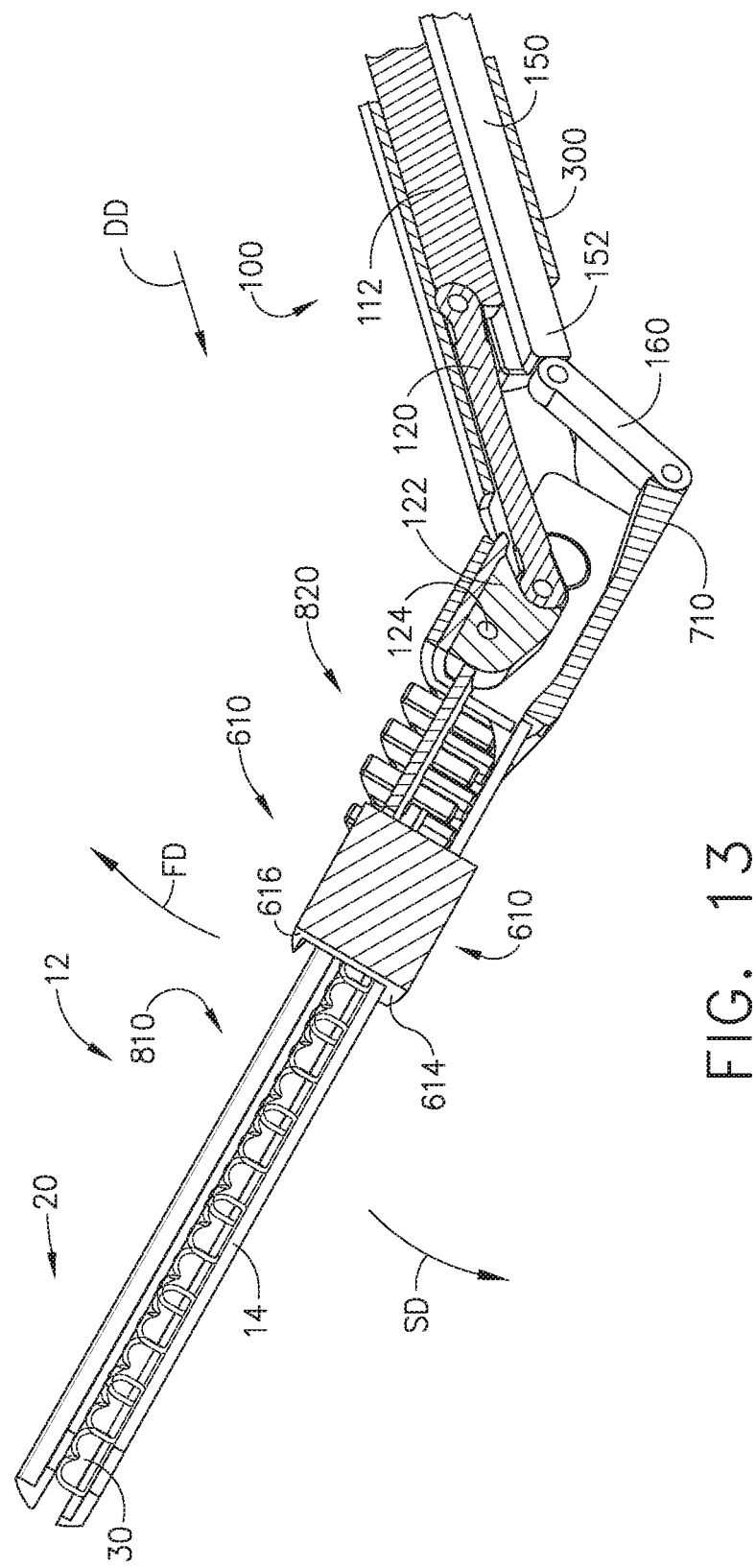
FIG. 13 is a cross-sectional view of the end effector and elongated shaft assembly portion of FIGS. 2, 9 and 12 in an articulated position and after the cutting head assembly has been retracted to a starting position after being fired.

Ratcheting rotation of the actuator 210 causes articulation of the elongated channel 14 in the first or second directions relative to the longitudinal tool axis LT-LT. FIGS. 1, 2, 9 and 12 illustrate the elongated channel 14 in an unarticulated position. When the drive gear 240 on the articulation body 220 of the articulation transmission 200 is rotated to thereby push the articulation rod 150 in the distal direction "DD", the elongated channel 14 will articulate in the first articulation direction "FD" relative to the longitudinal tool axis LT-LT as shown in FIG. 13. When the drive gear 240 on the articulation body 220 of the articulation transmission 200 has been rotated to thereby pull the articulation rod 112 in the proximal direction "PD", the elongated channel 14 will pivot in a second direction "SD" relative to the longitudinal tool axis LT-LT. The second direction "SD" is the same as the closure direction "CD". See FIG. 9.

The surgical instrument 10 may include a firing system generally designated as 410 that is supported within the housing assembly 400 and is operable to actuate various components of the instrument 10. Referring to FIG. 8, the firing system 410 may, for example, include an actuation bar 470. The actuation bar 470 has a first actuation rack 472 formed thereon that is configured for meshing engagement with the firing rack 446 on the primary trigger 440. Thus, when the firing rack 446 is in meshing engagement with the first actuation rack 472, the actuation bar 470 is driven in the distal direction "DD" when the primary trigger 440 is pivoted toward the pistol grip 406. The actuation bar 470 has a second actuation rack 474 formed thereon configured to meshingly engage clutch teeth 484 on a clutch shaft 482 of a clutch assembly 480. In various embodiments, the clutch shaft 482 is rotatably is supported within the housing assembly 400 and is also laterally movable therein. The clutch shaft 482 has a hub portion 486 that has a plurality of spaced teeth 488 that are configured to drivingly engage teeth openings 492 in a drive gear 490 that is rotatably supported on the clutch shaft 482. The drive gear 490 has a segment of drive gears 494 thereon that are adapted for meshing engagement with a firing rack 500 that is movably supported in the housing assembly 400.

Various embodiments of the clutch assembly 480 may further comprise a clutch plate 510 that is slidably journaled on a clutch pin 449 provided on the primary drive portion 444 of the primary trigger 440. The clutch pin 449 may be movably received within a vertical slot 512 in the clutch plate 510. The clutch plate 510 also has a distally-extending clutch arm 514 that is adapted to actuatably engage a bevel plate 489 formed on the clutch shaft 482. In addition, a clutch spring 520 is employed to bias the clutch shaft 480 laterally such that the teeth 488 on the clutch shaft 482 are brought into meshing engagement with the teeth openings 492 in the drive gear 490.

As can be seen in FIG. 8, the firing rack 500 is coupled to a firing rod 530 that is attached to the proximal end of a knife bar assembly 600. In various embodiments, the knife bar assembly 600 may comprise a three-ply flexible knife bar 602 that is flexible enough to accommodate articulation of the end effector 12, while remaining sufficiently rigid to be driven distally through the elongated shaft assembly 100. An axial passage 157 may be provided in the articulation bar 150 for axially receiving the knife bar 602 therein. See FIG. 10. In the depicted embodiment, the knife bar 602 is attached to an I beam cutting head 610. As can be seen in FIG. 3, for example, the I-beam cutting head 610 includes a vertically oriented body portion 612 that has a bottom foot 614 and an upper tab 616 formed thereon. A tissue cutting edge 620 is formed on the vertically oriented body portion 612.

Figure 14:
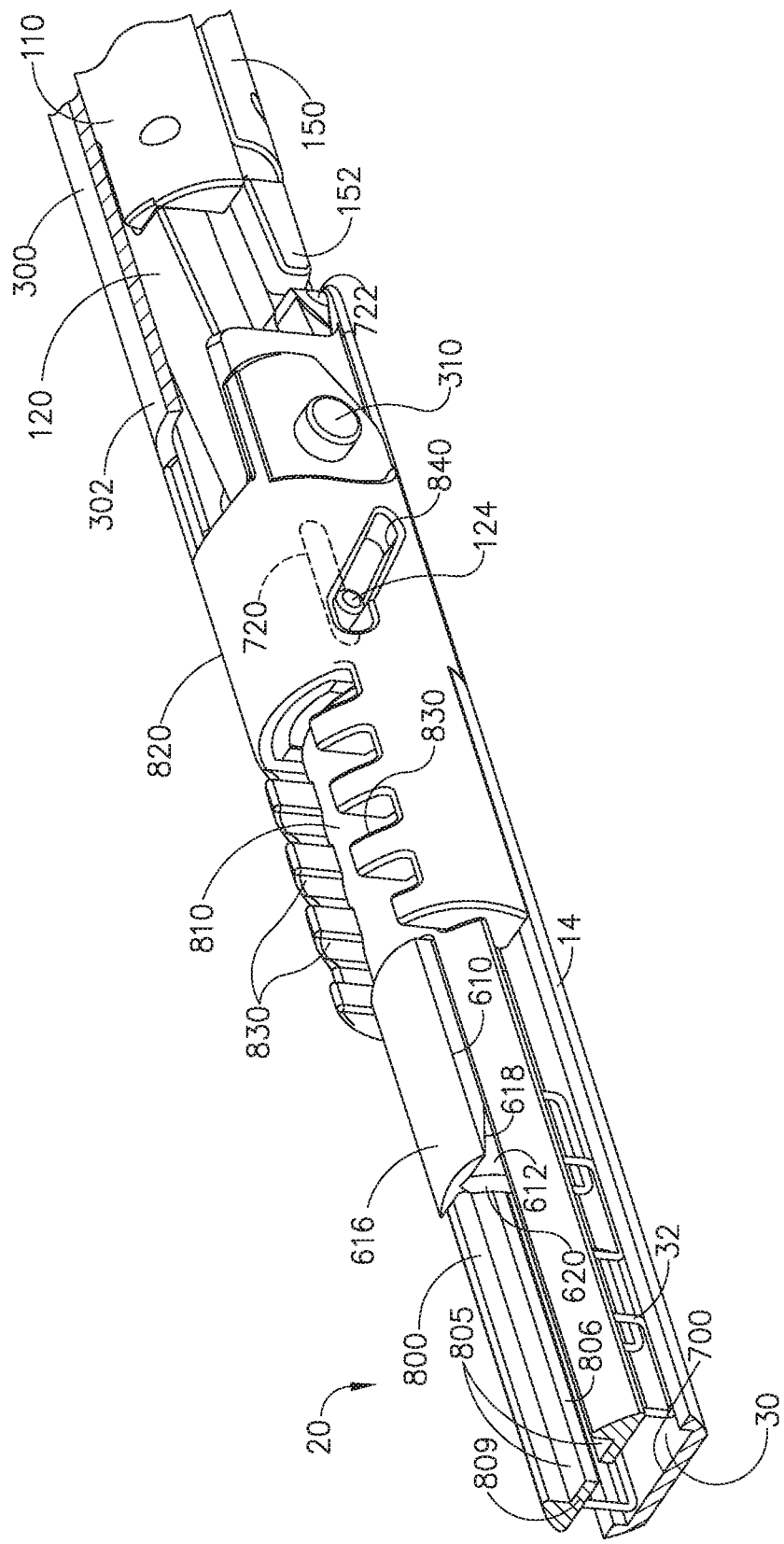
FIG. 14 is a partial perspective view of the end effector and portion of the elongated shaft assembly after the cutting head assembly has been retracted to a starting position after being fired.

Still referring to FIG. 3, the vertically oriented body portion 612 extends through a longitudinally extending slot 704 in the elongated channel 14 and a longitudinally extending slot 806 in the distal anvil portion 800. The distal anvil portion 800 further has a trough 809 formed in the upper surface for slidably receiving the upper tab 616 therein. The distal end 618 of the upper tab 616 is sloped to interface with sloped surfaces 811 formed on the portions 805 of the distal anvil portion 800 forming the slot 806. See FIG. 14. The flexible firing bar 602 extends through the elongated shaft assembly 100 to be coupled to a distal end portion 532 of a firing rod 530 are supported in a contiguous orientation relative to each other as shown in FIG. 10. The proximal end of the firing bar 602 may be attached to the distal end portion 532 of the firing rod 530 by a coupler member 650. As will be discussed in further detail below, the firing rod 530 facilitates the application of firing and refraction motions to the knife bar assembly 600 by the firing system 410.

Referring again to FIG. 8, the firing rod 530 extends through a closure bushing 540 that is mounted within the housing assembly 400. In at least one form, a pair of mounting studs 407 protrude from the handle case members 402, 404 and extend through corresponding slots in the closure carriage 420 to be received in a retaining slot in the bushing 540. A closure spring 550 that is attached to a retainer clip 552 is journaled on the closure bushing 540. The closure spring 550 extends between the nozzle body 252 and an internal wall 425 in the closure carriage 420. Thus, the closure spring 550 serves to bias the closure carriage 420 in the proximal direction "PD".

Various embodiments may also include a releasable closure locking assembly 560 that interfaces with the closure carriage 420 to selectively retain the closure carriage 420 in its distal-most closed or clamped position. In at least one form, the closure locking assembly 560 includes a locking button 562 that is pivotally supported in the housing assembly 400. The locking button 562 has a latch arm 564 that is configured to abut a locking ledge 421 formed on the closure carriage 420 when the button 562 is in the locked position. In addition, the latch arm 564 has a catch 566 formed thereon that is configured to releasably latch with a locking latch 502 on the proximal end of the firing rack 500. A locking spring 568 serves to bias the locking button 562 into the locked position.

Operation of the surgical instrument 10 will now be described. FIG. 9 illustrates the jaws 13 and 15 of the end effector 12 in an open position. When the end effector 12 is in the open position, the latch arm 564 is located on top of the locking ledge 421 formed on the closure carriage 420 such that the catch 566 of the latch arm 564 is in retaining engagement with the locking latch 502 on the firing rack 500. See FIG. 8. Thus, when in this initial starting position, the knife bar assembly 600 cannot be inadvertently actuated. The clutch plates 510, as well as the closure carriage, are each in their proximal-most unactuated positions. When in those positions, the clutch drive bevel 489 on the clutch shaft 482 is in contact with a portion of the closure carriage 420, which prevents the clutch shaft 482 from laterally moving into meshing engagement with the drive gear 490 under the bias of the clutch spring 520.

To initiate the closure process, a first stroke is applied to the trigger assembly 430. That is, the trigger assembly 430 is initially pivoted toward the pistol grip 406. Such pivoting action serves to drive the closure carriage 420 in the distal direction "DD" by virtue of the meshing engagement between the closure gear segment 466 on the secondary trigger 460 and the carriage rack 423 formed on the underside of the closure carriage 420. Such distal movement of the closure carriage 420 also axially advances the anvil closure rod 112 in the distal direction "DD". As the anvil closure rod 112 moves distally, the closure link 120 moves the anvil pin slide 122 distally. As the anvil pin slide 122 moves distally, anvil pin 124 moves up cam slots 840 in the proximal anvil portion 820 to cam the anvil assembly 20 towards the elongated channel 14 and the staple cartridge 30 supported therein. If the surgeon desires to simply grasp and manipulate tissue prior to clamping it between the anvil assembly 20 and the surgical staple cartridge 30, the trigger assembly 430 may be pivoted to open and close the anvil assembly 20 without fully pivoting the trigger assembly 430 to the fully closed position.

Those of ordinary skill in the art will understand that, as the trigger assembly 430 is pivoted toward the pistol grip 406, the actuation bar 470 will necessarily also be driven distally by virtue of the meshing engagement between the primary gear segment 446 on the primary trigger 440 and the first actuation rack 472 on the actuation bar 470. The distal movement of the actuation bar 470 will also result in the an application of a rotary actuation motion to the clutch shaft 482 by virtue of the meshing engagement between the clutch teeth 484 on the clutch shaft 482 and the second actuation rack 474 on the actuation bar 470. However, such rotary motion is not applied to the drive gear 490 because the clutch arm 514 of the clutch plate 510, in contact with the clutch drive bevel 489 on the clutch shaft 482, prevents the axial movement of the clutch shaft 482 into meshing engagement with the drive gear 490. Thus, the clutch shaft 482 freely rotates relative to the drive gear 490. Accordingly, the clutch assembly 480 automatically prevents the activation of the firing rack 500 during the initial actuation of the trigger assembly 430.

Once the trigger assembly 430 has been initially fully compressed into the closed position, the anvil assembly 20 will be locked in the closed position by the closure locking assembly 560 which prevents the proximal movement of the closure carriage 420. To drive the knife bar assembly 600 distally through the tissue clamped in the end effector 12, the surgeon again pivots the primary trigger 440 toward the pistol grip 406 of the housing assembly 400. As the primary trigger 440 is pivoted, the firing rack 500, the firing rod 530, and the knife bar assembly 600 are driven in the distal direction "DD". As the knife bar assembly 600 is driven in the distal direction, the cutting head 610 also moves distally. As the cutting head 610 moves distally, the sloped surface 618 on the upper tab 616 travels up the sloped surfaces 811 on the distal anvil portion 800 moving the floating distal anvil portion 800 in the down direction "D" towards the staple cartridge 30. As the distal anvil portion 800 is driven downwardly towards the clamped tissue and the staple cartridge 30, the clamping or crushing action causes the staples to be formed against the underside of the distal anvil portion 800. Thus, as the cutting head 610 is driven distally through the end effector 12, the tissue cutting surface 620 thereon severs the clamped tissue while forming the staples in the staple cartridge 30 on both sides of the cut tissue. Such two part anvil assembly enables the distal anvil portion to essentially remain parallel to the elongated channel and top of the surgical staple cartridge during firing. Stated even more succinctly, the two part floating anvil arrangement enables the staple-forming undersurfaces to remain parallel with the top of the surgical staple cartridge and the elongated channel during firing.

After the cutting head 610 has been driven through the tissue clamped in the end effector 12, the surgeon then releases the primary trigger 440 to thereby permit the primary trigger 440 to pivot to its unactuated position under the bias of the firing spring 432. As the primary trigger 440 pivots back to the starting position, the firing rack 500, firing rod 530, and knife bar assembly 600 are drawn proximally back to their respective starting positions. The end effector 12 remains in its clamped position as shown in FIG. 13.

To unlock the closure carriage 420 and the secondary trigger 460, the surgeon depresses the locking button 562. As the locking button 562 is depressed, the locking arm 564 is pivoted out of abutting engagement with the locking ledge 421 on the closure carriage 420. Further details regarding the operation of the firing and closure systems may be found in U.S. Patent Application Publication No. US 2012/0074200 which has been herein incorporated by reference in its entirety. As the closure carriage 420 moves proximally, the anvil closure rod 112 is also drawn proximally. As the anvil closure rod 112 moves proximally, the anvil pin slide 122 and anvil pin 124 move proximally camming the anvil assembly 20 to the open position.

The surgical instrument 10 provides a host of advantages over prior surgical instruments. For example, the unique and novel floating anvil arrangement is able to automatically adjust the anvil gap between the undersurface of the anvil and the staple cartridge or elongated channel. Thus, the floating anvil arrangement can automatically compensate for different thickness of tissue while enabling the staple forming undersurface(s) of the anvil to remain parallel to the staple cartridge and elongated channel. This is all accomplished without sacrificing anvil stability.

Another distinct advantage that the surgical instrument 10 enjoys over prior surgical instruments with articulatable end effector is the nature in which the present end effector is articulatable relative to the elongated shaft assembly. As described in detail above, the elongated channel portion of the end effector is pivotally mounted to the elongated shaft assembly for selective pivotal travel relative thereto about a pivot axis. The pivot axis is transverse to the longitudinal tool axis defined by the elongated shaft assembly. The anvil assembly is also pivotally coupled to the elongated channel for selective pivotal travel relative thereto about the same pivot axis. This provides another distinct advantage over prior articulatable end effector arrangements for at least the following reason.

During typical surgical procedures, the surgeon is viewing the surgical site and the end effector through a camera that can provide somewhat limited viewing. For example, such camera arrangements commonly only afford the surgeon with a view of a portion of the surgical end effector. When using an endocutter for example, the camera may only afford the surgeon a view of a portion of the endocutter's anvil and/or channel. In prior articulatable endocutter arrangements, the endocutter was coupled to the end of the elongated shaft by a flexible joint or other arrangement that did not always afford a consistent reference axis about which the end effector would pivot relative to the elongated shaft. So it was difficult for the surgeon when viewing a portion of the end effector to have a reliable frame of reference to know where the pivot axis resided. By having the articulation axis also be the axis about which the anvil pivots, the surgeon has a much more reliable frame of reference regarding the location of the pivot axis when viewing the endocutter's anvil through the camera. Stated another way, when using the end effector arrangement of the surgical instrument 10 the surgeon can determine where the elongated channel is going to pivot relative to the elongated shaft by viewing where the anvil is pivotally mounted to the elongated channel.

The surgical instrument 10 also employs separate control systems for moving the end effector jaws 13 and 15 relative to each other. For example, the clinician may elect to move or articulate the lower jaw 13 (elongated channel 14) about the pivot axis A-A toward or way from the upper jaw 15 (anvil assembly 20) without actuating the upper jaw 15 (anvil assembly 20). This may be accomplished by actuating the articulation control system (or first jaw closure system) without actuating the second jaw closure system 110. Thus, the elongated channel 14 may be selectively pivoted about the pivot axis A-A while the anvil assembly 20 remains in an open or closed position. Similarly, the anvil assembly 20 may be actuated or moved without moving the elongated channel 14 by actuating the closure system 110 without actuating the articulation control system. Such unique and novel arrangement provides the clinician with more flexibility when positioning the end effector jaws within the patient.

FIGS. 15-19 illustrate another surgical instrument 1010 that is capable of practicing several unique benefits of the present invention. The surgical instrument 1010 is designed to manipulate and/or actuate various forms and sizes of end effectors 1012 that are operably attached to an elongated shaft assembly 1100 of the surgical instrument. In the depicted embodiment, for example, the end effector 1012 comprises a surgical stapling device that has openable and closable jaws 1013 and 1015. More specifically, the end effector 1012 includes a jaw channel 1014 that forms a lower jaw 1013 of the end effector 1012. See FIG. 16. In the illustrated arrangement, the jaw channel 1014 is configured to operably support a staple cartridge 30 and also movably supports an anvil assembly 1020 that functions as an upper jaw 1015 of the end effector 1012.

Figure 15:
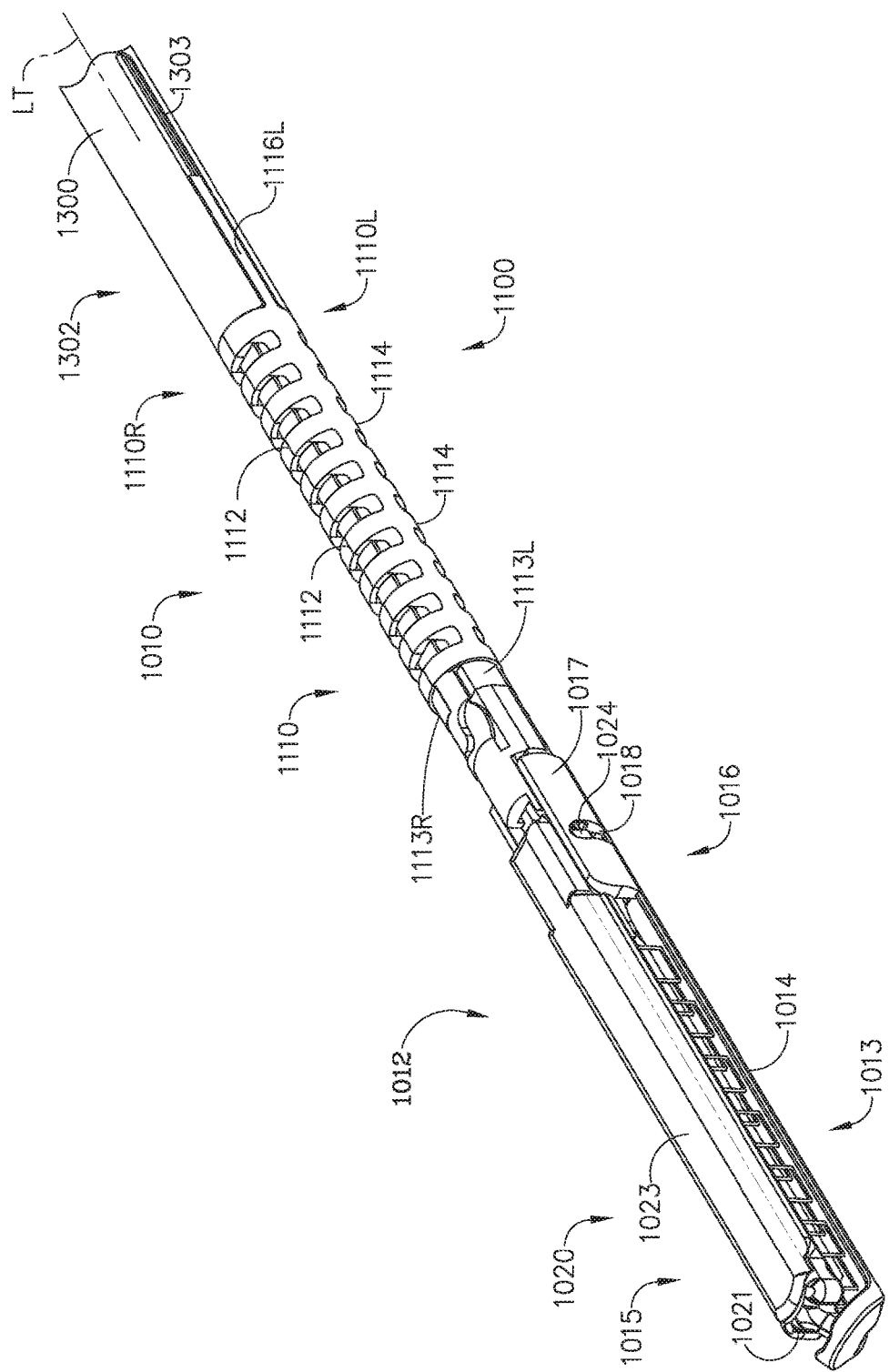
FIG. 15 is a partial perspective view of an another end effector and elongated shaft assembly with the end effector in a closed position.
Figure 17:
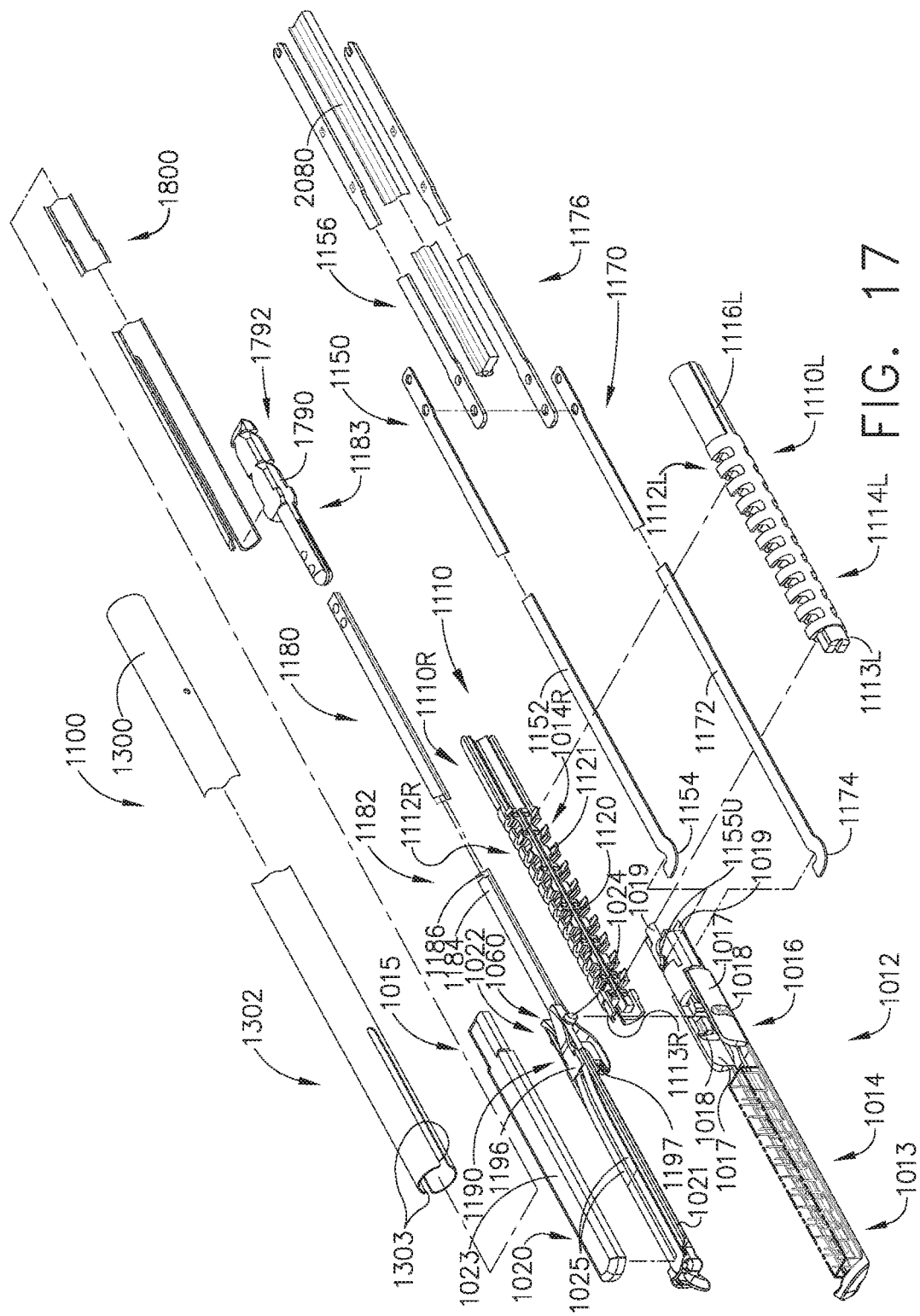
FIG. 17 is an exploded perspective assembly view of the end effector and elongated shaft assembly of FIGS. 15 and 16.

Referring now to FIGS. 15 and 17, the anvil assembly 1020 comprises a two-part arrangement including an anvil body portion 1021 and an anvil cap member 1023. The anvil body portion 1021 may include a mounting portion 1022 that has mounting trunnions 1024 protruding therefrom. The mounting trunnions 1024 are configured to be received in vertically elongated mounting slots 1018 in the upstanding side walls 1017 of a proximal mounting portion 1016 of the jaw channel 1014. Such arrangement permits the anvil assembly to somewhat float up and down relative to the elongated channel. Stated another way, the anvil body portion 1021 may move relative to the elongated channel or the top of a staple cartridge supported in the elongated channel such that the staple forming undersurfaces of the anvil body portion 1021 are parallel to the top of the staple cartridge and the elongated channel. As will be discussed in further detail below, the anvil assembly 1020 is moved between open and closed positions by manipulating the position of a tissue cutting head 1190.

In various arrangements, the end effector 1012 may be configured to be selectively articulated about a longitudinal tool axis LT-LT that is defined by the elongated shaft assembly 1100. As can be seen in FIGS. 15-18, for example, the elongated shaft assembly 1100 may include a flexible neck assembly 1110 to facilitate such articulation. Various flexible neck assemblies are know and may be employed. For example, flexible neck assemblies are disclosed in U.S. Provisional Patent Application Ser. No. 61/386,117, filed Sep. 24, 2010, the entire disclosure of which is herein incorporated by reference. Other flexible neck assemblies which may be employed are disclosed in U.S. Pat. No. 5,704,534, entitled ARTICULATION ASSEMBLY FOR SURGICAL INSTRUMENTS, issued Jan. 6, 1998; U.S. Patent Application Publication No. 2012/0074200 A1, entitled SURGICAL INSTRUMENT WITH SELECTIVELY ARTICULATABLE END EFFECTOR, filed Sep. 23, 2011; and U.S. Pat. No. 7,909,220, entitled SURGICAL STAPLER HAVING AN ARTICULATION MECHANISM, issued Mar. 22, 2011 the entire disclosures of each being hereby incorporated by reference herein in their respective entireties. As will be discussed in further detail below, however, the flexible neck assembly 1110 is configured to facilitate articulation of the end effector 1012 in directions that are the same directions in which the jaws of the end effector travel between open and closed positions.

In at least one implementation, the flex neck assembly 1110 may, for example, be fabricated in two pieces 1110R and 1110L that are configured to be coupled together by, fasteners such as snap features, screws, bolts, adhesive, etc. The flexible neck pieces 1110R and 1110L may be composed of rigid thermoplastic polyurethane sold commercially as ISOPLAST grade 2510 by the Dow Chemical Company. The right flexible neck portion 1110R includes a right upper rib segment 1112R and a right lower rib segment 1112L that are separated by an elongated right lateral spine (not shown). Similarly, the left flexible neck portion 1110L includes a left upper rib segment 1112L and a left lower rib segment 1114L that are separated by a left elongated lateral spine 1116. See FIG. 17. When assembled together, the right upper rib segments 1112R and the left upper rib segments 1112L form upper ribs 1112 and the right lower rib segments 1114R and the left lower rib segments 1114L form lower ribs 1114 that are spaced from each other and which together form a cylindrical configuration as shown in FIG. 15. Such arrangement enables the end effector 1012 to articulate in a first direction "FD" that is essentially the same direction that the anvil assembly 1020 moves in when the anvil assembly 1020 is moved from a closed position to an open position (hereinafter referred to as the anvil opening direction "OD"). See FIG. 18. The flexible neck assembly 1110 will further facilitate articulation of the end effector 1012 in a second articulation direction "SD" that is essentially the same as the direction that the anvil moves from an open position to a closed position (hereinafter referred to the anvil closing direction "CD"). In various embodiments, the right flexible neck portion 1110R further has a right tubular portion 1113R and the left flexible neck portion 1110L has a left tubular portion 1113L. When joined together, the right and left tubular portions 1113R, 1113L serve to receive therein two distally protruding attachment arms 1019 that protrude proximally from the jaw channel 1014. See FIGS. 16 and 17. The attachment arms 1019 have attachment tabs thereon that engage the tubular portions 1113R, 1113L to affix the jaw channel 1014 to the elongated shaft assembly 1100. Other methods of attaching the jaw channel 1014 to the elongated shaft assembly 1100 may also be employed. In at least one embodiment, the elongated shaft assembly 1100 includes a substantially rigid proximal outer shaft segment 1300 that has a distal end 1302. The distal end 1302 has a pair of opposed lateral slots 1303 therein for receiving the corresponding proximally protruding ends of the lateral spine portions 1116L (the right spine portion is not shown). See FIGS. 15 and 17. The outer shaft segment 1300 may be pressed onto the flexible neck assembly 1110 or otherwise attached thereto by fasteners, pins, screws, etc.

The proximal end of the outer shaft segment 1300 may be attached to a handle assembly of the type disclosed in U.S. Patent Application Publication No. US 2012/0074200 A1, entitled SURGICAL INSTRUMENT WITH SELECTIVELY ARTICULATABLE END EFFECTOR, which has been herein incorporated by reference in its entirety. Further details regarding at least one method of attaching the outer shaft segment to the handle assembly and operation of the outer shaft segment and related components may be gleaned from reference to that publication. Such arrangement permits the surgeon to rotate the outer shaft segment 1300 and the end effector 1012 operably coupled thereto about the longitudinal tool axis LT-LT by rotating the nozzle member relative to the handle assembly as discussed in detail therein.

Figure 16:
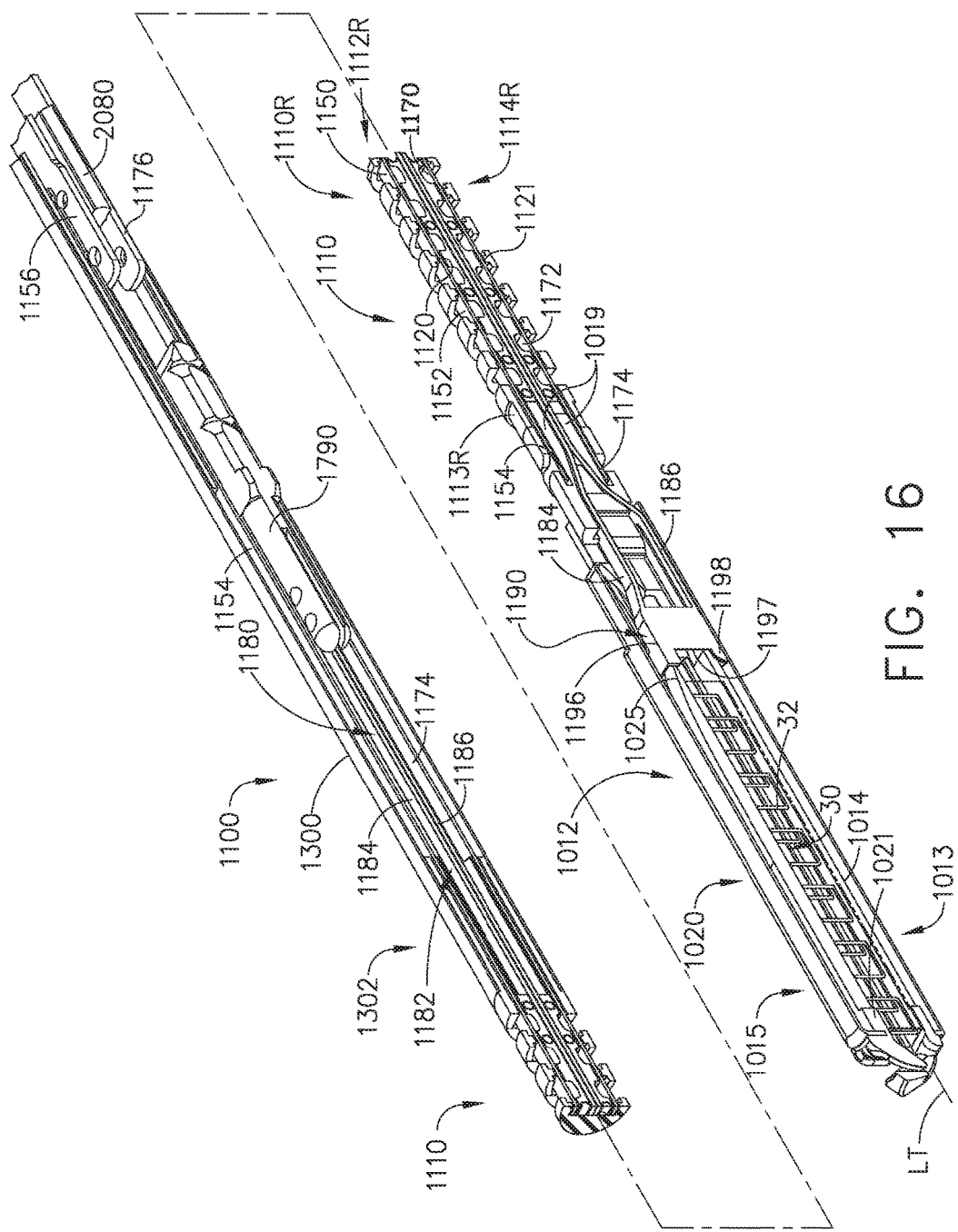
FIG. 16 is a cross-sectional perspective view of the end effector and elongated shaft assembly of FIG. 15.
Figure 18:
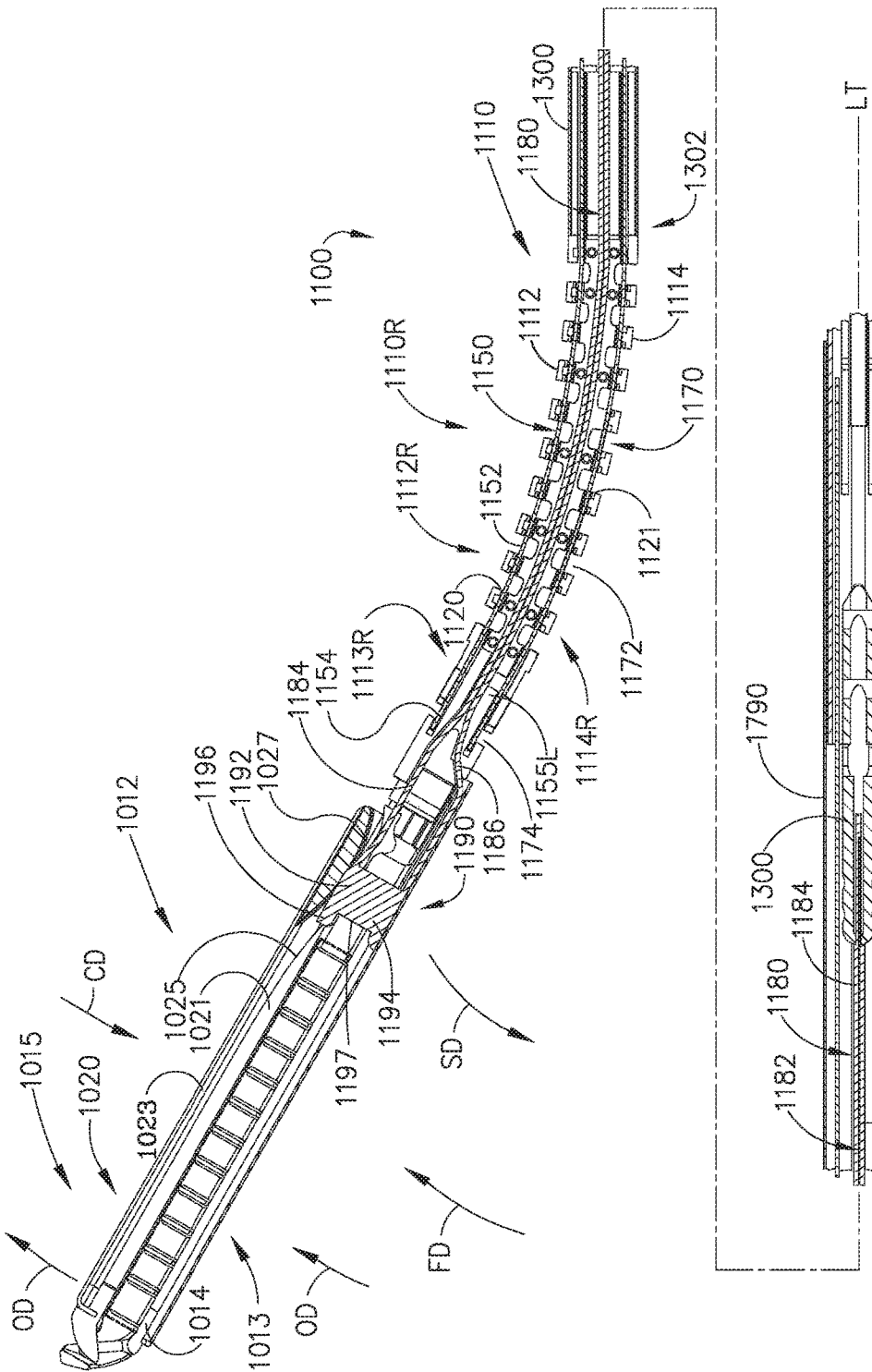
FIG. 18 is a cross-sectional perspective view of the end effector and elongated shaft assembly of FIGS. 15-17.

Referring to FIGS. 16 and 18, an upper slot 1120 extends through each of the upper ribs 1112 to form a passage through the flexible neck assembly 1110 for receiving a first flexible articulation band assembly 1150 therethrough. Similarly, a lower slot 1121 extends through each of the lower ribs 1114 in the flexible neck assembly 1110 to form a passage for receiving a second flexible articulation band assembly 1170 therethrough. Referring to FIG. 17, in at least one embodiment, the first flexible articulation band assembly 1150 comprises a flexible first distal segment 1152 that is fabricated from, for example, spring steel, 420 stainless steel, titanium, 400 or 300 grade stainless steel and has a first hook 1154 formed in its distal end. The first hook 1154 is configured to hookingly engage a first or upper hook-receiving feature 1155U formed in the proximal end of the jaw channel 1014. The first articulation band assembly 1150 further includes a first structural band portion 1156 that is attached to (e.g., pinned) to the first distal segment 1152. The first structural band portion 1156 may be fabricated from, for example, spring steel, 420 stainless steel, titanium. Likewise, the second articulation band assembly 1170 comprises a flexible second distal segment 1172 that is fabricated from, for example, spring steel, 420 stainless steel, and titanium and has a second or lower hook 1174 formed in its distal end. See FIG. 17. The second hook 1174 is configured to hookingly engage a second or lower hook-receiving feature 1155L formed in the jaw channel 1014. See FIG. 18. The second articulation band assembly 1170 further includes a second structural band portion 1176 that is attached to (e.g., pinned) to the second distal segment 1172. The second structural band portion 1176 may be fabricated from, for example, 400 or 300 grade stainless steel. The upper and lower articulation band assemblies 1150, 1170 may interface with and be controlled by an articulation transmission and control system 2000 of the type described in U.S. Patent Publication No. US 2012/0074200 A1 which has been incorporated by reference herein in its entirety.

Figure 19:
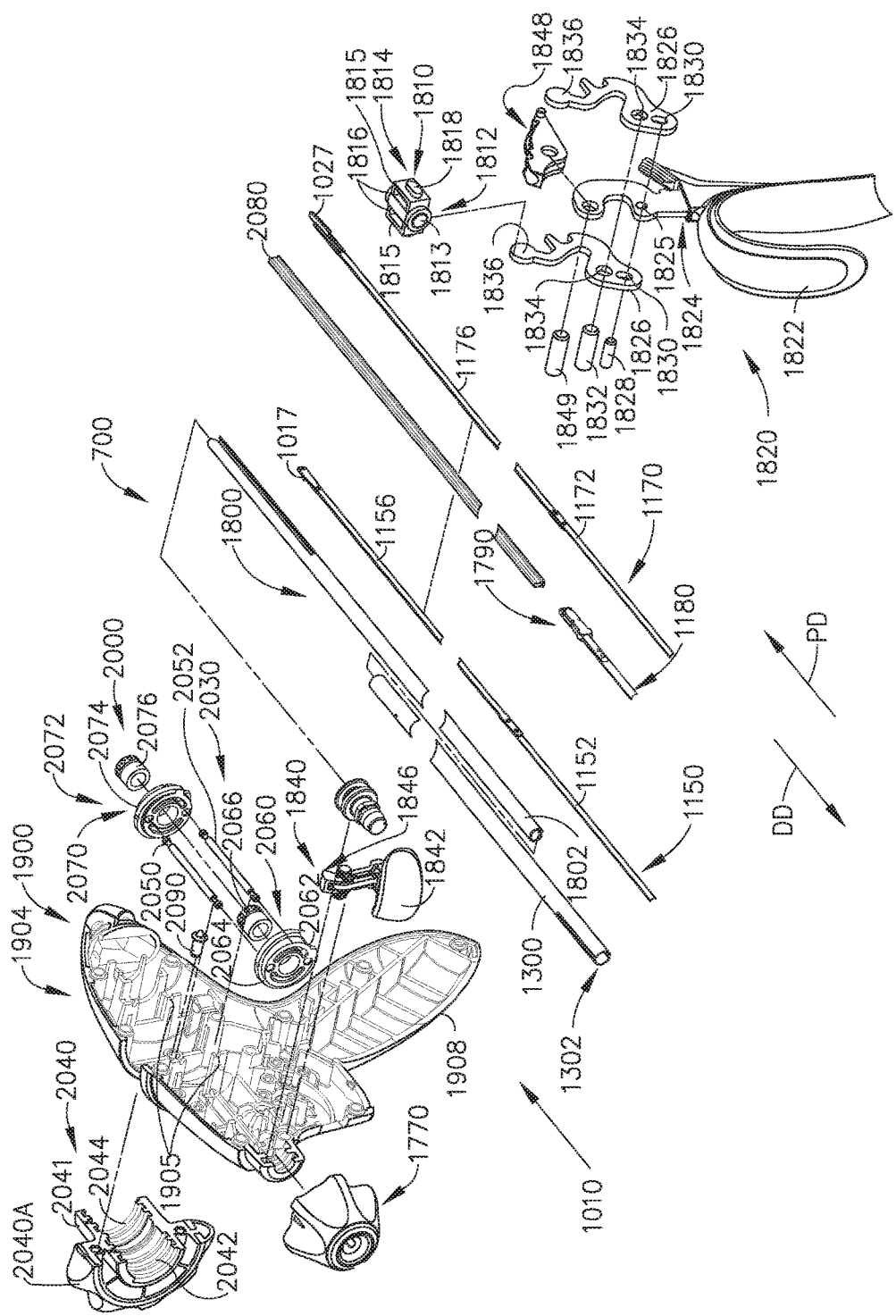
FIG. 19 is an exploded perspective assembly view of a handle assembly portion of a surgical instrument.
Figure 20:
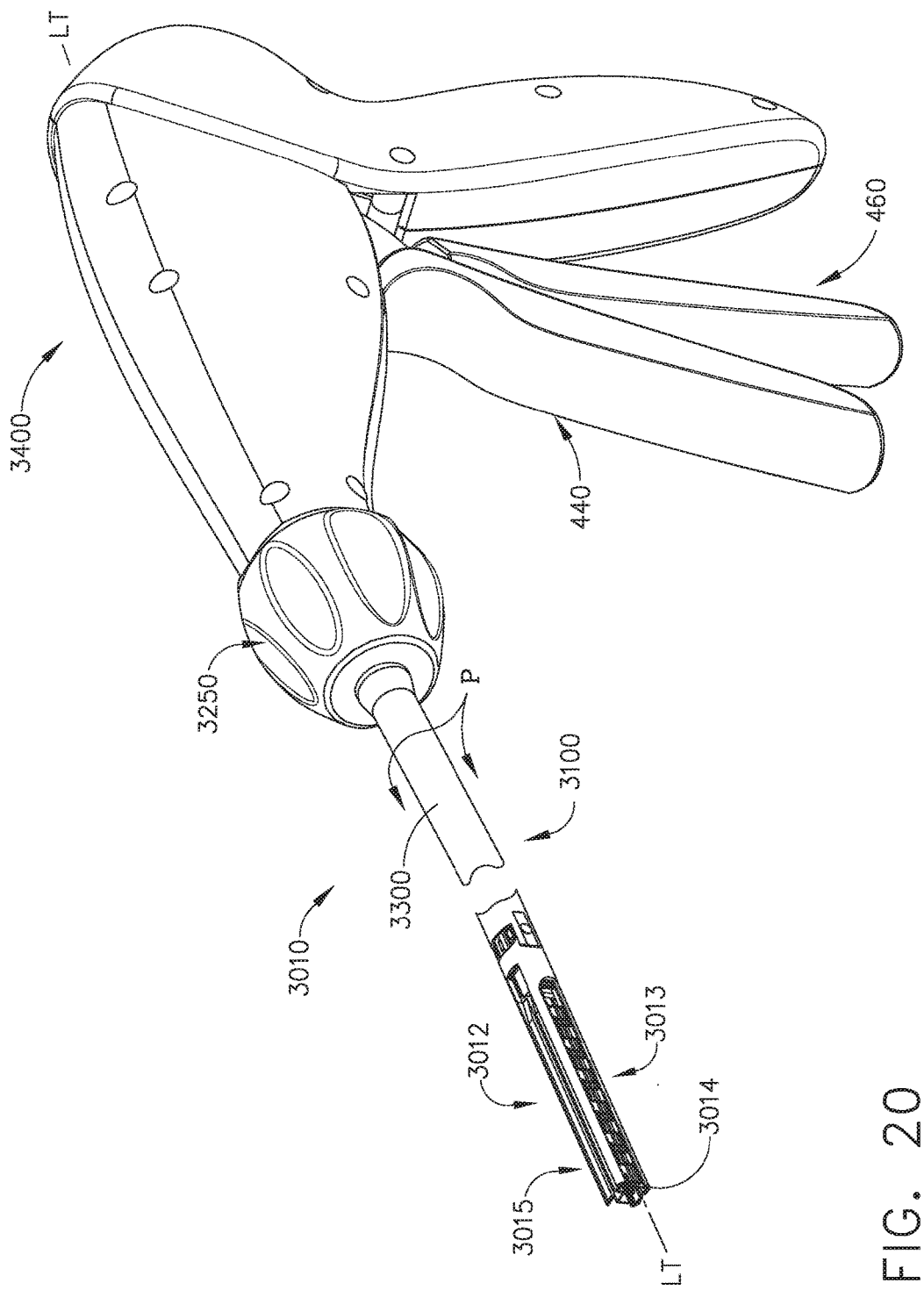
FIG. 20 is a perspective view of another surgical instrument.

Referring to FIG. 19, various embodiments of the articulation system 2000 include a novel articulation transmission 2030 that is supported within the handle assembly 1900 for applying articulation motions to the first and second articulation band assemblies 1150, 1170. In various forms, the articulation transmission 2030 includes an actuator wheel 2040 that is rotatably supported on the handle assembly 1900 for selective rotation about an actuation axis. In at least one embodiment, the actuation axis coincides with or is substantially coaxial with the longitudinal tool axis LT-LT. Thus the actuation axis does not transversely intersect the longitudinal axis. In other embodiments, the actuation axis may be substantially parallel to the longitudinal axis. To facilitate ease of assembly and manufacturing, the actuator wheel 2040 is fabricated in two pieces 2040A that may be attached together by screws, snap features, adhesive etc. When assembled, the actuator wheel 2040 has a first set of actuator threads 2042 which are configured in a first direction for threaded engagement with a first thread nut assembly 2060. In addition, the actuator wheel 2040 also has a second set of actuator threads 2044 which are configured in a second direction that differs from the first direction. For example, the first threads 2042 may comprise "right hand" threads and the second threads 2044 may comprise "left hand" threads or visa versa. The second threads 2044 are adapted to threadably engage a second threaded nut assembly 2070.

In various embodiments, the first threaded nut assembly 2060 comprises a first disc 2062 that has first threads 2064 formed thereon. The first disc 2062 is supported on a knife tube 1800 by a first bearing bushing 2066. The first bearing bushing 2066 facilitates movement of the first disc 2062 relative to the knife tube 1800. Similarly, the second threaded nut assembly 2070 comprises a second disc 2072 that has second threads 2074 formed thereon. The second disc 2072 is supported on the knife tube 1800 by a second bearing bushing 2076 that facilitates movement of the second disc 2072 relative to the knife tube 1800. The first and second discs 2062, 2072 are also movably supported on upper and lower nut rails 2050, 2052 that are mounted to standoff posts 1905 molded into the handle cases 1904. See FIG. 19. The upper and lower nut rails 2050, 2052 serve to prevent the first and second discs 2062, 2072 from rotating relative to the handle housing and therefore, as the actuator wheel 2040 is rotated relative to the handle housing, the first and second bearing bushings 2066, 2076 move axially on the knife tube 1800 in different directions.

The first and second articulation band assemblies 1150, 1170 are controlled by rotating the actuator wheel 2040 relative to the handle assembly 1900. To facilitate the application of such control motions, the first structural band portion 1156 has a first catch member configured to retainingly engage the first bearing bushing 2066 and the second structural band portion 1176 has a second catch member configured to retainingly engage the second bearing bushing 2076. In addition, the articulation system 2000 in at least one form includes an elongated support beam 2080 that extends longitudinally within the knife tube 1800 to provide lateral support to the first and second structural band portions 1156, 1176 within the knife tube 1800. The support beam 2080 may be fabricated from, for example, 400 or 300 grade stainless steel and is configured to facilitate axial movement of the first and second structural band portions 1156, 1176 while providing lateral support thereto.

FIGS. 15 and 16 illustrate the surgical instrument 1010 in an unarticulated position. That is, when in an unarticulated position, the end effector 1012 is substantially axially aligned on the longitudinal tool axis LT-LT. When in that "neutral" position, the first and second discs 2062, 2072 are spaced away from each other. To provide the surgeon with an indication when the articulation system 2000 has been parked in the neutral position, a detent assembly 2090 is mounted within the handle housing. The detent assembly 2090 into the housing and is adapted to engage a recess (not shown) in the hub portion 2041 of the actuator wheel 2040. See FIG. 19. The detent assembly 2090 is configured to engage the recess when the actuator wheel 2040 is in the neutral position. When the detent 2090 engages the recess, the surgeon may receive a tactile and/or audible indication.

The articulation system 2000 may articulate the end effector 1012 about the flexible neck assembly 1110 in the following manner. First, the surgeon rotates the articulation actuator wheel 2040 in a first rotary direction which causes the first and second discs 2062, 2072 to move toward each other. As the first disc 2062 moves in the proximal direction "PD", the first articulation band assembly 1150 is pulled in the proximal direction "PD" by virtue of the first catch feature 2017 which is coupled to the first bearing bushing 2066. Likewise, as the second disc 2072 moves in the distal direction "DD", the second articulation band assembly 1170 is pushed in the distal direction "DD" by virtue of the second catch feature 2027 which is coupled to the second bearing bushing 2076. Such action of the first and second articulation band assemblies 1150, 1170 causes the end effector 612 to articulate in the first articulation direction "FD" by virtue of the first and second articulation bands 1150, 1170 interconnection with the end effector 1012. To articulate the end effector in the second articulation direction "SD", the user simply rotates the articulation actuator wheel 2040 in a second rotary direction that is opposite to the first rotary direction.

As indicated above, the articulation system 2000 in at least one form also includes an elongated support beam 2080 that extends longitudinally within the knife tube 1800 to provide lateral support to the first and second structural band portions 1150 and 1170 within the knife tube 1800. The support beam 2080 may be fabricated from, for example, 400 or 300 grade stainless steel and is configured to facilitate axial movement of the first and second structural band portions 1156, 1176 while providing lateral support thereto. In addition, the right and left segments 1110R, 1110L of the flexible neck assembly 1110, when joined together, form a passage 1118 for receiving a knife bar assembly 1180. In various forms, the knife bar assembly 1180 includes a distal knife bar portion 1182 that includes an upper knife bar 1184 and a lower knife bar 1186 that are attached to a tissue cutting head 1190. The upper knife bar 1184 is attached to a top portion 1192 of the tissue cutting head 1190 and the lower knife bar 1186 is attached to a lower portion 1194 of the tissue cutting head 1190. The upper knife bar 1184 and the lower knife bar 1186 are configured to flex as the flexible neck assembly 1110 flexes.

As will be discussed in further detail below, in at least one embodiment, the axial advancement and withdrawal of the knife bar assembly 1180 may be controlled by, for example, the manual activation of a firing trigger that is operably supported on the handle assembly 1900. As can be seen in FIG. 19, a connector member 1790 is coupled to a proximal end 1183 of the distal knife bar portion 1182. In at least one embodiment, for example, the connector member 1790 is pinned to the proximal end 1787 of the distal knife bar portion 1182 and has a proximally protruding attachment feature 1792 that is configured to be coupled to a distal end 1802 of the hollow knife tube 1800. The hollow knife tube 1800 extends through the outer shaft segment 1300 and into the handle assembly 1900 and is attached to a carriage assembly 1810. In various embodiments, for example, the carriage assembly 1810 comprises a flanged carriage bushing 1812 that is press fit onto a portion of the knife tube 1800. The carriage assembly 1810 further comprises a firing carriage 1814 that has a saddle formed therein configured to extend over the carriage bushing 1812 between the bushing flanges 1813. In at least one form, the firing carriage 1814 also has a pair of laterally extending portions 1816 that each have a support tab 1818 formed thereon. The support tabs 1818 are configured to be slidably received in a corresponding slide passage (not shown) formed in the handle housing 1904. Such arrangement permits the firing carriage 1814 to move axially within the handle assembly 1900 and thereby apply axial actuation motions to the knife tube 1800 while permitting the knife tube 1800 to rotate about the longitudinal tool axis LT-LT relative to the firing carriage 1814 as the nozzle assembly 1770 is rotated.

In at least one embodiment, actuation motions may be manually applied to the firing carriage 1814 by a firing trigger assembly 1820 that is pivotally supported on the handle assembly 1900. The firing trigger assembly 1820 includes a firing trigger 1822 that has an attachment plate 1824 that is configured to operably interface with a pair of actuation plates 1826. As can be seen in FIG. 19, the attachment plate 1824 is located between the actuation plates 1826 and is pivotally pinned thereto by a first pivot pin 1828 that extends through slots 1830 in the actuation plates 1826 and a hole 1825 in the attachment plate 1824. A second pivot pin 1832 is received within or is supported by mounting lugs in the handle cases 1904 and extends between holes 1834 in the actuation plates 1826. Each of the actuation plates 1826 have a lug 1836 that extends into a corresponding pocket or opening 1815 in the firing carriage 814. Such arrangement facilitates the application of axial actuation motions to the knife tube 1800 by pivoting the firing trigger 1822 relative to the handle housing 1900. As the firing trigger 822 is pivoted towards the pistol grip portion 1908 of the handle housing 1900, the firing carriage 1814 is driven in the distal direction "DD". As the firing trigger 1822 is pivoted away from the pistol grip portion 1908 of the handle housing 1900, the firing carriage 1814 draws the knife tube 1800 in the proximal direction "PD".

Various embodiments of the surgical instrument 1010 may further include a locking system 1840 that includes a locking trigger 1842 that is pivotally coupled to the handle housing 1900. The locking trigger 1842 includes a locking bar portion that is configured to operably engage a locking member 1846 that is pivotally attached to the attachment plate 1824 of the firing trigger 1822 by pin 1849. Further discussion regarding the operation of the locking system 1840 may be found in U.S. Patent Application Publication No. US 2012/0074200 A1.

Actuation of the end effector 1012 will now be explained. While grasping the pistol grip portion 1908 of the handle assembly 1900, the surgeon may apply a closing motion to the anvil assembly 1020 of the end effector 1012 by applying an actuation force to the firing trigger 1822. Such action results in the application of an actuation motion to the firing carriage 1814 by the actuation plates 1826 which ultimately results in the axial displacement of the knife tube 1800 in the distal direction "DD". As the knife tube 1800 is advanced in the distal direction "DD", the knife bar assembly 1180 is likewise driven in the distal direction "DD". As the knife bar assembly 1180 and, more particularly the tissue cutting head 1190, is driven in the distal direction "DD", the upper tab portions 1196 on the tissue cutting head 1190 contact sloped surfaces 1025 on the anvil body 1021 to start to apply a closing motion to the anvil assembly 1020. Further application of the actuation force to the firing trigger 1822 results in further axial displacement of the knife tube 1800 and the tissue cutting head 1090. Such action further moves the anvil assembly 1020 towards the elongated jaw channel 1014. As the firing trigger 1822 is pivoted towards the pistol grip portion 1908 of the handle assembly 1900, the locking member 1848 also pivots in the counterclockwise "CCW" direction about the pin 1849. At this point, the tissue cutting head 1190 is prevented from moving any further in the distal direction "DD" by virtue of the locking system 1840. Thus, the surgeon may move the anvil assembly 1020 to capture and manipulate tissue in the end effector 1012 without risk of actually "firing" the end effector 1012 (i.e., or cutting the tissue and forming the staples).

Once the surgeon desires to cut tissue and form staples, a second actuation force is applied to the locking trigger 1842. When the locking trigger 842 is depressed, the locking bar portion 1844 pivots to a forward position which thereby permits the locking member 1848 to continue to pivot in the counterclockwise direction as the surgeon continues to apply the actuation force to the trigger 1822. Such actuation of the firing trigger 1822 results in the axial displacement of the tissue cutting head 1190 through the anvil assembly 1020 and the elongated jaw channel 1014. At this point, the upper tab portions 1196 and the lower foot 1198 on the tissue cutting head 1190 serves to space the anvil assembly 1020 relative to the elongated jaw channel 1014 such that the staples 32 in the staple cartridge 30 are formed into the tissue on each side of the tissue cut line.

After completing the cutting and stapling process, the firing trigger 1822 may be released. A return spring (not shown) attached to the firing trigger 1822 returns the firing trigger 1822 to the unactuated position. Alternative, the user can use the hook feature of the trigger to "pull" open the trigger if no spring is used. As the firing trigger 1822 moves in the clockwise "CW" direction, the firing carriage 1814 is moved in the proximal direction "PD" which also moves the knife bar assembly 1180 in the proximal direction "PD". As the tissue cutting head 1190 returns to its starting position, the upper tabs 1196 on the tissue cutting head 1190 contact an arcuate opening surface 1027 on the underside of the anvil cap 1023 as shown in FIG. 18. Continued movement of the tissue cutting head 1190 in the proximal direction "PD" causes the anvil assembly 1020 to pivot open by virtue of its contact with the arcuate surface 1027.

The surgical instrument 1010 also provides advantages over prior surgical instruments. For example, the unique and novel floating anvil arrangement is able to automatically adjust the anvil gap between the undersurface of the anvil and the staple cartridge or elongated channel. Thus, the floating anvil arrangement can automatically compensate for different thickness of tissue while enabling the staple forming undersurface(s) of the anvil to remain parallel to the staple cartridge and elongated channel. This is all accomplished without sacrificing anvil stability.

FIGS. 20-26 depict another surgical instrument 3010 that is capable of practicing several unique benefits of the present invention. The surgical instrument 3010 is designed to manipulate and/or actuate various forms and sizes of end effectors 3012 that are operably attached to an elongated shaft assembly 3100 of the surgical instrument. In the depicted embodiment, for example, the end effector 3012 comprises a surgical stapling device that has openable and closable jaws 3013 and 3015. More specifically, the end effector 3012 includes an elongated channel 3014 that forms a lower jaw 3013 of the end effector 3012. See FIGS. 21 and 22. In the illustrated arrangement, the elongated channel 3014 is configured to operably support a staple cartridge 30 of the type and construction described herein. For example, the surgical staple cartridge includes a cartridge body 31 that operably supports a plurality of unformed surgical staples 32 therein. The elongated channel 3014 also movably supports an anvil assembly 3020 that functions as an upper jaw 3015 of the end effector 3012.

In various implementations, the end effector 3012 is configured to be coupled to an elongated shaft assembly 3100 that protrudes from a handle assembly or housing 3400. See FIG. 20. The handle assembly 3400 may be similar to one of the handle assemblies disclosed herein and/or in U.S. Patent Application Publication No. US 2012/0074200 A1 except for the differences discussed herein.

Figure 23:
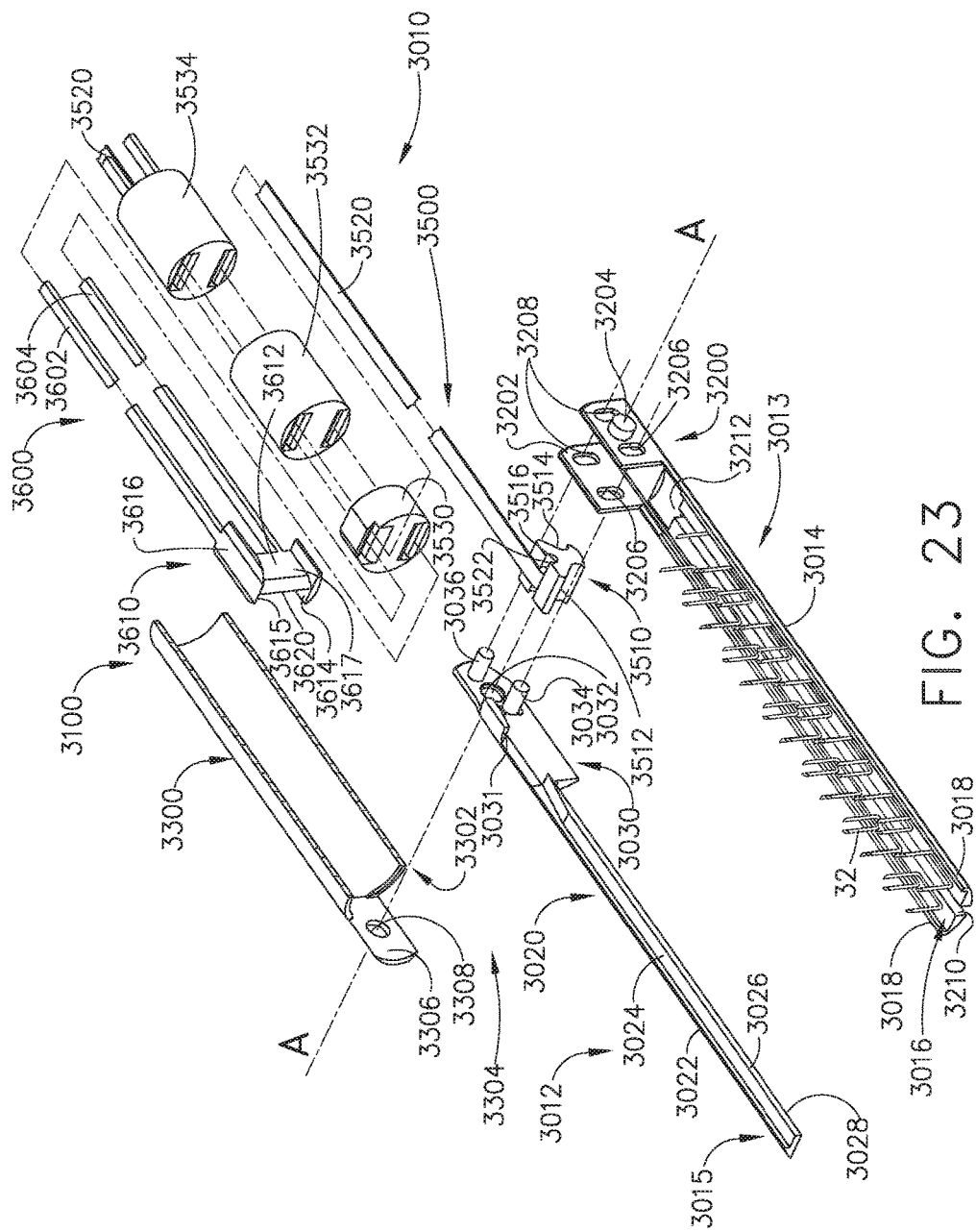
FIG. 23 is an exploded perspective assembly view of the end effector of FIGS. 21 and 22.
Figure 24:
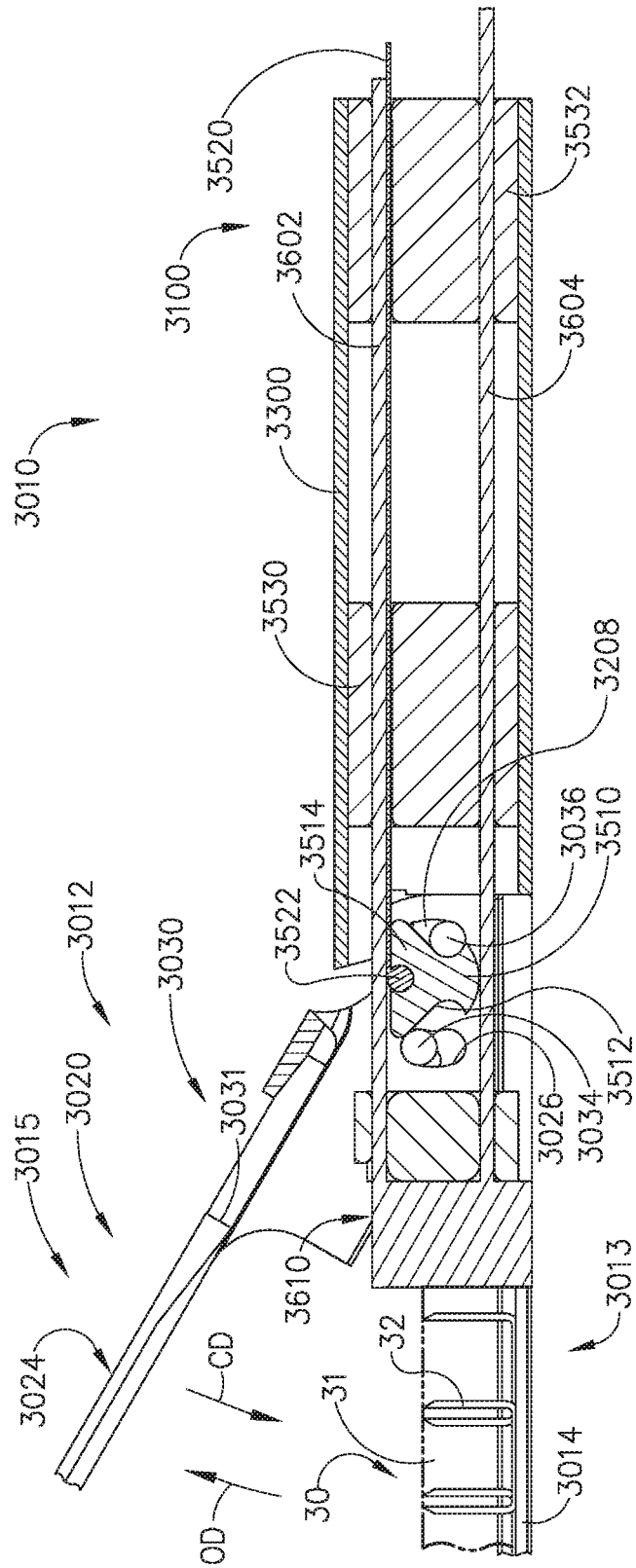
FIG. 24 is a cross-sectional elevational view of the end effector of FIGS. 21-23 with the anvil assembly thereof in an open position.
Figure 25:
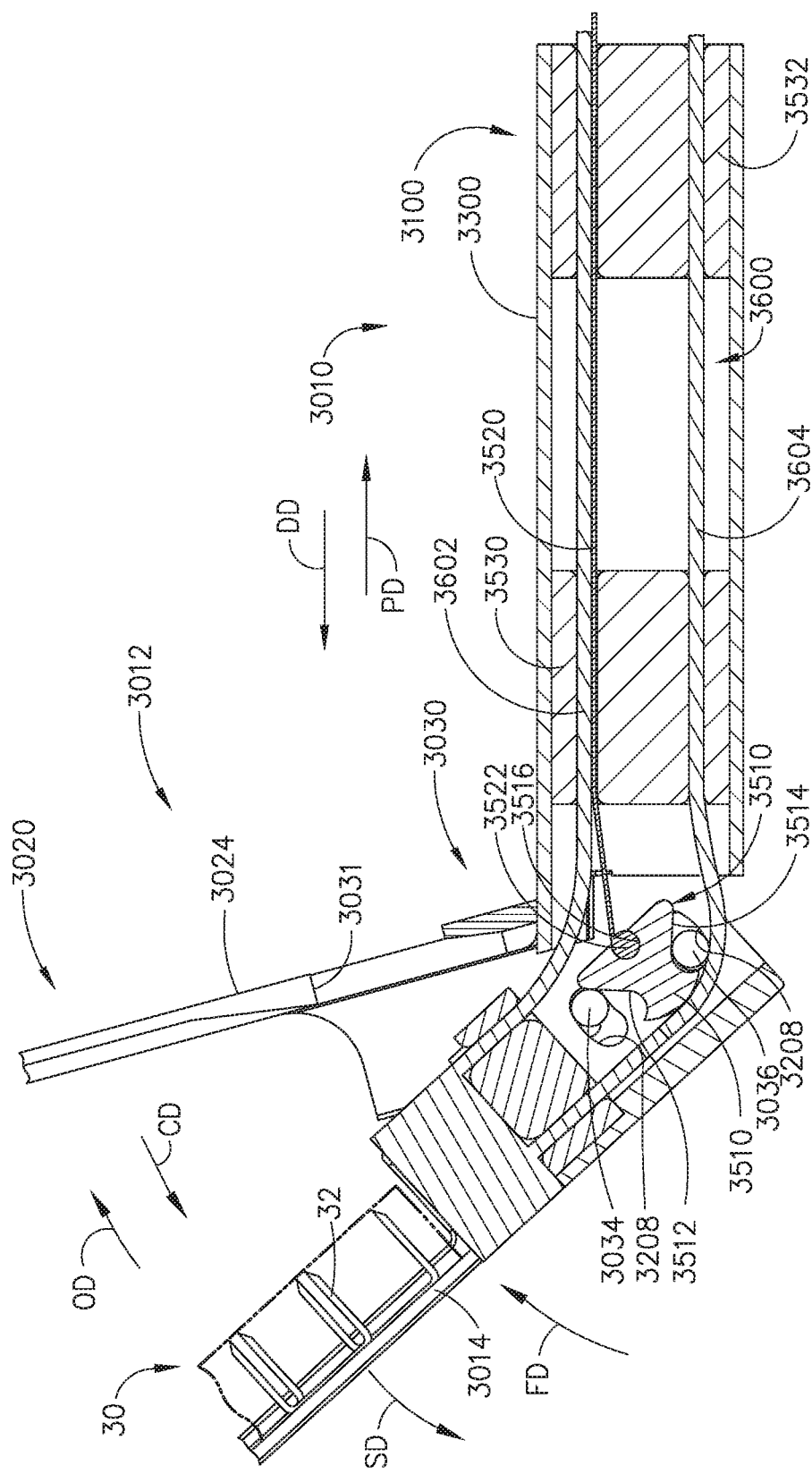
FIG. 25 is another cross-sectional view of the end effector of FIGS. 21-24 in an articulated position and with the anvil assembly thereof in an open position.

Referring to FIG. 23, the elongated channel 3014 may comprise an elongated trough 3016 that is configured to removably support a surgical staple cartridge 30 thereon. In various implementations, for example, the elongated channel 3014 may be fabricated from, for example, 300 & 400 Series, 17-4 & 17-7 stainless steel, titanium, etc. and be formed with spaced side walls 3018. The body 31 of staple cartridge 30 is sized to be removably supported within the elongated channel 3014 as shown such that each staple 32 therein is aligned with corresponding staple forming pockets in the anvil assembly 3020 when the anvil assembly 3020 is driven into forming contact with the staple cartridge 30. The elongated channel 3014 may further include a proximal end 3200 that includes a pair of spaced side walls 3202. In at least one implementation, the end effector 3012 is configured to be articulated relative to the elongated shaft assembly 3100 about an articulation and pivot axis A-A about which the anvil assembly 3020 is pivoted relative to the elongated channel 3014. The elongated shaft assembly 3100 defines a longitudinal tool axis LT-LT. The articulation and pivot axis A-A is transverse to the longitudinal tool axis LT-LT. The elongated shaft assembly 3100 comprises a hollow outer shaft 3300 and serves to function as the shaft spine of the elongated shaft assembly 3100. The proximal end of the outer shaft 3300 may be rotatably supported by the handle assembly 3400 so that the clinician may selectively rotate the elongated shaft assembly 3100 and the end effector 3012 attached thereto about the longitudinal tool axis LT-LT. For example, the proximal end of the elongated shaft assembly may be operably coupled to a nozzle assembly 3250 that is rotatably supported on the handle assembly 3400. Rotation of nozzle assembly 3250 relative to the handle assembly 3400 (represented by arrow "R") will result in rotation of the elongated shaft assembly 3100 as well as the end effector 3012 coupled thereto. See FIG. 20.

Referring again to FIG. 23, the distal end 3302 of the outer shaft 3300 is formed with a clevis arrangement 3304 that comprises a pair of spaced attachment tabs 3306. Each attachment tab 3306 has a mounting hole 3308 therein that is adapted to receive a corresponding pivot pin 3204 that is formed on each upstanding side wall 3202. Thus, the elongated channel 3014 is selectively pivotable or articulatable about the pivot axis A-A relative to the elongated shaft assembly 3100. The anvil assembly 3020 includes a distal anvil portion 3022 and a proximal anvil mounting portion 3030. The distal anvil portion 3022 may, for the most part, be substantially coextensive with the portion of the elongated channel 3014 that supports the staple cartridge 30 and be fabricated from, for example, 300 & 400 Series, 17-4 & 17-7 stainless steel, titanium, etc. The distal anvil portion 3022 comprises two spaced apart anvil arms 3024 that protrude distally from the anvil mounting portion 3030 to define an elongated slot 3026 therebetween. Each of the spaced-apart anvil arms 3024 has a staple forming undersurface, generally labeled as 3028 that has a plurality of staple forming pockets (not shown) formed therein.

Figure 21:
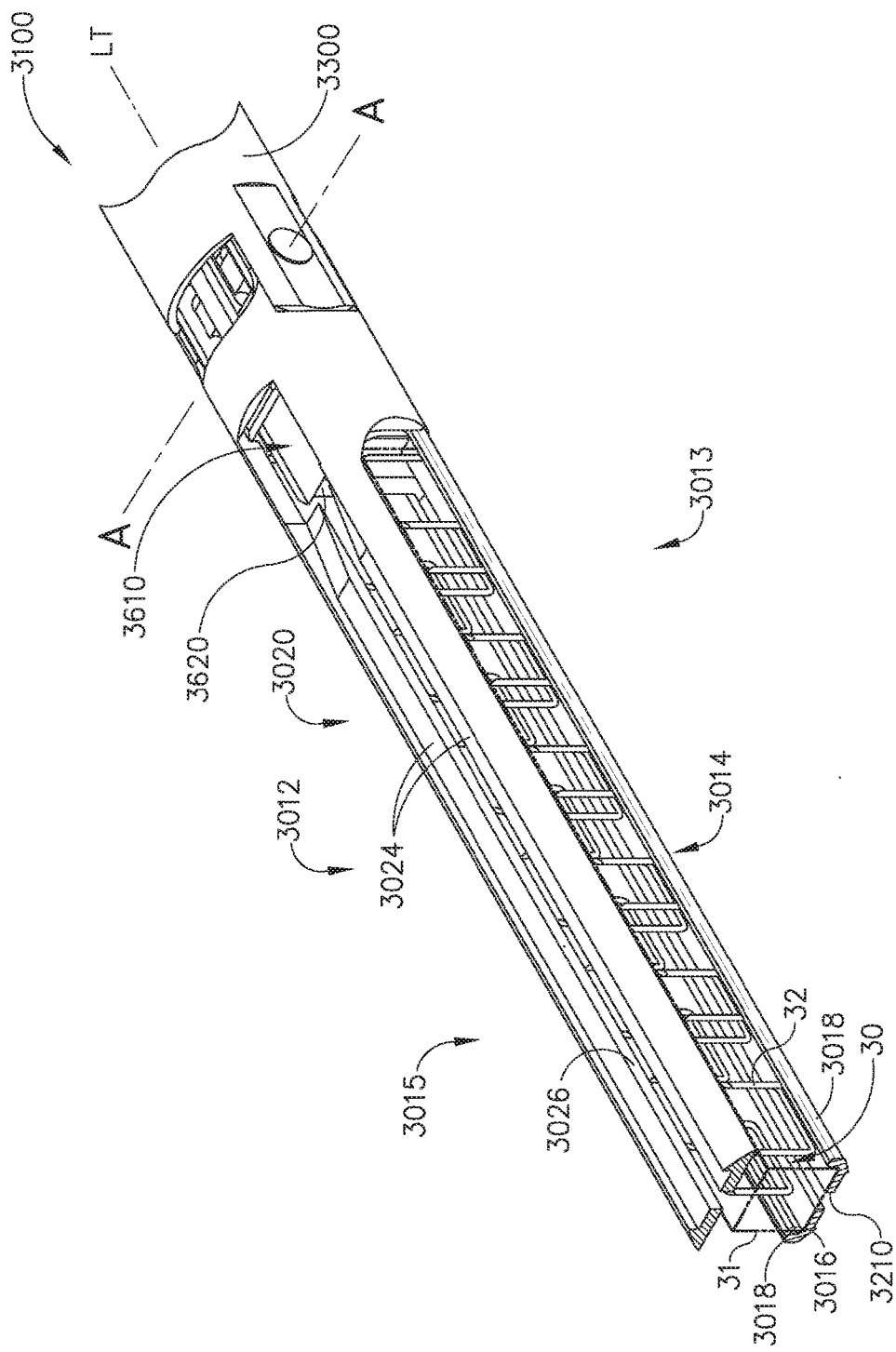
FIG. 21 is a partial perspective view of the end effector of the surgical instrument of FIG. 20 in a closed position.
Figure 22:
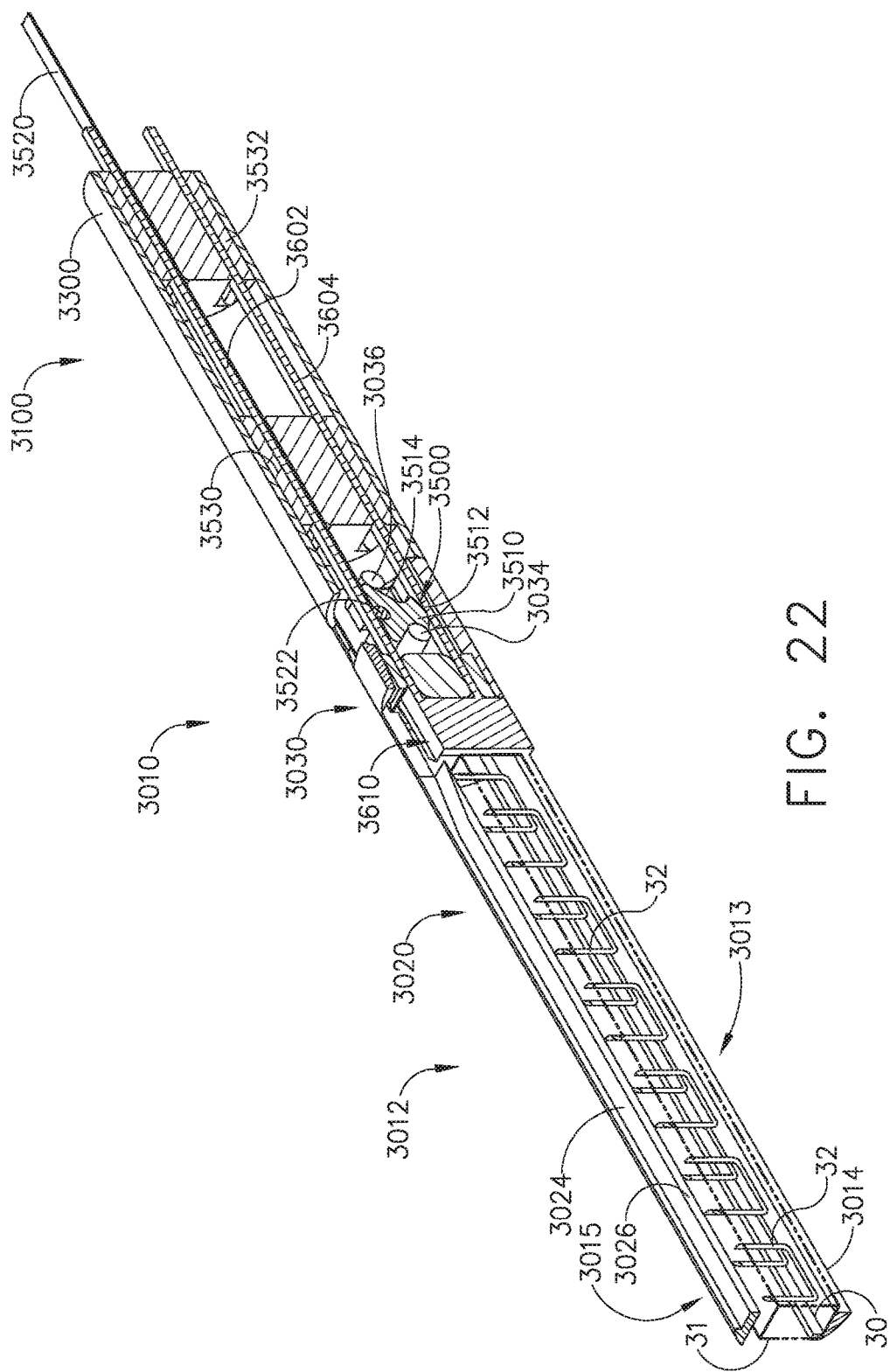
FIG. 22 is a cross-sectional perspective view of the end effector of FIG. 21.
Figure 26:
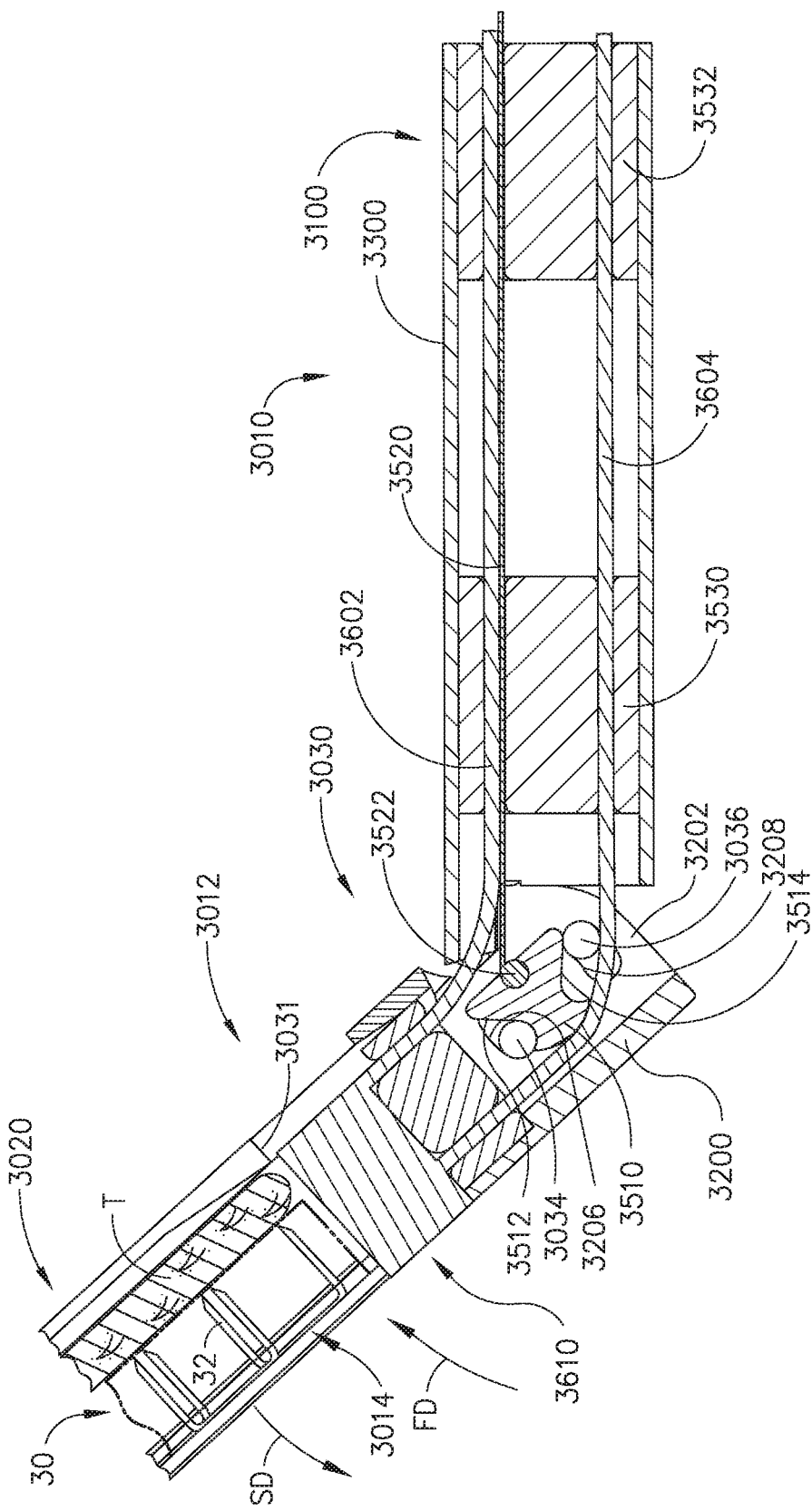
FIG. 26 is another cross-sectional view of the end effector of FIG. 24 after the anvil has been closed onto tissue.

The anvil mounting portion 3030 has a pair of mounting holes 3032 (only one is shown in FIG. 23) that are adapted to pivotally receive therein the corresponding pivot pins 3204 that protrude from the side walls 3202 of the proximal end 3200 of the elongated channel 3014. Such arrangement serves to pivotally mount the anvil assembly 3020 to the elongated channel 3014 for selective pivotal travel about pivot axis A-A between an open position (FIGS. 24 and 25) and a closed position (FIGS. 21, 22 and 26).

Articulation of the end effector 3012 about the pivot axis A-A as well as actuation of the anvil assembly 3020 between open and closed positions may be controlled by a single firing system generally designated as 3500. In at least one implementation, for example, the firing system 3500 includes an actuation pivot 3510 that is movably supported between the upstanding side walls 3202 of the elongated channel 3014. The actuation pivot 3510 includes a distal cam surface 3512 and a proximal cam surface 3514. The distal cam surface 3512 is configured to operably interface with an inwardly protruding distal anvil pin 3034 that protrudes from the anvil mounting portion 3030. The proximal cam surface 3514 is configured to operably interface with an inwardly protruding proximal anvil pin 3036 that also protrudes inwardly from the anvil mounting portion 3030. As can be seen in FIG. 23, the distal anvil pin 3034 extends inwardly through the corresponding elongated distal slots 3206 in the upstanding side walls 3202 of the proximal end 3200 of the elongated channel 3014. Likewise, the proximal anvil pin 3036 extends inwardly through corresponding elongated slots 3208 in the upstanding side walls 3202 of the proximal end 3200 of the elongated channel 3014.

The firing system 3500 may be controlled, for example, by a closure trigger arrangement on a handle assembly 3400 of the type disclosed in U.S. Patent Application Publication No. US 2012/0074200 A1. For example, the firing system 3500 may include an actuation bar 3520 that is movably coupled to the actuation pivot 3510. The actuation bar 3520 may have, for example, an attachment ball member 3522 formed on the distal end thereof that is rotatably received within a semi-circular groove 3516 in the actuation pivot 3510. Such arrangement permits the actuation pivot 3510 to pivot or otherwise move relative to the actuation bar 3520. Other methods of movably coupling the actuation bar 3520 to the actuation pivot 3510 may also be employed. The actuation bar 3520 may extend through the hollow outer shaft 3300 and be operably coupled to, for example, the closure carriage arrangement disclosed in the aforementioned published patent application such that actuation of the trigger 440 will result in the axial travel of the actuation bar 3520 within the outer shaft 3330. In various implementations, a series of support collars 3530, 3532, 3534 may be provided in the outer shaft 3300 to provide support to the actuation bar 3520 within the outer shaft 3300.

In use, the end effector 3012 is articulated into a desired position prior to closing the anvil assembly 3020. Of course, if the end effector 3012 must be inserted through a trocar or other opening in the patient, the clinician can move the anvil assembly 3020 to the closed position (FIG. 21) without articulating the end effector 3012 so that the end effector 3012 is coaxially aligned with the elongated shaft assembly 3100. The clinician manipulates the trigger 440 to position the actuation pivot 3510 so that the cam surfaces 3512 and 3514 interact with the pins 3034, 3036 to result in the closure of the anvil assembly 3020 without articulating the end effector 3012. Once the end effector 3012 has been inserted through the trocar or other opening, the clinician may actuate the trigger 440 to move the actuation pivot 3510 to the position shown in FIG. 24. When in that position, the actuation pivot 3510 causes the anvil assembly 3520 to move to the open position without being articulated. The clinician may then articulate the end effector 3012 about the pivot axis A-A relative to the elongated shaft assembly 3100 by further actuating the trigger 440 to move the actuation pivot 3510 to the position shown, for example, in FIG. 25. As can be seen in that Figure, the end effector 3012 has pivoted in a first direction "FD" which is the same general direction that the anvil assembly 3020 moves when it moves from a closed position to the open position (referred to herein as the "opening direction 'OD'"). If desired, the user may actuate the trigger 440 to thereby cause the end effector 3012 to move in a second direction "SD" that is the same general direction that the anvil assembly 3020 moves when it is moved from the open position to a closed position (referred to herein as the "closing direction "CD""). Once the user has positioned the end effector 3012 in the desired position, the user further actuates trigger 440 to manipulate the actuation pivot to the position illustrated in FIG. 26 to thereby clamp the target tissue "T" between the anvil assembly 3020 and the staple cartridge 30.

The surgical instrument 3010 further includes a knife bar assembly 3600 that can be attached to the firing bar and firing rack arrangement disclosed herein and/or in U.S. Patent Application Publication US 2012/0074200 A1 such that it can be controlled by actuating the secondary trigger 460. In various embodiments, the knife bar assembly 3600 may comprise an upper bar segment 3602 and a lower bar segment 3604. Such arrangement may enable the knife bar assembly 3600 to flex as the end effector 3012 is articulated, while remaining sufficiently rigid to be driven distally through the shaft assembly 3100. In the depicted embodiment, the upper and lower knife bar segments 3602, 3604 are each attached to a cutting head 3610. In the depicted configuration, the cutting head 3610 includes a vertically oriented body portion 3612 that has an upper portion 3615 and a lower portion 3617. A bottom foot 3614 is formed on or attached to the lower portion 3617. Similarly, an upper tab 3616 is formed on or otherwise attached to the upper portion 3615 of the vertically oriented body portion 3612. In addition, as can be seen in FIG. 23, the vertically oriented body portion 612 further includes a tissue cutting edge 3620.

Referring to FIG. 23, the vertically oriented body portion 3612 extends through a longitudinally extending slot 3210 in the elongated channel 3014 and the longitudinally extending slot 3026 in the anvil assembly 3020. When assembled, the upper portion 3615 of the cutting head 3610 extends through a proximal upper opening 3031 in the anvil mounting portion 3030 of the anvil assembly 3020. Thus, when the cutting head 3610 is distally advanced, the upper tab portions 3616 ride on the anvil arms 3024. Likewise the bottom foot 3614 protrudes through a lower opening 3212 in the elongated channel 3014 such that it rides below the elongated channel as the cutting head 3610 is advanced distally. As the cutting head 3610 is advanced distally, the cutting edge 3620 thereon severs the tissue clamped in the end effector 3012. The surgical staple cartridge 30 is crushed between the anvil assembly 3020 and the elongated channel 3014 thereby causing the staples 32 supported therein to be formed on both sides of the tissue cut line as they are brought into contact with the staple forming underside of the anvil assembly 3020. After the cutting head 3610 has been advanced to the distal end of the end effector, 3012, the user retracts the cutting head 3610 to the starting position in the manner discussed herein and the trigger 440 is actuated to open the anvil assembly 3020 to release the staple cartridge and stapled tissue.

As was discussed in detail above, by having the articulation axis also be the axis about which the anvil pivots, the surgeon has a much more reliable frame of reference regarding the location of the pivot axis when viewing the endocutter's anvil through the camera. Stated another way, when using the end effector arrangement of the surgical instrument 10 the surgeon can determine where the elongated channel is going to pivot relative to the elongated shaft by viewing where the anvil is pivotally mounted to the elongated channel.

FIGS. 27-35 illustrate another surgical instrument arrangement 4010 that may employ various components of other surgical instruments disclosed herein except for the differences discussed below. The surgical instrument 4010 is designed to manipulate and/or actuate various forms and sizes of end effectors 4012 that are operably attached to an elongated shaft assembly 4100 of the surgical instrument. In the depicted embodiment, for example, the end effector 4012 comprises a surgical stapling device that has openable and closable jaws 4013 and 4015. More specifically, the end effector 4012 includes an elongated channel 4014 that forms a lower jaw 4013 of the end effector 4012. See FIG. 28. In the illustrated arrangement, the elongated channel 4014 is configured to operably support a staple cartridge 30 and also movably supports an anvil assembly 4020 that functions as an upper jaw 4015 of the end effector 4012.

In various implementations, the end effector 4012 is configured to be coupled to an elongated shaft assembly 4100 that protrudes from a handle assembly or housing 4400. See FIG. 27. The handle assembly 4400 may be similar to one of the handle assemblies disclosed herein and/or in U.S. Patent Application Publication No. US 2012/0074200 A1 except for any differences discussed below. Alternative embodiments, however, may be employed with and actuated by robotic systems as was discussed hereinabove.

Figure 28:
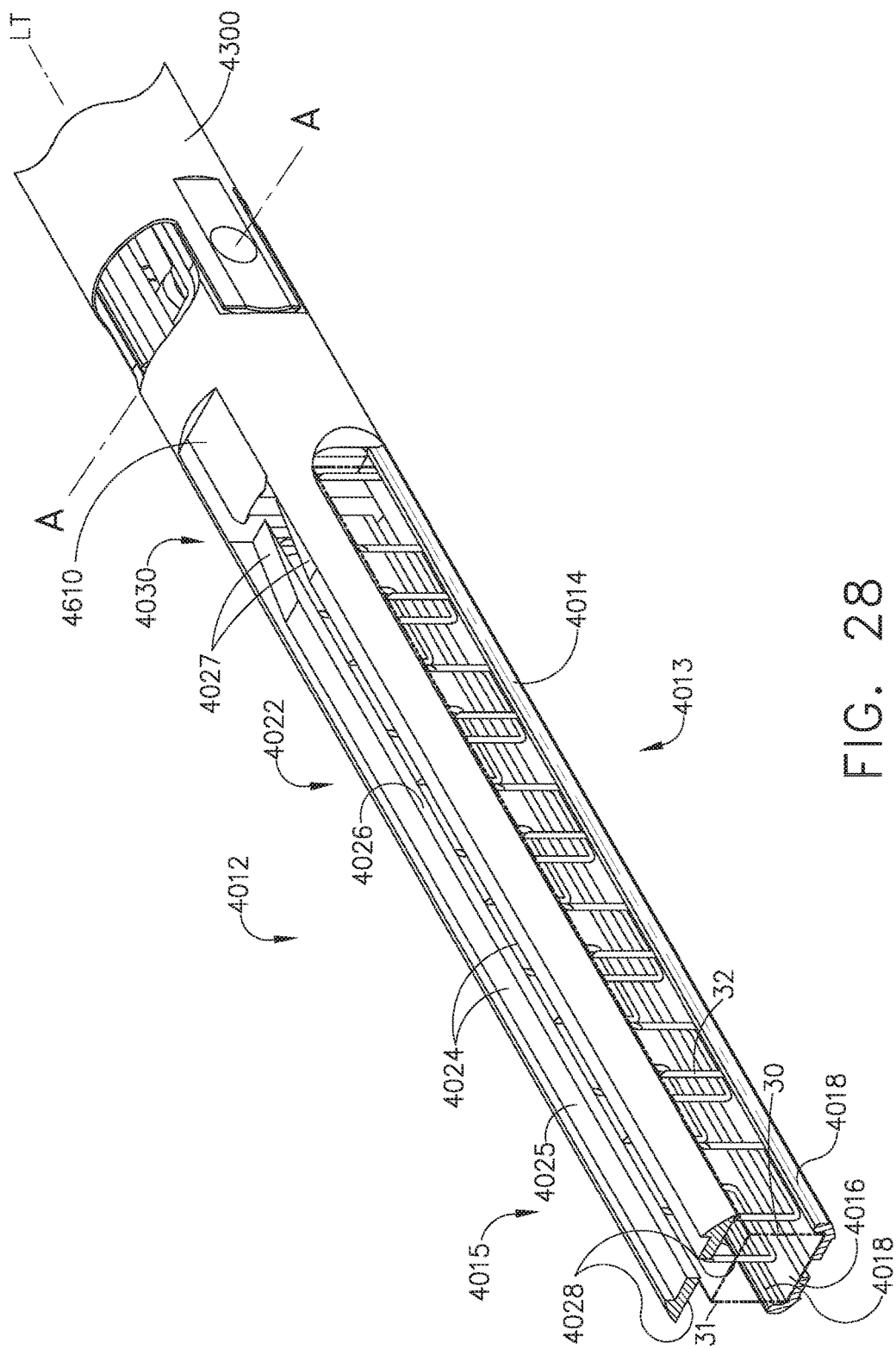
FIG. 28 is a partial perspective view of the end effector of the surgical instrument of FIG. 27 in a closed position.
Figure 29:
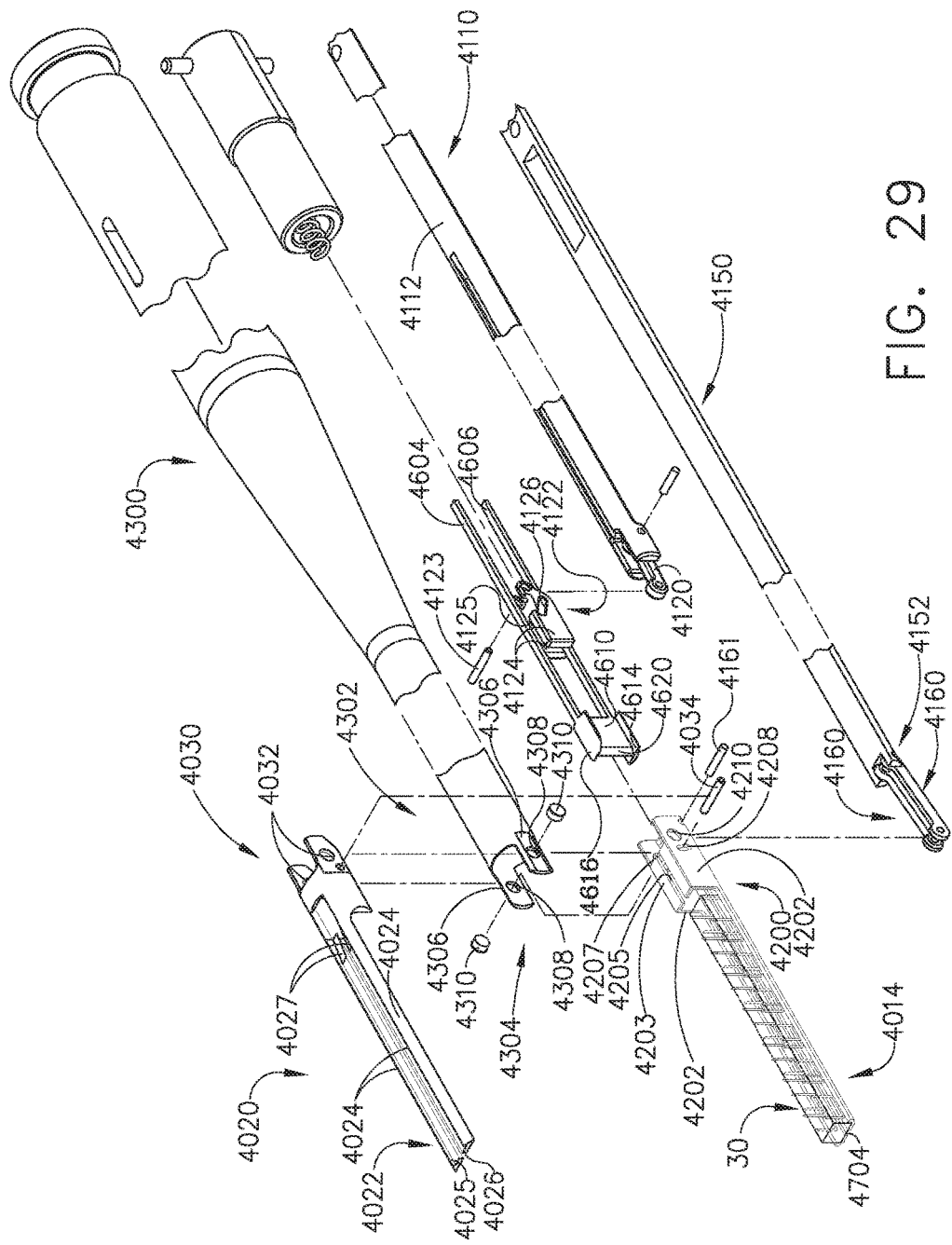
FIG. 29 is an exploded perspective assembly view of the end effector and elongated shaft assembly of FIGS. 27 and 28.

Referring to FIGS. 28 and 29, the elongated channel 4014 may comprise an elongated trough 4016 that is configured to removably support a surgical staple cartridge 30 thereon. In various implementations, for example, the elongated channel 3014 may be fabricated from, for example, 300 & 400 Series, 17-4 & 17-7 stainless steel, titanium, etc. and be formed with spaced side walls 4018. The body 31 of staple cartridge 30 is sized to be removably supported within the elongated channel 3014 as shown such that each staple 32 therein is aligned with corresponding staple forming pockets in the anvil assembly 4020 when the anvil assembly 4020 is driven into forming contact with the staple cartridge 30. The elongated channel 4014 may further include a somewhat box-like proximal end 4200 that includes a pair of spaced side walls 4202 that have a top flap 4203 protruding inwardly therefrom to define a slot 4205 therebetween. The sidewalls 4202 are coupled together by a support bar 4207 that extends therebetween. See FIGS. 29, 31 and 32.

In at least one implementation, the elongated channel 4014 is configured to be moved or articulated relative to the elongated shaft assembly 4100 and the anvil assembly 4020 about a pivot axis A-A about which the anvil assembly 4020 is also pivotally mounted. The elongated shaft assembly 4100 defines a longitudinal tool axis LT-LT. The pivot axis A-A is transverse to the longitudinal tool axis LT-LT. The elongated shaft assembly 4100 comprises a hollow outer shaft 4300 and serves to function as the shaft spine of the elongated shaft assembly 4100. The proximal end of the outer shaft 4300 may be rotatably supported by the handle assembly 4400 so that the clinician may selectively rotate the elongated shaft assembly 4100 and the end effector 4012 attached thereto about the longitudinal tool axis LT-LT.

Referring again to FIG. 29, the distal end 4302 of the outer shaft 4300 is formed with a clevis arrangement 4304 that comprises a pair of spaced attachment tabs 4306. Each attachment tab 4306 has a mounting hole 4308 therein that is adapted to receive a corresponding pivot pin 4310 that defines the pivot axis A-A. The pivot pins 4310 also extend through corresponding openings 4210 in the upstanding side walls 4202 of the proximal mounting end 4200 of the elongated channel 4014. Thus, the elongated channel 4014 is selectively pivotable or articulatable about the pivot axis A-A relative to the elongated shaft assembly 4100 and the anvil assembly 4020. The anvil assembly 4020 includes a distal anvil portion 4022 and an proximal anvil mounting portion 4030. The distal anvil portion 4022 may, for the most part, be substantially coextensive with the portion of the elongated channel 3014 that supports the staple cartridge 30 and be fabricated from, for example, 300 & 400 Series, 17-4 & 17-7 stainless steel, titanium, etc. The distal anvil portion 4022 comprises two spaced apart anvil arms 4024 that protrude distally from the anvil mounting portion 4030 to define an elongated slot 4026 therebetween. Each of the spaced-apart anvil arms 4024 has a staple-forming undersurface, generally labeled as 4028 that has a plurality of staple forming pockets (not shown) formed therein. The anvil mounting portion 4030 has a pair of mounting holes 4032 that are adapted to pivotally receive therein the corresponding pivot pins 4310. Such arrangement serves to pivotally mount the anvil assembly 4020 to the outer shaft 4300 for selective pivotal travel about pivot axis A-A between an open position (FIGS. 32 and 33) and a closed position (FIGS. 28, 30 and 31) relative to the elongated channel assembly 4014.

Initial closure of the anvil assembly 4020 relative to the elongated channel assembly 4014 and the surgical staple cartridge 30 operably supported therein may be accomplished by a unique and novel closure system, generally designated as 4110. The closure system 4110 may also be referred to herein as the "second jaw closure system". In one implementation, the closure system 4110 includes an anvil closure rod 4112 that has a proximal end that may be operably coupled to the closure carriage in the handle assembly 4400 in the various manners discussed herein and also disclosed in further detail in U.S. Patent Application Publication No. US 2012/0074200 A1. For example, the proximal end of the closure rod 4112 may have a flange (not shown) that is configured to be rotatably attached to a closure carriage that is operably supported within the housing assembly 4400. Thus, actuation of the trigger 440 will result in the axial advancement of the anvil closure rod 4112 within the outer shaft 4300. Such arrangement also enables the elongated shaft assembly 4100 and the end effector 4012 that is operably coupled thereto may be selectively rotated about the longitudinal tool axis LT-LT relative to the housing assembly 4400. The anvil closure rod 4112 may also be referred to herein as the "second jaw actuator bar."

Figure 31:
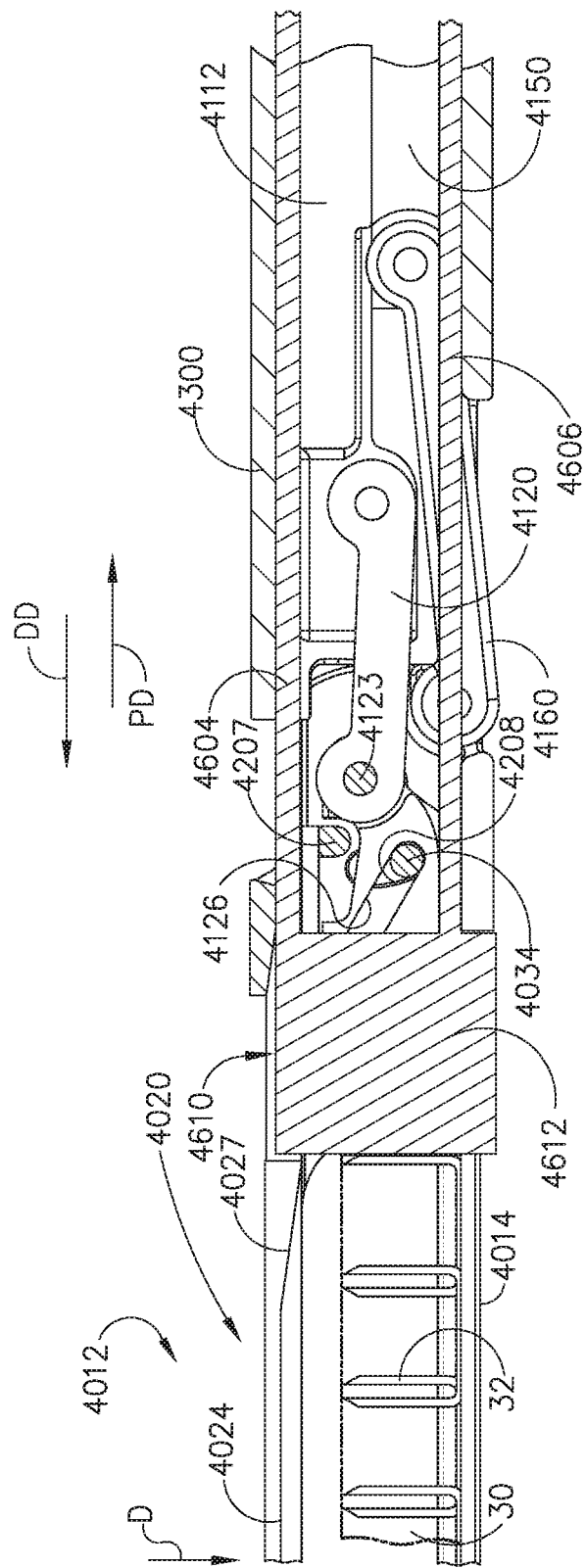
FIG. 31 is a cross-sectional side view of the end effector of FIGS. 28-30 with the anvil assembly thereof in a closed position.
Figure 32:
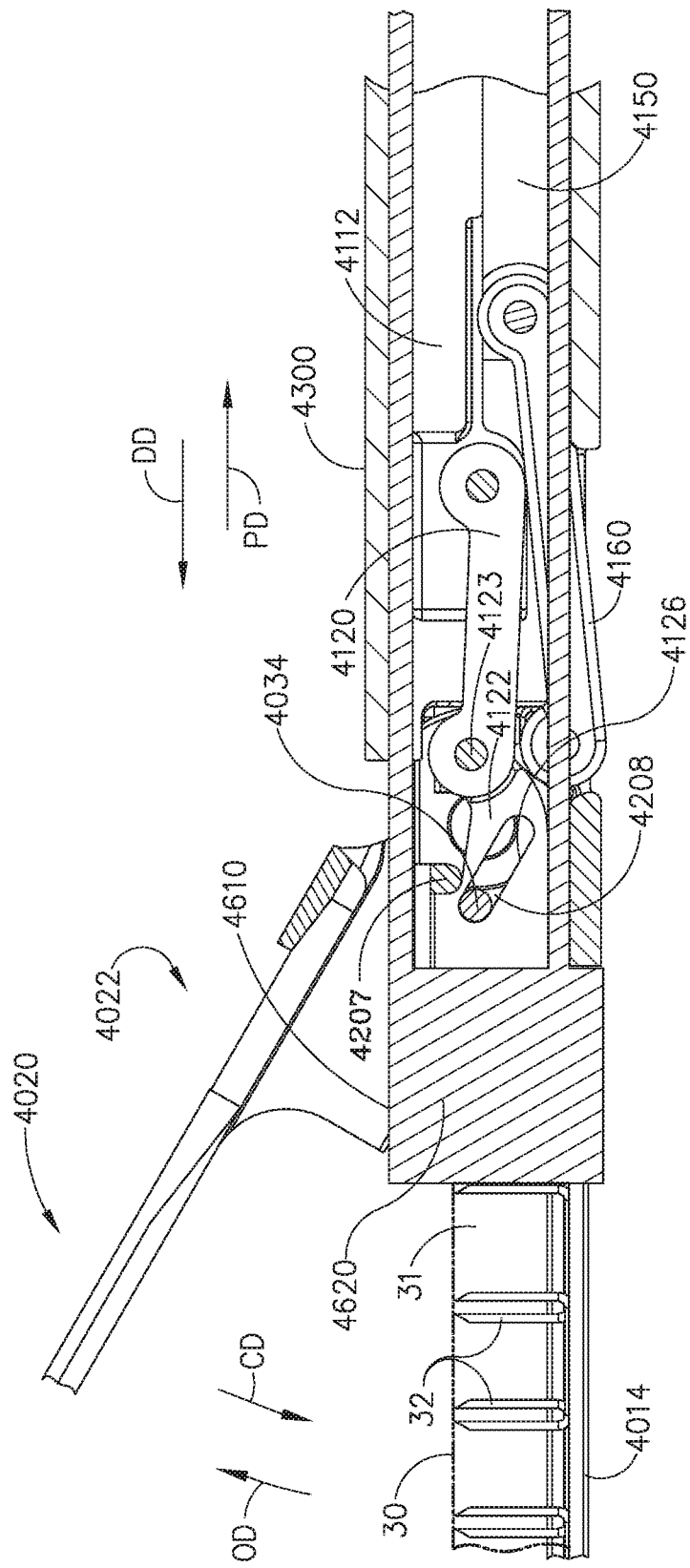
FIG. 32 is another cross-sectional side view of the end effector of FIGS. 28-31 with the anvil assembly thereof in an open position.

Referring again to FIG. 29, a distal end 4118 of the anvil closure rod 4112 is configured to be pinned to an anvil closure link 4120. The anvil closure link 4120 is pivotally pinned to an anvil pin slide 4122 by a pin 4123. The anvil pin slide 4122 includes two spaced side walls 4124 that define a space 4125 therebetween that is configured to receive a portion of a tissue cutting head 4610 as will be discussed in further detail below. An anvil cam pin 4034 is mounted to the anvil mounting portion 4030 and extends through elongated slots 4208 in the upstanding side walls 4202 of the proximal end 4200 of the elongated channel 4014 as well as through cam slots 4126 provided through the side walls 4124 of the anvil pin slide 4122. FIG. 32 illustrates the positions of the anvil slide 4122 and the anvil cam pin 4034 when the anvil assembly 4020 is in the open position. To move the anvil assembly 4020 to a closed position relative to the elongated channel assembly 4014 (FIG. 31), the clinician can actuate the trigger 440 which drives the anvil closure rod 4112 in the distal direction "DD". Such movement of the anvil closure rod 4112 in the distal direction also moves the anvil pin slide 4122 in the distal direction "DD". As the anvil pin slide 4122 moves in the distal direction, the camming action of the anvil pin 4034 in the slots 4126 and 4208 cams the anvil assembly 4020 in the closing direction "CD" to the closed position as shown in FIG. 31. Movement of the anvil closure rod 4112 in the proximal direction "PD" will cause the anvil assembly 4020 to move in the opening direction "OD".

Figure 30:
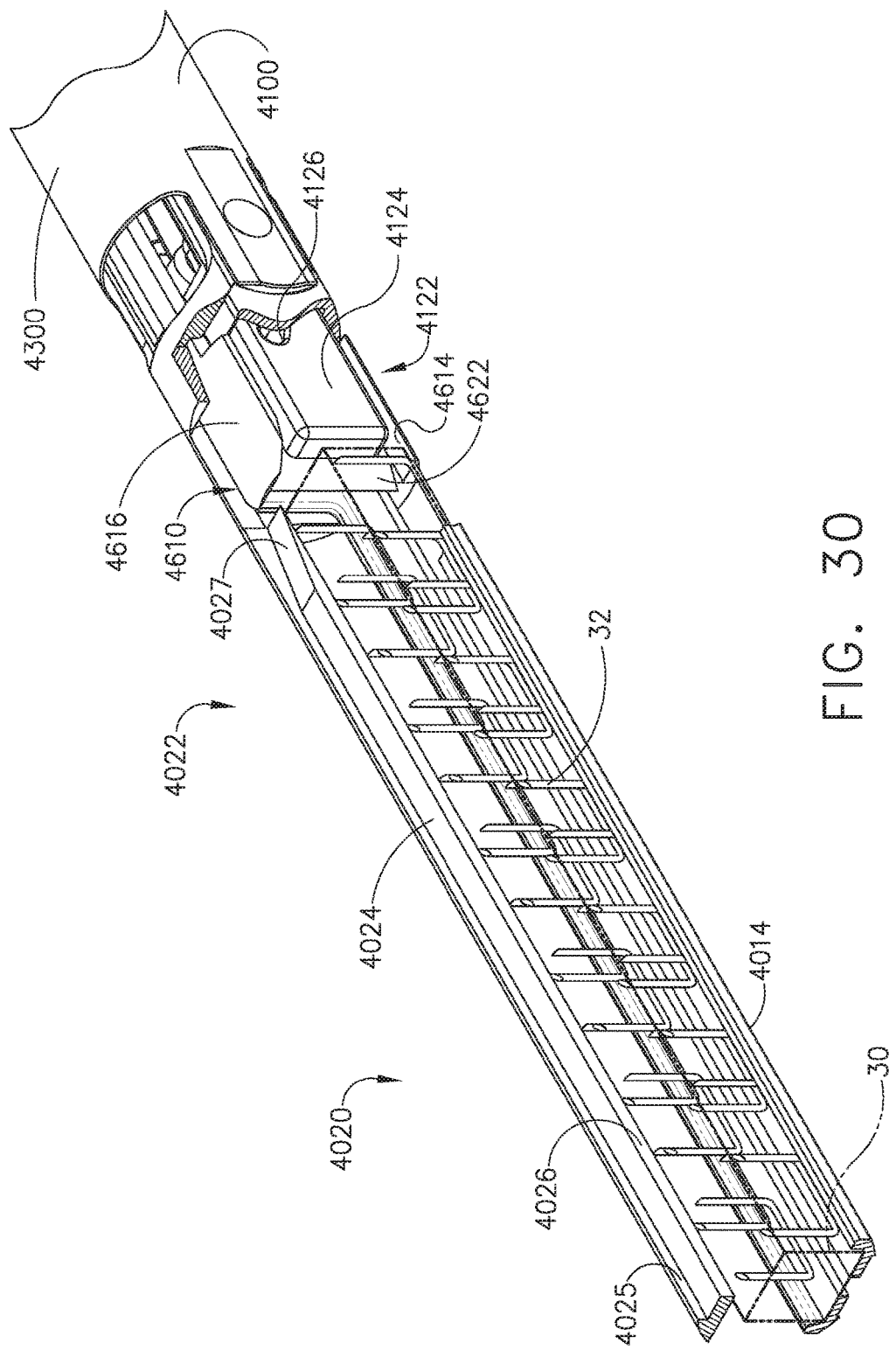
FIG. 30 is a cross-sectional perspective view of the end effector of FIGS. 28 and 29.
Figure 33:
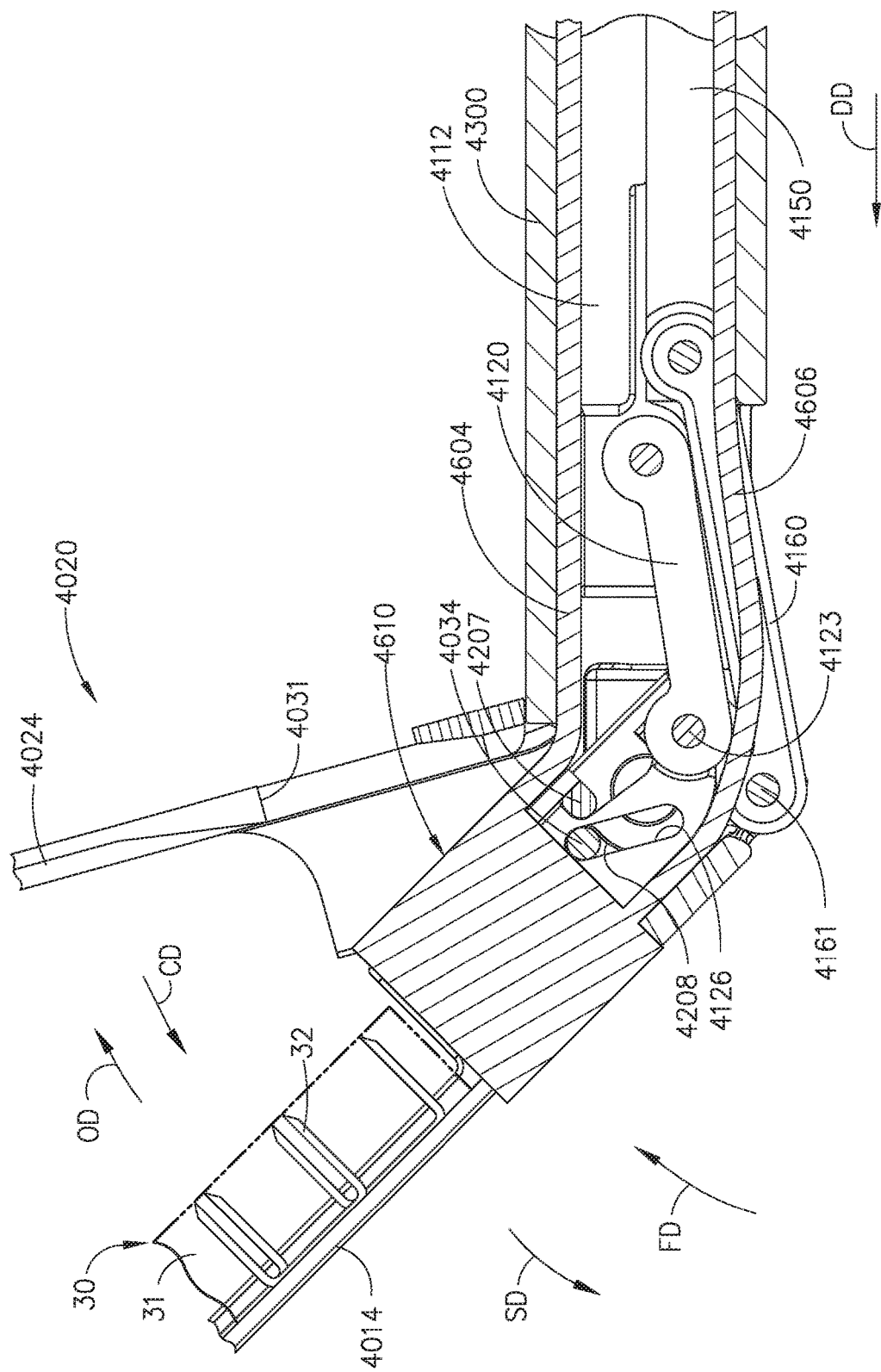
FIG. 33 is a cross-sectional side view of the end effector of FIGS. 28-32 in an articulated position and with the anvil assembly thereof in an open position.
Figure 34:
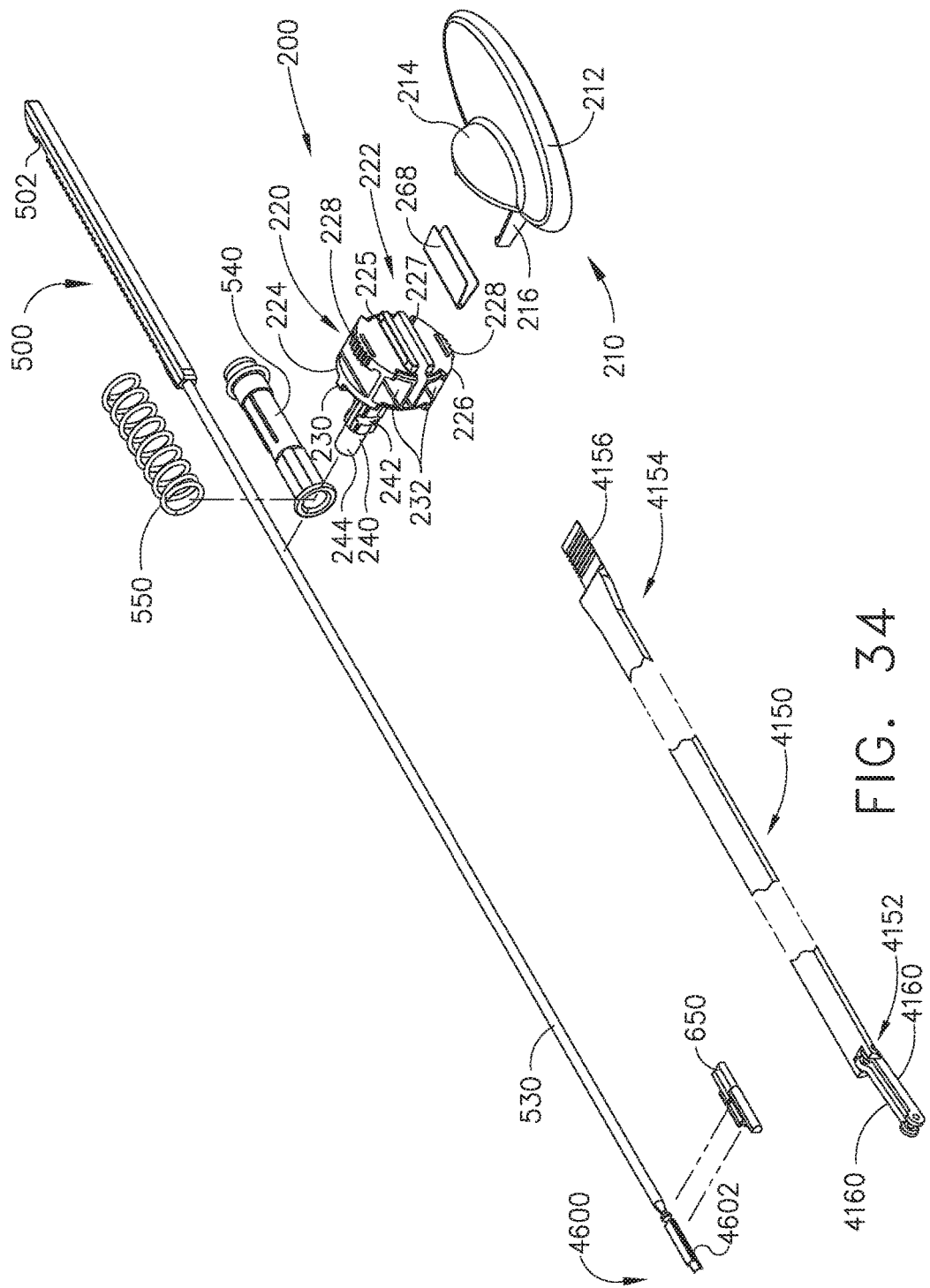
FIG. 34 is a perspective assembly view of portions of the articulation system and firing system of the surgical instrument of FIG. 27.
Figure 35:
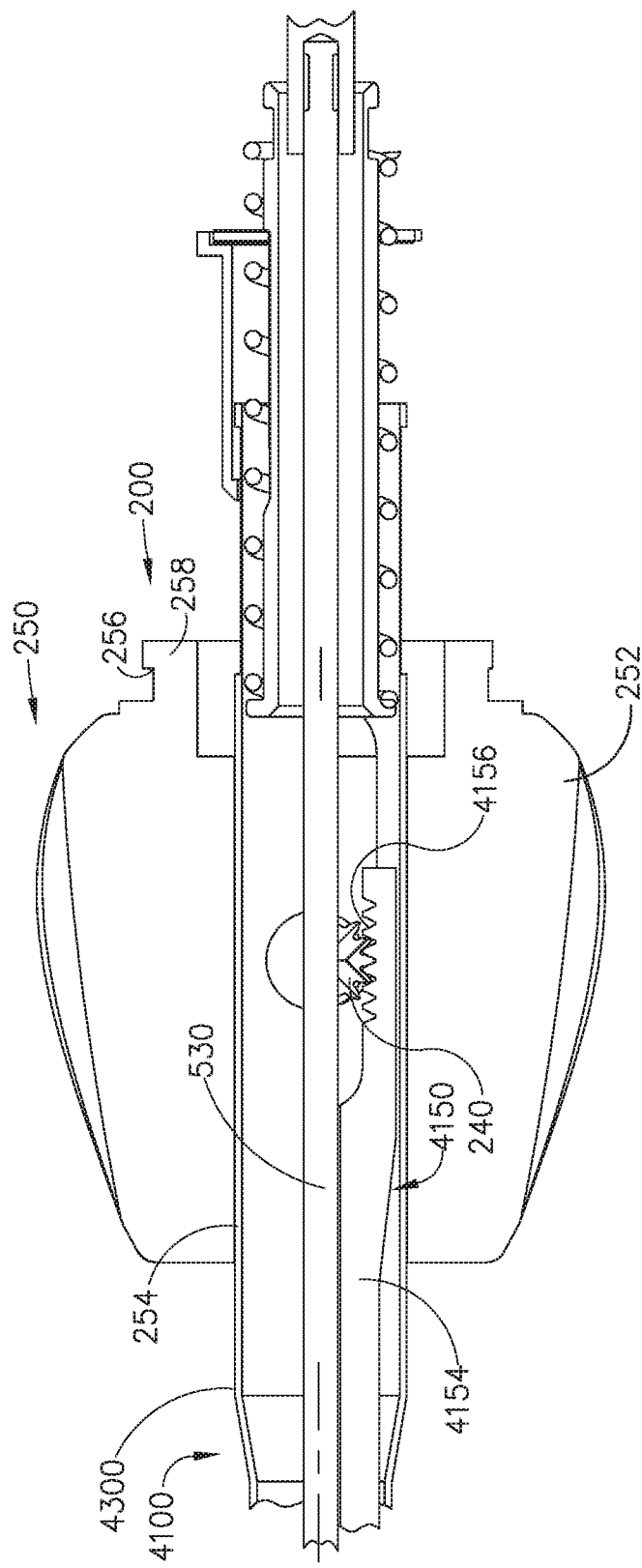
FIG. 35 is a side view of a portion of the articulation system of FIG. 34 with portions thereof shown in cross-section.
Figure 36:
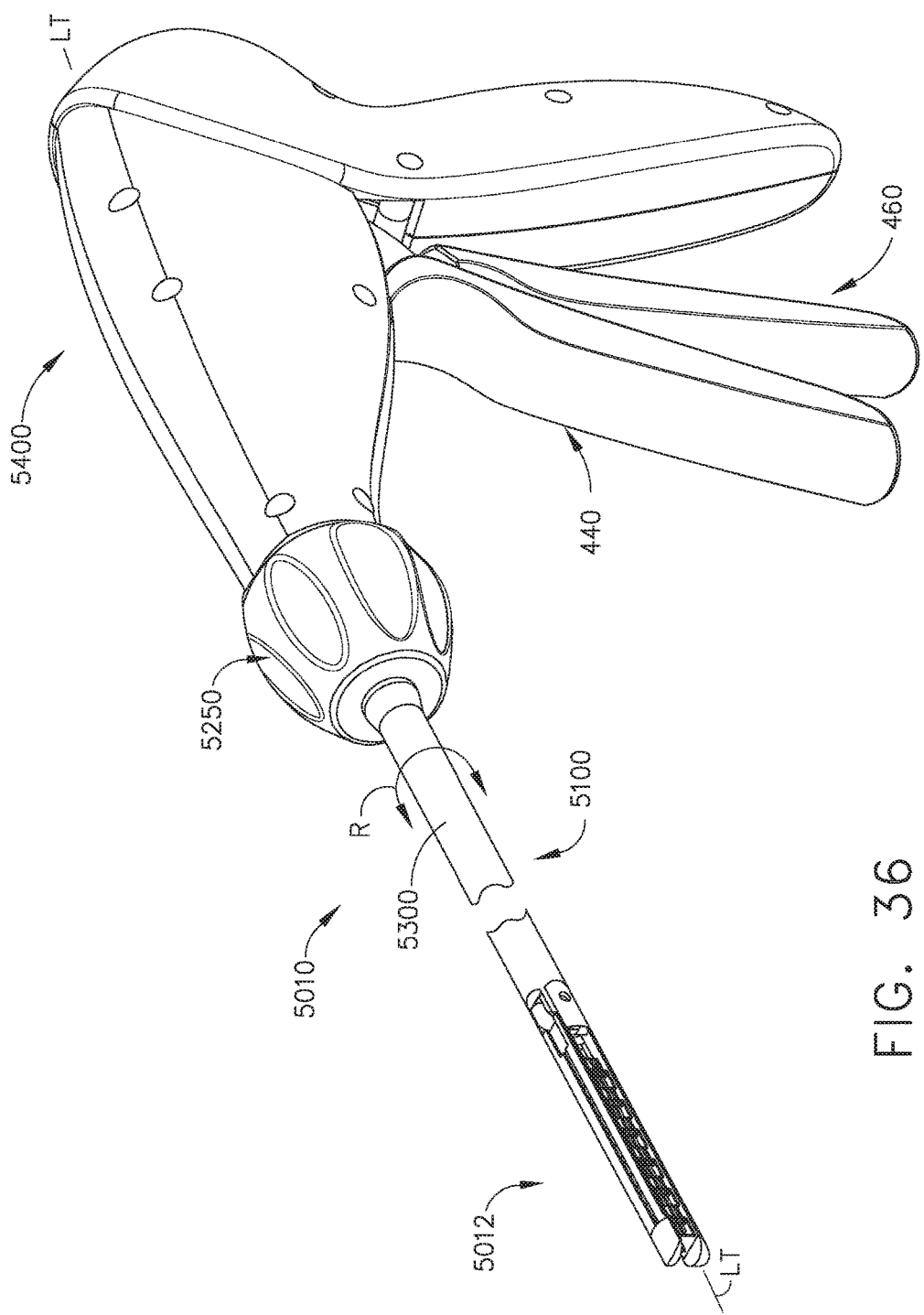
FIG. 36 is a perspective view of another surgical instrument.
Figure 37:
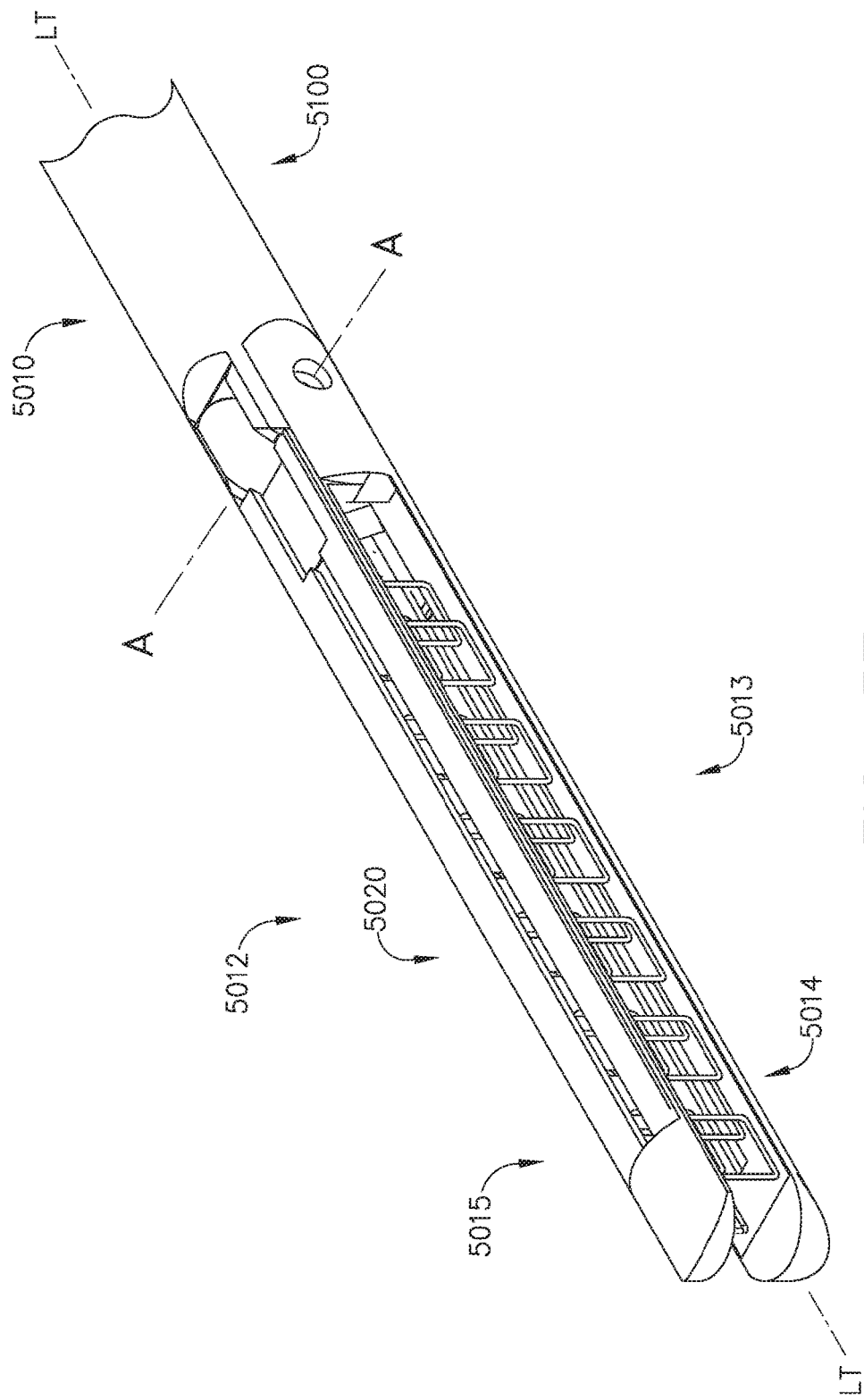
FIG. 37 is a partial perspective view of the end effector of the surgical instrument of FIG. 36 in a closed position.

In various arrangements, the end effector 4012 may be configured to be selectively articulated relative to the longitudinal tool axis LT-LT. Stated another way, the elongated channel assembly 4014 may be selectively articulatable or movable relative to the anvil assembly 4020. As described above, the elongated channel 4014 is pivotally coupled to the distal end 4302 of the outer tube 4300 by pivot pins 4310. Such attachment arrangement permits the end elongated channel assembly 4014 to articulate in a first direction "FD" about the articulation and pivot axis A-A which is essentially the same direction that the anvil assembly 4020 moves in when the anvil assembly 4020 is moved from a closed position to an open position (the anvil opening direction "OD"). Such arrangement further facilitates articulation or movement in a second articulation direction "SD" that is essentially the same as the direction that the anvil assembly 4020 moves from an open position to a closed position (the anvil closing direction "CD"). To facilitate such movement of the elongated channel assembly 4014 relative to the anvil assembly 4020, a reciprocatable articulation rod 4150 is employed. The articulation rod 4150 may also be referred to herein as the "first jaw actuator bar". More specifically and with reference to FIG. 29, the articulation rod 4150 is sized to be movably received with the outer tube 4300 and has a distal end 4152 that is pivotally pinned to a pair of articulation links 4160. The articulation links 4160 are pivotally pinned to the proximal portion of the elongated channel 4014 by an articulation pin 4161. As can be seen in FIG. 34, a proximal end 4154 of the articulation rod 4150 has an articulation rack 4156 formed thereon that drivingly interfaces with an articulation control system 200 of the type described hereinabove. As indicated above, the articulation control system 200 may also be referred to herein as the "first jaw closure system". Ratcheting rotation of the actuator 210 of the articulation transmission 200 causes articulation of the elongated channel assembly 4014 in the first or second directions relative to the anvil assembly 4020. FIGS. 28, 30, 31 and 31 illustrate the elongated channel assembly 4014 in an unarticulated position. When the drive gear 240 on the articulation body 220 of the articulation transmission 200 is rotated to thereby push the articulation rod 4150 in the distal direction "DD", the elongated channel assembly 4014 will move in the first articulation direction "FD" relative to the anvil assembly 4020 as shown in FIG. 33. When the drive gear 240 on the articulation body 220 of the articulation transmission 200 has been rotated to thereby pull the articulation rod 112 in the proximal direction "PD", the elongated channel assembly 4014 will pivot in a second direction "SD" relative to the anvil assembly 4020. The second direction "SD" is the same as the closure direction "CD". See FIG. 33.

Figure 27:
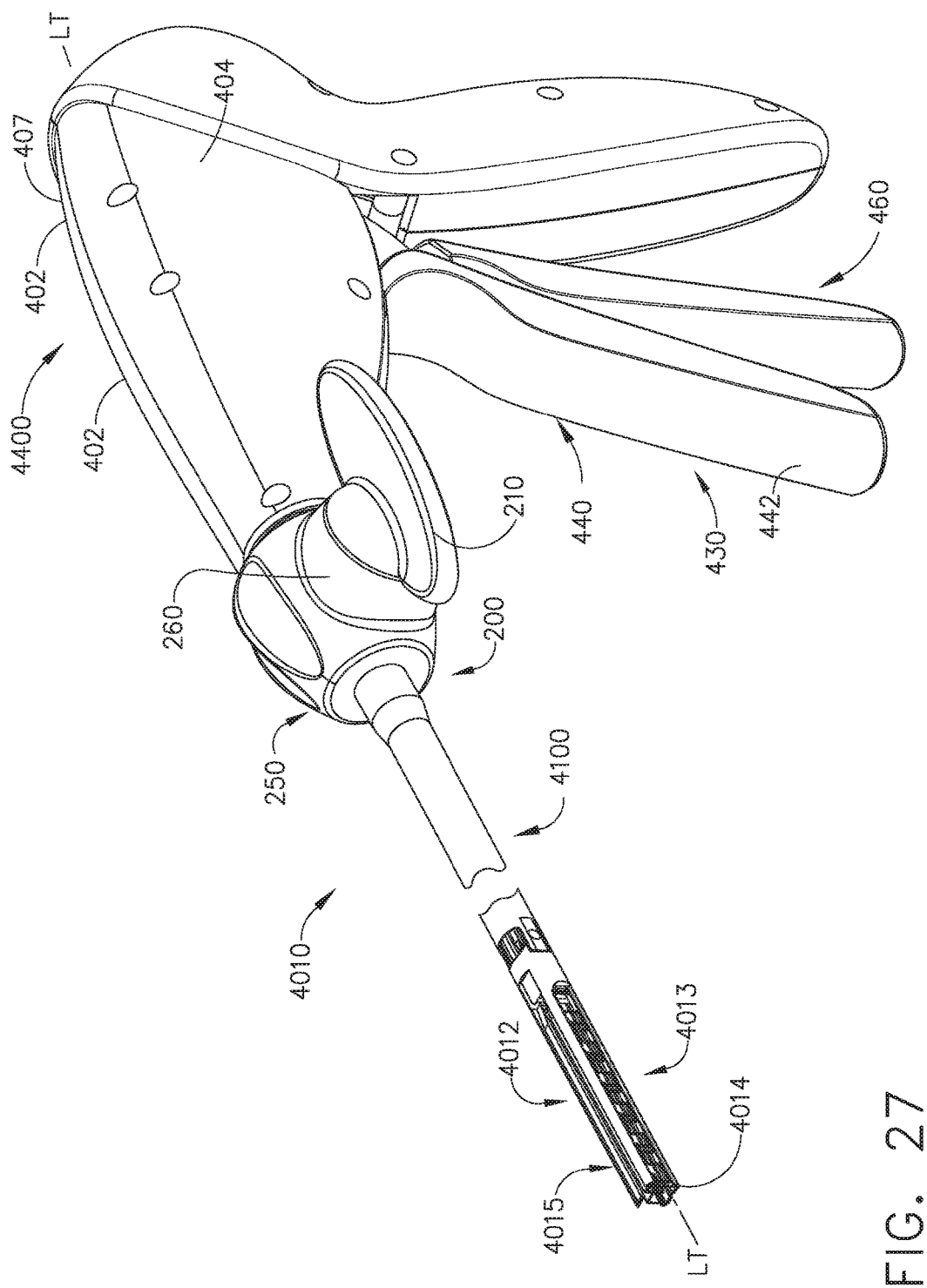
FIG. 27 is a perspective view of another surgical instrument.

The surgical instrument 4010 as illustrated in FIG. 27 may further include an firing system of the type described herein and/or in U.S. Patent Application Publication No. US 2012/0074200 A1 that may be controlled by actuating trigger 460. Referring to FIG. 34, a firing rack 500 is coupled to a firing rod 530 that is attached to the proximal end of a knife bar assembly 4600. In various forms, the knife bar assembly 4600 includes a distal knife bar portion 4602 that includes an upper knife bar 4604 and a lower knife bar 4606 that are attached to an I-beam cutting head 4610. The upper knife bar 4604 and the lower knife bar 4606 are configured to flex as the end effector 4012 is articulated. As can be seen in FIG. 29, for example, the I-beam cutting head 4610 includes a vertically oriented body portion 4612 that has a bottom foot 4614 and an upper tab 4616 formed thereon. A tissue cutting edge 4620 is formed on the vertically oriented body portion 4612.

Still referring to FIG. 29, the vertically oriented body portion 4612 extends through a longitudinally extending slot 4704 in the elongated channel 4014 and the longitudinally extending slot 4026 in the distal anvil portion 4024. The distal anvil portion 4024 further has a trough 4025 formed in the upper surface for slidably receiving the upper tab 4616 therein. The distal end of the upper tab 6616 may be sloped to interface with sloped surfaces 4027 formed on the anvil arms 4024 of the distal anvil portion 4022. The flexible firing bars 4604, 4606 extend through the elongated shaft assembly 4100 to be coupled to a distal end portion 532 of a firing rod 530 by a coupler member 650. As was discussed above, actuation of the trigger 460 will result in the axial advancement of the firing rod 530 within the elongated shaft assembly 4100 to apply firing and retraction motions to the knife bar assembly 4600.

Operation of the surgical instrument 4010 will now be described. To initiate the closure process, a first stroke is applied to the trigger assembly 430. That is, the trigger assembly 430 is initially pivoted toward the pistol grip 406. Such pivoting action serves to drive the closure carriage in the distal direction "DD". Such distal movement of the closure carriage also axially advances the anvil closure rod 4112 in the distal direction "DD". As the anvil closure rod 4112 moves distally, the closure link 4120 moves the anvil pin slide 4122 distally. As the anvil pin slide 4122 moves distally, the anvil assembly 4020 is pivoted to the closed position by virtue of the camming interaction of the anvil pin 4034 within the slots 4208, 4126. See FIG. 31. In the various manners discussed herein, if the surgeon desires to simply grasp and manipulate tissue prior to clamping it between the anvil assembly 4020 and the surgical staple cartridge 30, the trigger assembly 430 may be pivoted to open and close the anvil assembly 4020 without fully pivoting the trigger assembly 430 to the fully closed position. Once the trigger assembly 430 has been initially fully compressed into the closed position, the anvil assembly 4020 will be retained in the locked or clamped position by the closure locking assembly which prevents the proximal movement of the closure carriage as was discussed above. To drive the knife bar assembly 4600 distally through the tissue clamped in the end effector 4012, the surgeon again pivots the primary trigger 440 toward the pistol grip 406 of the housing assembly 400. As the primary trigger 440 is pivoted, the firing rack 500, the firing rod 530, and the knife bar assembly 4600 are driven in the distal direction "DD". As the knife bar assembly 4600 is driven in the distal direction, the cutting head 4610 also moves distally. As the cutting head 4610 moves distally, the sloped surface on the upper tab 4616 travels up the sloped surfaces 4027 on the distal anvil portion 4022 moving the floating distal anvil portion 4022 in the down direction "D". As the distal anvil portion 4022 is driven downwardly towards the clamped tissue and the staple cartridge 30, the clamping or crushing action causes the staples to be formed against the underside of the distal anvil portion 4022. Thus, as the cutting head 4610 is driven distally through the end effector 4012, the tissue cutting surface 4620 thereon severs the clamped tissue while forming the staples in the staple cartridge which are situation on both sides of the cut tissue. After the knife bar assembly 4600 has been driven through the tissue clamped in the end effector 4012, the surgeon then releases the primary trigger 440 to thereby permit the primary trigger 440 to pivot to its unactuated position under the bias of the firing spring. As the primary trigger 440 pivots back to the starting position, the firing rack 500, firing rod 530, and knife bar assembly 4600 are drawn proximally back to their respective starting positions. The end effector 4012 remains in its clamped position as shown in FIG. 31. The anvil assembly 4020 may then be unlocked and moved to the open position in the manner discussed above.

As was discussed in detail above, by having the articulation axis also be the axis about which the anvil pivots, the surgeon has a much more reliable frame of reference regarding the location of the pivot axis when viewing the endocutter's anvil through the camera. Stated another way, when using the end effector arrangement of the surgical instrument 10 the surgeon can determine where the elongated channel is going to pivot relative to the elongated shaft by viewing where the anvil is pivotally mounted to the elongated channel.

The surgical instrument 4010 also employs separate control systems for moving the end effector jaws 4013 and 4015. For example, the clinician may elect to move or articulate the lower jaw 4013 (elongated channel 14) about the pivot axis A-A toward or way from the upper jaw 4015 without actuating the upper jaw 4015 (anvil assembly 4020). This may be accomplished by actuating the articulation control system 200 without actuating the closure system 4110. Thus, the elongated channel 4014 may be selectively pivoted about the pivot axis A-A while the anvil assembly 4020 is open or closed. Similarly, the anvil assembly 4020 may be actuated or moved without moving the elongated channel 4014 by actuating the closure system 4110 without actuating the articulation control system 200. Such unique and novel arrangement provides the clinician with more flexibility when positioning the end effector jaws within the patient.

FIGS. 36-42 depict another surgical instrument 5010 that is capable of practicing several unique benefits of the present invention. The surgical instrument 5010 is designed to manipulate and/or actuate various forms and sizes of end effectors 5012 that are operably attached to an elongated shaft assembly 5100 of the surgical instrument. In the depicted embodiment, for example, the end effector 5012 comprises a surgical stapling device that has openable and closable jaws 5013 and 5015. More specifically, the end effector 5012 includes an elongated channel 5014 that forms a lower jaw 5013 of the end effector 5012. See FIG. 37. In the illustrated arrangement, the elongated channel 5014 is configured to operably support a staple cartridge 30 of the type and construction described herein. For example, the surgical staple cartridge includes a cartridge body 31 that operably supports a plurality of unformed surgical staples 32 therein. The elongated channel 5014 also movably supports an anvil 3020 that functions as an upper jaw 5015 of the end effector 5012.

In various implementations, the end effector 5012 is configured to be coupled to an elongated shaft assembly 5100 that protrudes from a handle assembly or housing 5400. See FIG. 36. The handle assembly 5400 may be similar to one of the handle assemblies disclosed herein and/or in U.S. Patent Application Publication No. US 2012/0074200 A1 except for the differences discussed below.

Figure 38:
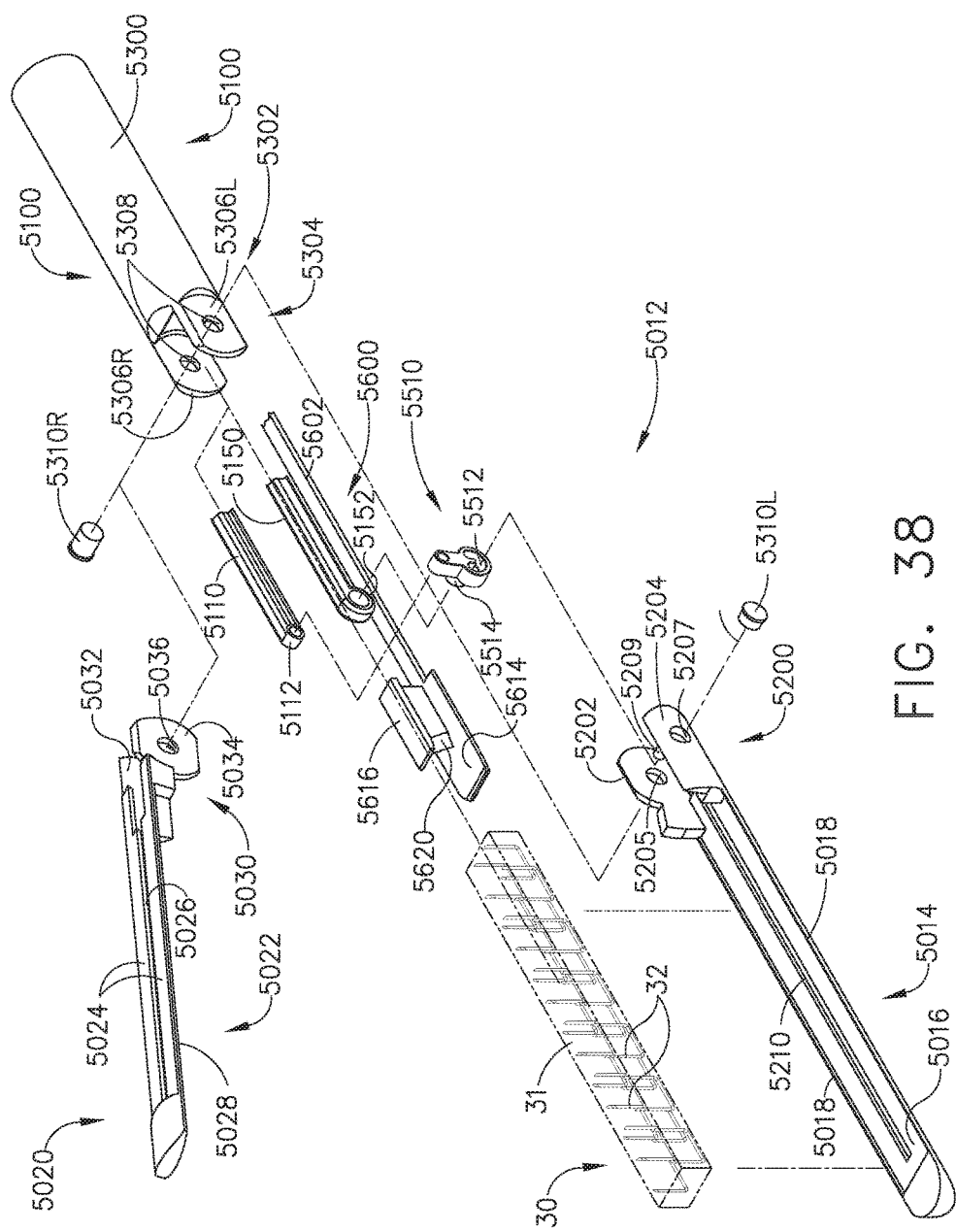
FIG. 38 is a distal exploded perspective assembly view of the end effector and elongated shaft assembly of FIGS. 36 and 37.

Referring to FIG. 38, the elongated channel 5014 may comprise an elongated trough 5016 that is configured to removably support a surgical staple cartridge 30 thereon. In various implementations, for example, the elongated channel 5014 may be fabricated from, for example, 300 & 400 Series, 17-4 & 17-7 stainless steel, titanium, etc. and be formed with spaced side walls 5018. The body 31 of staple cartridge 30 is sized to be removably supported within the elongated channel 5014 as shown such that each staple 32 therein is aligned with corresponding staple forming pockets in the anvil 5020 when the anvil 5020 is driven into forming contact with the staple cartridge 30. The elongated channel 5014 may further include a proximal end 5200 that includes a pair of spaced side walls 5202 and 5204. Each side wall 5202, 5204 has a hole 5205, 5207, respectively therethrough for attachment to the elongated shaft assembly 5100 by corresponding pivot pins 5310R and 5310L.

In at least one implementation, for example, the end effector 5012 is configured to be articulated relative to the elongated shaft assembly 5100 about an articulation and pivot axis A-A about which the anvil assembly 5020 is pivoted relative to the elongated channel 5014. The elongated shaft assembly 5100 defines a longitudinal tool axis LT-LT. The articulation and pivot axis A-A is transverse to the longitudinal tool axis LT-LT. The elongated shaft assembly 5100 comprises a hollow outer shaft 5300 and serves to function as the shaft spine of the elongated shaft assembly 5100. The proximal end of the elongated shaft assembly 5100 may be rotatably supported by the handle assembly 5400 so that the clinician may selectively rotate the elongated shaft assembly 5100 and the end effector 5012 attached thereto about the longitudinal tool axis LT-LT. For example, the proximal end of the elongated shaft assembly 5100 may be operably coupled to a nozzle assembly 5250 that is rotatably supported on the handle assembly 5400. Rotation of nozzle assembly 5250 relative to the handle assembly 5400 (represented by arrow "R") will result in rotation of the elongated shaft assembly 5100 as well as the end effector 5012 coupled thereto. See FIG. 36.

Referring again to FIG. 38, the distal end 5302 of the outer shaft 5300 is formed with a clevis arrangement 5304 that comprises a pair of spaced attachment tabs 5306R and 5306L. Each attachment tab 5306R, 5306L has a mounting hole 5308R, 5308L, respectively therein that is adapted to receive a corresponding pivot pin 5310R, 5310L, respectively. Thus, the elongated channel 5014 is selectively pivotable or articulatable about the pivot axis A-A relative to the elongated shaft assembly 5100. The anvil assembly 5020 includes a distal anvil portion 5022 and a proximal anvil mounting portion 5030. The distal anvil portion 5022 may, for the most part, be substantially coextensive with the portion of the elongated channel 5014 that supports the staple cartridge 30 and be fabricated from, for example, 300 & 400 Series, 17-4 & 17-7 stainless steel, titanium, etc. The distal anvil portion 5022 comprises two spaced apart anvil portions 5024 that protrude distally from the anvil mounting portion 5030 to define an elongated slot 5026 therebetween. Each of the spaced-apart anvil portions 5024 has a staple forming undersurface, generally labeled as 5028 that has a plurality of staple forming pockets (not shown) formed therein. The anvil mounting portion 5030 includes a right mounting wall 5032 and a left mounting wall 5034. Each mounting wall 5032, 5034 has a mounting hole 5036 extending therethrough that are adapted to pivotally receive therein the corresponding pivot pins 5310R, 5310L. Such arrangement serves to pivotally mount the anvil assembly 5020 to the elongated channel 5014 for selective pivotal travel about pivot axis A-A between an open position and a closed position.

Figure 41:
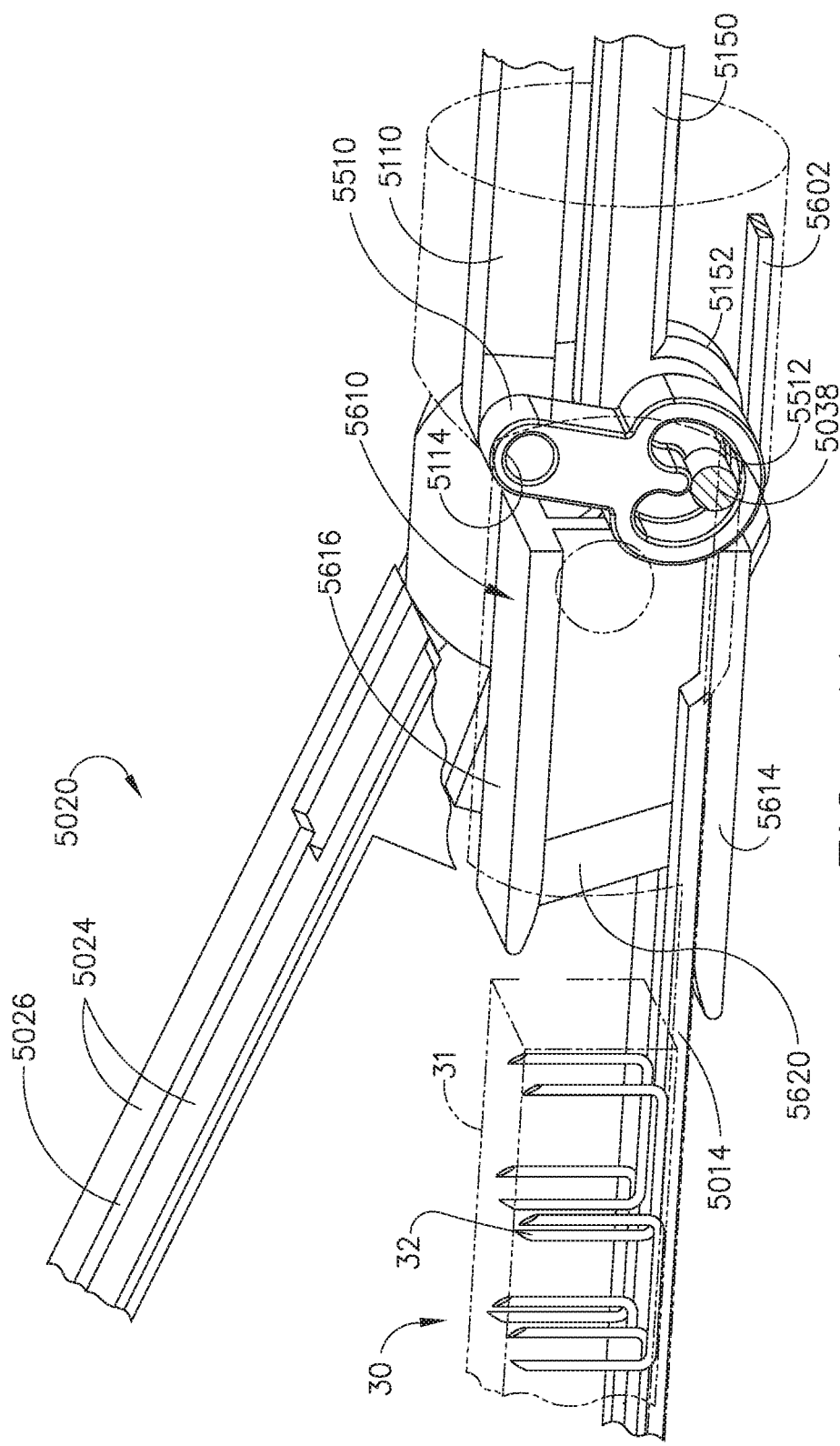
FIG. 41 is a partial perspective view of portions of the end effector of FIGS. 36-40 with the anvil assembly thereof in an open position.

The anvil assembly 5020 is selectively movable between open and closed positions by means of an anvil bar 5110. The anvil bar 5110 may be coupled to a closure carriage of the type disclosed herein and/or in U.S. Patent Application Publication No. US 2012/0074200 A1 such that actuation of a trigger mounted on the handle assembly will result in the axial movement of the anvil bar 5110 within elongated shaft assembly 5100. The anvil bar 5110 is configured for movable attachment to an actuator cam 5510 that is pivotally journaled on an anvil pin 5038 that protrudes inwardly from the left mounting wall 5034 of the anvil mounting portion 5030. See FIGS. 39 and 40. As can be seen in FIG. 41, for example, the anvil pin 5034 is rotatably received within a corresponding anvil cam slot 5512 within the actuator cam 5510. The distal end 5112 of the anvil bar 5110 is pivotally pinned to the actuator cam 5510 by a pivot pin 5114 defines an anvil actuation axis B-B. See FIG. 40.

Figure 39:
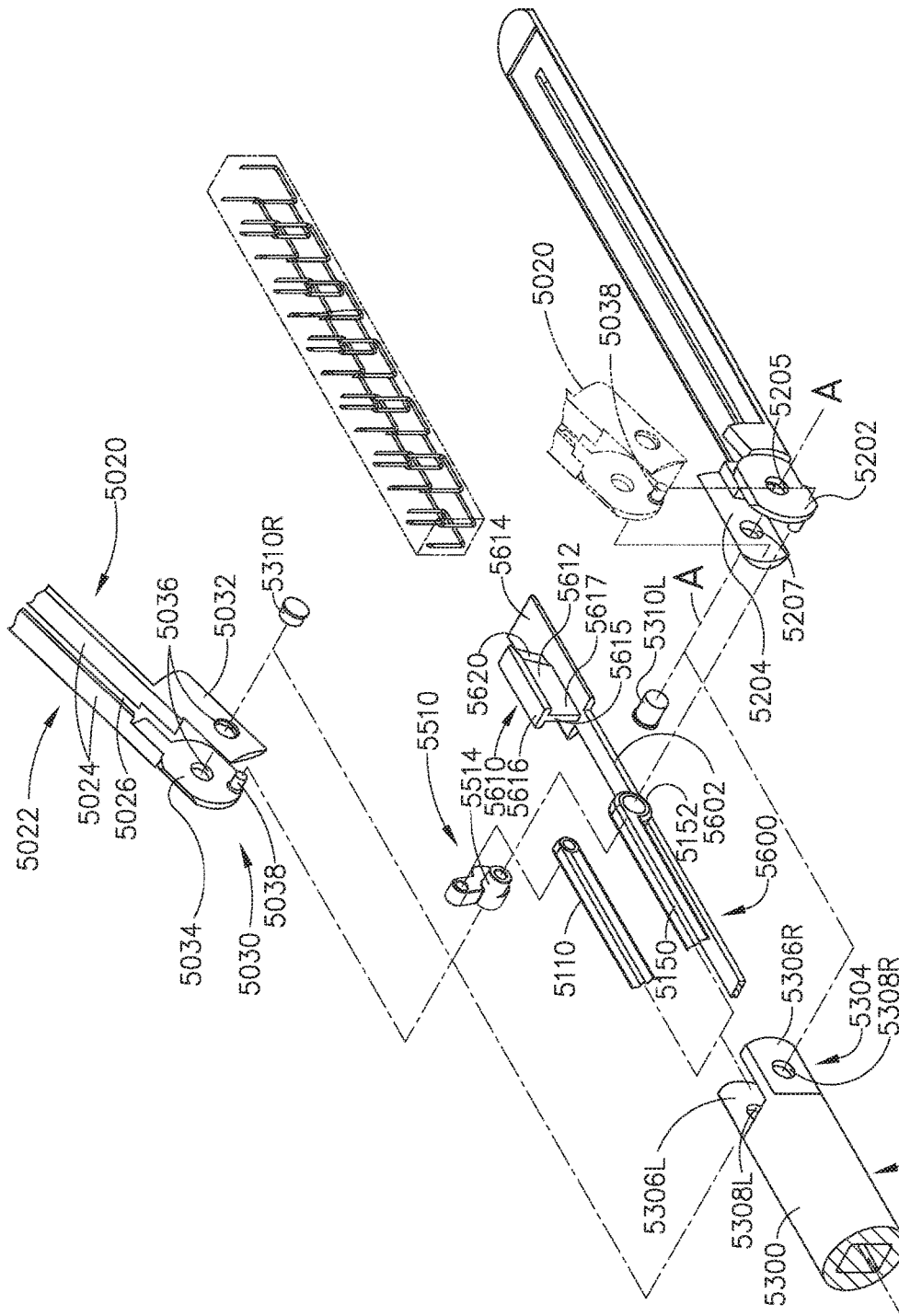
FIG. 39 is a proximal exploded perspective assembly view of the end effector and elongated shaft assembly of FIGS. 36-38.
Figure 40:
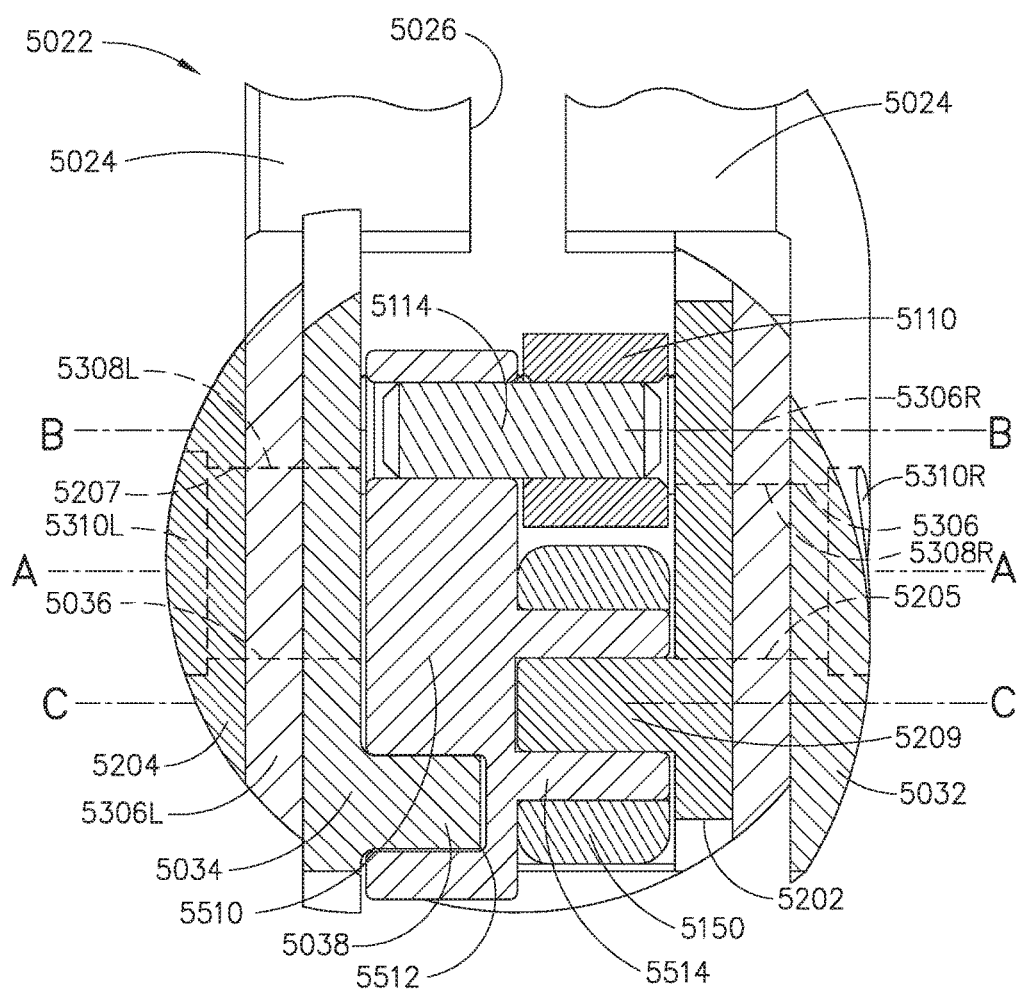
FIG. 40 is a cross-sectional end view of a portion of the end effector of FIGS. 36-39.

The end effector 5012 may also be articulatable or pivotable relative to the elongated shaft assembly 5100 about the pivot axis A-A by an articulation system of the type described herein and/or in U.S. Patent Application Publication No. US 2012/0074200 A1. The articulation system may be employed to axially actuate an articulation bar 5150 that is pivotally coupled to the actuator cam 5510. Referring to FIGS. 38 and 39 for example, the distal end 5152 of the articulation bar 5150 pin is rotatably mounted on a pin hub 5514 protruding from the actuator cam 5510. The pin hub 5514 has a cavity 5516 therein for rotatably receiving an inwardly protruding channel pin 5209 for selective rotation relative thereto about a channel axis C-C. See FIG. 40.

Figure 42:
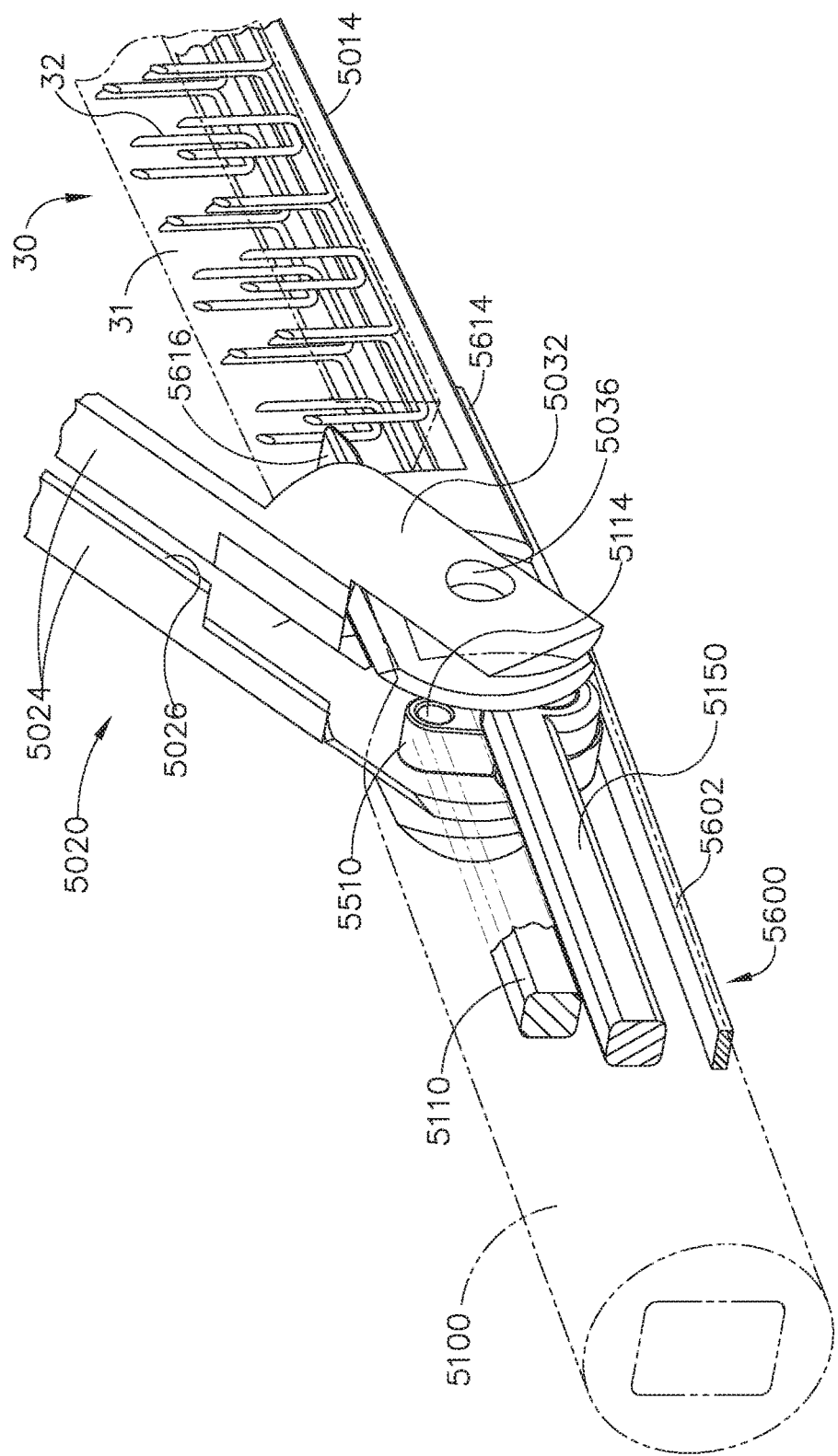
FIG. 42 is another partial perspective view of portions of the end effector of FIGS. 36-41 with the anvil assembly thereof in an open position.

FIGS. 41 and 42 illustrate the position of the end effector 5012 in a neutral or unarticulated position with the anvil assembly 5020 thereof in an open position. When the user desires to close the anvil assembly 5020, the anvil rod 5110 is advanced distally in the distal direction "DD". Movement of the anvil rod 5110 in the distal direction causes the actuator cam 5510 to interact with the anvil pin 5038 to pivot the anvil assembly 5020 to a closed position about the pivot axis A-A. When the clinician desires to articulate the end effector 5012, the articulation rod 5150 is moved axially within the elongated shaft 5100. Movement of the articulation rod in the distal direction "DD" will, for example, cause the end effector 5012 to pivot in a first direction "FD" that is essentially the same direction in which the anvil assembly 5020 is moved from a closed position to an open position (referred to herein as the opening direction "OD"). Movement of the articulation rod in a proximal direction "PD" will cause the end effector 5012 to pivot in a second direction "SD" about the pivot axis A-A which is essentially the same direction in which the anvil assembly 5020 moves when moving from an open position to a closed position (referred to herein as the closing direction "CD").

As can also be seen in FIGS. 38 and 39, the surgical instrument 5010 further includes a knife bar assembly 5600 that can be attached to the firing bar and firing rack arrangement disclosed herein and/or in U.S. Patent Application Publication US 2012/0074200 A1 such that it can be controlled by actuating the secondary trigger in the various manners described herein 460. The knife bar assembly 5600 may comprise a knife bar 5602 that may flex as the end effector 5012 is articulated, while remaining sufficiently rigid to be driven distally through the shaft assembly 5100. In the depicted embodiment, the knife bar 5602 is attached to a cutting head 5610. In the depicted configuration, the cutting head 5610 includes a vertically oriented body portion 5612 that has an upper portion 5615 and a lower portion 5617. A bottom foot 5614 is formed on or attached to the lower portion 5617. Similarly, an upper tab 5616 is formed on or otherwise attached to the upper portion 5615 of the vertically oriented body portion 5612. In addition, as can be seen in FIGS. 38 and 39, the vertically oriented body portion 5612 further includes a tissue cutting edge 5620. The vertically oriented body portion 5612 extends through a longitudinally extending slot 5210 in the elongated channel 5014 and the longitudinally extending slot 5026 in the anvil assembly 5020. Thus, when the cutting head 5610 is distally advanced, the upper tab portions 5616 ride on the anvil arms 5024. Likewise the bottom foot 5614 protrudes through a lower opening in the elongated channel 5014 such that it rides below the elongated channel 5014 as the cutting head 5610 is advanced distally. As the cutting head 5610 is advanced distally, the cutting edge 5620 thereon severs the tissue clamped in the end effector 5012. The surgical staple cartridge 30 is crushed between the anvil assembly 5020 and the elongated channel 5014 thereby causing the staples 32 supported therein to be formed on both sides of the tissue cut line as they are brought into contact with the staple forming underside of the anvil assembly 5020. After the cutting head 5610 has been advanced to the distal end of the end effector 5012, the user retracts the cutting head 5610 to the starting position in the manner discussed herein and the trigger is actuated to open the anvil assembly 5020 to release the staple cartridge and stapled tissue.

As was discussed in detail above, by having the articulation axis also be the axis about which the anvil pivots, the surgeon has a much more reliable frame of reference regarding the location of the pivot axis when viewing the endocutter's anvil through the camera. Stated another way, when using the end effector arrangement of the surgical instrument 10 the surgeon can determine where the elongated channel is going to pivot relative to the elongated shaft by viewing where the anvil is pivotally mounted to the elongated channel.

In various implementations, when employing surgical end effectors of the types disclosed herein, the end effector is configured to be coupled to an elongated shaft assembly that protrudes from a housing. The housing may comprise a hand-manipulatable handle arrangement or it may, for example, comprise a portion of a robotic system or other automated control system arrangement. The end effector and elongated shaft may typically be introduced to the surgical site within the patient through a trocar tube or working channel in another form of access instrument. In at least some surgical procedures, it is desirable and indeed, even sometimes necessary, to limit the size of trocar tubes/access tubes that are employed. This limits the size of end effector and elongated shaft arrangements that may be employed. For example, if a trocar is employed that has a 5 mm diameter opening through the trocar tube, the end effector as well as the elongated shaft must be sized to enable them to be passed through that opening. When employing cutting and stapling end effectors that essentially comprise jaws that are moveable between open and closed positions, the clinician passes the end effector through the trocar when the jaws are in their closed position. Typically when the jaws are in their fully closed position, the end effector is in its smallest cross-sectional shape to facilitate such insertion through the tube or access opening. Once the end effector has been passed through the tube or opening, the clinician may then open the jaws to grasp and manipulate the target tissue. Once the target tissue is properly positioned between the jaws, the clinician may cause the jaws to be closed onto or clamped onto the tissue in preparation for firing the instrument (i.e., causing the instrument to cut and staple the tissue). Thus, the size of the end effector that may be employed to complete a surgical procedure may necessarily be limited by the size of access opening or access tube that it must pass through. Such limitations can become problematic, however, in instances wherein the jaws cannot sufficiently accommodate the target tissue due to the thickness of the target tissue to be cut and stapled. In some applications, for example, the tissue may be over compressed by the jaws if the tissue is thicker than anticipated.

Over the years, a variety of end effector arrangements have been developed to effectively accommodate various tissue thicknesses. For example, U.S. Pat. No. 7,665,647, entitled SURGICAL CUTTING AND STAPLING DEVICE WITH CLOSURE APPARATUS FOR LIMITING MAXIMUM TISSUE COMPRESSION, issued Feb. 23, 2010, the entire disclosure of which is hereby incorporated by reference herein discloses cutting head configurations referred to as "E-Beam" arrangements that are configured to limit an amount of compression applied to the tissue as the E-beam is fired down the end effector. While effective, there is a need for an end effector that has a fully closed height that is smaller than a closed "operating height" or "stapling height" when stapling tissue.

Figure 43:
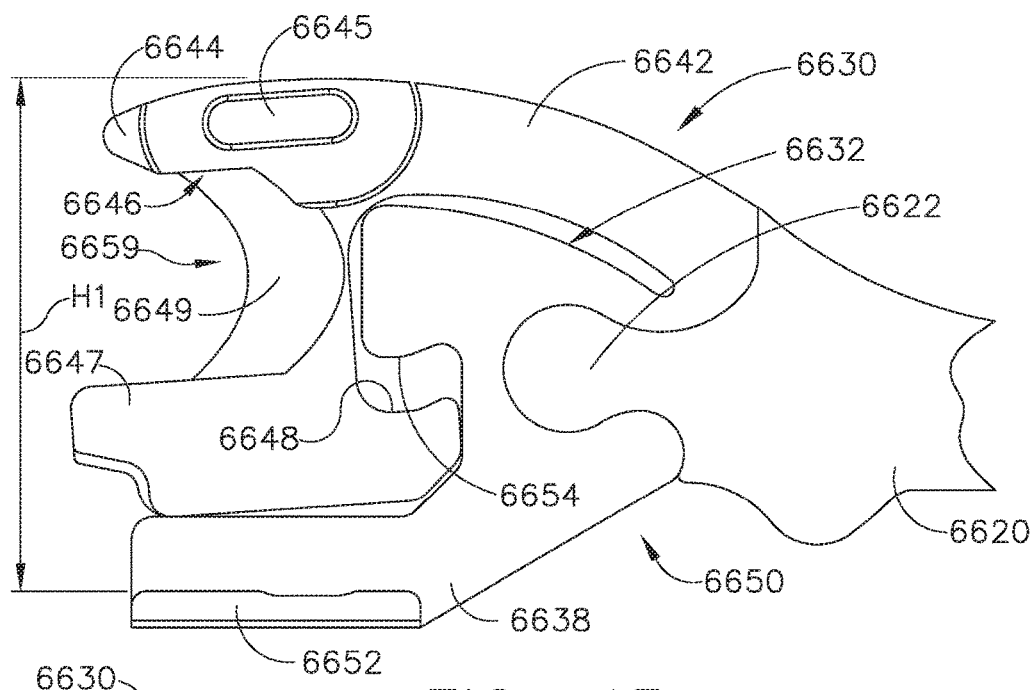
FIG. 43 is a partial side view of a cutting beam head in its uncompressed state.
Figure 44:
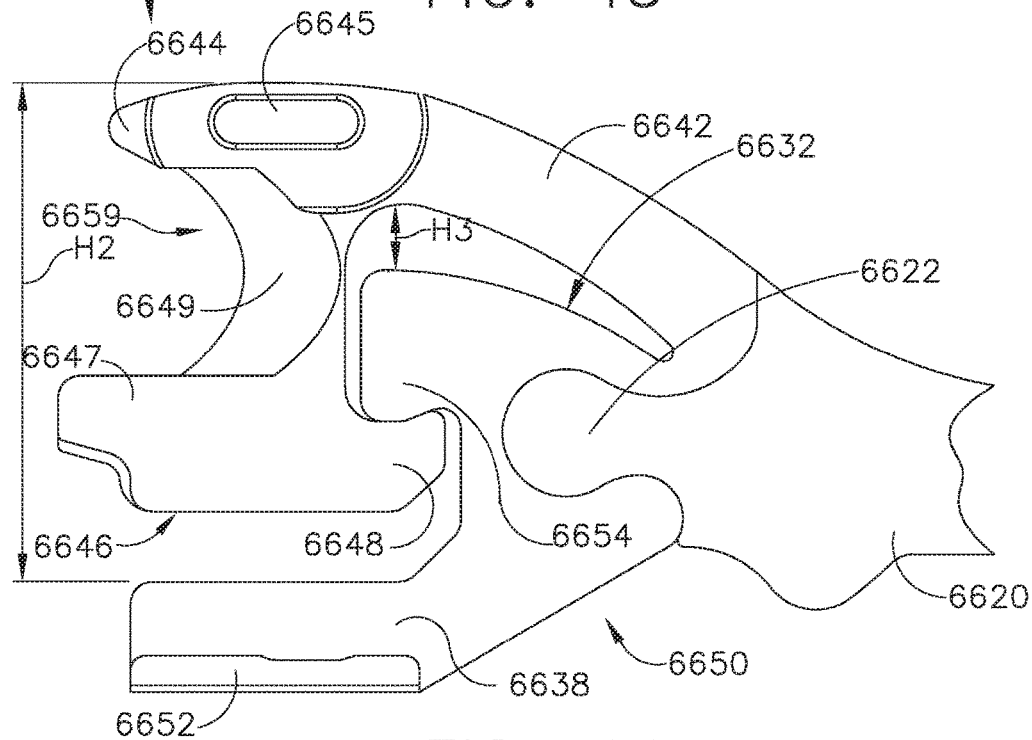
FIG. 44 is another partial side view of the cutting beam head of FIG. 43 in its maximum compressed state.

FIGS. 43-46 illustrate a cutting beam assembly 6610 that may be employed with various end effectors 6012 of the type, for example, disclosed herein as well as those disclosed in U.S. Pat. No. 7,665,647. As can be seen in FIGS. 43 and 44, the cutting beam assembly 6610 may include a firing bar 6620 that has a proximal portion 6622 that is attached to a distal cutting beam head 6630 that translates within a staple cartridge 6670. See FIGS. 45 and 46. The distal cutting beam head 6630 may also be referred to as a "firing member". The staple cartridge 6670 may comprise a staple cartridge of the type disclosed in U.S. Pat. No. 7,665,647 and be configured to be operably supported in the elongated channel 6014 of the end effector 6012. As discussed therein, the staple cartridge 6670 includes a series of staple drivers 6642 that operably support the surgical staples 6674 thereon. The drivers 6672 are driven upwardly toward the anvil 6020 as a wedge sled 6676 is advanced distally through the staple cartridge 6670.

Referring to FIGS. 43 and 44, the distal cutting beam head 6630 includes a body portion 6632 that is attached to the proximal portion 6622 of the firing bar 6620. The firing bar 6622 may be actuated by any of the firing arrangements disclosed herein including those firing arrangements disclosed in U.S. Pat. No. 7,665,647. As can be seen in those Figures, the body portion includes an upper portion 6640 and a lower portion 6650. The upper portion 6640 includes a flexible extension arm 6642 that protrudes from the lower portion 6650. Essentially, the extension arm 6642 comprises a cantilever-type beam arrangement that includes a distally protruding nose 6644 that includes upper pins or tabs 6645 that protrude laterally therefrom. The upper portion 6640 further includes a lower tab portion 6646 that includes a distally-protruding lower nose portion 6647 and a proximally-protruding hook, bumper, or catch formation 6648 that is designed to engage a complementary body hook 6654 formed on the lower portion 6650 as shown in FIG. 44. As can be most particularly seen in FIGS. 43 and 44, a cutting surface 6649 is provided on the movable upper portion 6640 and is oriented such that it located proximal to the end of the upper nose 6644 and the end of the lower nose portion 6647 such that a tissue-capturing pocket 6659 is established between the upper nose 6644 and the lower nose 6647. Such pocket 6659 enables tissue to be captured therein just distal of cutting surface 6649. As can be appreciated from reference to FIGS. 43 and 44, the cutting surface 6649 as well as the upper nose portion 6644 and upper tabs 6645 move as a unit (e.g., they move together) relative to the lower portion 6650 of the cutting beam head 6630. As will be discussed in further detail below, such arrangement enables the cutting beam head 6630 to assume a compressed state that facilitates passage of the cutting beam head 6630 through, for example, an access opening or a trocar port that has a somewhat limited cross-sectional area, while still being able to accommodate various thicknesses of tissue when the end effector has exited though the opening and has been clamped onto the tissue in preparation for firing.

Figure 45:
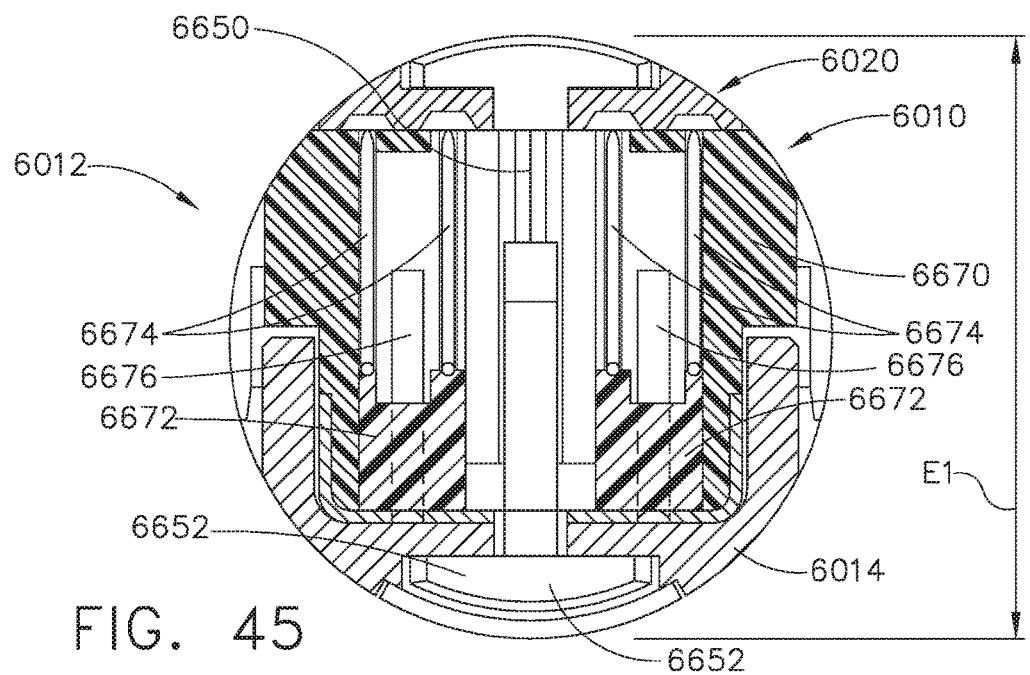
FIG. 45 is a cross-sectional end view of an end effector and a cutting beam head of FIGS. 43 and 44 in its maximum compressed state.
Figure 46:
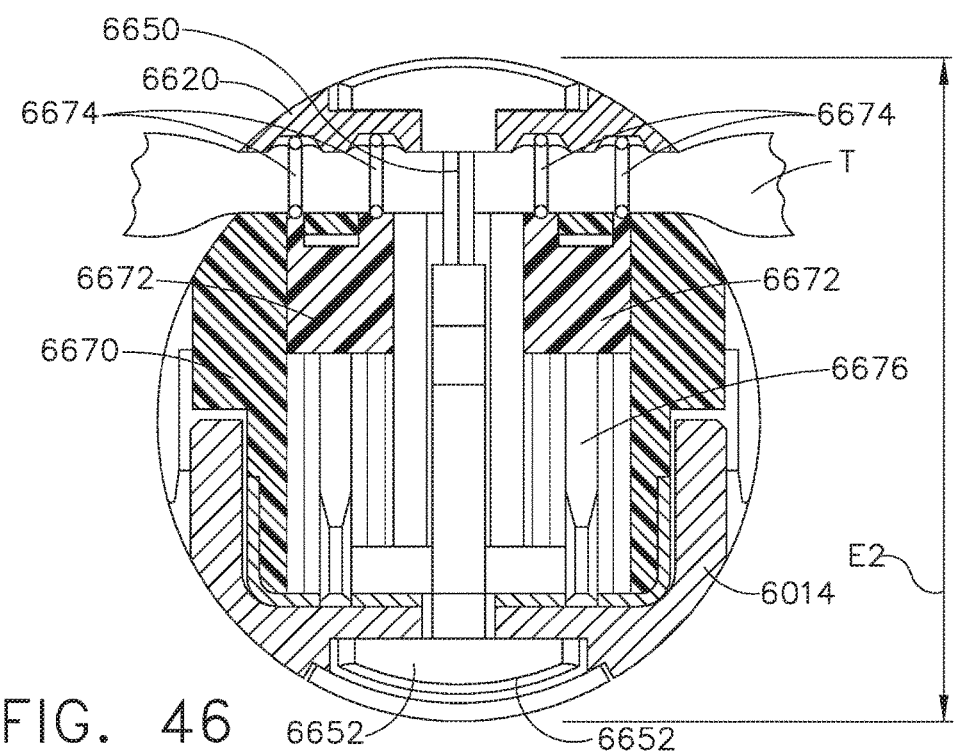
FIG. 46 is another cross-sectional view of the end effector and cutting beam head of FIG. 45 after the end effector has cut and stapled tissue.
Figure 47:
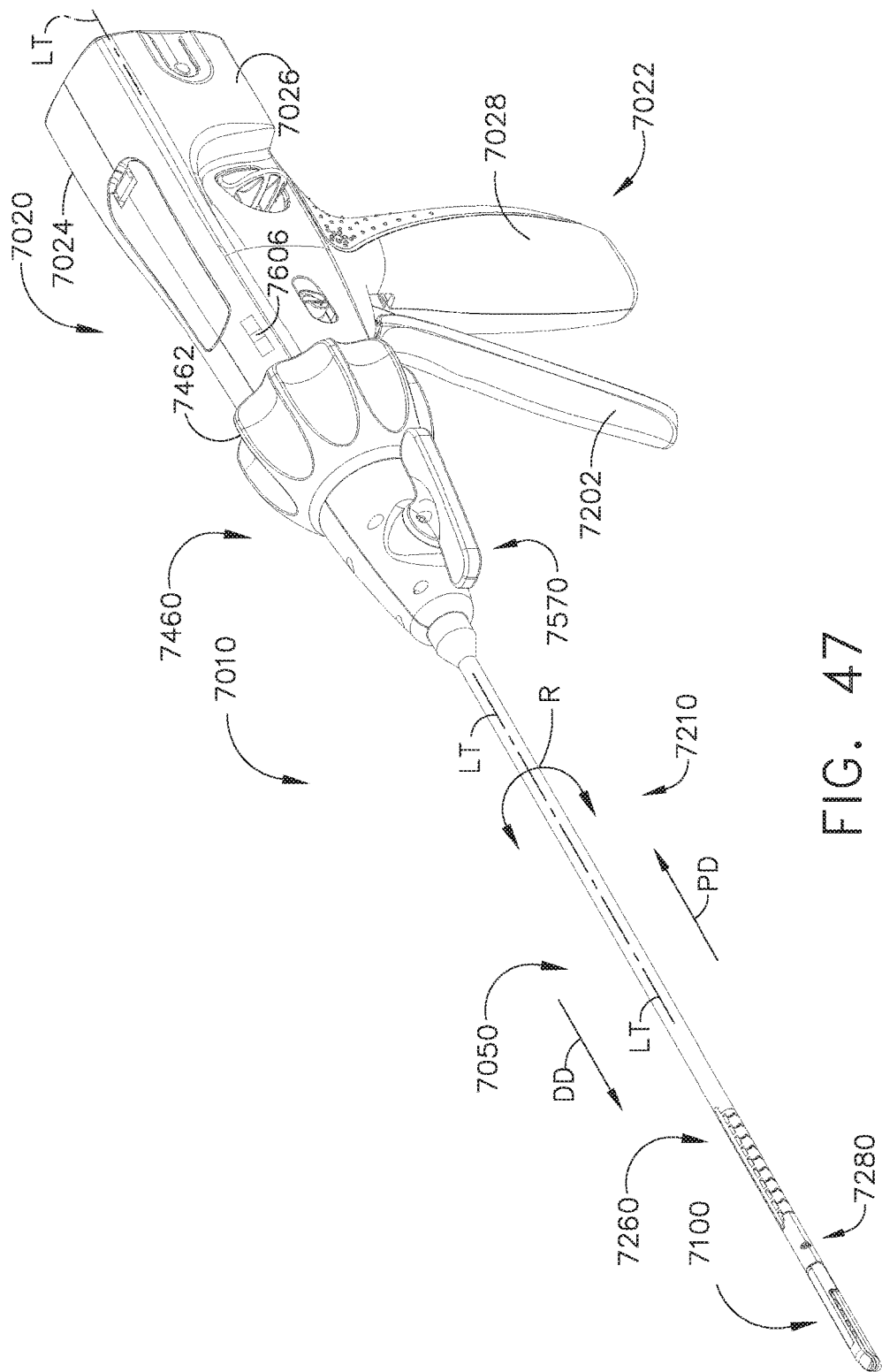
FIG. 47 is a perspective view of another surgical instrument.

The lower portion 6650 of the cutting beam head 6630 further includes lower foot tabs 6652 that protrude laterally from the lower portion 6650. As can be seen in FIGS. 45 and 46, the elongated channel 6014 includes an elongated slot 6016 that corresponds with an elongated slot 6678 in the staple cartridge 6670 for accommodating the body portion 6632 of the cutting beam head 6630. The elongated channel further has a channel track 6018 that is configured to receive the lower foot tabs 6652. Likewise, the anvil assembly 6020 includes an elongated slot 6022 that accommodates the body portion 6632 and an upper anvil track 6024 that accommodates the upper tabs 6645 therein.

FIG. 43 illustrates the cutting beam head 6630 in its compressed state. The overall maximum height of the cutting beam head in this compressed state is represented by "H1". FIG. 44 illustrates the cutting beam head 6630 in its uncompressed maximum height state. The overall maximum height of the cutting beam head in this uncompressed state is represented by "H2". It will be understood that the overall height of the E-beam 6630 can vary between H1 and H2 depending upon the cutting beam head's compressed state. Referring now to FIG. 45, the end effector 6012 is illustrated in its most cross-sectionally compact state which may be referred to herein as its insertion state or position. The overall height (or diameter) of the end effector 6012 is represented in FIG. 45 by "E1". This would be the state, for example, in which the end effector 6012 might be inserted through an access opening or a trocar port. Once the end effector 6012 has been inserted through the opening or trocar port to the surgical site, the clinician may open and close the anvil assembly 6020 as needed to grasp and manipulate the target tissue T. Once the target tissue T has been captured between the anvil assembly 6020 and the staple cartridge 6670, the clinician may lock the anvil assembly 6020 in the closed position in the various manners disclosed herein or otherwise known. The unique and novel cutting beam head 6630 enables the over all height of the end effector 6012 to increase to accommodate various thicknesses of tissue and or different surgical staple cartridges that have different lengths/sizes of staples/fasteners. FIG. 46 illustrates the target tissue T after it has been "fully clamped" in the end effector 6012 and the end effector 6012 has been fired to cut and sever the tissue T. The overall height of the end effector 6012 is represented by "E2". Such cutting beam head arrangement is capable of assuming a compressed insertion height for insertion into the surgical site and then automatically reconfiguring to a firing height. Such reconfiguration is accomplished by the extension arm 6642 which acts as a spring and which is normally biased into its uncompressed state as illustrated in FIG. 44. Thus, the cutting beam head 6630 has a range of operating heights extending between H1 and H2. This range may be represented by "H3" and may be equal to the distance between the lower edge of the extension arm 6642 and the upper-most edge of the body hook portion 6636. See FIG. 44.

FIGS. 47-54 depict another surgical instrument 7010 that is capable of practicing several unique benefits of the present invention. The surgical instrument 7010 depicted in the FIG. 47 comprises a housing 7020 that consists of a handle 7022 that is configured to be grasped, manipulated and actuated by a clinician. The handle 7022 may comprise a pair of interconnectable housing segments 7024, 7026 that may be interconnected by screws, snap features, adhesive, etc. As the present Detailed Description proceeds, however, it will be understood that the various unique and novel arrangements of the various forms of shaft arrangements and end effector arrangements disclosed herein may also be effectively employed in connection with robotically-controlled surgical systems such as those robotic systems and arrangements disclosed in U.S. patent application Ser. No. 13/536, 323, entitled ROBOTICALLY-POWERED SURGICAL DEVICE WITH MANUALLY ACTUATABLE REVERSING SYSTEM, filed Jun. 28, 2012, now U.S. Pat. No. 9,408,606, the entire disclosure of which is has been herein incorporated by reference.

Figure 48:
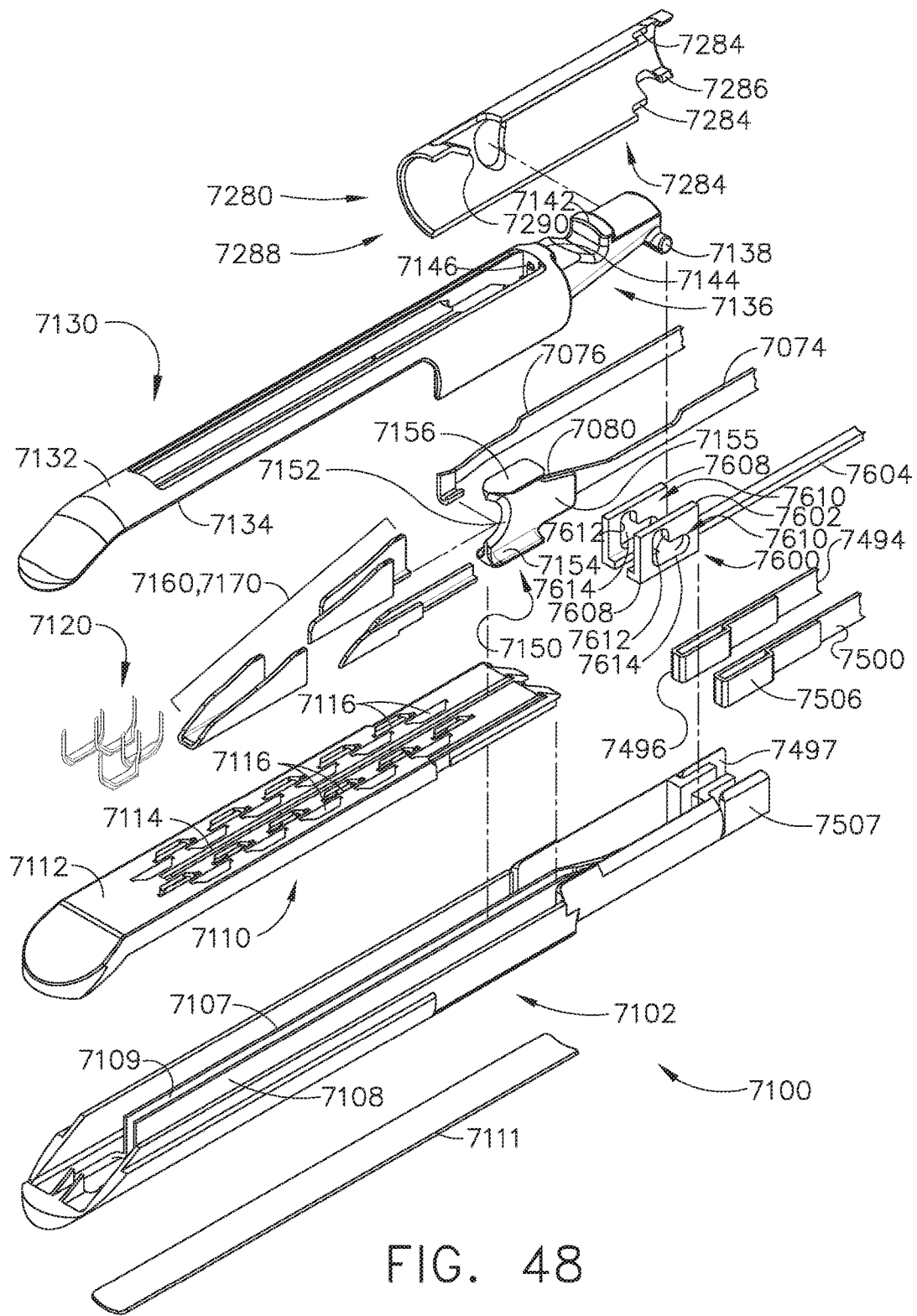
FIG. 48 is an exploded perspective view of another surgical end effector of the present invention.

As can be seen in FIG. 48, the surgical end effector 7100 may comprise an elongated channel 7102 that is configured to receive a surgical fastener cartridge 7110 therein. The surgical fastener cartridge 7110 may include a cartridge body 7112 that has a centrally disposed elongated slot 7114 therein. The cartridge body 7112 may further include rows of fastener pockets 7116 that are located on each side of the elongated slot 7114 and which are configured to support corresponding surgical fasteners 7120 therein. The elongated channel 7102 may further operably support a "firing member" in the form of a tissue-cutting member or knife assembly 7150. The knife assembly 7150 is configured to axially travel in the slot 7114 in the cartridge body 7112 when the cartridge body 7112 has been installed in the elongated channel 7102. The knife assembly 7150 may be configured with a tissue cutting edge 7152 that is centrally disposed between a lower foot 7154 and an upper foot or tab 7156. In a preferred arrangement, the knife assembly 7150 has the same construction and features as cutting head assembly 6610 described in detail above. As will be discussed in further detail below, the knife assembly 7150 is configured to be axially driven within the elongated channel 7102 and the surgical fastener cartridge 7110 in response to motions applied thereto by a firing drive system 7300.

As can also be seen in FIG. 48, the surgical end effector 7100 may further include an anvil assembly 7130 that is supported for movement relative to the elongated channel 7102. The anvil assembly 7130 may be movable relative to the surgical fastener cartridge 7110, for example, in response to "actuation motions" which may comprise, for example, closing and opening motions that are transferred thereto from a closure drive system 7200. In one arrangement, for example, the anvil assembly 7130 includes an anvil body portion 7132 that has a fastener forming surface 7134 formed on the underside thereof. The fastener forming surface 7134 may comprise a series of forming pockets (not shown) that correspond to the surgical fasteners 7120 supported in the surgical fastener cartridge 7110. As the legs of the surgical fasteners 7120 are driven into forming contact with the corresponding forming pockets in the anvil assembly 7130, they are formed into a desired tissue-retaining configuration. The anvil assembly 7130 may further includes an anvil mounting portion 7136 that has a pair of trunnions 7138 protruding therefrom that are received within corresponding trunnion slots 7610 formed in a U-shaped control insert 7602 that is movably supported in a proximal mounting portion 7104 of the elongated channel 7102. In various arrangements, the surgical fasteners 7120 are driven out of their respective fastener pockets 7116 in the surgical fastener cartridge 7110 by corresponding sled assemblies 7160 and 7170 that are movably supported within the elongated channel 7102 and are movable in response to firing motions applied thereto by the firing drive system 7300.

Figure 49:
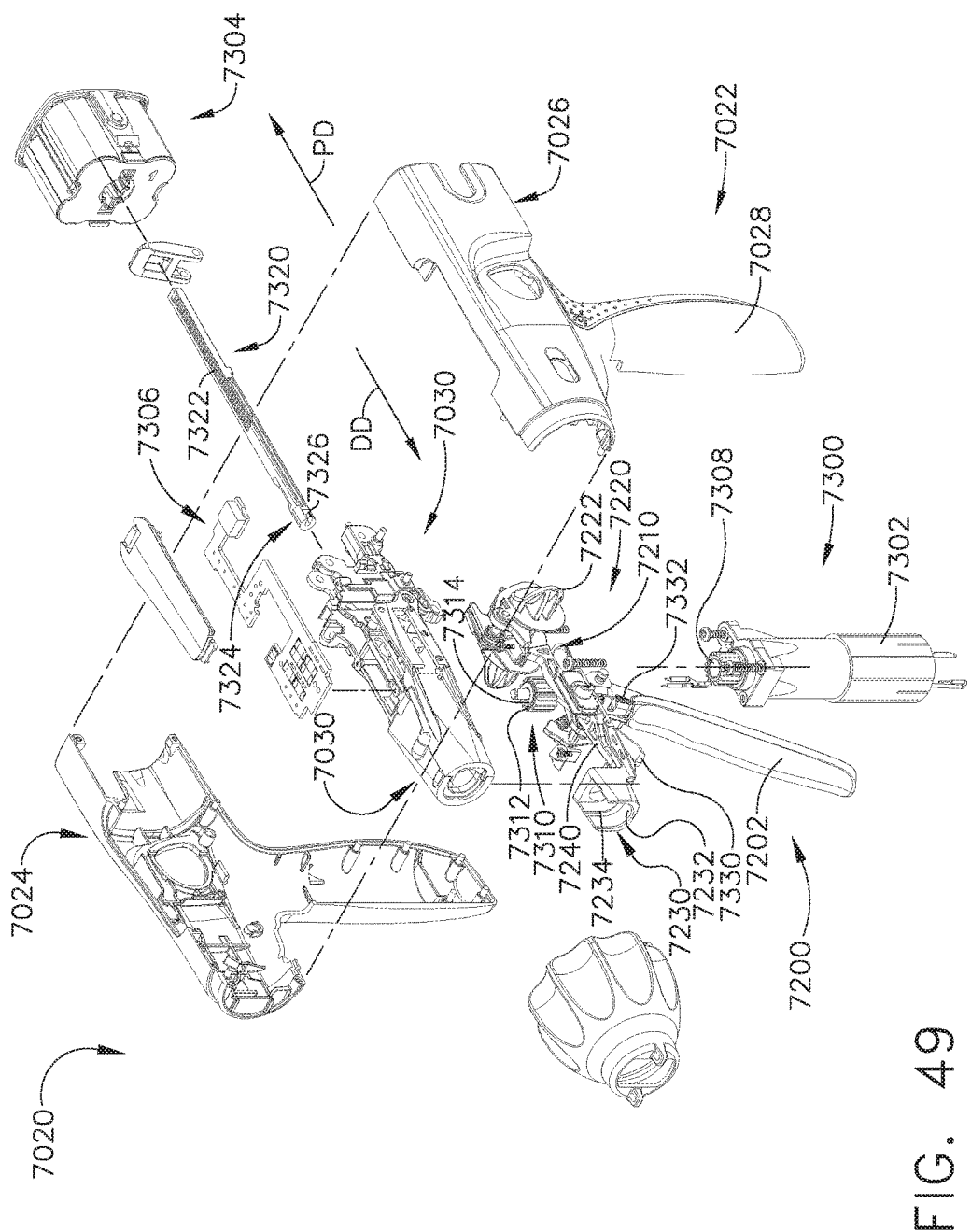
FIG. 49 is an exploded assembly view of the handle assembly of the surgical instrument of FIG. 47.

As indicated above, the anvil assembly 7130 is also responsive to actuation motions in the form of opening and closing motions that are applied thereto by a closure drive system 7200. Various details regarding the certain aspects of the construction and operation of the closure drive system 7200 may be found in U.S. patent application Ser. No. 13/803,097, filed Mar. 14, 2013, entitled ARTICULATABLE SURGICAL INSTRUMENT COMPRISING A FIRING DRIVE, now U.S. Patent Application Publication No. 2014/0263542, the entire disclosure of which is incorporated by reference herein. As discussed in that reference and as shown in FIG. 49 herein, the closure drive system 7200 includes a closure trigger 7202 that is configured to cooperate with a closure release assembly 7220 that is pivotally coupled to a frame 7030. In at least one form, the closure release assembly 7220 may comprise a release button assembly 7222 that may be pivoted in a counterclockwise direction by a release spring (not shown). As the clinician depresses the closure trigger 7202 from its unactuated position towards the pistol grip portion 7028 of the handle 7022, the closure release assembly 7220 serves to lock the closure trigger 7202 in the fully actuated position. When the clinician desires to unlock the closure trigger 7202 to permit it to be biased to the unactuated position, the clinician simply pivots the closure release button assembly 7220 to cause it to disengage the closure trigger arrangement and thereby permit the closure trigger 7202 to pivot back to the unactuated position. Other closure trigger locking and release arrangements may also be employed.

Figure 50:
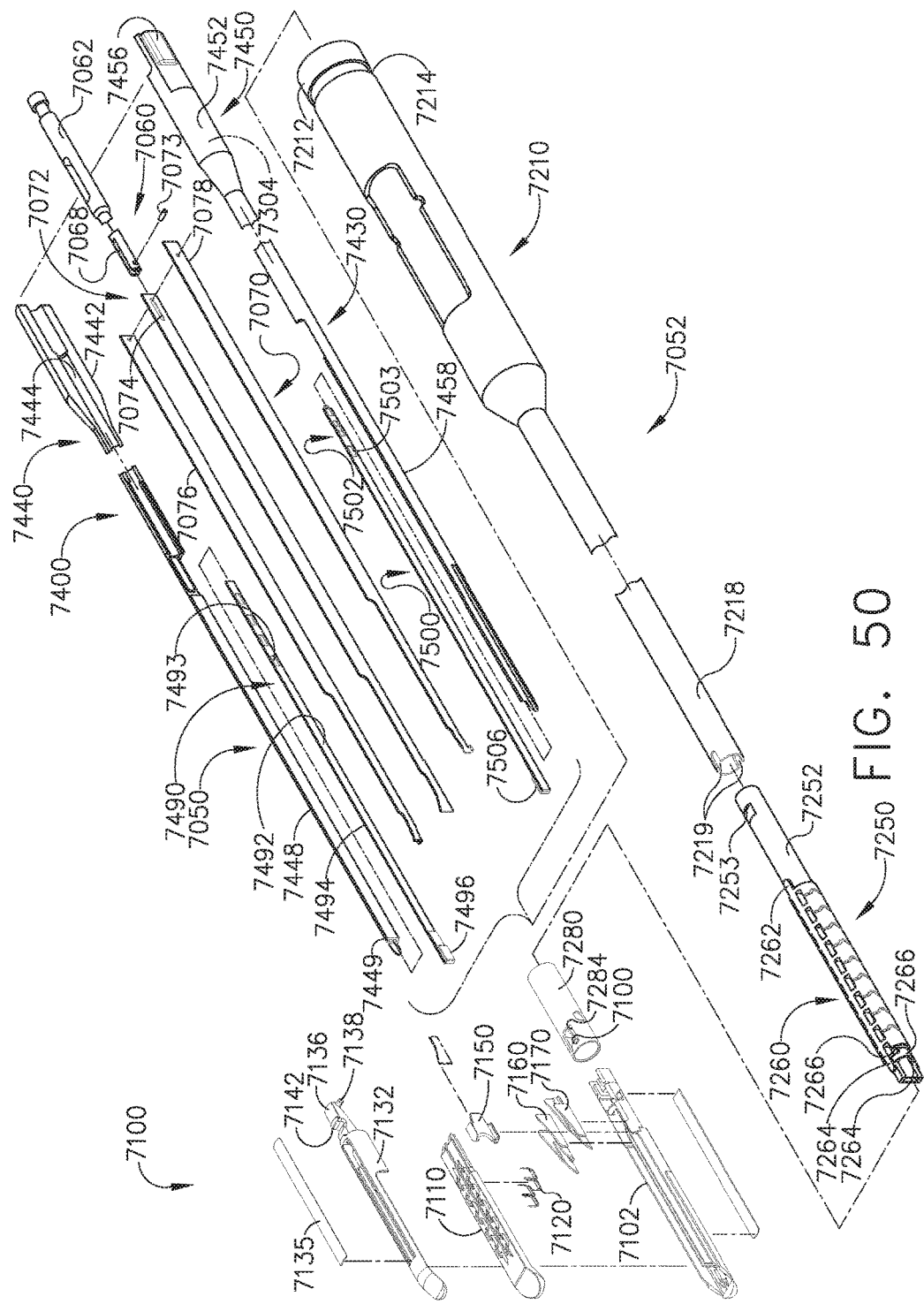
FIG. 50 is an exploded assembly view of an elongated shaft assembly of the surgical instrument of FIGS. 47-49.

Referring to FIGS. 49-50, the closure drive system 7200 may further comprise a proximal closure tube segment 7210 that has a proximal end 7212 that is adapted to be rotatably coupled to a closure tube attachment yoke 7230. The proximal end 7212 of the proximal closure tube segment 7210 is configured to be received within a cradle 7232 (FIG. 49) in the closure tube attachment yoke 7230 to permit relative rotation relative thereto. The proximal closure tube segment 7210 may be rotatably attached to the closure tube attachment yoke 7230 by a U-shaped connector (not shown) that is configured to be received in an annular slot 7214 in the proximal end 7212 of the proximal closure tube segment 7210 and be seated in a slot 7234 (FIG. 49) in the closure tube attachment yoke 7230. Such arrangement serves to rotatably couple the proximal closure tube segment 7210 to the closure tube attachment yoke 7230 such that the proximal closure tube segment 7210 may rotate relative thereto. More specifically, such arrangement facilitates manual rotation of the elongated shaft assembly 7050 relative to the handle 7022 about a longitudinal tool axis "LT-LT" defined by the elongated shaft assembly 7050 to enable the clinician to rotate the surgical end effector 7100 in the manner represented by arrow "R" in FIG. 47.

In various arrangements, the closure tube attachment yoke 7230 is movably mounted on a proximal articulation tube 7402 of an articulation system 7400 which will be discussed in further detail below. Such arrangement permits the closure tube attachment yoke 7230 to move axially on the proximal articulation tube 7402 in response to actuation of the closure trigger 7202. In particular, the closure tube attachment yoke 7230 may be pivotally coupled to the closure trigger 7202 by a closure linkage bar 7240. See FIG. 49. Thus, when the clinician pivots the closure trigger 7202 inward toward the pistol grip portion 7028 of the handle 7022, the closure tube attachment yoke 70230 will be advanced in the distal direction "DD". When the firing trigger 7202 is returned to the unactuated position, the closure tube attachment yoke 7230 will be advanced proximally (direction "PD") on the proximal articulation tube 7402 to a starting position.

The closure drive system 7200 may further include an intermediate tube segment 7250 that is configured for attachment to the distal end 7218 of the proximal closure tube segment 7210. As can be seen in FIG. 50, the intermediate tube segment 7250 may include a flexible articulation portion 7260 and an attachment stem portion 7252. The attachment stem portion 7252 may be sized to extend into the open distal end 7218 of the proximal closure tube segment 7210 in frictional engagement therewith. The flexible articulation portion 7260 may be integrally formed with the attachment stem portion 7252 and include an articulation spine 7262 that includes proximal end portions 7264 (only one can be seen in FIG. 50) that are configured to be received in corresponding notches 7219 in the distal end 7218 of the proximal closure tube segment 7210 to prevent relative rotation between the proximal closure tube segment 7210 and the intermediate tube segment 7250. The intermediate tube segment 7250 may be non-rotatably (i.e., attached to prevent relative rotation between these components) attached to the proximal closure tube segment 7210 by, for example, screws, detents, adhesive, etc.

The closure drive system 7200 may further include a distal closure tube segment 7280 that is configured to axially engage and apply opening and closing motions to the anvil assembly 7130. The distal closure tube segment 7280 may be attached to the distal end of intermediate tube segment 7250 for axial travel therewith. The articulation spine 7262 may further include distal end portions 7266 that are configured to be received in corresponding notches 7284 in the proximal end 7282 of the distal closure tube segment 7280 to prevent relative rotation between the distal closure tube segment 7280 and the intermediate tube segment 7250. See FIG. 50. The proximal end 7282 of the distal closure tube segment 7280 may inwardly extending attachment tabs 7286 that are adapted to be bent into corresponding notches 7266 in the intermediate tube segment 7250. See FIG. 50. Such arrangement serves to facilitate attachment of the distal closure tube segment 7280 to the intermediate tube segment 7250 for axial travel therewith.

The distal closure tube segment 7280 is configured to apply opening and closing motions to the anvil assembly 7130. The anvil mounting portion 7136 may be formed with an anvil tab 7142. The distal end 7288 of the distal closure tube segment 7280 has an inwardly extending actuation tab 7290 formed therein that is configured to interact with the anvil tab 7142. For example, when the distal closure tube segment 7280 is in the open position, the actuation tab 7290 is in biasing contact with the anvil tab 7142 which serves to pivot the anvil assembly 7130 to the open position.

Operation of the closure drive system 7200 will now be described. The anvil assembly 7130 may be moved relative to the surgical fastener cartridge 7110 by pivoting the closure trigger 7202 toward and away from the pistol grip portion 7028 of the handle 7022. Thus, actuating the closure trigger 7202 causes the proximal closure tube segment 7210, the intermediate tube segment 7250 and the distal closure tube segment 7280 to move axially in the distal direction "DD" to contact the end wall 7144 of the anvil body portion 7132 to pivot or otherwise move the anvil assembly 7130 toward the surgical fastener cartridge 7110. The clinician may grasp and manipulate tissue between the anvil assembly 7130 and the fastener cartridge 7110 by opening and closing the anvil assembly 7130. Once the target tissue is captured between the anvil assembly 7130 and fastener cartridge 7110, the clinician may pivot the closure trigger 7202 to the fully actuated position wherein it is locked in place for firing.

Referring again to FIG. 49, the frame 7030 may also be configured to operably support the firing drive system 7300 that is configured to apply firing motions to corresponding portions of the elongated shaft assembly 7050 and ultimately to the knife assembly 7150 and the sled assemblies 7160, 7170. As can be seen in FIG. 49, the firing drive system 7300 may employ an electric motor 7302 that is supported in the pistol grip portion 7028 of the handle 7022. In various forms, the motor 7302 may be a DC brushed driving motor having a maximum rotation of, approximately, 25,000 RPM, for example. In other arrangements, the motor 7302 may include a brushless motor, a cordless motor, a synchronous motor, a stepper motor, or any other suitable electric motor. A battery 7304 (or "power source" or "power pack"), such as a Li ion battery, for example, may be coupled to the handle 7022 to supply power to a control circuit board assembly 7306 and ultimately to the motor 7302.

The electric motor 7302 can include a rotatable shaft 7308 that operably interfaces with a gear reducer assembly 7310 that is mounted in meshing engagement with a with a set, or rack, of drive teeth 7322 on a longitudinally-movable drive member 7320. The gear reducer assembly 7310 can include, among other things, a housing and an output pinion gear 7314. In certain embodiments, the output pinion gear 7314 can be directly operably engaged with the longitudinally-movable drive member 7320 or, alternatively, operably engaged with the drive member 7320 via one or more intermediate gears. In use, the electric motor 7302 can move the drive member distally, indicated by an arrow "DD", and/or proximally, indicated by an arrow "PD", depending on the direction in which the electric motor 7302 rotates. For example, a voltage polarity provided by the battery can operate the electric motor 7302 in a clockwise direction wherein the voltage polarity applied to the electric motor by the battery can be reversed in order to operate the electric motor 7302 in a counter-clockwise direction. When the electric motor 7302 is rotated in one direction, the drive member 7320 will be axially driven in the distal direction "DD". When the motor 7302 is driven in the opposite rotary direction, the drive member 320 will be axially driven in a proximal direction "PD". The handle 7022 can include a switch which can be configured to reverse the polarity applied to the electric motor 7302 by the battery. The handle 7022 can also include a sensor that is configured to detect the position of the movable drive member 7320 and/or the direction in which the movable drive member 7320 is being moved.

Actuation of the motor 7302 can be controlled by a firing trigger 7330 that is pivotally supported on the handle 7022. The firing trigger 7330 may be pivoted between an unactuated position and an actuated position. The firing trigger 7330 may be biased into the unactuated position by a spring (not shown) or other biasing arrangement such that when the clinician releases the firing trigger 7330, it may be pivoted or otherwise returned to the unactuated position by the spring or biasing arrangement. In at least one form, the firing trigger 7330 can be positioned "outboard" of the closure trigger 7202 as discussed in further detail in U.S. patent application Ser. No. 13/803,097 which has been previously incorporated by reference in its entirety herein. In at least one form, a firing trigger safety button 7332 may be pivotally mounted to the closure trigger 7202. The safety button 7332 may be positioned between the firing trigger 7330 and the closure trigger 7202 and have a pivot arm (not shown) protruding therefrom. When the closure trigger 7202 is in the unactuated position, the safety button 7332 is contained in the handle housing where the clinician cannot readily access it and move it between a safety position preventing actuation of the firing trigger 7330 and a firing position wherein the firing trigger 7330 may be fired. As the clinician depresses the closure trigger 7202, the safety button 7332 and the firing trigger 7330 pivot down to a position wherein they can then be manipulated by the clinician.

As indicated above, in at least one form, the longitudinally movable drive member 7320 has a rack of teeth 7322 formed thereon for meshing engagement with a corresponding drive gear of the gear reducer assembly 7310. At least one form may also include a manually-actuatable "bailout" assembly that is configured to enable the clinician to manually retract the longitudinally movable drive member 7320 should the motor become disabled. U.S. patent application Ser. No. 13/803,097, now U.S. Patent Application Publication No. 2014/0263542 contains further details of one form of bailout assembly that may be employed. U.S. Patent Application Publication No. 2010/0089970, now U.S. Pat. No. 8,608,045, also discloses "bailout" arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is incorporated by reference in its entirety.

Referring to FIG. 50, various forms of the elongated shaft assembly 7050 may include a firing member assembly 7060 that is supported for axial travel within an articulation shaft assembly 7400 that essentially functions as shaft frame or spine. The firing member assembly 7060 may further include a proximal firing shaft 7062 that has a proximal end portion 7064 that is configured to be rotatably received in a distal cradle 7326 provided in a distal end 7324 of the movable drive member 7320. Such arrangement permits the proximal firing shaft 7062 to rotate relative to the movable drive member 7320 while also axially moving therewith. The proximal firing shaft 7062 may further have a slot 7068 formed in its distal end for receiving a proximal end 7072 of a flexible distal firing shaft assembly 7070 therein. See FIG. 50. As can be seen in that Figure, the proximal end 7072 of the distal firing shaft assembly 7070 may be received within the slot 7068 in the distal firing shaft 7062 and may be pinned thereto with a pin 7073.

The distal firing shaft assembly 7070 may include a central firing beam 7074 that is located between a right sled pusher beam 7076 and a left sled pusher beam 7078. The central firing beam 7074 and the pusher beams 7076, 7078 may, for example, each be fabricated from metal that facilitates axial actuation of the sled assemblies 7160, 7170 in the surgical end effector 7100 while also facilitating flexing thereof when the end effector 7100 is articulated. In at least one arrangement, the central pusher beam 7074, the right sled pusher beam 7076 and the left sled pusher beam 7078 may extend through a slot 7146 in the anvil mounting portion 7136. The right sled pusher beam 7076 corresponds to the right sled assembly 7160 and the left sled pusher beam 7078 corresponds to the left sled assembly 7170 movably supported within the elongated channel 7102. Axial movement of the right sled pusher beam 7076 and the left sled pusher beam 7078 will result in the axial advancement of the right and left sled assemblies 7160, 7170, respectively, within the elongate channel 7102. As the right sled assembly 7160 is axially advanced within the elongated channel 7102, it drives the surgical fasteners 7120 supported in the cartridge body 7112 on the right side of the slot 7114 out of their respective pockets 7116 and as the left sled assembly 7170 is axially advanced within the elongated channel 7102, it drives the surgical fasteners 7120 supported within the cartridge body 7112 on the left side of the slot 7114 out of their respective pockets 7116.

The central firing beam 7074 has a distal end 7080 that may be configured to be received within a slot provided in the body portion 7155 of the knife assembly 7154 and retained therein by, for example, a frictional fit, adhesive, welding, etc. In at least one form, the elongated channel 7102 is formed with a right upstanding wall 7107 and a left upstanding wall 7108 that define a centrally-disposed channel slot 7109. Once the knife assembly 7150 is inserted into the bottom window in the elongated channel 7102, the body portion 7151 of the knife assembly 7150 may be inserted into the channel slot 7109 and advanced proximally in the elongated channel 7102 to be coupled with the distal end 7080 of the central firing beam 7074. A lower channel cover 7111 may be attached to the bottom of the elongated channel 7102 to prevent tissue, body fluids, etc. from entering into the elongated channel 7102 which might hamper the movement of the knife assembly 7150 therein.

The surgical instrument 7010 may also include an articulation system 7400 of the type described in detail in U.S. patent application Ser. No. 13/803,097, now U.S. Patent Application Publication No. 2014/0263542. In one implementation, for example, the articulation system 7400 includes an articulation shaft assembly 7430 that may be operably controlled by an articulation control system 7460. In one form, for example, the articulation shaft assembly 7430 may include a right articulation shaft segment 7440 and a left articulation shaft segment 7450. The right articulation shaft segment 7440 includes a proximal end 7442 that has a right passage segment 7444 formed therein. Likewise the left articulation shaft segment 7450 includes a proximal end portion 7452 that has a left passage segment 7454 formed therein. When the right articulation shaft segment 7440 and the left articulation shaft segment 7450 are installed within the proximal closure tube segment 7210, they form the articulation shaft assembly 7430. The right passage segment 7444 and the left passage segment 7454 cooperate to receive a portion of the proximal firing shaft 762 therein. The right articulation shaft segment 7440 and the left articulation shaft segment 7450 may be, for example, composed of a plastic, especially a glass fiber-reinforced amorphous polyamide, sold commercially under the trade name Grivory GV-6H by EMS-American Grilon.

Still referring to FIG. 50, the articulation shaft assembly 7430 may further include a right articulation band 7490 and a left articulation band 7500. In one form, a proximal end portion 7492 of the right articulation band 7490 may be attached to a distal portion 7448 of the right articulation shaft segment such that a distal portion 7494 of the right articulation band 7490 protrudes out of a right passage 7449 therein. The proximal end portion 7492 of the right articulation band 7490 may include holes or cavities 7493 that are configured to receive corresponding lugs (not shown) in the right articulation shaft segment 7440 to facilitate attachment of the right articulation band 7490 to the right articulation shaft segment 7440. Likewise, a proximal end portion 7502 of the left articulation band 7500 may have holes or cavities 7503 therein that are configured to receive lugs (not shown) in the distal portion 7458 of the left articulation shaft segment 7450 to facilitate attachment of the left articulation band 7500 to the articulation shaft segment 7450. The articulation bands 7490 and 5700 may be composed of a metal, advantageously full hard 301 stainless steel or its equivalent. The distal end of the left articulation band 7500 may have a left hook portion 7506 that is adapted to be coupled to a left attachment portion 7507 of the elongated channel 7102. Likewise, the distal end of the right articulation band 7494 has a right hook portion 7496 for attachment to a right attachment portion 7497. As discussed in further detail in U.S. patent application Ser. No. 13/803,097, now U.S. Patent Application Publication No. 2014/0263542, when the clinician wishes to articulate the end effector 7100 to the right relative to the longitudinal tool axis LT-LT, the clinician simply rotates the articulation control knob 7570 in the appropriate direction.

The surgical instrument 7010 may be used in a minimally invasive procedure wherein it is inserted through a trocar port that has been installed in a patient. In such applications, it is generally advantageous to minimize the overall cross-sectional shape of the end effector during insertion into the patient in order to minimize the size of the trocar port that must be employed. The smallest cross-sectional configuration that the end effector 7100 may adopt is achieved when the upper jaw or anvil assembly 7130 is in its a "first insertion position" relative to the lower jaw or more specifically relative to the surgical staple cartridge 7110 installed in the elongated channel 7102. Thus, to facilitate insertion of the end effector 7100 through the trocar port, the cross-sectional area or footprint is sized relative to the cross-sectional size of the port opening in the trocar port to permit the end effector 7110 to slidably pass therethrough.

In at least one implementation, the end effector 7100 employs an active anvil control system 7600 that is configured to enable the anvil assembly 7130 to move to the first insertion position to enable the end effector 7100 to be inserted through the trocar port and then once the end effector 7100 has passed through the trocar port, enables the anvil assembly 7130 to assume an operating configuration for stapling tissue. Referring to FIGS. 48 and 51-54, one form of anvil control system 7600 includes a U-shaped control insert 7602 that is movably supported on the elongated channel 7102 and is attached to a control bar 7604. The control bar 7604 extends through the elongated shaft assembly 7050 and is movably supported for axial travel therein. The control bar 7604 may be attached to a movable actuator slide 7606 or other form of actuator arrangement supported on the handle assembly. See FIG. 47. Movement of the actuator slide 7606 in the distal direction "DD" will cause the control bar 7604 to move in the distal direction "DD". Similarly, movement of the actuator slide 7606 in the proximal direction "PD" will cause the control bar 7604 to move in the proximal direction "PD".

Figure 51:
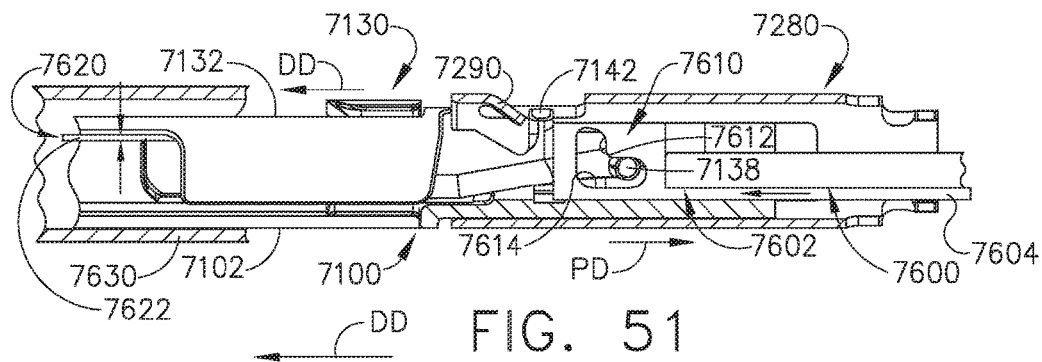
FIG. 51 is a cross-sectional side view of a portion of the surgical instrument of FIGS. 47-50 inserted through a portion of a trocar port.
Figure 52:
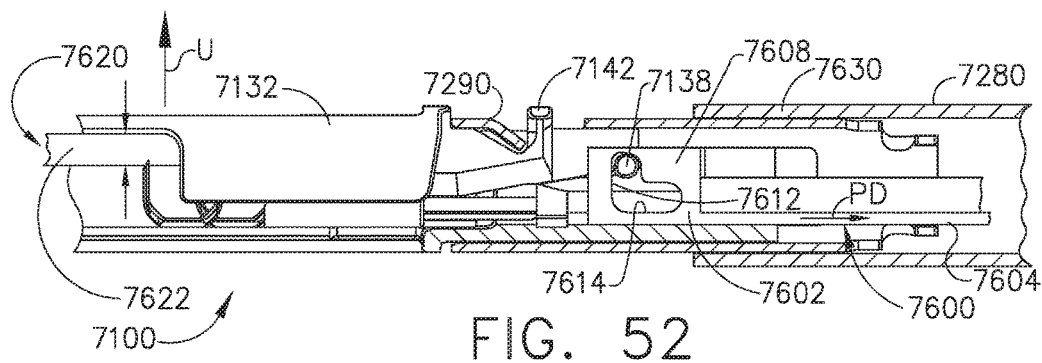
FIG. 52 is another cross-sectional side view of the surgical instrument of FIG. 51 after it has exited through the trocar port inside the patient.

As can be seen in FIG. 48, the U-shaped control insert 7602 is formed with two upstanding walls 7608 that each have a somewhat L-shaped trunnion slot 7610 therein. More specifically, each trunnion slot 7610 has a vertical slot portion 7612 and a horizontal slot portion 7614. The trunnion slots 7610 are sized to movably receive a corresponding anvil trunnion 7138 therein. FIG. 51 illustrates the anvil assembly 7130 in its first insertion position. As can be seen in that Figure, for example, the anvil assembly 7130 is being inserted through a distal end portion of a trocar port 7630. To enable the anvil assembly 7130 to assume that first insertion position, the clinician moves the control bar 7604 in the distal direction "DD" to cause the movable anvil trunnions 7130 to be retained within the horizontal slot portions 7614 as shown. When in that position, the anvil mounting portion 7136 is in is lowest position within the elongated channel 7102.

Figure 53:
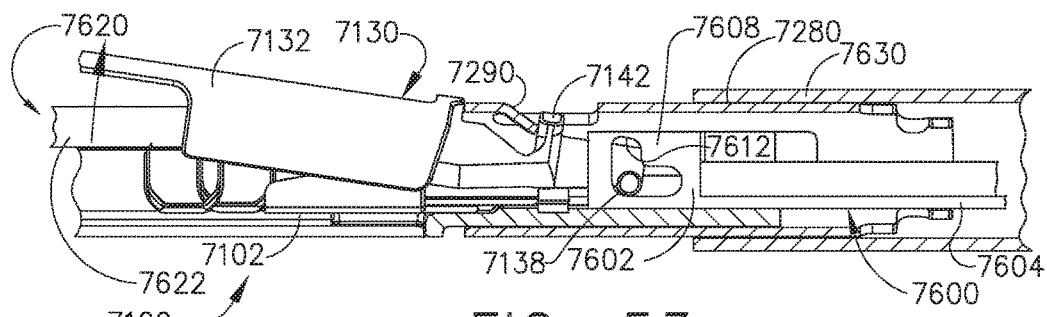
FIG. 53 is another cross-sectional side view of the surgical instrument of FIGS. 51 and 52 after the anvil assembly has been moved to an open position.
Figure 54:
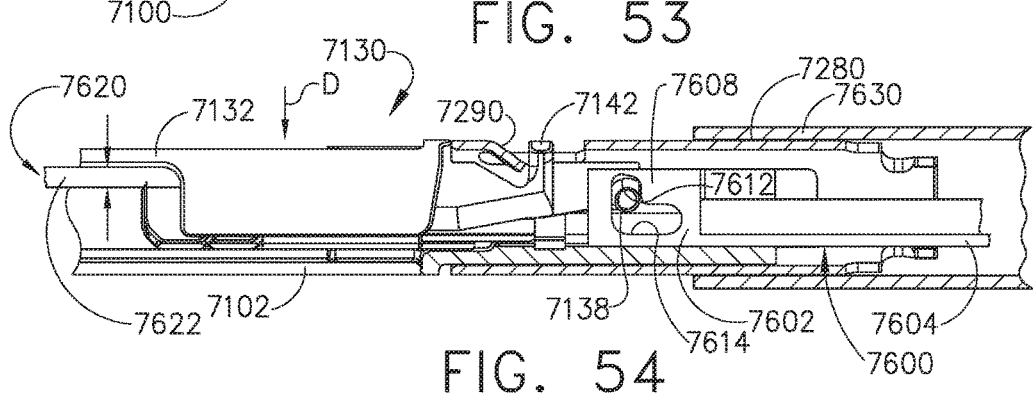
FIG. 54 is another cross-sectional side view of the surgical instrument of FIGS. 51-53 with the anvil in the closed firing position.

The elongated channel 7102 is equipped with an elastic "biasing means" 7620 that serves to bias the anvil body portion 7132 away from the elongated channel 7102. In various embodiments, the elastic biasing means 7620 may comprise any form of resilient member(s) and/or spring(s) that are attached directly to the elongated channel 7102. For example, in the depicted arrangement, the biasing means comprises strips of compressible or elastic foam material 7622 attached along the sides of the elongated channel 7102. When the anvil assembly 7130 is inside the trocar port 7630, the foam strips 7622 will be compressed as shown in FIG. 51. After the end effector 7100 has passed through the trocar port 7630, the clinician may move the control bar 7604 in the proximal direction "PD" such that the control insert 7602 is also moved proximally to the position illustrated in FIG. 52. When in that position, the foam strips 7622 bias the anvil assembly 7130 upward (represented by arrow "U" in FIG. 52) to a "primary opened position" thereby causing the anvil trunnions 7138 to move to the upper end of the vertical trunnion slots 7612 as shown. When the anvil assembly 7130 is in that "primary opened position", the clinician may then actuate the closure trigger to move the distal closure tube 7280 in the proximal direction "PD" to cause the anvil assembly 7130 to move to a "fully open position" as illustrated in FIG. 53. Once the clinician has positioned the target tissue between the anvil assembly 7130 and the staple cartridge 7110, the anvil assembly 7130 can be closed using the closure trigger 7202 to move the anvil assembly 7130 to the closed or fully clamped position illustrated in FIG. 54.

Figure 57:
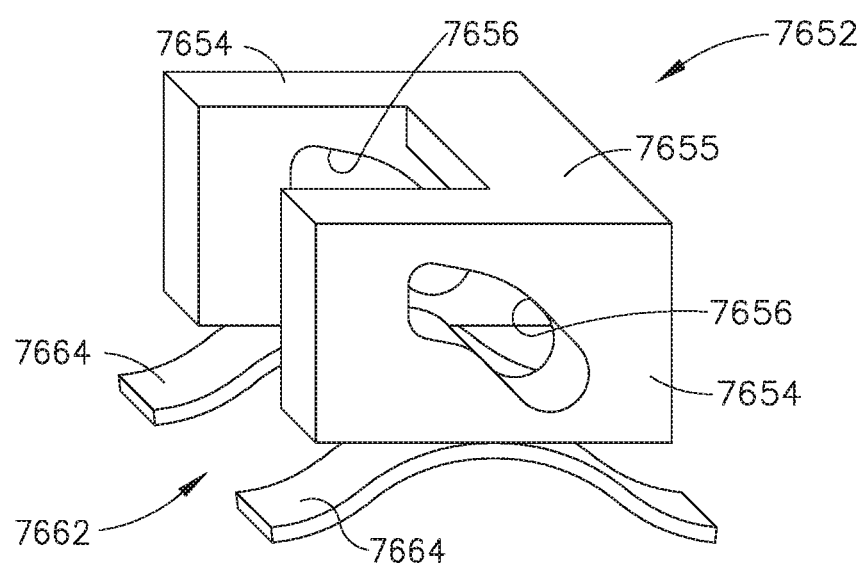
FIG. 57 is a perspective view of one form of a control insert.

FIGS. 55 and 56 illustrates a "passive" anvil control arrangement 7650 that is configured to enable the anvil assembly 7130 to move to the first insertion position for insertion through a hollow trocar port 7630 and then, once the end effector 7100 has passed through the hollow trocar port 7630, to be biased into a "primary opened position" whereupon further actuation motions may be applied to the anvil assembly 7130 for acquiring and clamping the target tissue. In this arrangement, for example, the anvil control arrangement 7650 includes a U-shaped control insert 7652 that is movably supported on the elongated channel 7102 for vertical travel therein. One form of control insert 7652 is depicted in FIG. 57. As can be seen in that Figure, the control insert includes a pair of vertical side walls 7654 that are spaced from each other and connected together by an upper bar 7655. Each vertical side wall has an arcuate trunnion slot 7656 therein. Referring again to FIGS. 55 and 56, the control insert 7652*t* is movable relative to the elongated channel 7102 along an insert axis "IA-IA" which is transverse to the longitudinal tool axis "LT-LT" that is defined by the elongated shaft assembly 7050. The control insert 7652 may movably interface with vertically extending guide ribs 7660 formed in the elongated channel 7102 to guide the control insert 7652 as it moves up and down along the insert axis IA-IA between a first lower position that corresponds to the insert position of the anvil assembly 7130 and a second upper position that corresponds to the "primary opened position" wherein actuation motions may be applied to the anvil assembly 7130. As can be seen in FIGS. 55 and 56, the anvil trunnions 7138 are received within the trunnion slots 7656. Control member biasing means 7662 is provided between the control insert 7652 and the bottom of the elongated channel 7102 to bias the control insert 7652 in the upward direction "U" to the second or upper-most position. As shown in FIG. 55, the control member biasing means 7662 comprises leaf springs 7664. However, other biasing materials, members, springs, materials, etc. may be employed.

FIG. 55 illustrates the end effector 7100 wherein the upper jaw or anvil assembly 7130 is in the insertion position as it is being and being inserted through the trocar port 7630. As can be seen in that Figure, the control insert 7652 is compressed into its lowest position within the elongated channel 7102 referred to herein as the first position. After the end effector 7100 has been inserted through the trocar port 7630, the "biasing means" 7620 serves to bias the anvil body portion 7132 away from the elongated channel 7102 to the primary opened position as shown in FIG. 56. As can be seen in that Figure, when the anvil assembly 7130 is in that position, the springs 7664 bias the control insert 7652 to its upper-most or second position and the clinician may then operate the closure system to apply an actuation motion to the anvil assembly 7130 to move the anvil assembly 7130 relative to the elongated channel 7102 to a fully opened position for receiving the target tissue therebetween. The clinician may then again operate the closure system to move the anvil assembly to the fully clamped position wherein the end effector is ready for firing.

FIGS. 58 and 59 illustrate another anvil control configuration that facilitates initial positioning of the anvil assembly in a fully compressed, first insertion position wherein the end effector 7720 can be inserted through the trocar port and then once the end effector 7100 has passed through the trocar port, enables the anvil assembly 7730 to assume a primary opened position whereupon application of an actuation motion to the anvil assembly 7730 may cause the anvil assembly 7730 to move to a fully opened position. As shown in those Figures, the end effector 7720 is coupled to a surgical instrument 7710 of the types and construction disclosed herein. The anvil assembly 7730 may be similar in construction to other anvil assemblies disclosed herein. For example, the anvil assembly 7730 may include an anvil body portion 7732 and an anvil mounting portion 7736 that has a pair of trunnions 7738 protruding therefrom as well as an upstanding anvil tab 7742. The anvil tab 7742 is configured to interact with the actuation tab 7290 of the distal closure tube segment 7280 has in the various manners described herein.

As can be seen in FIGS. 58 and 59, the end effector 7720 includes an elongated channel 7721 that is similar in construction and operation to other elongated channel arrangements described herein. The elongated channel 7721 is configured to operably support a surgical staple cartridge therein and includes a proximal mounting portion 7722 that comprises two upstanding wall portions 7723 that each has a trunnion slot 7724 therein. In at least one implementation, each trunnion slot 7724 has a distal portion 7726 that allows the trunnions to be parked therein during the initial insertion process. Each trunnion slot 774 further has an arcuate portion 7727 that facilitates travel of the trunnions 7738 during opening and closing of the anvil assembly 7730.

In various implementations, biasing means 7750 are provided on portions of the underside 7733 of the anvil body portion 7732 as well as on the sides of the elongated channel 7721 and/or on portions of the surgical staple cartridge. For example, anvil biasing member(s) 7752 may be provided on the anvil body portion 7732 in confronting arrangement with anvil biasing member(s) 7756 on the elongated channel 7721. The biasing means 7752, 7754 may comprise any form of resilient member(s) and/or spring(s). For example, in the depicted arrangement, the biasing means comprises strips of compressible or elastic foam material. When the anvil assembly 7730 is inside the trocar port 7630, the biasing members 7752, 7754 will be compressed as shown in FIG. 58. After the end effector 7720 has passed through the trocar port 7630, the biasing members 7752, 7754 bias the anvil assembly 7730 upward to a "primary opened position" as shown in FIG. 59. When the anvil assembly 7730 is in that "primary opened position", the clinician may then actuate the closure trigger to move the distal closure tube 7280 in the proximal direction "PD" to cause the anvil assembly 7730 to move to a "fully open position". Once the clinician has positioned the target tissue between the anvil assembly 7730 and the staple cartridge, the anvil assembly 7730 can be moved to the closed or fully clamped position. The amount of resistance and biasing forces generated by the biasing members may be altered by employing different biasing members having different durometers or spring members with different spring compression characteristics. Another method is to alter the geometry of the biasing members. FIGS. 60 and 61 depict different biasing member configurations 7752', 7754' (FIG. 60) and 7752", 7754" (FIG. 61).

FIGS. 62 and 63 illustrate use of the end effector 7720 with an alternative distal closure tube arrangement 7280' that is essentially identical as distal closure tube 7280 except that a biasing member 7292 is mounted on the inwardly extending actuation tab 7290. In the illustrated embodiment, the biasing member 7292 comprises a leaf-type spring. It will be appreciated however, that the biasing member could comprise an elastic material that is attached, for example, to the anvil mounting portion 7736 (distal from the anvil tab 7742). FIG. 62 illustrates the end effector 7720 the insertion position as it is being inserted through the trocar port 7630. As can be seen in that Figure, the anvil body portion 7732 is compressed into its lowest position relative to the elongated channel 7102 by trocar portion 7630 which also places a biasing force or motion on the biasing member 7292. After the end effector 7100 has been inserted through the trocar port 7630, the biasing member 7292 biases the anvil body portion 7132 away from the elongated channel 7102 to the primary opened position as shown in FIG. 63. The clinician may then again operate the closure system to move the anvil assembly 7730 to the fully clamped position wherein the end effector is ready for firing.

Figure 64:
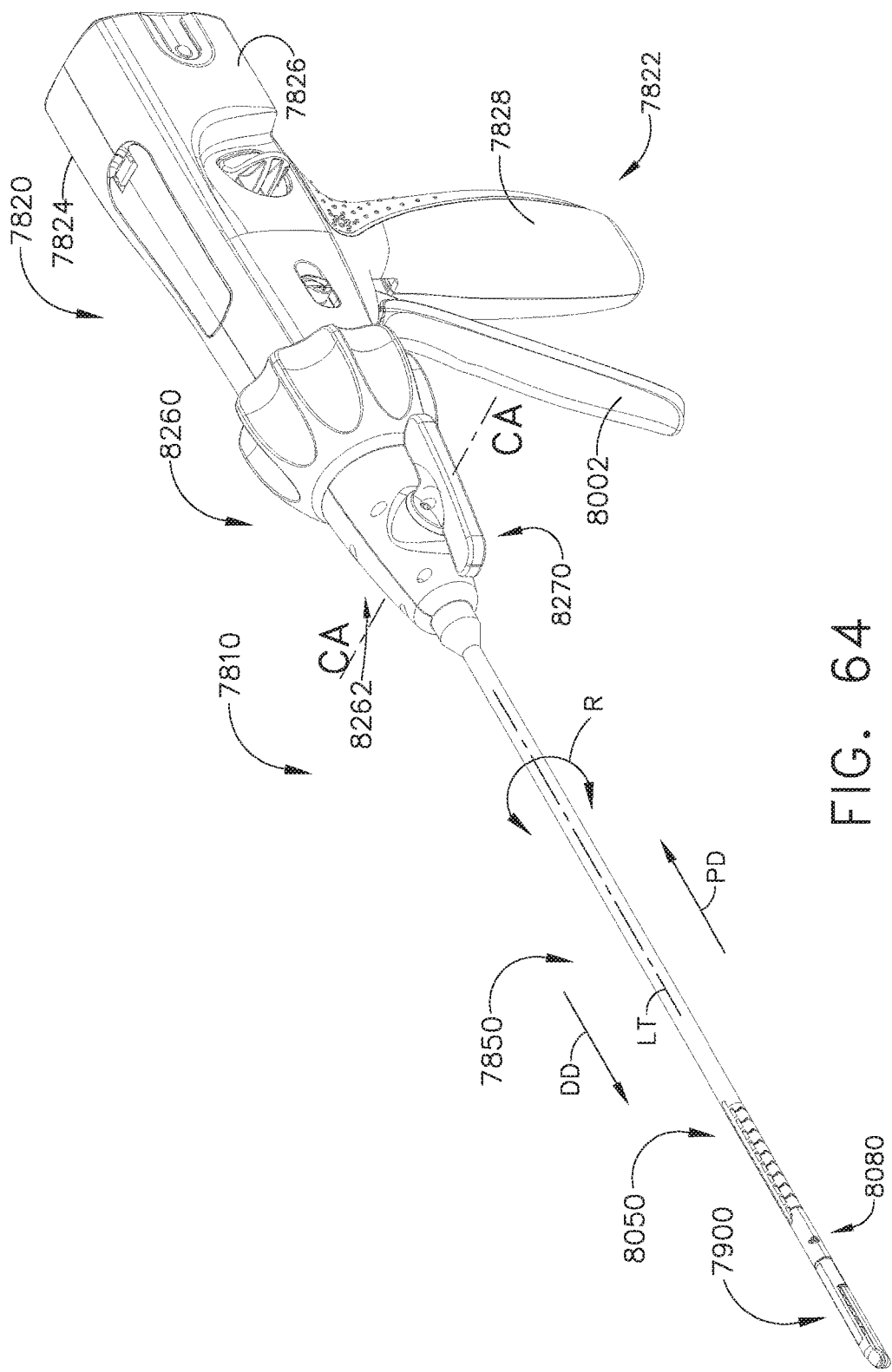
FIG. 64 is a perspective view of one form of a surgical instrument of the present invention.

FIG. 64 illustrates an exemplary surgical instrument 7810 which can include a housing 7820, an elongated shaft assembly 7850 that operably protrudes from the housing 7820 and which is operably coupled to a surgical end effector 7900. The surgical instrument 7810 depicted in the FIG. 64 comprises a housing 7820 that consists of a handle 7822 that is configured to be grasped, manipulated and actuated by a clinician. As the present Detailed Description proceeds, however, it will be understood that the various unique and novel arrangements of the various forms of shaft arrangements and end effector arrangements disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate various forms of surgical end effectors attached thereto. The term "frame" may refer to a portion of a handheld surgical instrument. The term "frame" may also represent a portion of a robotically controlled surgical instrument and/or a portion of the robotic system that may be used to operably control a surgical instrument. For example, U.S. patent application Ser. No. 13/536,323, entitled "Robotically Powered Surgical Device With Manually Actuatable Reversing System", filed Jun. 28, 2012, now U.S. Pat. No. 9,408,606, the entire disclosure of which is incorporated by reference herein discloses various robotic system arrangements that may also be effectively employed. Furthermore, as will be discussed in further detail below, the surgical instrument 7810 depicted in at least some of the accompanying drawings employs a motor for generating control motions for actuating various components and features of the surgical end effector. As the present Detailed Description proceeds, however, those of ordinary skill in the art will appreciate that certain features and advantages of the present invention may also be effectively attained in connection with surgical instruments that are equipped with manually generated (i.e., non-motor generated) actuation and control motions.

Figure 66:
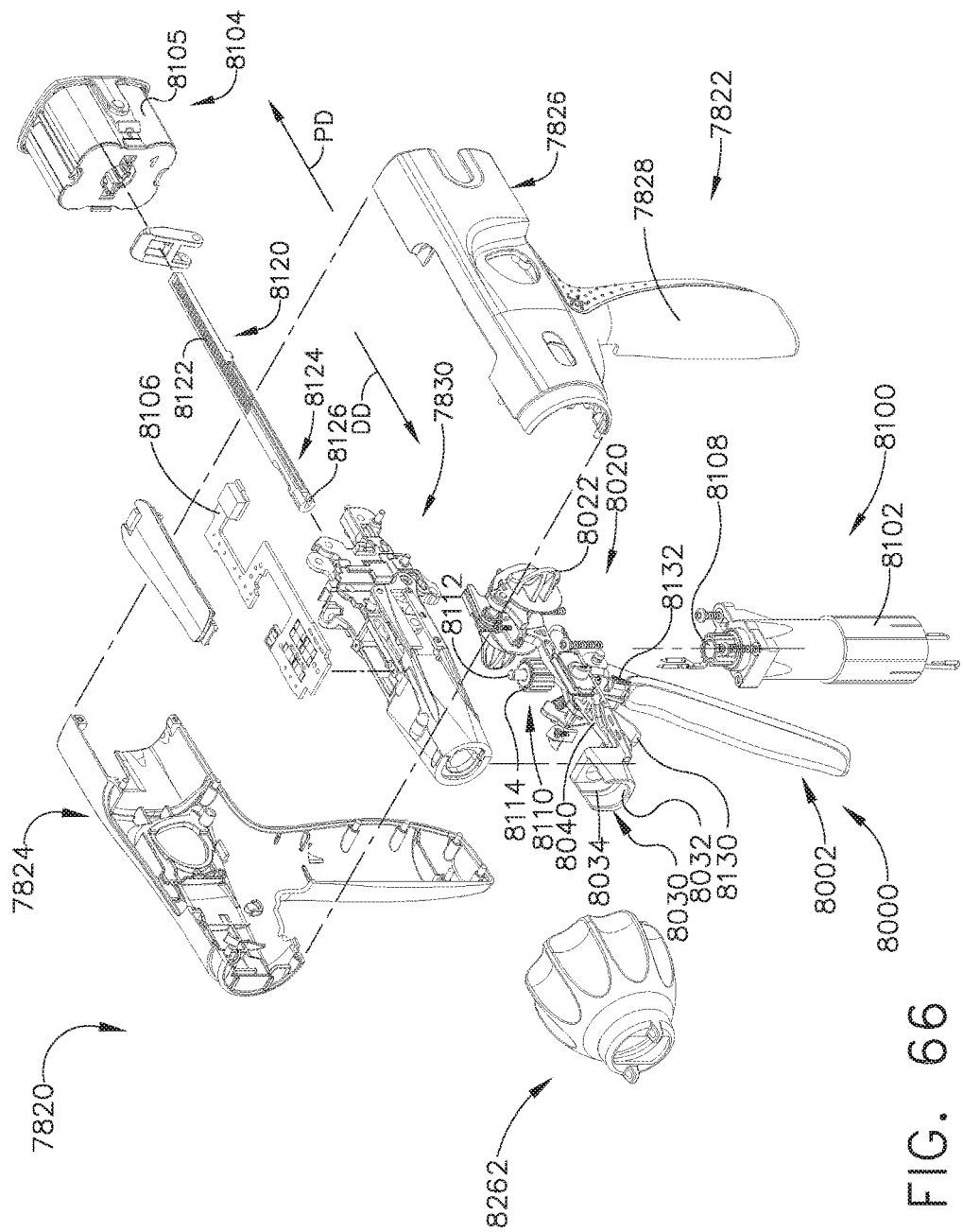
FIG. 66 is an exploded perspective view of a portion of the surgical instrument of FIG. 64.

As illustrated in FIGS. 64 and 66, the handle 7822 may comprise a pair of interconnectable housing segments 7824, 7826 that may be interconnected by screws, snap features, adhesive, etc. As used herein, the term "snap feature" includes, but is not limited to, for example, a tab that has a protrusion thereon that is configured to retainingly engage a corresponding mating portion of another component. Such features may be designed to releasably engage the mating portion or it may not be designed or intended to be removed. In the illustrated arrangement, the handle housing segments 7824, 7826 cooperate to form a pistol grip portion 7828 that can be gripped and manipulated by the clinician. As will be discussed in further detail below, the handle 7822 operably supports a plurality of drive systems or control systems therein that are configured to generate and apply various control motions to corresponding component portions of the elongated shaft assembly 7850 that is operably attached to the surgical end effector 7900. In the illustrated embodiment, the surgical end effector 7900 is configured to cut and fasten tissue, for example.

Figure 65:
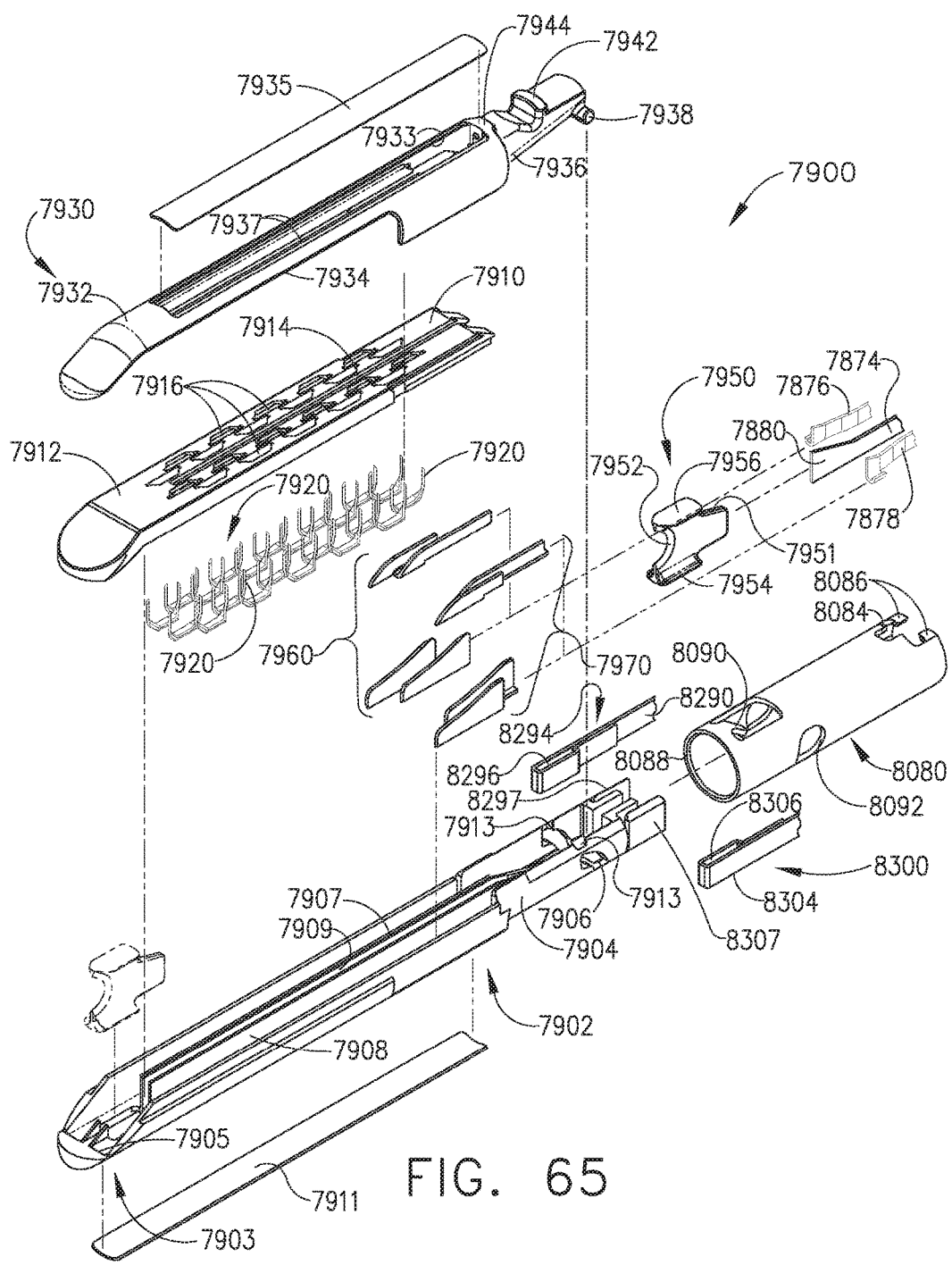
FIG. 65 is an exploded perspective view of one form of surgical end effector of the present invention.

FIG. 65 illustrates one form of surgical end effector 7900 that may be employed. As can be seen in that Figure, the surgical end effector 7900 may comprise an elongated channel 7902 that is configured to receive a surgical fastener cartridge 7910 therein. The surgical fastener cartridge 7910 may include a cartridge body 7912 that has a centrally disposed elongated slot 7914 therein. The cartridge body 7912 may further include rows of fastener pockets 7916 that are located on each side of the elongated slot 7914 and which are configured to support corresponding surgical fasteners 7920 therein. The elongated channel 7902 may further operably support a tissue-cutting member or knife assembly 7950 therein that is configured to axially travel in the slot 7914 in the cartridge body 7912 when installed in the elongate channel 7902. The knife assembly 7950 may be configured with a tissue cutting edge 7952 that is centrally disposed between a lower foot 7954 and an upper foot or tab 7956. As will be discussed in further detail below, the knife assembly 7950 is configured to be axially driven within the elongated channel 7902 and the surgical fastener cartridge 7910 in response to motions applied thereto by a firing drive system 8100.

As can also be seen in FIG. 65, the surgical end effector 7900 may further include an anvil assembly 7930 that is movably supported on the elongate channel 7902. The anvil assembly 7930 may be movable relative to the surgical fastener cartridge 7910, for example, in response to closing and opening motions transferred thereto from a closure drive system 8000. In other arrangements, however, the anvil assembly may be fixed and the surgical fastener cartridge may be configured to move relative to the anvil assembly upon application of closure motions thereto. In one arrangement, for example, the anvil assembly 7930 includes an anvil body portion 7932 that has a fastener forming surface 7934 formed on the underside thereof. The fastener forming surface 7934 may comprise a series of forming pockets (not shown) that correspond to the surgical fasteners 7920 supported in the surgical fastener cartridge 7910. As the legs of the surgical fasteners 7920 are driven into forming contact with the corresponding forming pockets in the anvil assembly 7930, they are formed into a desired tissue-retaining configuration. The anvil assembly 7930 may further include an anvil mounting portion 7936 that has a pair of trunnions 7938 protruding therefrom that are received within corresponding arcuate slots 7906 formed in a proximal mounting portion 7904 of the elongated channel 7902. In various arrangements, the surgical fasteners 7920 are driven out of their respective fastener pockets 7916 in the surgical fastener cartridge 7910 by corresponding sled assemblies 7960 and 7970 that are movably supported within the elongated channel 7902 and are movable in response to firing motions applied thereto by the firing drive system 8100.

Referring now to FIG. 66, the handle 7822 may further include a frame 7830 that operably supports various components of the closure drive system 8000 and the firing drive system 8100. In at least one form, the closure drive system 8000 may include an actuator in the form of a closure trigger 8002 that is pivotally supported by the frame 7830. The closure trigger 8002 may be pivotally supported by frame 7830 such that when the clinician grips the pistol grip portion 7828 of the handle 7822, the closure trigger 8002 may be easily pivoted from a starting or unactuated position to an actuated position and more particularly to a fully compressed or fully actuated position. The closure trigger 8002 may be biased into the unactuated position by spring or other biasing arrangement (not shown). Various details regarding the certain aspects of the construction and operation of the closure drive system 8000 may be found in U.S. patent application Ser. No. 13/803,097, filed Mar. 14, 2013, entitled ARTICULATABLE SURGICAL INSTRUMENT COMPRISING A FIRING DRIVE, now U.S. Patent Application Publication No. 2014/0263542, the entire disclosure of which is incorporated by reference herein. As discussed in that reference and as shown in FIG. 66 herein, the closure trigger 8002 may be configured to cooperate with a closure release assembly 8020 that is pivotally coupled to the frame 7830. In at least one form, the closure release assembly 8020 may comprise a release button assembly 8022 that may be pivoted in a counterclockwise direction by a release spring (not shown). As the clinician depresses the closure trigger 8002 from its unactuated position towards the pistol grip portion 7828 of the handle 7822, the closure release assembly 8020 serves to lock the closure trigger 8002 in the fully actuated position. When the clinician desires to unlock the closure trigger 8002 to permit it to be biased to the unactuated position, the clinician simply pivots the closure release button assembly 8020 to cause it to disengage the closure trigger arrangement and thereby permit the closure trigger 8002 to pivot back to the unactuated position. Other closure trigger locking and release arrangements may also be employed.

Figure 67:
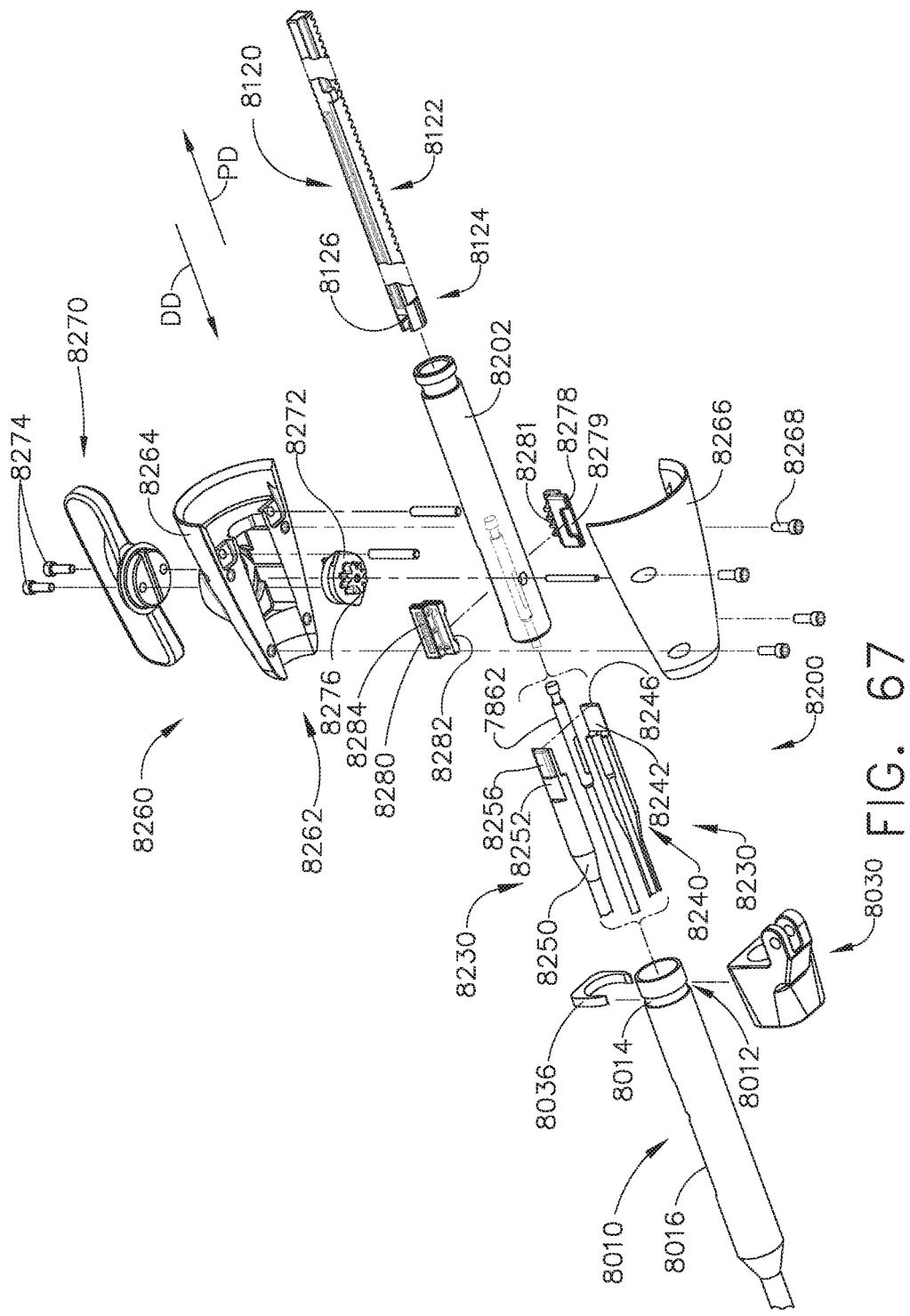
FIG. 67 is an exploded perspective assembly view of another portion of the surgical instrument of FIG. 64.

Referring to FIGS. 66 and 67, the closure drive system 8000 may further comprise a proximal closure tube segment 8010 that has a proximal end 8012 that is adapted to be rotatably coupled to a closure tube attachment yoke 8030. The proximal end 8012 of the proximal closure tube segment 8010 is configured to be received within a cradle 8032 (FIG. 66) in the closure tube attachment yoke 8030 to permit relative rotation relative thereto. The proximal closure tube segment 8010 may be rotatably attached to the closure tube attachment yoke 8030 by a U-shaped connector 8036 that is configured to be received in an annular slot 8014 in the proximal end 8012 of the proximal closure tube segment 8010 and be seated in a slot 8034 (FIG. 66) in the closure tube attachment yoke 8030. Such arrangement serves to rotatably couple the proximal closure tube segment 8010 to the closure tube attachment yoke 8030 such that the proximal closure tube segment 8010 may rotate relative thereto. More specifically, such arrangement facilitates manual rotation of the elongated shaft assembly 7850 relative to the handle 7822 about a longitudinal tool axis "LT-LT" defined by the elongated shaft assembly 7850 to enable the clinician to rotate the surgical end effector 7900 in the manner represented by arrow "R" in FIG. 64.

In various arrangements, the closure tube attachment yoke 8030 is movably mounted on a proximal articulation tube 8202 of an articulation system 8200 which will be discussed in further detail below. Such arrangement permits the closure tube attachment yoke 8030 to move axially on the proximal articulation tube 8202 in response to actuation of the closure trigger 8002. In particular, the closure tube attachment yoke 8030 may be pivotally coupled to the closure trigger 8002 by a closure linkage bar 8040. See FIG. 66. Thus, when the clinician pivots the closure trigger 8002 inward toward the pistol grip portion 7828 of the handle 7822, the closure tube attachment yoke 8030 will be advanced in the distal direction "DD". When the firing trigger 8002 is returned to the unactuated position, the closure tube attachment yoke 8030 will be advanced proximally (direction "PD") on the proximal articulation tube 8202 to a starting position.

Figure 68:
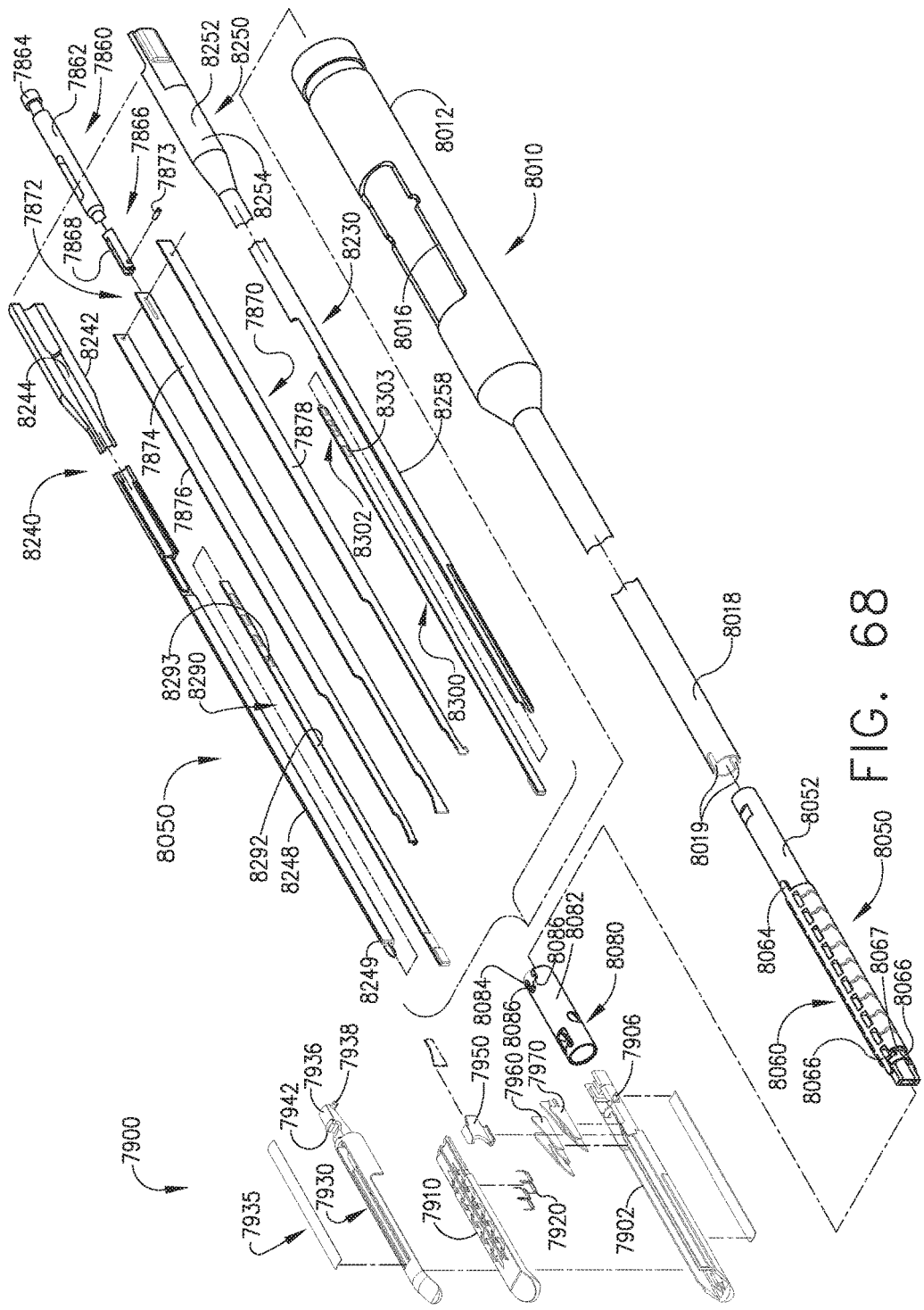
FIG. 68 is an exploded perspective assembly view of a portion of the elongated shaft assembly of the surgical instrument of FIG. 64.

The closure drive system 8000 may further include an intermediate flexible tube segment 8050 that is configured for attachment to the distal end 8018 of the proximal closure tube segment 8010. As can be seen in FIG. 68, the intermediate tube segment 8050 may include a flexible articulation portion 8060 and an attachment stem portion 8052. The attachment stem portion 8052 may be sized to extend into the open distal end 8018 of the proximal closure tube segment 8010 in frictional engagement therewith. The flexible articulation portion 8060 may be integrally formed with the attachment stem portion 8052 and include an articulation spine 8062 that includes proximal end portions 8064 (only one can be seen in FIG. 5) that are configured to be received in corresponding notches 8019 in the distal end 8018 of the proximal closure tube segment 8010 to prevent relative rotation between the proximal closure tube segment 8010 and the intermediate tube segment 8050. The intermediate tube segment 8050 may be non-rotatably (i.e., attached to prevent relative rotation between these components) attached to the proximal closure tube segment 8010 by, for example, screws, detents, adhesive, etc.

The closure drive system 8000 may further include a distal closure tube segment 8080 that is configured to axially engage and apply opening and closing motions to the anvil assembly 7930. The distal closure tube segment 8080 may be attached to the distal end of intermediate tube segment 8050 for axial travel therewith. The articulation spine 8062 may further include distal end portions 8066 that are configured to be received in corresponding notches 8084 in the proximal end 8082 of the distal closure tube segment 8080 to prevent relative rotation between the distal closure tube segment 8080 and the intermediate tube segment 8050. See FIG. 68. The proximal end 8082 of the distal closure tube segment 8080 may inwardly extending attachment tabs 8086 that are adapted to be bent into corresponding notches 8067 in the intermediate tube segment 8050. See FIG. 68. Such arrangement serves to facilitate attachment of the distal closure tube segment 8080 to the intermediate tube segment 8050 for axial travel therewith.

Figure 69:
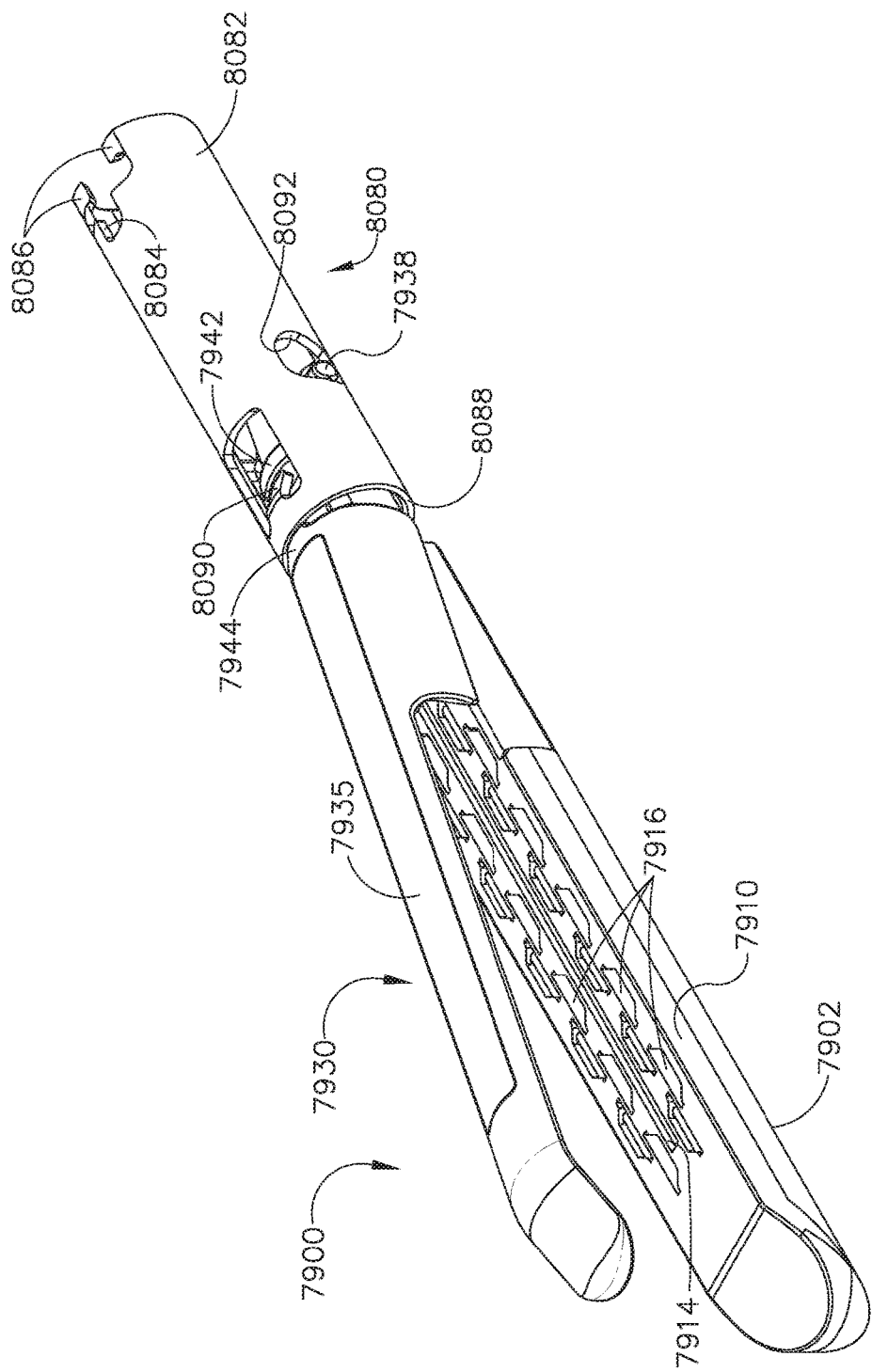
FIG. 69 is a perspective view of the surgical end effector of FIG. 65 and a distal closure tube segment.
Figure 70:
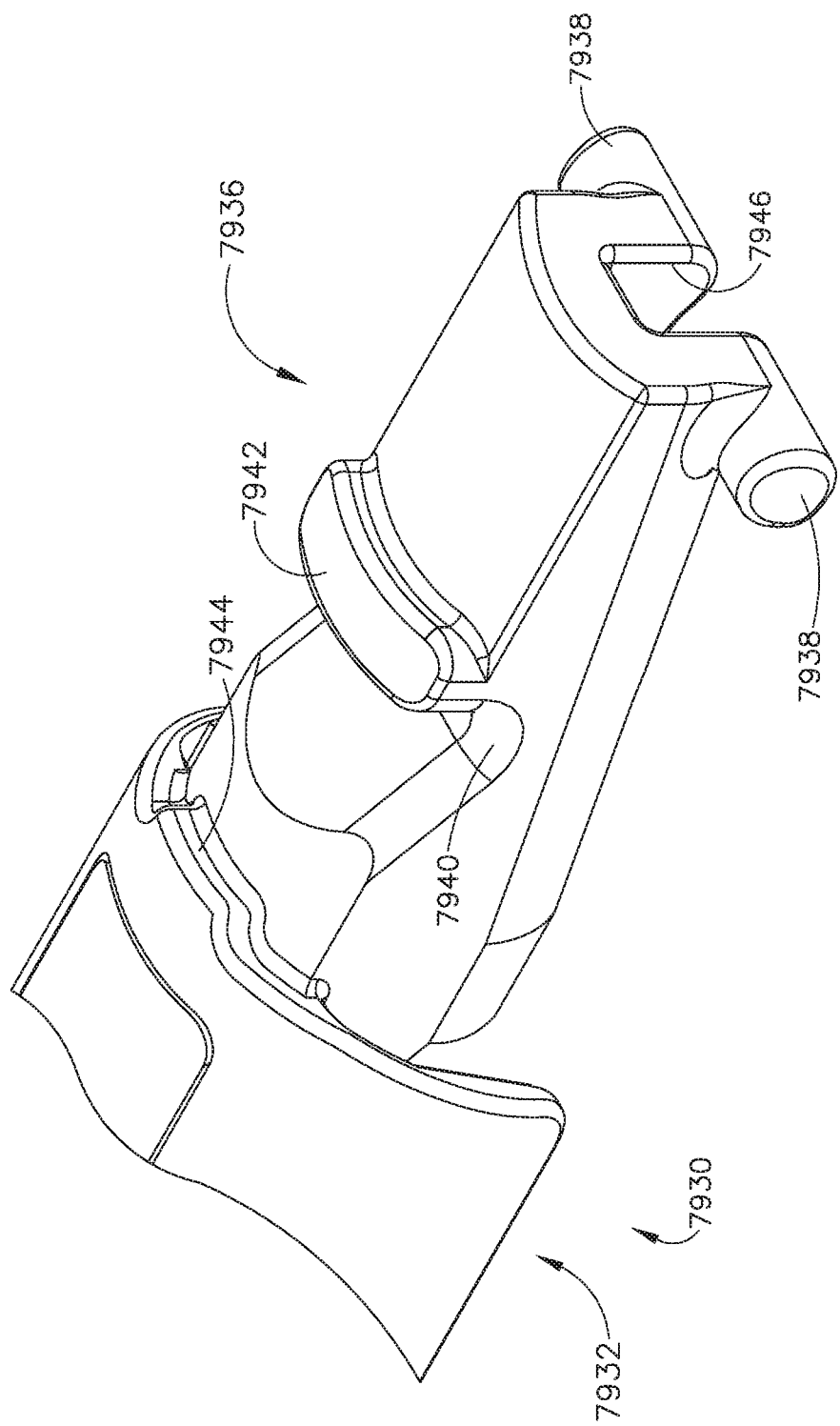
FIG. 70 is a rear perspective view of a portion of an anvil embodiment.

The distal closure tube segment 8080 is configured to apply opening and closing motions to the anvil assembly 7930. As can be seen in FIG. 70, one form of the anvil mounting portion 7936 may be formed with a groove 7940 that defines an anvil tab 7942. As can be seen in FIGS. 69 and 71, the distal end 8088 of the distal closure tube segment 8080 has an inwardly extending actuation tab 8090 formed therein that is configured to interact with the anvil tab 7942. For example, when the distal closure tube segment 8080 is in the open position (FIGS. 69 and 71), the actuation tab 8090 is in biasing contact with the anvil tab 7942 which serves to pivot the anvil assembly 7930 to the open position. As shown in FIG. 72, when the anvil assembly 7930 is in an open position, the trunnions 7938 are located in the bottom of the trunnion slots 7906 in the proximal mounting portion 7904 of the elongated channel 7902. When the distal closure tube segment 8080 is advanced distally, the distal end 8088 contacts an upstanding end wall 7944 on the anvil body 7932 to cause the anvil assembly 7930 to pivot or otherwise move toward the surgical fastener cartridge 7910. When assembled, the trunnions 7938 each extend into a corresponding opening 8092 in the distal closure tube segment 8080. See FIG. 69.

Operation of the closure drive system 8000 will now be described. The anvil assembly 7930 may be moved relative to the surgical fastener cartridge 7910 by pivoting the closure trigger toward and away from the pistol grip portion 7828 of the handle 7822. Thus, actuating the closure trigger 8002 causes the proximal closure tube segment 8010, the intermediate tube segment 8050 and the distal closure tube segment 8080 to move axially in the distal direction "DD" to contact the end wall 7944 of the anvil body portion 7932 to pivot or otherwise move the anvil 7930 toward the surgical fastener cartridge 7910. The clinician may grasp and manipulate tissue between the anvil assembly 7930 and the fastener cartridge 7910 by opening and closing the anvil assembly 7930. Once the target tissue is captured between the anvil assembly 7930 and fastener cartridge 7910, the clinician may pivot the closure trigger 8002 to the fully actuated position wherein it is locked in place for firing.

Figure 73:
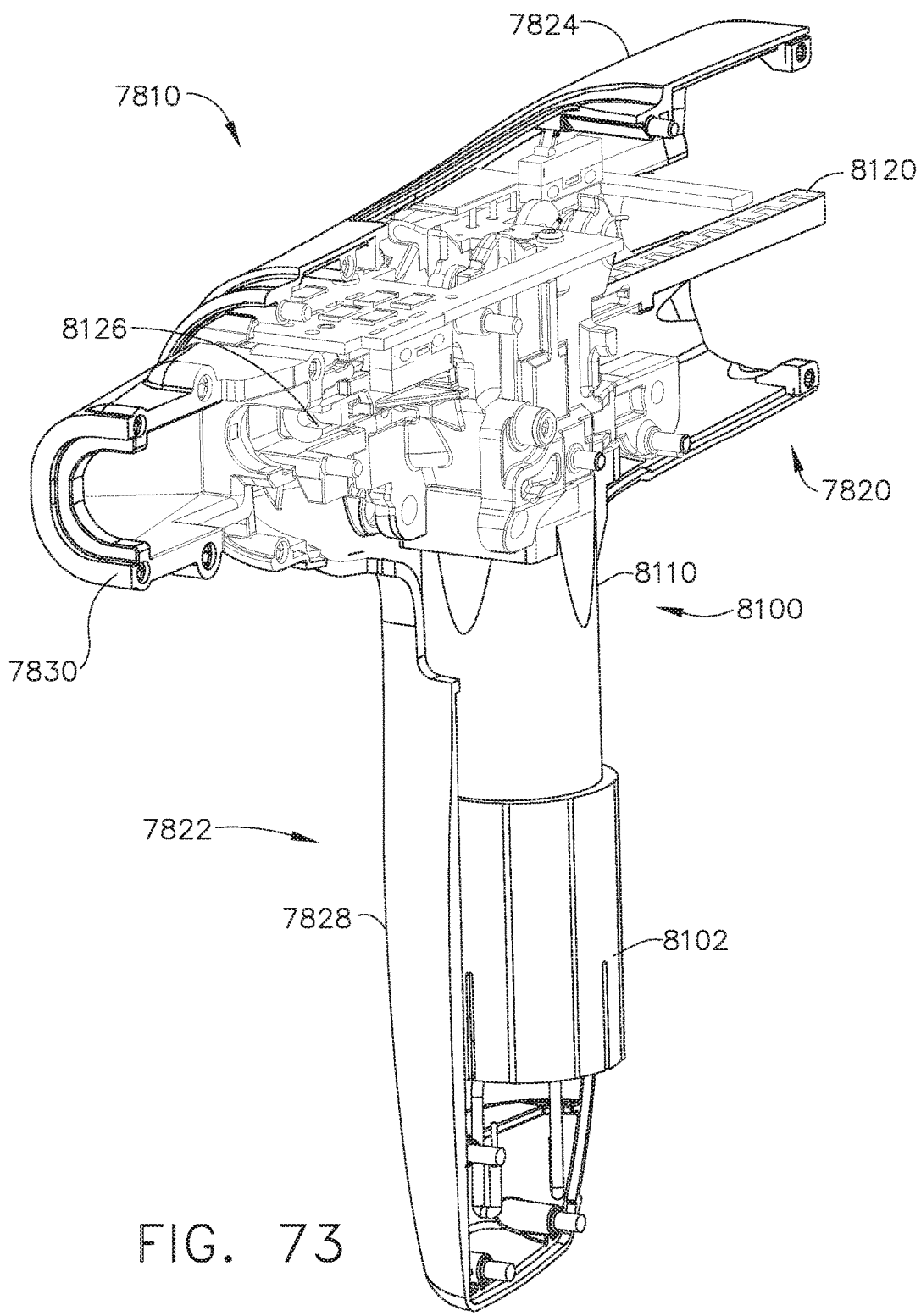
FIG. 73 is a perspective view of a portion of the surgical instrument of FIG. 64 with a portion of the handle housing removed.
Figure 74:
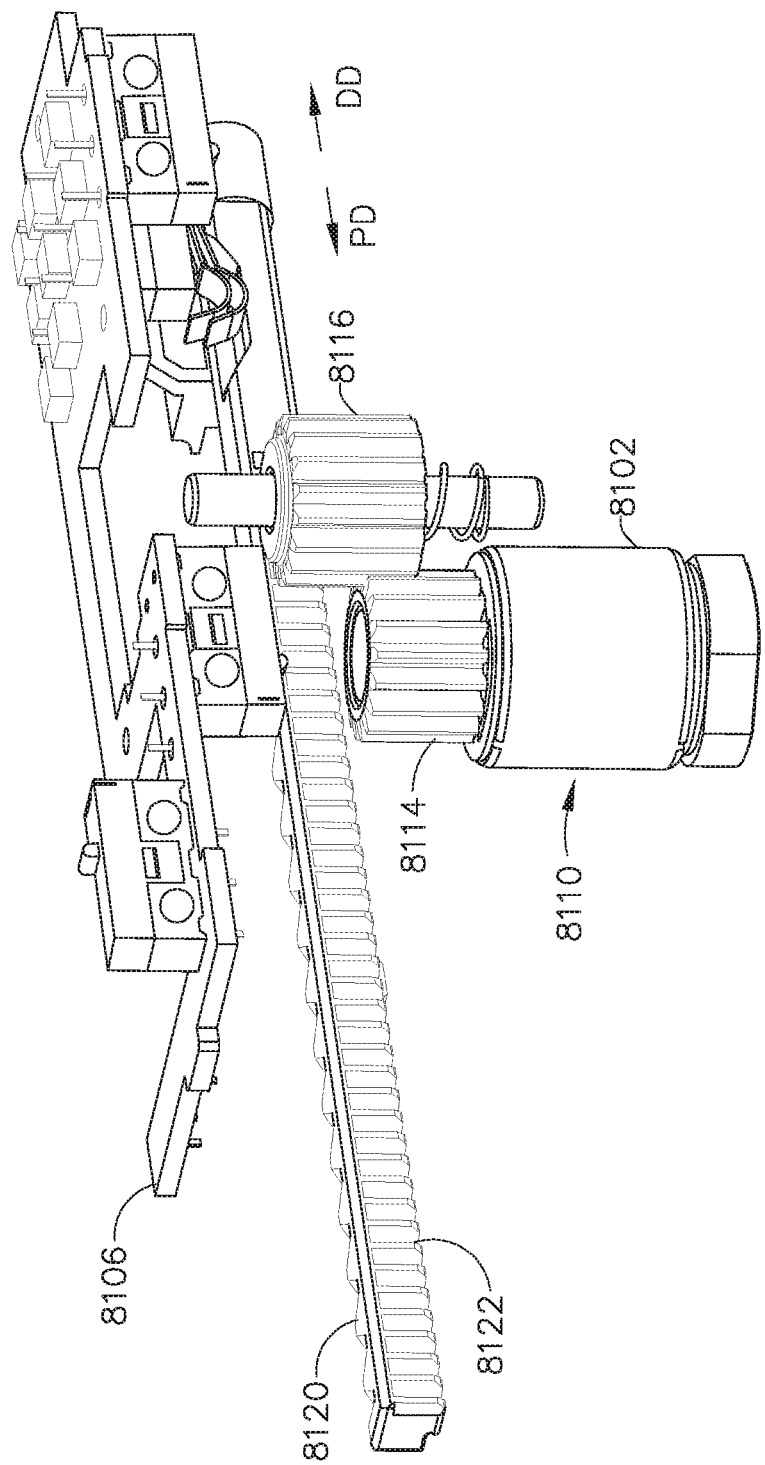
FIG. 74 is a perspective view of a portion of a firing drive system.

As indicated above, the frame 7830 may also be configured to operably support the firing drive system 8100 that is configured to apply firing motions to corresponding portions of the elongated shaft assembly 7850 and ultimately to the knife assembly 7950 and the sled assemblies 7960, 7970. As can be seen in FIGS. 64 and 73, the firing drive system 8100 may employ an electric motor 8102 that is supported in the pistol grip portion 7828 of the handle 7022. In various forms, the motor 8102 may be a DC brushed driving motor having a maximum rotation of, approximately, 25,000 RPM, for example. In other arrangements, the motor 302 may include a brushless motor, a cordless motor, a synchronous motor, a stepper motor, or any other suitable electric motor. A battery 8104 (or "power source" or "power pack"), such as a Li ion battery, for example, may be coupled to the handle 22 to supply power to a control circuit board assembly 8106 and ultimately to the motor 8102. FIG. 66 illustrates a battery pack housing 8105 that is configured to be releasably mounted to the handle 7822 for supplying control power to the surgical instrument 7810. A number of battery cells connected in series may be used as the power source to power the motor 8102. In addition, the power source may be replaceable and/or rechargeable.

As outlined above with respect to other various forms, the electric motor 8102 can include a rotatable shaft 8108 that operably interfaces with a gear reducer assembly 8110 that is mounted in meshing engagement with a with a set, or rack, of drive teeth 8122 on a longitudinally-movable drive member 8120. The gear reducer assembly 8110 can include, among other things, a housing 8112 and an output pinion gear 8114. See FIG. 10. In certain embodiments, the output pinion gear 8114 can be directly operably engaged with the longitudinally-movable drive member 8120 or, alternatively, operably engaged with the drive member 8120 via one or more intermediate gears 8116. The intermediate gear, in at least one such embodiment, can be meshingly engaged with the set, or rack, of drive teeth 8122 defined in the drive member 8120. In use, the electric motor 8102 can move the drive member distally, indicated by an arrow "DD", and/or proximally, indicated by an arrow "PD", depending on the direction in which the electric motor 8102 rotates the intermediate gear. In use, a voltage polarity provided by the battery can operate the electric motor 8102 in a clockwise direction wherein the voltage polarity applied to the electric motor by the battery can be reversed in order to operate the electric motor 8102 in a counter-clockwise direction. When the electric motor 8102 is rotated in one direction, the drive member 8120 will be axially driven in the distal direction "DD". When the motor 8102 is driven in the opposite rotary direction, the drive member 8120 will be axially driven in a proximal direction "PD". The handle 7822 can include a switch which can be configured to reverse the polarity applied to the electric motor 8102 by the battery. The handle 7822 can also include a sensor that is configured to detect the position of the movable drive member 8120 and/or the direction in which the movable drive member 8120 is being moved.

Actuation of the motor 8102 can be controlled by a firing trigger 8130 that is pivotally supported on the handle 7822. The firing trigger 8130 may be pivoted between an unactuated position and an actuated position. The firing trigger 8130 may be biased into the unactuated position by a spring (not shown) or other biasing arrangement such that when the clinician releases the firing trigger 8130, it may be pivoted or otherwise returned to the unactuated position by the spring or biasing arrangement. In at least one form, the firing trigger 8130 can be positioned "outboard" of the closure trigger 8002 as discussed in further detail in U.S. patent application Ser. No. 13/803,097, now U.S. Patent Application Publication No. 2014/0263542, which has been previously incorporated by reference in its entirety herein. In at least one form, a firing trigger safety button 8132 may be pivotally mounted to the closure trigger 8002. The safety button 8132 may be positioned between the firing trigger 8130 and the closure trigger 8002 and have a pivot arm (not shown) protruding therefrom. When the closure trigger 8002 is in the unactuated position, the safety button 8132 is contained in the handle housing where the clinician cannot readily access it and move it between a safety position preventing actuation of the firing trigger 8130 and a firing position wherein the firing trigger 8130 may be fired. As the clinician depresses the closure trigger 8002, the safety button 8132 and the firing trigger 8130 pivot down to a position wherein they can then be manipulated by the clinician.

As indicated above, in at least one form, the longitudinally movable drive member 8120 has a rack of teeth 8122 formed thereon for meshing engagement with a corresponding drive gear of the gear reducer assembly 8110. At least one form may also include a manually-actuatable "bailout" assembly that is configured to enable the clinician to manually retract the longitudinally movable drive member 8120 should the motor become disabled. U.S. patent application Ser. No. 13/803,097, now U.S. Patent Application Publication No. 2014/0263542, contains further details of one form of bailout assembly that may be employed. U.S. Patent Application Publication No. 2010/0089970, now U.S. Pat. No. 8,608,045, also discloses "bailout" arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is incorporated by reference in its entirety herein.

Referring to FIGS. 67 and 68, various forms of the elongated shaft assembly 7850 may include a firing member assembly 7860 that is supported for axial travel within an articulation shaft assembly 8230 that is part of the articulation system 8200 and which essentially functions as shaft frame or spine. The firing member assembly 7860 may further include a proximal firing shaft 7862 that has a proximal end portion 7864 that is configured to be rotatably received in a distal cradle 8126 provided in a distal end 8124 of the movable drive member 8120. Such arrangement permits the proximal firing shaft 7862 to rotate relative to the movable drive member 8120 while also axially moving therewith. The proximal firing shaft 7862 may further have a slot 7868 formed in its distal end 7866 for receiving a proximal end 7872 of a flexible distal firing shaft assembly 7870 therein. See FIG. 68. As can be seen in that Figure, the proximal end 7872 of the distal firing shaft assembly 7870 may be received within the slot 7868 in the distal firing shaft 7862 and may be pinned thereto with a pin 7873.

The distal firing shaft assembly 7870 may include a central firing beam 7874 that is located between a right sled pusher beam 7876 and a left sled pusher beam 7878. The central firing beam 7874 and the pusher beams 7876, 7878 may, for example, each be fabricated from metal that facilitates axial actuation of the sled assemblies 7960, 7970 in the surgical end effector 7900 while also facilitating flexing thereof when the end effector 7900 is articulated as will be discussed in further detail below. In at least one arrangement, the central pusher beam 7874, the right sled pusher beam 7876 and the left sled pusher beam 7878 may extend through a slot 7946 in the anvil mounting portion 7936. The right sled pusher beam 7876 corresponds to the right sled assembly 7960 and the left sled pusher beam 7878 corresponds to the left sled assembly 7970 movably supported within the elongated channel 7902. Axial movement of the right sled pusher beam 7876 and the left sled pusher beam 7878 will result in the axial advancement of the right and left sled assemblies 7960, 7970, respectively, within the elongated channel 7902. As the right sled assembly 7960 is axially advanced within the elongated channel 7902, it drives the surgical fasteners 7920 supported in the cartridge body 7912 on the right side of the slot 7914 out of their respective pockets 7916 and as the left sled assembly 7970 is axially advanced within the elongated channel 7902, it drives the surgical fasteners 7920 supported within the cartridge body 7912 on the left side of the slot 7914 out of their respective pockets 7916.

The central firing beam 7874 has a distal end 7880 that may be configured to be received within a slot 7951 provided in the knife assembly 7954 and retained therein by, for example, a frictional fit, adhesive, welding, etc. A bottom window 7905 may be formed in a distal end 7903 of the elongated channel 7902 to enable the knife assembly 7950 to be inserted therethrough. In at least one form, the elongated channel 7902 is formed with a right upstanding wall 7907 and a left upstanding wall 7908 that define a centrally-disposed channel slot 7909. Once the knife assembly 7950 is inserted into the bottom window 7905 in the elongated channel 7902, the body portion 7951 of the knife assembly 7950 may be inserted into the channel slot 7909 and advanced proximally in the elongated channel 7902 to be coupled with the distal end 7980 of the central firing beam

7874. A lower channel cover 7911 may be attached to the bottom of the elongated channel 7902 to prevent tissue, body fluids, etc. from entering into the elongated channel 7902 which might hamper the movement of the knife assembly 7950 therein.

In one form, the anvil assembly 7930 may be installed onto the elongate channel 7902 as follows. To commence the installation process, the anvil assembly 7930 is positioned over the elongated channel 7902 such that the trunnions 7938 may be inserted into notches 7913 in the proximal mounting portion 7904 of the elongated channel 7902 which enable the trunnions 7938 to enter the corresponding trunnion slots 7906 in the elongated channel 7902. See FIG. 65. This installation may be performed before the distal closure tube segment 8080 has been attached to the intermediate tube segment 8050 or after the distal closure tube segment 8080 has been moved sufficiently proximally to permit the anvil to be so positioned. Once the trunnions 8038 are received within their respective trunnion slots 7906, the distal closure tube segment 8080 may be moved to the position shown in FIGS. 71 and 72 wherein the distal closure tube segment 8080 retains the trunnions 7938 in their respective trunnion slots 7906 and the actuation tab 8090 is in biasing contact with the anvil tab 7942 which serves to pivot the anvil assembly 7930 to the open position. When in that position, each trunnion 7938 protrudes into a corresponding opening 8092 in the distal closure tube segment 8080. See FIG. 69. As shown in FIGS. 65 and 71, when the anvil assembly 7930 is in an open position, the upper end of the knife assembly 7950 enters a window 7933 in the anvil body portion 7932. Such window 7933 provides clearance for the anvil assembly 7930 to be moved to the closed positions while the knife assembly 7950 remains in the unactuated position. Once the anvil assembly 7930 has been installed with the knife assembly 7950 in place, an anvil cover 7935 may be attached to the anvil body 7934 to prevent tissue, body fluids, etc. from entering into the anvil body 7934 which might hamper the movement of the knife assembly 7950 therein. As the knife assembly 7950 is advanced distally in the end effector 7900, the upper tab 7956 of the knife assembly 7950 engages ledges in the anvil body and the lower foot 7954 engages portions 7915 of the elongated channel 7902 and serves to retain the anvil assembly 7930 in the closed position and essentially maintain the spacing between the anvil assembly 7930 and the fastener cartridge 7910.

Figure 70A:
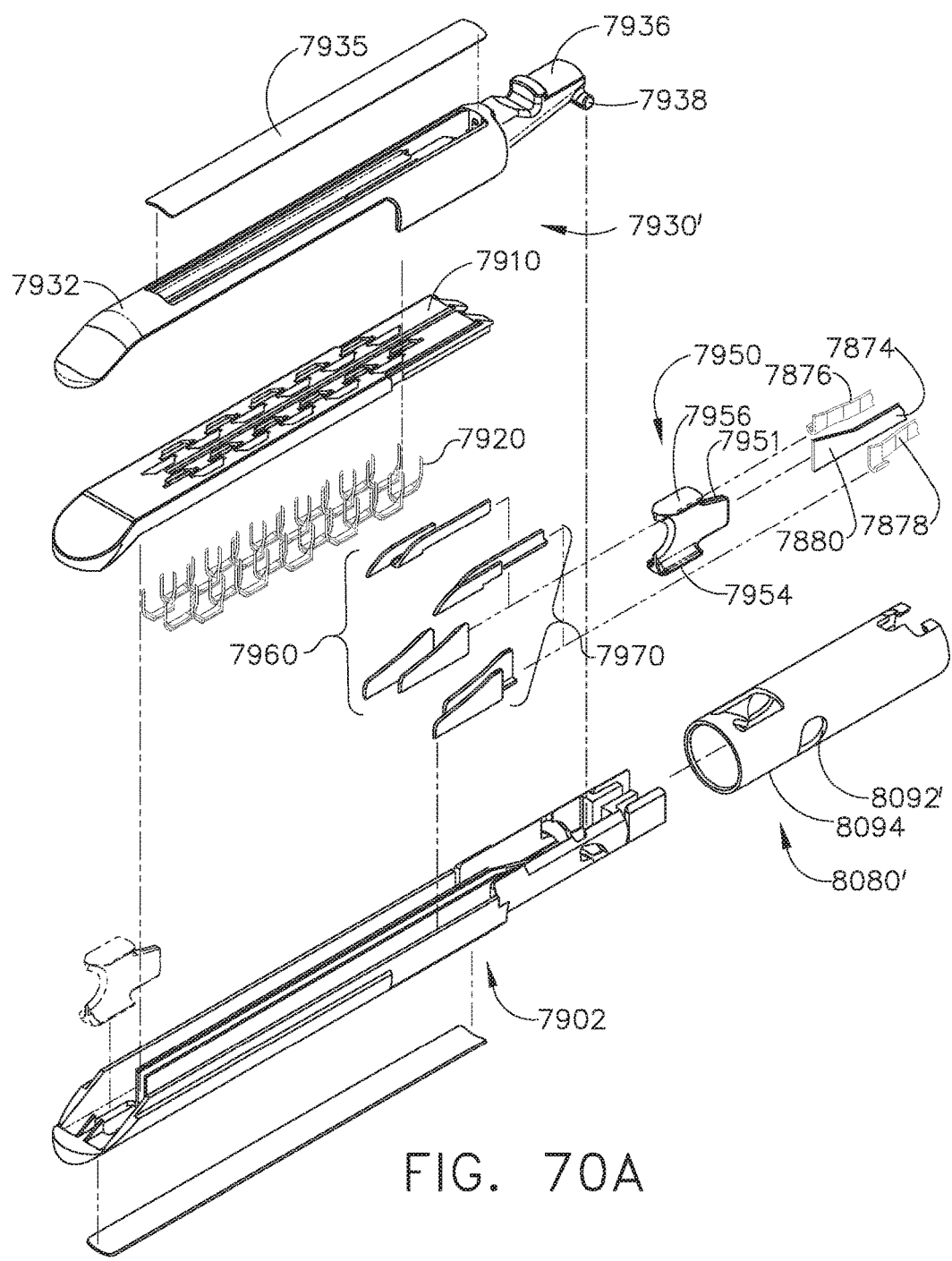
FIG. 70A is an exploded perspective assembly view of another surgical end effector assembly.
Figure 70B:
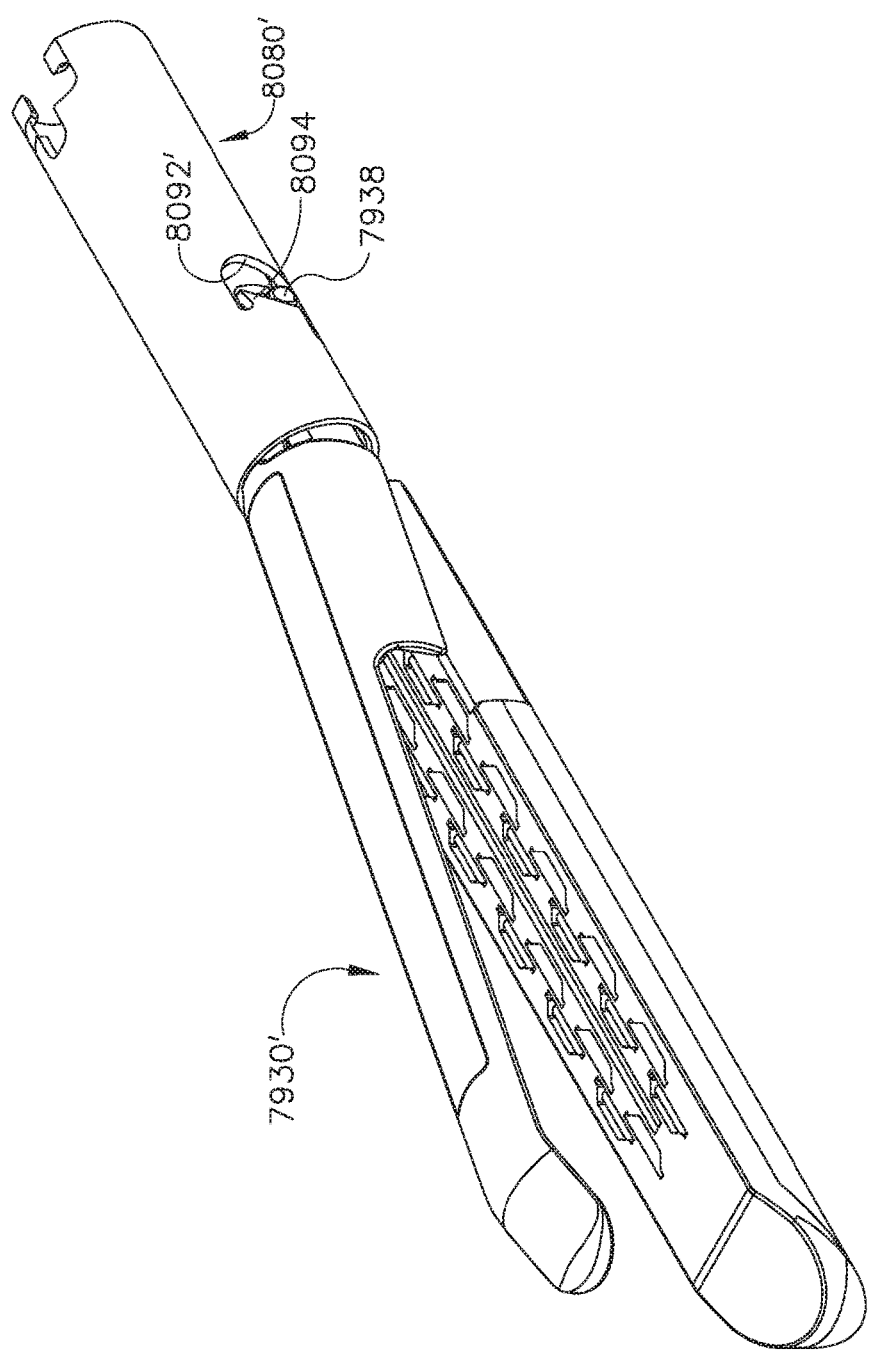
FIG. 70B is a rear perspective view of a portion of another anvil assembly embodiment and another closure tube segment embodiment.
Figure 70C:
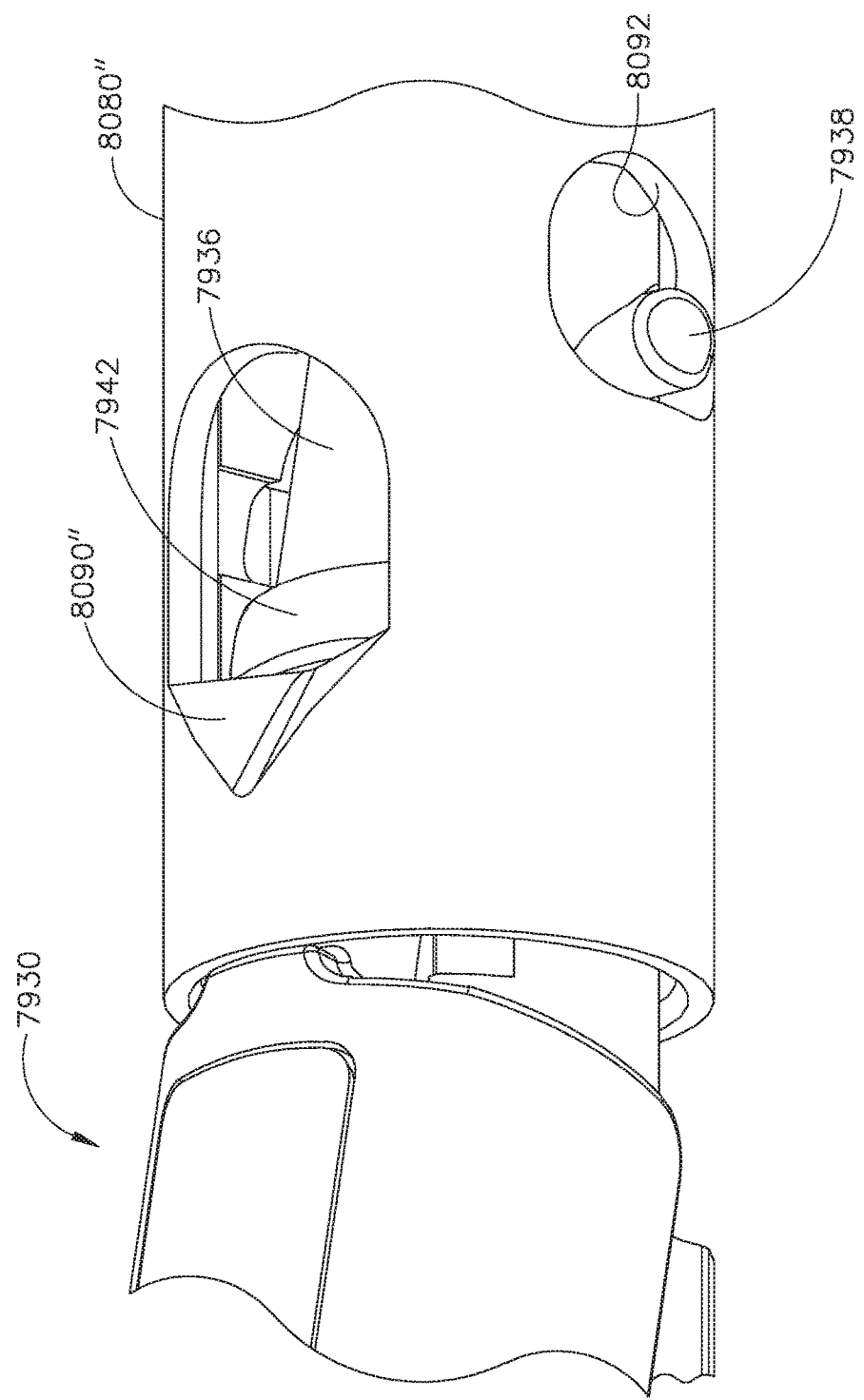
FIG. 70C is a perspective view of a portion of another anvil assembly and another distal closure tube segment.

FIGS. 70A and 70B illustrate an alternative distal closure tube arrangement 8080' that may work with an anvil assembly 7930' that may be substantially identical to anvil assembly 7930 except that anvil assembly 7930' lacks an anvil tab. In such an arrangement, for example, each trunnion 7938 extends into a corresponding opening 8092' in the distal closure tube segment 8080'. The distal closure tube segment 8080' further includes an inwardly extending gill tab 8094 that protrudes inward for contact with the corresponding anvil trunnion 7938. When the distal closure tube segment 8080' is drawn in the proximal direction "PD", each gill tab 8094 contacts the corresponding trunnion 7938 to cause the trunnion to move downwardly in its corresponding trunnion slot 7906 in the elongated channel 7902 to pivot or otherwise move the anvil assembly 7930' into open positions. FIG. 70C illustrates yet another distal closure tube arrangement 8080" wherein the actuation tab is formed by an indentation 8090" in the distal closure tube segment 8080" for interaction with the anvil tab 7942 in the above-described manner.

Figure 70D:
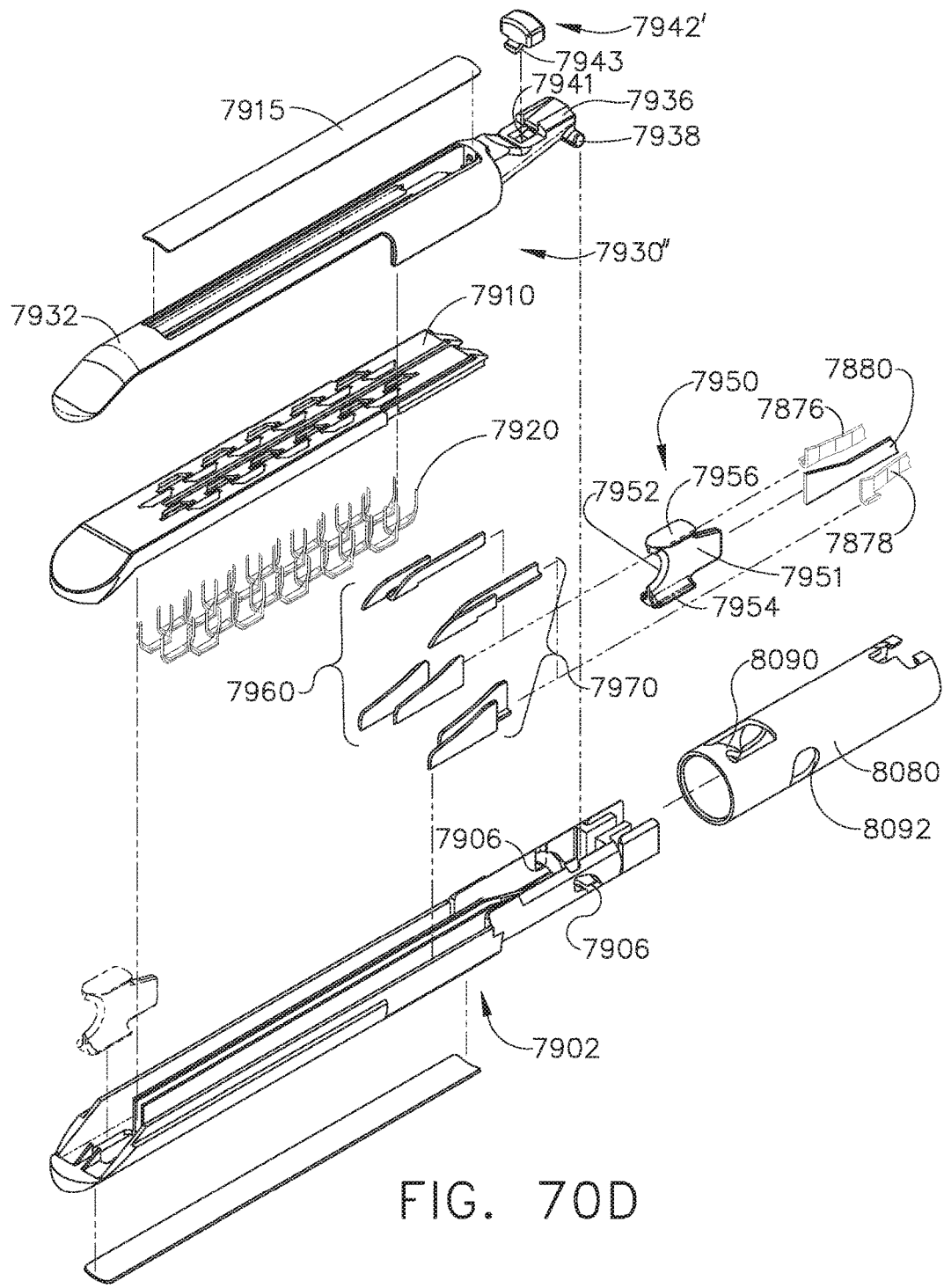
FIG. 70D is an exploded perspective assembly view of another surgical end effector embodiment.
Figure 70E:
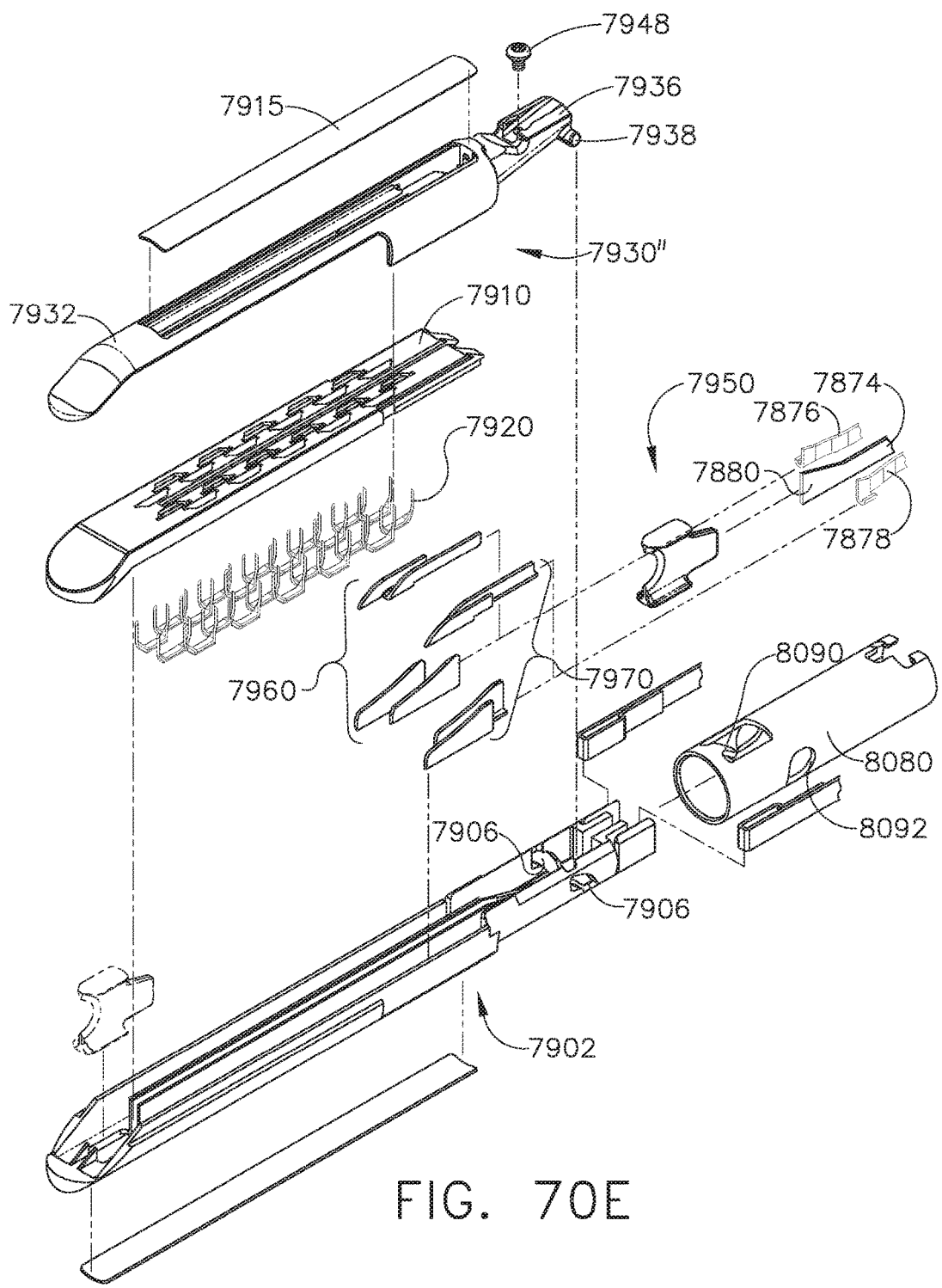
FIG. 70E is an exploded perspective assembly view of another surgical end effector embodiment.

FIG. 70D illustrates an alternative anvil assembly 7930"' wherein the anvil tab 7942' is removably attached to the anvil mounting portion 7936. In one arrangement for example, the anvil tab 7942' is configured with a snap tab 7943 arranged to retainingly engage an opening 7941 in the anvil mounting portion 7936. The anvil assembly 7930"' may otherwise be the same as anvil assembly 7930 described above and be opened and closed in similar manners by the distal closure tube segment 8080. FIG. 70E illustrates yet another anvil assembly 7930"" wherein the anvil tab is formed by a screw 7948 that is removably attachable to the anvil mounting portion 7936. Such removable anvil tab/screw arrangements may facilitate ease of installation of the anvil assembly 7930"".

Referring to FIGS. 67 and 68, one form of articulation system 8200 includes an articulation shaft assembly 8230 that may be operably controlled by an articulation control system 8260. In one form, for example, the articulation shaft assembly 8230 may include a right articulation shaft segment 8240 and a left articulation shaft segment 8250. The right articulation shaft segment 8240 includes a proximal end 8242 that has a right passage segment 8244 formed therein. Likewise the left articulation shaft segment 8250 includes a proximal end portion 8252 that has a left passage segment 8254 formed therein. When the right articulation shaft segment 8240 and the left articulation shaft segment 8250 are installed within the proximal closure tube segment 8010, they form the articulation shaft assembly 8230. The right passage segment 8244 and the left passage segment 8254 cooperate to receive a portion of the proximal firing shaft 7862 therein. The right articulation shaft segment 8240 and the left articulation shaft segment 8250 may be, for example, composed of a plastic, especially a glass fiber-reinforced amorphous polyamide, sold commercially under the trade name Grivory GV-6H by EMS-American Grilon.

In various arrangements, for example, the articulation control system 8260 may include a nozzle assembly 8262 that is supported for rotational travel relative to the handle 7822. As can be seen in FIG. 67, the nozzle assembly 8262 may comprise an upper nozzle segment 8264 and a lower nozzle segment 8266 that are attached together by a series of fasteners (e.g., screws) 8268. The upper nozzle segment 8264 may be configured to rotatably support an articulation control knob 8270 thereon. In one arrangement, for example, the articulation control knob 8270 extends through an opening (not shown) in the upper nozzle segment 8264 and is coupled to an articulation gear member 8272 by screws 8274. The articulation gear member 8272 may include articulation spur gear 8276 that extends into an opening 8016 in the proximal end portion 8012 of the proximal closure tube segment 8010. As can be further seen in FIG. 67, the articulation system 8200 further includes a right actuation tube adapter 8278 and a left articulation tube adapter 8280. The right articulation tube adapter 8278 has a right recess 8279 formed therein that is adapted to receive a right adapter lug 8246 formed on the proximal end 8242 of the right articulation shaft segment 8240. Likewise, the left articulation tube adapter 8280 includes a left recess 8282 that is adapted to engage a left adapter lug 8256 formed on the proximal end 8252 of the left articulation shaft segment 8250. The right articulation tube adapter 8278 further has a series of right articulation drive gears 8281 that are configured for meshing engagement with the articulation spur gear 8276. The left articulation tube adapter 8280 has a series of left articulation drive gears 8284 formed therein that are adapted to intermesh with the articulation spur gear 8276. Thus, when the articulation control knob 8270 is rotated about a control axis CA-CA that is transverse to the longitudinal tool axis LT-LT relative to the handle 7822 (FIG. 64), the left articulation shaft segment 8250 is, for example, driven axially in the distal direction "DD" within the proximal closure tube segment 8010 and the right articulation shaft segment 8240 is simultaneously axially driven in the proximal direction "PD".

Still referring to FIG. 68, the articulation shaft assembly 8230 may further include a right articulation band 8290 and a left articulation band 8300. In one form, a proximal end portion 8292 of the right articulation band 8290 may be attached to a distal portion 8248 of the right articulation shaft segment such that a distal portion 8294 of the right articulation band 8290 protrudes out of a right passage 8249 therein. The proximal end portion 8292 of the right articulation band 8290 may include holes or cavities 8293 that are configured to receive corresponding lugs (not shown) in the right articulation shaft segment 8240 to facilitate attachment of the right articulation band 8290 to the right articulation shaft segment 8240. Likewise, a proximal end portion 8302 of the left articulation band 8300 may have holes or cavities 8303 therein that are configured to receive lugs (not shown) in the distal portion 8258 of the left articulation shaft segment 8250 to facilitate attachment of the left articulation band 8300 to the articulation shaft segment 8250. The articulation bands 8290 and 8300 may be composed of a metal, advantageously full hard 301 stainless steel or its equivalent.

Referring now to FIGS. 75-78, as was briefly discussed above, the intermediate tube segment 8050 may have an attachment stem portion 8052 and a flexible articulation portion 8060. In various arrangements, the intermediate tube segment 8050 may be fabricated from, for example, rigid thermoplastic polyurethane sold commercially as ISO-PLAST grade 2510 by the Dow Chemical Company and include a centrally disposed, vertically-extending articulation spine 8062. The articulation spine 8062 includes a proximal spine end 8064 and a distal spine end 8066 that facilitate attachment to the proximal closure tube segment 8010 and the distal closure tube segment 8080, respectively as was discussed above. The articulation spine 8062 further includes a centrally disposed component or knife slot 8070 for facilitating the passage of various control components therethrough. In the illustrated arrangement, the slot 8070 movably supports the central firing beam 7874, the right pusher beam 7876 and the left pusher beam 7878. In various forms, the centrally disposed slot 8070 is substantially enclosed to retard or prevent infiltration of body fluids and tissue therein which might otherwise hamper the movement of the control components operably passing therethrough.

Figure 78:
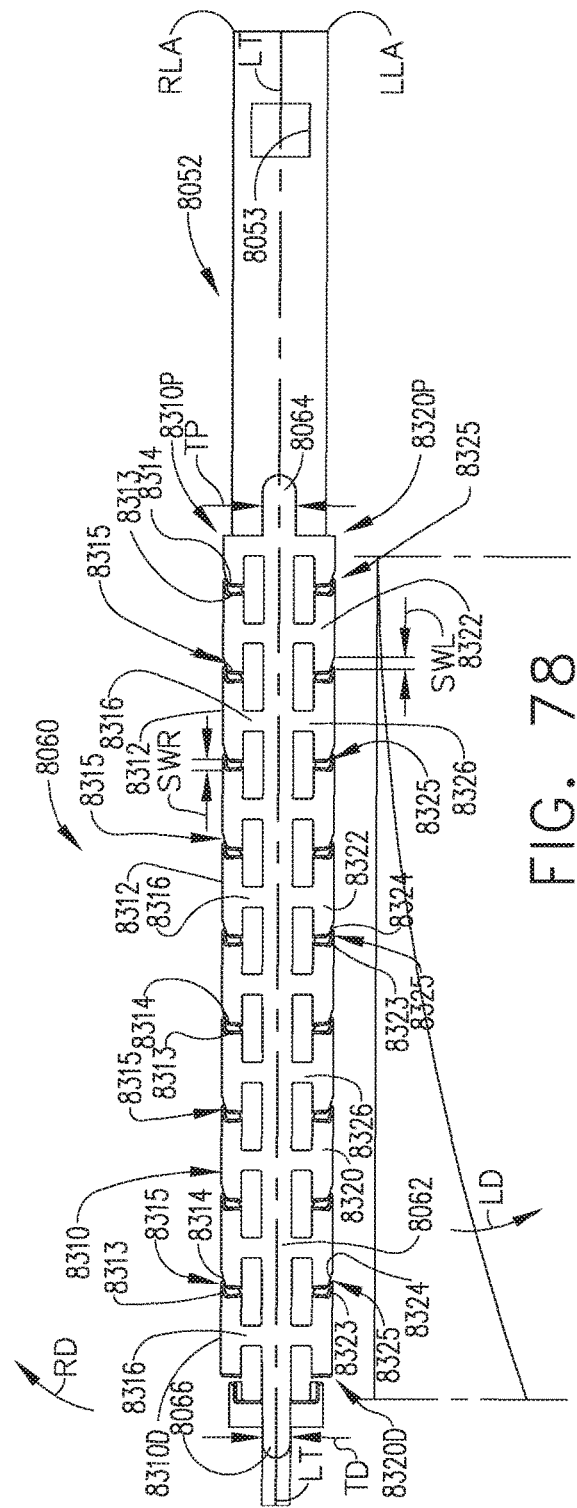
FIG. 78 is a plan view of the intermediate shaft portion of FIGS. 74-77.

As can be most particularly seen in FIG. 78, the flexible articulation portion 8060 further includes a plurality of right ribs 8310 and a plurality of left ribs 8320 that may be integrally-formed with, and laterally protrude from, the articulation spine 8062. In various forms, for example, each right rib 8310 may comprise a rib body portion 8312 that is spaced from the articulation spine 8062 by a corresponding right rib neck portion 8316. Likewise, each left rib 8320 may comprise a left rib body portion 8322 that is spaced from the articulation spine 8062 by a left rib neck portion 8326. As can be seen in FIG. 76, the left and right rib body portions 8312, 8322 have an arcuate shape to provide the flexible articulation portion 8060 of the intermediate tube segment 8050 with a substantially-circular cross-sectional shape. Such shape may facilitate easy passage of the intermediate tube segment 8050 through a circular passage such as, for example, an appropriately sized trocar.

In various arrangements, each of the right rib neck portions 8016 serves to define a right articulation passage 8318 for movably receiving the right articulation band 8290 therethrough. The right articulation band 8290 may extend through the right articulation passage 8318 and be coupled to the proximal mounting portion 7904 of the elongate channel 7902. For example, the distal end 8294 of the right articulation band 8290 may have a right hook portion 8296 that is adapted to be coupled to a right attachment portion 8297 of the elongated channel 7902. See FIG. 65. Similarly, each of the left rib neck portions 8326 serves to define a left articulation passage 8328 for movably receiving the left articulation band 8300 therethrough. The left articulation band 8300 may extend through the left articulation passage 8328 and be coupled to the proximal mounting portion 7904 of the elongated channel 7902. For example, the distal end 8304 of the left articulation band 8300 may have a left hook portion 8306 that is adapted to be coupled to a left attachment portion 8307 of the elongated channel 7902.

One method of operating the articulation system 8200 will now be described. When the clinician wishes to articulate the end effector 7900 to the right relative to the longitudinal tool axis LT-LT (the right direction is represented by arrow "RD" in FIG. 78), the clinician simply rotates the articulation control knob 8270 in the appropriate direction. For example, turning the control knob 8270 in a clockwise direction (when viewed from above) causes the left articulation band to be pushed in the distal direction "DD" and the right articulation band 8290 is drawn in the proximal direction "PD" which serve to apply an articulation motion to the elongated channel 102. As the articulation motion is applied to the elongated channel 7902, the flexible articulation portion 8060 flexes to accommodate the movement of the surgical end effector 7900 in the "right" direction. Conversely, if the clinician wishes to articulate the end effector 7900 in the left direction "LD", the clinician simply rotates the control knob 8270 in a counterclockwise direction which causes the right articulation band 8290 to be pushed in the distal direction "DD" and the left articulation band 8300 to be drawn in the proximal "PD" direction thereby causing the surgical end effector 7900 to move to the left. The end effector 7900 may also be articulated by a robotic system (not shown) that is configured to apply control motions to the articulation bands 8290, 8300.

Upon application of the above-described articulation motions to the surgical end effector 7900, it may be desirable to avoid twisting or torquing the flexible articulation portion 8060 of the intermediate tube segment 8050. If such torque or twisting were to occur, the possibility exists for hampering or, in instances of severe twisting, completely jamming the operation of the central firing beam 7874 and the right and left sled pusher beams 7876, 7878. To avoid this problem, the right and left ribs 8310, 8320 may be uniquely configured to prevent twisting between the ribs.

In at least one arrangement, for example, each rib body 8312 has lateral ends that are arranged in spaced, confronting relationship with the lateral ends of the rib bodies of adjacent ribs. Referring again to FIG. 78, for example, the rib body 8312 of each right rib 8310 has a first right lateral end 8313 and a second right lateral end 8314. With the exception of the proximal-most right rib 8310P and the distal-most right rib 8310D, the first right lateral end 8313 of one right rib 8310 is in confronting relationship with the second right lateral end 8314 of an adjacent right rib 8310. When the flexible articulation portion 8060 of the intermediate tube segment 8050 is unarticulated (e.g., the flexible articulation portion 8060 is substantially aligned on the longitudinal tool axis LT-LT), the first right lateral end 8313 of each right ribs 8310 is spaced from the second right lateral end 8314 of the adjacent right rib 8310 by a right rib space 8315. In the arrangement depicted in FIG. 78, for example, all of the right rib spaces 8315 have substantially the same space width "SWR". Likewise, the rib body 8322 of each left rib 8320 has a first left lateral end 8323 and a second left lateral end 8324. With the exception of the proximal-most left rib 8320P and the distal most left rib 8320D, the first left lateral end 8323 of one left rib 8320 is in confronting relationship with the second left lateral end 8324 of an adjacent left rib 8320. When the flexible articulation portion 8060 of the intermediate tube segment 8050 is unarticulated, the first left lateral end 8323 of each left rib 8320 is spaced from the second left lateral end 8324 of the adjacent left rib 8320 by a left rib space 8325. In the arrangement depicted in FIG. 78, for example, all of the left rib spaces 8325 have substantially the same space width "SWL". In at least one form, the right rib space widths SWR are substantially the same as the left rib space widths SWL. However, the right and left rib space widths may differ from each other.

Figure 77:
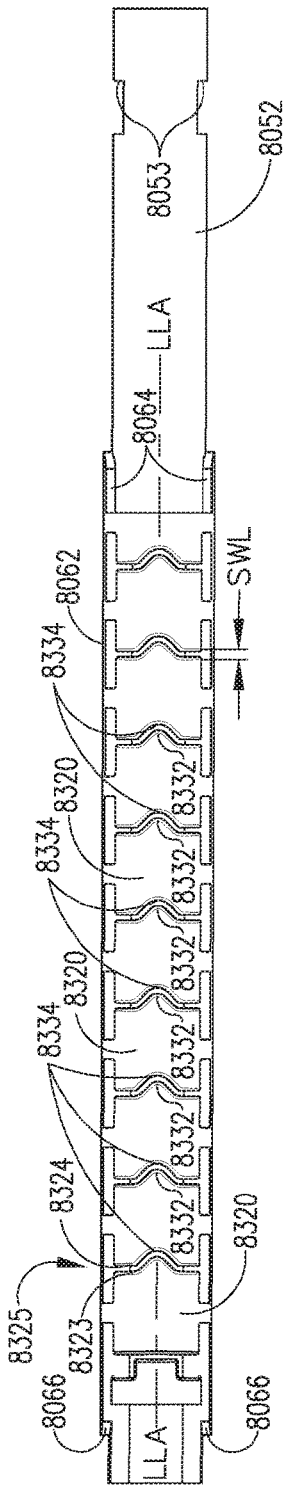
FIG. 77 is side elevational view of the intermediate shaft portion of FIGS. 74 and 75.

Still referring to FIG. 78, each rib may be provided with a twist-preventing configuration, generally designated as 8330. In at least one arrangement, for example, an anti-twist protrusion 8332 may be formed on each of the first right lateral ends 8313 of the right rib bodies 8312 and on each of the first left lateral ends 8323 of each of the left rib bodies 8322. Each anti-twist protrusion 8332 corresponds with a substantially complementary-shaped recces 8334 formed in the rib that is immediately adjacent and in confronting relationship therewith. FIG. 77 illustrates this arrangement on the left ribs 8320. In at least one arrangement, the right ribs 8310 employ an identical configuration. In at least one form, the protrusions 8332 may be substantially aligned along a lateral axis. That is, the protrusions 8332 formed on the right ribs 8310 may be substantially aligned along a right lateral axis RLA-RLA on the right side of the articulation spine 8062 and the protrusions 8332 formed on the left ribs 8320 may be substantially aligned on the left side of the articulation spine 8062 along a left lateral axis LLA-LLA. When the flexible portion 8060 is unarticulated, the right lateral axis RLA-RLA, the left lateral axis LLA-LLA and the longitudinal tool axis LT-LT may be substantially parallel to each other. As can be see in FIG. 78, the right lateral axis RLA-RLA and the left lateral axis LLA-LLA are spaced from the longitudinal tool axis LT-LT.

Figure 79:
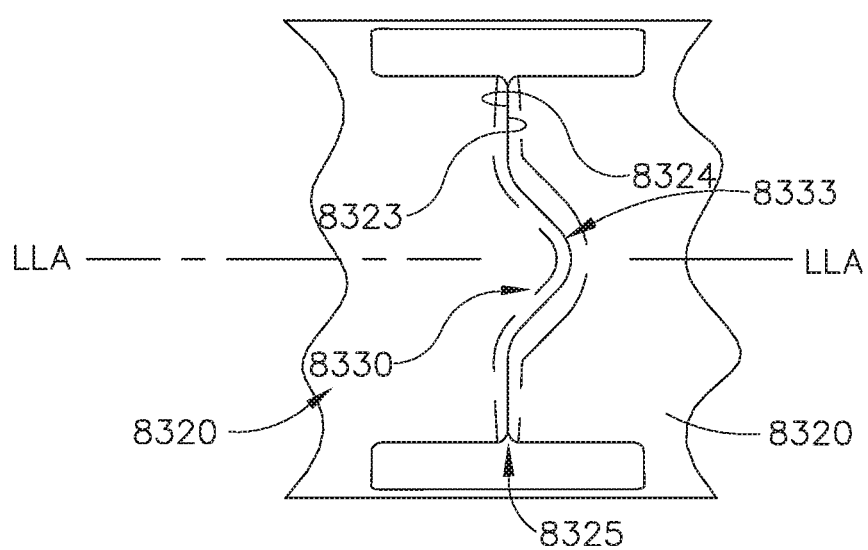
FIG. 79 is an enlarged side elevational view of portions of adjacent ribs of the intermediate shaft portion of FIGS. 74-78.

As the flexible articulation portion 8060 is articulated in the right direction "RD", at least some of the protrusions 8332 on the right ribs 8310 will frictionally engage a portion of a corresponding recess 8332 in an adjacent right rib 8310 to prevent the flexible portion 8060 from twisting. Similarly, as the flexible articulation portion 8060 is articulated in the left direction "LD", at least some of the protrusions 8332 on the left ribs 8320 will engage a portion of the recess 8332 in an adjacent left rib 8320 in a "twist-preventing orientation" to prevent the flexible portion 8060 from twisting. This engagement/orientation between the protrusion 8332 and the bottom of the cavity 8334 in an adjacent left rib 8320, for example, is illustrated in FIG. 79. As can be seen in that Figure, in that example, the first left lateral end 8323 of one of the second rib 8320 is in abutting contact with the second left lateral end 8324 of an adjacent left rib 8320 to thereby prevent or retard twisting of the flexible portion 8060 of the intermediate tube segment 8050.

Various alternative anti-twist arrangements are also contemplated. For example, the anti-twist features may not provided on, for example, the proximal-most four ribs. In still other arrangements, the anti-twist features may be provided in a plurality of ribs comprising a central area of the flexible segment, but not in the proximal-most and distal most ribs. In, other arrangements, the anti-twist features may be employed on every other pair of ribs along the length of the flexible segment. For example, the proximal-most pair of adjacent ribs may have anti-twist features, then the next rib or ribs (distal to those ribs) may not have anti-twist features and the next ribs (distal thereto) may have the anti-twist features and so on. These alternative arrangements may be applied only to the ribs on one side of the articulation spine or they may be employed on the ribs on both sides of the articulation spine. By altering the number, location and/or spacing of the ribs with the anti-twist features, as well as the space widths between the ribs (with and without anti-twist features), as well as the geometric shape of the articulation spine, one can advantageously adjust the overall flexibility of the flexible segment, its degree of articulation, its degree of stiffness and its rate of articulation.

Referring to FIGS. 75 and 76, in the illustrated arrangement, the articulation spine 8062 is elongated and has a height, generally designated as "H". In at least one arrangement, the height "H" is substantially consistent for the length "L" of the articulation spine 8062. In addition, the articulation spine 8062 may decreasingly taper from the proximal end portion 8064 to the distal end portion 8066. More specifically, as can be seen in FIG. 75, the proximal end portion 8064 has a proximal width "PW" and the distal end portion 266 has a distal width "DW". In the illustrated embodiment, the "PW" is greater than the distal width "DW" and the width of the articulation spine 8062 gradually tapers in width (as opposed to height) from the proximal end 8064 to the distal end 8066 along length "L". Such tapered articulation spine arrangement further serves to retard twisting during articulation of the surgical end effector while facilitating increased articulation of the distal end of the flexible portion 8060 relative to the proximal end of the flexible portion 8060 and while facilitating movable passage of various control components (e.g., central firing beam 7874, right sled pusher beam 7876, left sled pusher beam 7878, etc.) therethrough.

Figure 82:
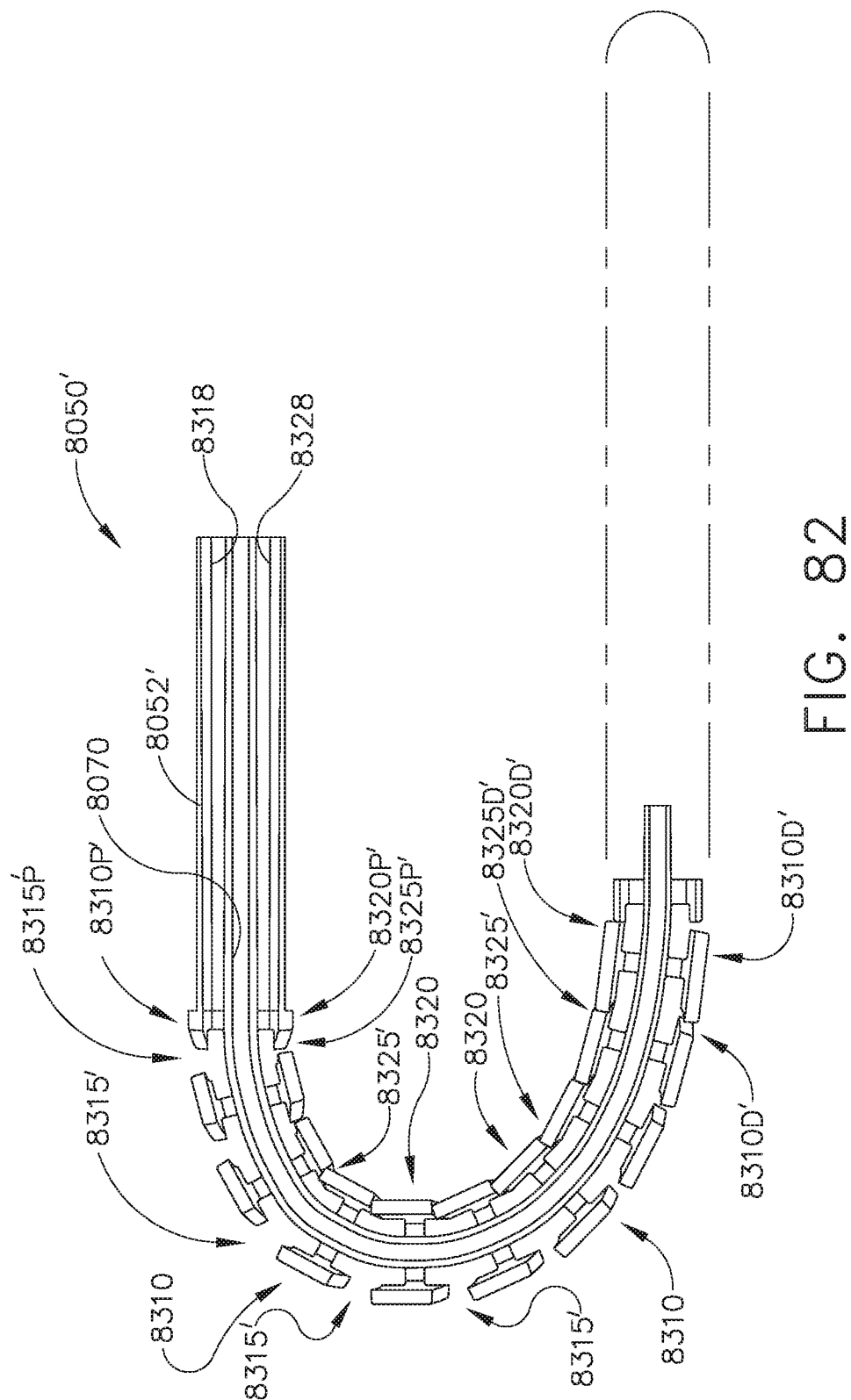
FIG. 82 is a cross-sectional plan view of the intermediate shaft portion of FIGS. 80 and 81 articulated into a substantial U-shape.

Further, in one arrangement, when the flexible portion 8060 is in an unarticulated or flexed position, all of the right rib spaces 8315 and left rib spaces 8325 have the same starting width. Thus, in that configuration, SWR=SWL. FIGS. 80 and 81 illustrate another intermediate tube segment 8050' that may be substantially identical to the intermediate tube segment 8050 described above, except that the right rib spaces 8315 and the left rib spaces 8325 decrease in magnitude going from the proximal end of the flexible articulation portion 8060' to the distal end of the flexible articulation portion 8060'. That is, the proximal-most right rib space 8315P' is the widest right rib space and the distal most right rib space 8315D' is the narrowest right rib space with the right rib spaces 8315' getting successively narrower going in the distal direction "DD". Similarly, the proximal-most left rib space 8325P' is the widest left rib space and the distal-most left rib space 8325D' is the narrowest left rib space with the left rib spaces 8325' getting successively narrower going in the distal direction. In such arrangement, when the articulation motion is applied to the surgical end effector, the flexible portion 8060 will have a faster rate of flexure at its distal end. That is, a distal portion of flexible segment 8060' will flex or articulate at a rate that is greater than a rate at which another portion of 8060' that is proximal to that distal segment will articulate upon application of an articulation motion to the end effector. Stated another way, relative movement between the ribs on the distal end will stop before the relative movement between the more proximal ribs stops because the spaces between the distal ribs are smaller than the spaces between the proximal ribs. In the illustrated arrangement the widths of the right and left rib spaces 8315' and 8325' that are laterally aligned with each other may be equal in magnitude. Such rib space width arrangements may enable the flexible articulation portion 8060' to assume a substantial "U"-shape if desired. See e.g., FIG. 82. It will be understood, however, that various other slot width arrangements, sizes and configurations may be employed to achieve a desired amount/range of articulation while preventing the intermediate tube from inadvertently twisting about the longitudinal tool axis.

Figure 83:
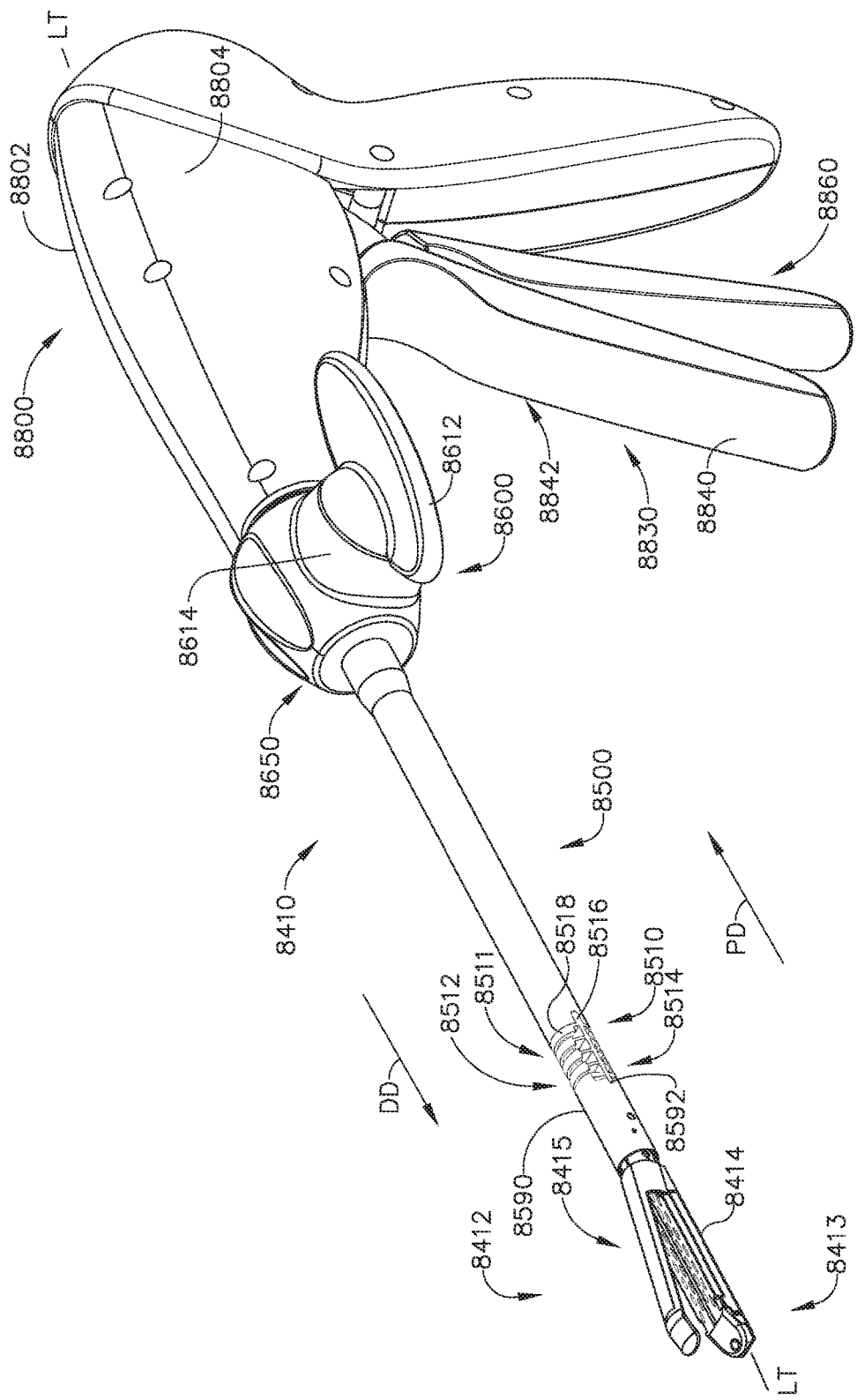
FIG. 83 is a perspective view of one surgical instrument arrangement.

FIG. 83 depicts another surgical instrument 8410 that is capable of practicing several unique benefits of the present invention. The surgical instrument 8410 is designed to manipulate and/or actuate various forms and sizes of end effectors 8412 that are operably attached to an elongated shaft assembly 8500 of the surgical instrument. In the depicted embodiment, for example, the end effector 8412 comprises a surgical stapling device that has openable and closable jaws 8413 and 8415. More specifically, the end effector 8412 includes an elongated channel 8414 that forms a lower jaw 8413 of the end effector 8412. See FIG. 84. In the illustrated arrangement, the elongated channel 8414 is configured to operably support a staple cartridge 8430 and also movably supports an anvil 8420 that functions as an upper jaw 8415 of the end effector 8412.

Figure 84:
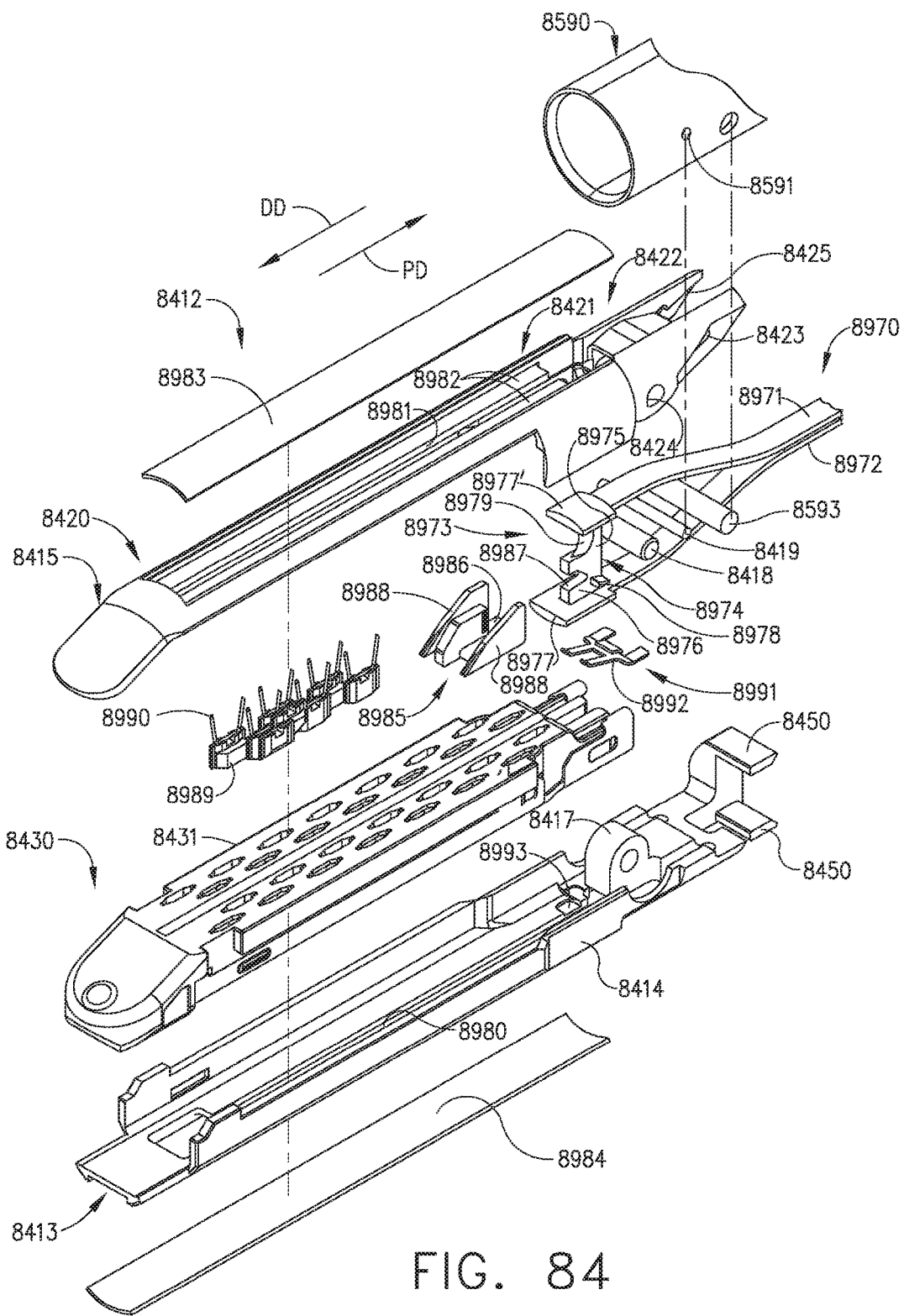
FIG. 84 is an exploded perspective assembly view of a surgical end effector arrangement.
Figure 85:
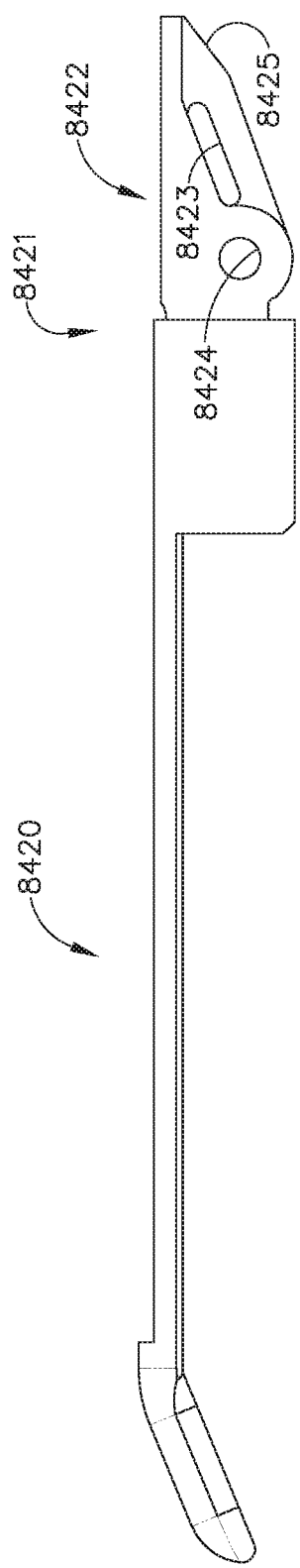
FIG. 85 is a side elevational view of an anvil.
Figure 86:
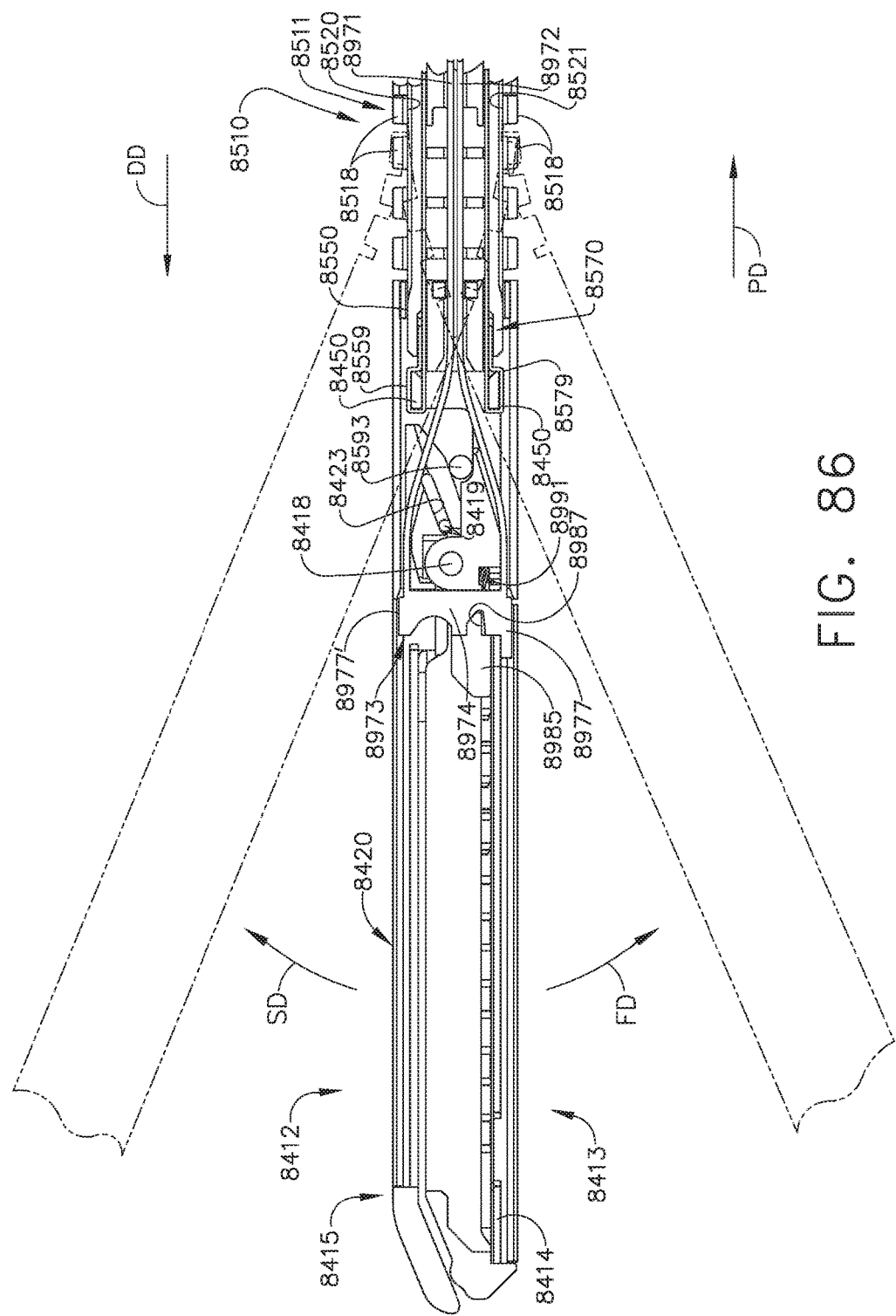
FIG. 86 is a side cross-sectional view of an end effector and portion of an elongated shaft assembly with the end effector shown in an unarticulated position in solid lines and the end effector shown in articulated positions in broken lines.
Figure 87:
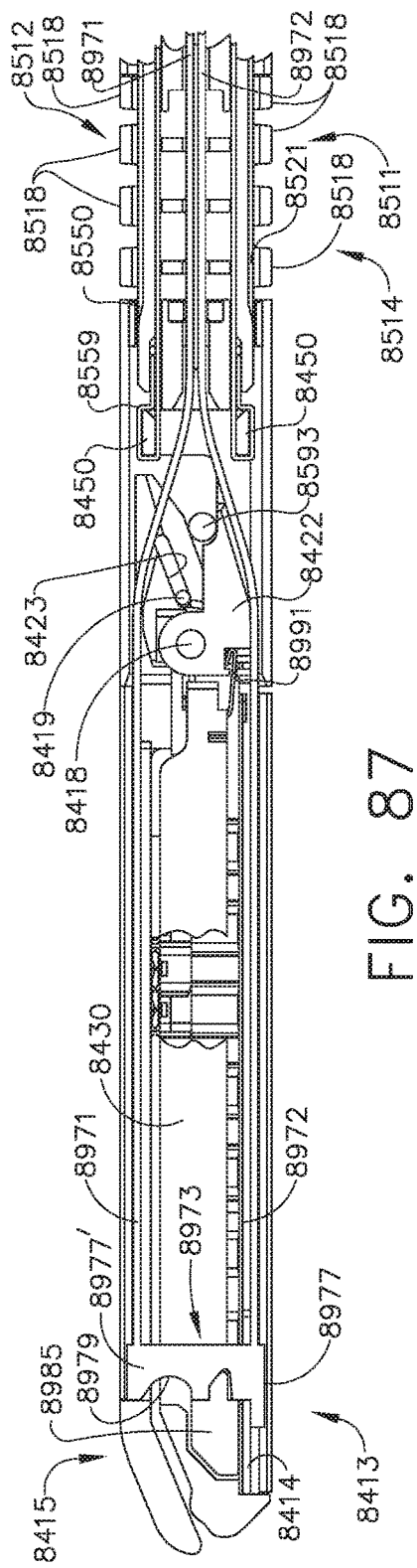
FIG. 87 is another side cross-sectional view of an end effector and portion of an elongated shaft assembly with the anvil in a closed position and the cutting head in an end position after being fired distally through the staple cartridge.
Figure 88:
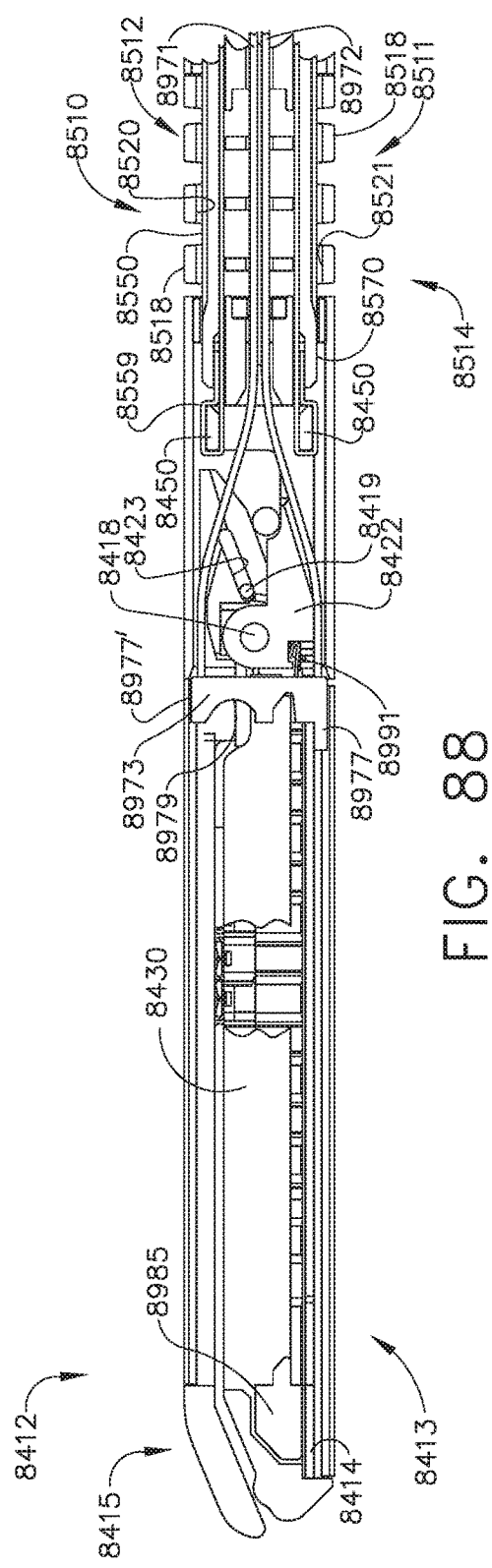
FIG. 88 is another side cross-sectional view of the end effector and elongated shaft assembly portion of FIG. 87 after the cutting head has been retracted proximally back to its starting position.
Figure 91:
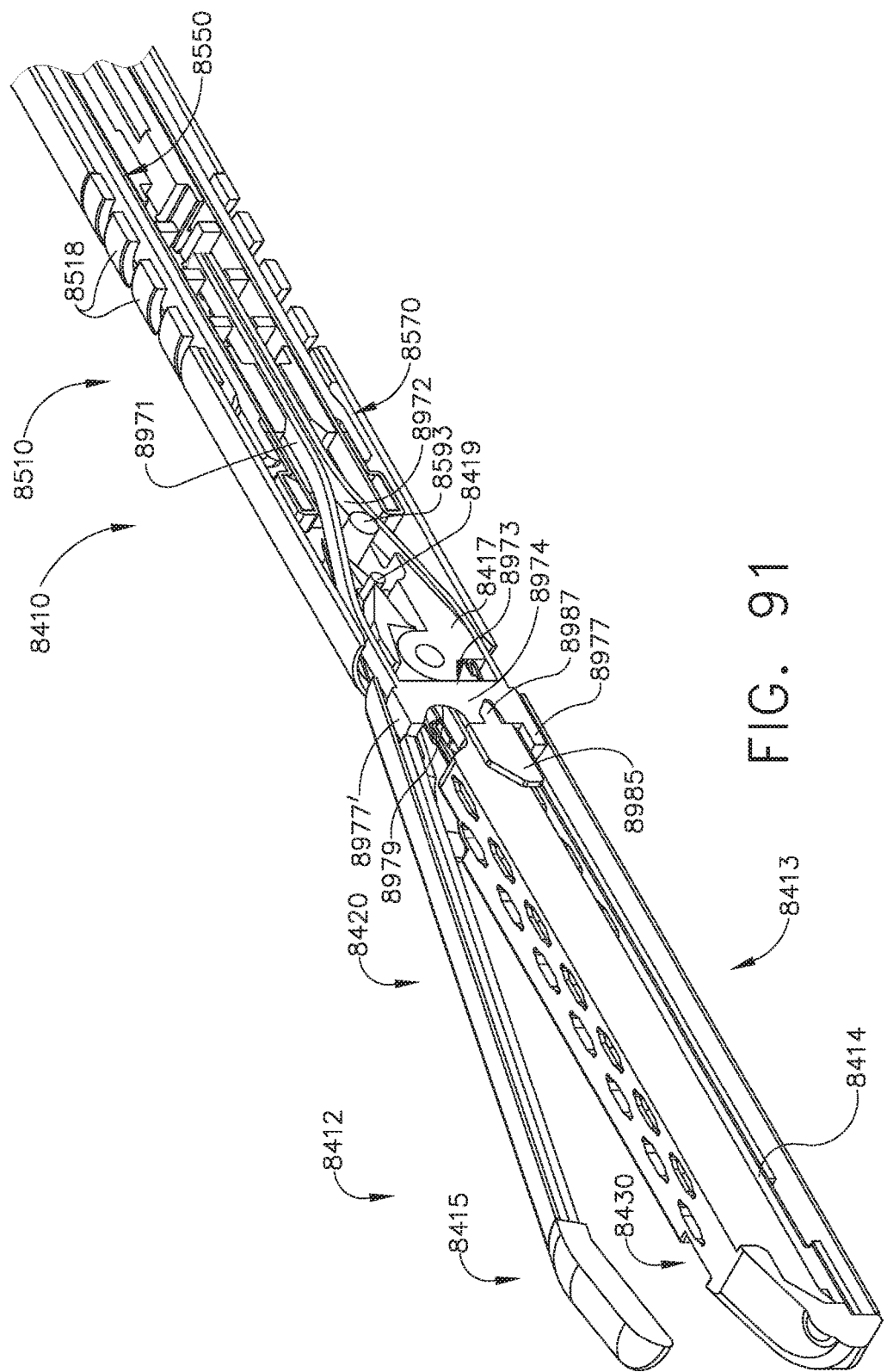
FIG. 91 is cross-sectional perspective view of the end effector and portion of the elongated shaft assembly of FIG. 8.

Referring now to FIGS. 84 and 85, the anvil 8420 may have a mounting portion 8422 that protrudes from its proximal end 8421. The mounting portion 8422 may have lateral mounting holes 8424 therethrough that enable the mounting portion 8422 to be pivotally pinned to an upstanding pivot boss 8417 formed in the elongated channel 8414 by an anvil pin 8418. The anvil 8420 may be selectively "moved" towards the surgical staple cartridge 8430 mounted in the elongated channel 8414 by axially advancing a distal closure tub segment 8590 in the distal direction "DD" as will be discussed in further detail below. In various implementations, for example, a first anvil actuation member in the form of an anvil camming pin 8419 may extend through a camming slot 8423 provided in the anvil mounting portion 8422. The camming pin 8419 is mounted in holes 8591 provided in the distal closure tube segment 8590 such that movement of the distal closure tube segment 8590 in the distal and proximal directions will result in the movement of the camming pin 8419 in the camming slot 8423. In addition, the distal closure tube segment 8590 may further include a second anvil actuation member in the form of, for example, an actuation pin 8593 that is positioned to interact with an angled actuation surface 8425 formed on the proximal end of the anvil mounting portion 8522. FIGS. 89-91 illustrate the anvil 8420 in a first or open position. The anvil 8420 may be moved to a closed position by moving the distal closure tube segment 8590 in the distal direction "DD". Movement of the distal closure tube segment 18590 in the distal direction "DD" causes the first camming pin 8419 to move within the camming slot 8423 in the anvil mounting portion 8422 which thereby causes the anvil 8420 to pivot about the anvil pin 8418 to the closed position as illustrated in FIGS. 86-88. To return the anvil 20 to the open position (FIGS. 89-91), the distal closure tube segment 8590 is moved in the proximal direction "PD" which causes the first camming pin 8419 to move in the camming slot 8423 in an opposite direction and cam the anvil 8420 to the open position. Such closure tube arrangement differs from prior closure tube arrangements wherein the distal end of the closure tube segment is configured to contact the anvil and pivot it to a closed position. Use of the present camming pin arrangements does not require use of an anvil that has a more robust portion configured for actuation contact with the closure tube segment.

In various arrangements, the end effector 8412 may be configured to be selectively articulated about a longitudinal tool axis LT-LT that is defined by the elongated shaft assembly 8500. For example, the elongated shaft assembly 8500 may include a flexible neck assembly 8510 that enables the end effector 8412 to articulate in a first direction "FD" that is essentially the same direction that the anvil 8420 moves in when the anvil 8420 is moved from an open position to a closed position (hereinafter referred to as the anvil closing direction "CD"). See FIGS. 86 and 90. The flexible neck assembly 8510 will further facilitate articulation of the end effector 8412 in a second articulation direction "SD" that is essentially the same as the direction that the anvil moves from a closed position to an open position (hereinafter referred to the anvil opening direction "OD"). See FIGS. 86, 89 and 90.

Various flexible neck assemblies are disclosed in U.S. Provisional Patent Application Ser. No. 61/386,117, filed Sep. 24, 2010, the entire disclosure of which is herein incorporated by reference. Other flexible neck assemblies are disclosed in U.S. Patent Application Publication No. US 2012/0074200 A1, entitled SURGICAL INSTRUMENT WITH SELECTIVELY ARTICULATABLE END EFFECTOR, filed Sep. 23, 2011, the entire disclosure of which is hereby incorporated by reference herein. The flexible neck assembly 110 may, for example, be composed of rigid thermoplastic polyurethane sold commercially as ISO-PLAST grade 2510 by the Dow Chemical Company. The flexible neck assembly 8510 may have a flexible neck segment 8511 that comprises a first or upper flexible neck portion 8512 and a second or lower flexible neck portion 8514. These neck portions 8512, 8514 may be separated by a longitudinal rib portion 8516. The neck portions 8512, 8514 may each have a plurality of neck ribs 8518 that are configured essentially as semi-circular disks which together generally form a cylindrical configuration. An upper slot 8520 extends through each of the neck ribs 8518 of the first or upper flexible neck portion 8512 to form a passage through the first flexible neck portion 8512 for receiving a first flexible transmission band assembly 8550 therethrough. Similarly, a lower slot 8521 extends through each of the neck ribs 8518 in the second or lower flexible neck portion 8514 to form a passage for receiving a second flexible transmission band assembly 8570 therethrough. See, for example, FIG. 86. The flexible neck assembly 8510 may include guide surfaces 8524 (only one can be seen in FIG. 92) that extend proximally from the flexible neck segment 8511 for supporting the reciprocating movement of the flexible transmission band assemblies 8550, 8570.

Figure 92:
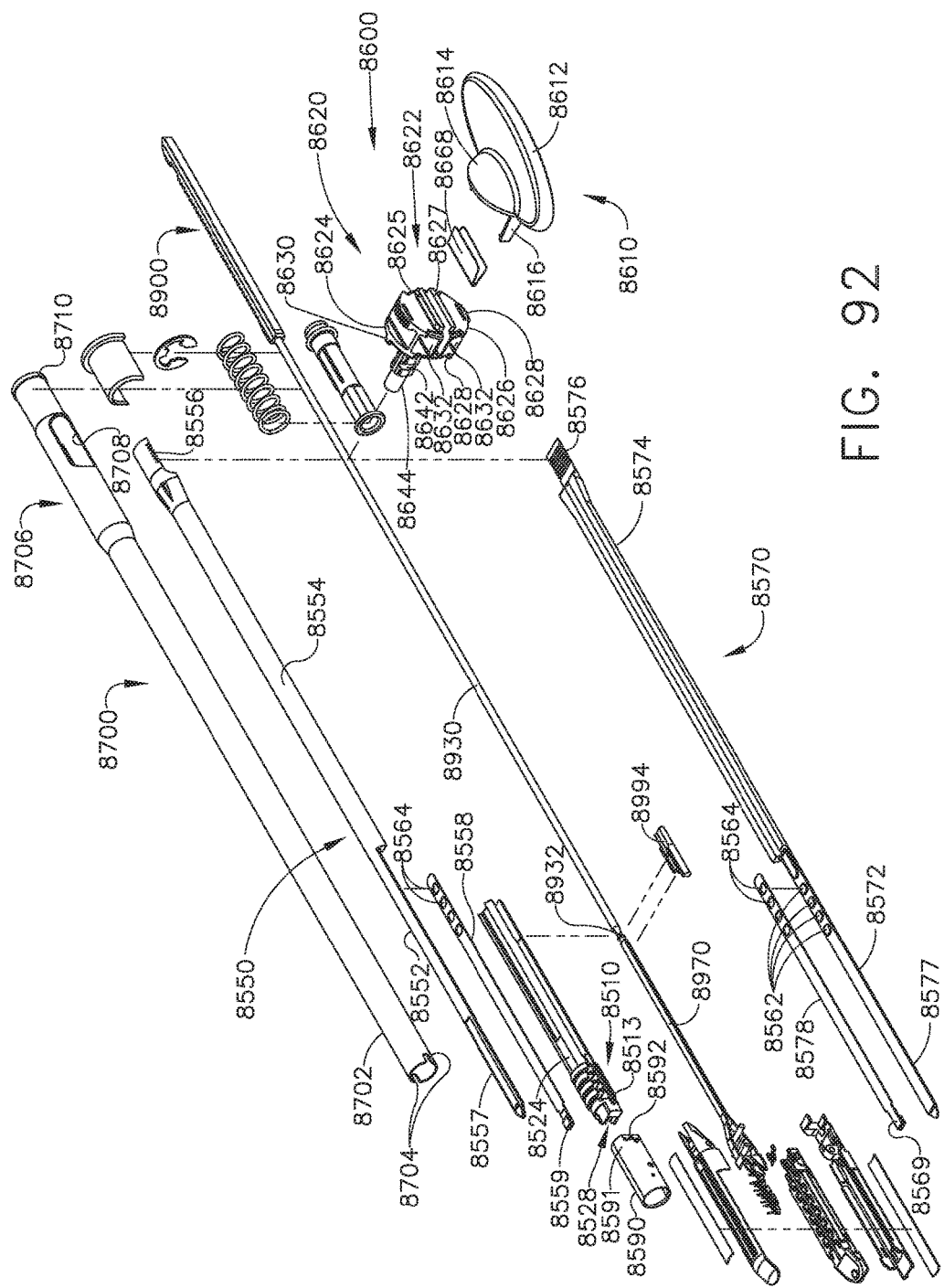
FIG. 92 is a perspective assembly view of an end effector and elongated shaft assembly.

As can be seen in FIG. 92, the first or upper transmission band assembly 8550 may include a first transmission band 8552 and the second transmission band assembly 8570 may include a second transmission band 8572. In addition, the first transmission band 8550 may have a first elongated structural portion 8554 and the second transmission band 8570 may have a second elongated structural portion 8574. When the first and second transmission bands 8550, 8570 are brought into contact with each other during assembly of the instrument, they form an elongated cylinder which has a longitudinal cavity 8560 extending concentrically through it to operably receive a firing rod 530 therethrough. See FIGS. 93 and 94. The first structural portion 8554 of the first transmission band 8552 has a first articulation rack 8556 formed thereon and the second structural portion 8574 of the second transmission band 8572 has a second articulation rack 8576 formed thereon which, as will be discussed in further detail below, drivingly interface with an articulation transmission assembly 8600.

Referring again to FIG. 92, the first transmission band 8552 may have a first exterior reinforcement band portion 8557 that extends distally from the first structural portion 8554. Likewise, the second transmission band 8572 may have a second exterior reinforcement band portion 8577 that extends distally from the second structural portion 8576. Each exterior reinforcement band portion 8557, 8577 may have a plurality of attachment lugs 8562 for securing first and second interior articulation bands 8558, 8578 thereto. For example, the first transmission band 8552 has a first interior articulation band 8558 attached thereto and the second transmission band 8572 has a second interior articulation band 8578 attached thereto. The first and second transmission bands 8552, 8572 may be composed of a plastic, especially a glass fiber-reinforced amorphous polyamide, sold commercially under the trade name Grivory GV-6H by EMS-American Grilon. In contrast, the interior articulation bands 8558, 8578 of the transmission band assembly may be composed of a metal, advantageously full hard 301 stainless steel or its equivalent. The attachment lugs 8562 on the exterior reinforcement band portions 8557, 8577 of the transmission bands 8552, 8572, respectively, are received into and secured within a plurality of lug holes 8564 on the corresponding interior articulation band 8558, 8578. See FIG. 92.

In at least one implementation, the proximal end of the elongated cartridge channel 8414 is provided with a pair of upper and lower band connector ears 8450. See FIGS. 84 and 86-88. These band connector ears 8450 are inserted into and through connector loops 8559, 8579 on the distal end of the interior articulation bands 8558, 8578, respectively. In this manner, the cartridge channel 8414 is coupled to the interior articulation bands 8558, 8578 of the flexible neck assembly 8510. Specifically, the reciprocation of the first and second flexible transmission band assemblies 8550, 8570 in opposite directions causes the interior articulation bands 8558, 8578 received in the upper and lower slots 8520, 8521 on the flexible neck segment 8511 to reciprocate in a like manner. Upon reciprocation of the interior articulation bands 8558, 8578, in particular when the first band 8558 is moved proximally in tandem with the second band 8578 moving distally, the first and second flexible neck portions 8514, 8516 bend as the neck ribs 8518 of the first flexible neck portion 8514 move toward each other and the neck ribs 8518 of the second flexible neck rib portion 8516 concurrently move away from each other. The coupling of the interior articulation bands 8558, 8578 to the exterior reinforcement band portions 8557, 8577 of the transmission bands 8552, 8572, respectively prevents the interior articulation bands 8558, 8578 from buckling between adjacent neck ribs.

In various arrangements, the distal closure tube segment 8590 is slid over the channel guide 8528 of the flexible neck assembly 8510. The proximal end 8591 of the distal closure tube segment 8590 has a pair of diametrically opposed slots 8592 therein (only one can be seen in FIGS. 83 and 92) for receiving distally protruding lugs 8513 protruding from the flexible neck portion 8511 to prevent rotation of the distal closure tube segment 8590 relative to the flexible neck portion 8511. In various embodiments, the distal closure tube segment 8590 may be retained on the channel guide 8528 by a retention tab (not shown) that extends into the fastener hole (not shown) in the channel guide 8528. However, other fastening arrangements may be employed, for example. Such arrangement causes the distal closure tube segment 8590 to move axially with the flexible neck assembly 8510.

Movement of the first and second transmission bands 8552, 8572 may be controlled by an articulation transmission assembly 8600. The component parts of one form of articulation transmission assembly 8600 are illustrated in FIG. 92. In one form, the articulation transmission assembly 8600 may include an actuator 8610, an articulation body 8620 and a nozzle 8650 (FIGS. 83 and 94). Rotational movement of the actuator 8610 causes corresponding rotation of the articulation body 8620 within the nozzle 8650. The first and second elongated transmission bands, 8552 and 8572, consequently reciprocate axially in opposite directions parallel to the longitudinal tool axis LT-LT of the elongated shaft assembly 100 to cause the remote articulation of the end effector 8412.

Still referring to FIG. 92, the articulation body 8620 has a deck 8622 consisting of first and second spaced-apart, semicircular deck halves, 8624, 8626. The deck halves are mutually opposed to each other and essentially represent mirror images of each other. The first and second deck halves 8624, 8626 have protruding from their surfaces mutually opposed first and second detents 8625, 8627, respectively. Each deck half 8624, 8626 has a set of deck teeth 8628 spaced about 180 degrees from the set of deck teeth on the other deck half. The articulation body 8620 has a pair of rotation stops 8630 protruding from its surface as well as a pair of finger recesses 8632. A drive gear 8640 protrudes laterally from the articulation body 8622. The drive gear 8640 has a flared opening 8642 through it, and a lateral pivot 8644. Within the flared opening 8642 of the drive gear 8640, there is a firing rod orifice (not shown) for receiving a firing rod 8930 therethrough enabling the application of a firing motion to the end effector 8412. The drive gear 8640 is configured to intermesh with the first and second drive racks 8556, 8576, respectively to effect the desired reciprocating movement of the first and second transmission bands 8552, 8572. See FIG. 94.

The nozzle 8650 of the articulation transmission assembly 8600 may include a nozzle body 8652. The nozzle body 8652 may have an axial bore 8654 therethrough that facilitates the passage of the first transmission band assembly 8550 and the second transmission band assembly 8570 as well as for the firing rod 8930 and other operative components of the instrument 8410 including a the proximal end 8706 of a proximal outer shaft segment 8700. See FIG. 94. The nozzle body 8652 may also have a frame groove 8656 and flange 8658 to rotatably fasten the nozzle body 8652 to a housing 8800. In various forms, a detent housing 8660 comprises a portion of the nozzle body 8652. See FIG. 95. An annular array of detent teeth (not shown) is formed within the detent housing 8660. A detent housing floor is spaced from the detent teeth. The floor may have a pair of ledges which interact within the rotation stops 8630 of the articulation body 8620 to limit the degree of rotation. When the articulation body 8620 is inserted into the detent housing 8660, the base of the articulation body 8620 is supported on the floor within the detent housing 8660, and the deck teeth 8628 of the first and second deck halves, 8624, 8626 are aligned for meshing engagement with the detent teeth of the detent housing 8660. A spring member 8668 is supported within the articulation body to bias the deck teeth 8628 into meshing engagement with the detent teeth.

Referring again to FIG. 92, the actuator 8610 may consist of a lever arm 8612, a cap 8614 and a pair of retaining fingers 8616. The lever arm 8612 is mounted on the top of the cap 8614. The pair of retaining fingers 8616 protrudes laterally from the underside of the cap 8614. Each of the retaining fingers 8616 has a retaining clip. The retaining fingers 8616 are received within the finger recesses 8632 of the articulation body 8620. First and second detents, 8625, 8627, on the deck halves of the articulation body are inserted into a slot depression within the underside of the circular cap 8614. Advantageously, each of the three significant components of the articulation transmission assembly, namely the actuator, articulation body and nozzle, may be injection molded components. Such components, for example, may be fabricated from a glass fiber-reinforced amorphous polyamide, sold commercially under the trade name Grivory GV-4H by EMS-American Grilon 150.

Ratcheting rotation of the actuator 8610 causes articulation of the end effector 8412 in the first or second directions relative to the longitudinal tool axis LT-LT. FIG. 86 illustrates the end effector 8412 in an unarticulated position in solid lines and exemplary ranges of articulation in broken lines. When the drive gear 8640 on the articulation body 8620 of the articulation transmission 8600 is rotated to thereby drive the first transmission band assembly 150 distally in the "DD" direction and the second transmission bar assembly 8570 proximally in the proximal direction "PD", the end effector 8412 will articulate in the first articulation direction "FD" relative to the longitudinal tool axis LT-LT. When the drive gear 8640 on the articulation body 8620 of the articulation transmission 8600 has been rotated to thereby drive the second articulation band assembly 8570 in the distal direction "DD" and the first articulation band assembly 8550 in the proximal direction "PD", the end effector 8412 will pivot in a second direction "SD" relative to the longitudinal tool axis LT-LT.

As can be seen in FIG. 93, the elongated shaft assembly 8500 further includes a proximal outer shaft segment 8700 that is attached to the flexible neck assembly 8510. The proximal outer shaft segment 8700 is substantially rigid and may be attached to the flexible neck portion 8511 of the flexible neck assembly 8510 by, for example, a press fit, adhesive or other suitable fastener arrangement. As can be seen in FIG. 94, in at least one embodiment, the distal end 8702 of the proximal outer shaft segment 8700 has a pair of opposed notches 8704 therein that are adapted to receive corresponding lugs 8515 protruding from the flexible neck portion 8511 such that rotation of the proximal outer shaft segment 8700 results in rotation of the flexible neck assembly 8510 and ultimately of the end effector 8412.

Still referring to FIG. 92, the proximal outer shaft segment 8700 has a proximal end 8706 that has a slot 8708 for receiving the drive gear 8640 therethrough such that the proximal outer shaft segment 8700 may move axially relative thereto. In addition, the proximal end 8706 of the proximal outer shaft segment 8700 has a flange 8710 formed thereon that facilitates rotational attachment to a closure carriage 8820 of an actuation system that is operably supported within the housing assembly 8800. The closure carriage and actuation system may be of the same or similar type, construction and operation as the closure carriage and actuation system disclosed in U.S. Patent Application Publication No. US 2012/0074200 A1 which has been incorporated by reference herein in its entirety.

Figure 96:
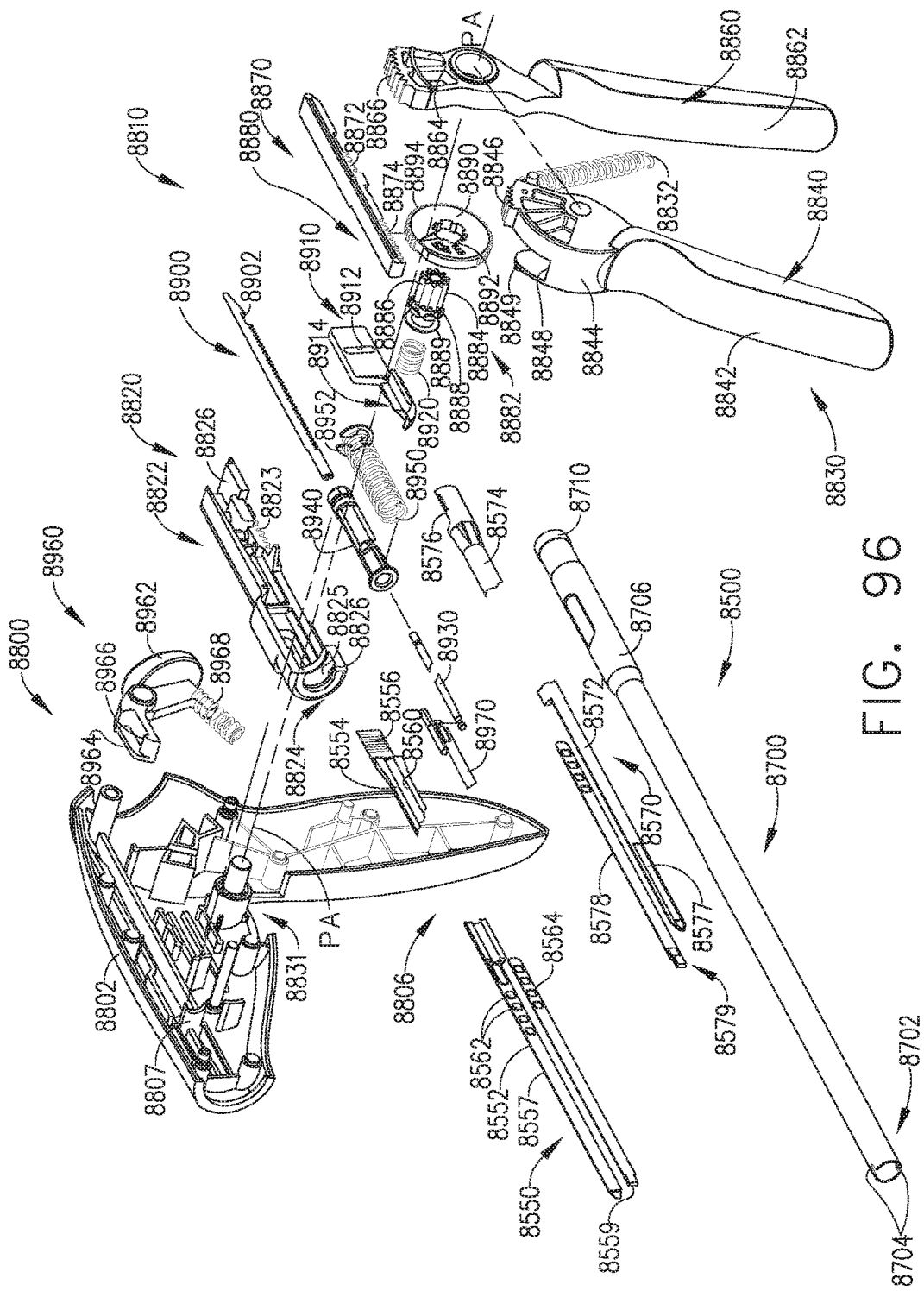
FIG. 96 is a partial perspective exploded view of a handle assembly.

Referring now to FIG. 96, the closure carriage 8820 may comprise two carriage segments 8822 (only one is illustrated) that are interconnected together by adhesive, snap features, screws, etc. As used herein, the term "snap feature" includes, but is not limited to, for example, a tab that has a protrusion thereon that is configured to retainingly engage a corresponding mating portion of another component. Such features may be designed to releasably engage the mating portion or it may not be designed or intended to be removed. In at least one form, the closure carriage 8820 has a distal end 8824 that has a groove arrangement 8826 that is adapted to receive the flanged end 8710 of the proximal outer shaft segment 8700. Such arrangement serves to attach the proximal end 8706 of the proximal outer shaft segment 8700 to the closure carriage 8820 while facilitating its selective rotation of the proximal outer shaft segment 8700 relative to the closure carriage 8820. Therefore, the elongated shaft assembly 8500 and the end effector 8412 that is operably coupled thereto may be selectively rotated about the longitudinal tool axis LT-LT relative to the housing assembly 8800.

In various implementations, the housing assembly 8800 comprises a pistol-shaped handle housing that may be fabricated in two or more pieces for assembly purposes. For example, the housing assembly 8800 as shown comprises a right hand case member 8802 and a left hand case member 8804 (FIG. 83) that are molded or otherwise fabricated from a polymer or plastic material and are designed to mate together. Such case members 8802 and 8804 may be attached together by snap features, pegs and sockets molded or otherwise formed therein and/or by adhesive, screws, etc. When assembled, the housing assembly 8800 movably supports the closure carriage 8820 for selective axial travel therein in response to actuation motions from a trigger, generally designated as 8830. As the present Detailed Description proceeds, however, it will be understood that the various unique and novel aspects and attributes of the various implementations of the present invention may be effectively attained when employed with robotically controlled or otherwise remotely controlled systems. Thus, the term "housing" or "housing assembly" may also encompass a housing or similar portion of a robotic system that houses or otherwise operably supports at least one drive system that is configured to generate and apply at least one control motion which could be used to actuate various forms of surgical end effectors attached thereto. For example, various implementations of the surgical instrument described herein may be used in connection with those robotic systems and arrangements disclosed in U.S. patent application Ser. No. 13/536,323, entitled ROBOTICALLY-POWERED SURGICAL DEVICE WITH MANUALLY ACTUATABLE REVERSING SYSTEM, filed Jun. 28, 2012, now U.S. Pat. No. 9,408,606, the entire disclosure of which is incorporated by reference herein.

The trigger assembly 8830 may, for example, comprise a primary trigger 8840 and a secondary trigger 8860. The primary and secondary triggers 8840 and 8860 are pivotally journaled on a pivot pin assembly 8831 formed in the housing assembly 8800 such that the triggers 8840 and 8860 may essentially move relative to each other. Such arrangement permits the trigger assembly 8830 to pivot relative to the housing assembly 8800 about a pivot axis PA-PA. See FIG. 96. The primary trigger 8840 has an elongated, grippable primary trigger paddle 8842 that protrudes from a primary drive portion 8844 that has a firing rack 8846 formed thereon. In one embodiment, the secondary trigger 8860 has a secondary trigger paddle 8862 that protrudes from a secondary drive portion 8864 as discussed in further detail that is pivotally journaled on the pivot pin assembly 8831. The primary drive portion 8844 has a slot 8848 that is adapted to receive the secondary drive portion 8864 of the secondary trigger 8860 therein as the primary trigger paddle 8842 is pivoted towards a pistol grip portion 8806 of the housing assembly 8800. Such arrangement essentially enables the secondary trigger 8860 to "nest" within the primary trigger 8840 during actuation. As will be discussed in detail below, the secondary trigger 8860 is pivotally actuated by pivoting the primary trigger 8840. Thus, in other embodiments, the secondary trigger 8860 may lack the secondary trigger paddle 8842. In various forms, the trigger assembly 8830 may be biased into the unactuated position by a trigger spring (not shown).

As can be seen in FIG. 96, the secondary drive portion 8864 of the secondary trigger 8860 may have a closure gear segment 8866 formed thereon that is configured for meshing engagement with a carriage gear rack 8823 formed on the underside of the closure carriage 8820. Thus, when the secondary trigger 8860 is pivoted toward the pistol grip 8806, the closure carriage 8820 is driven in the distal direction "DD".

In various implementations, the actuation system 8810 may further include an actuation bar 8870. The actuation bar 8870 has a first actuation rack 8872 formed thereon that is configured for meshing engagement with the primary gear segment 8846 on the primary trigger 8840. Thus, when the primary gear segment 8846 is in meshing engagement with the first actuation rack 8872, the actuation bar 8870 is driven in the distal direction "DD" when the primary trigger 8840 is pivoted toward the pistol grip 8806. The actuation bar 8870 has a second actuation rack 8874 formed thereon configured to meshingly engage clutch teeth 8884 on a clutch shaft 8882 of a clutch assembly 8880. In various embodiments, the clutch shaft 8882 is rotatably is supported within the housing assembly 8800 and is also laterally movable therein. The clutch shaft 8882 has a hub portion 8886 that has a plurality of spaced teeth 8888 that are configured to drivingly engage teeth openings 8892 in a drive gear 8890 that is rotatably supported on the clutch shaft 8882. The drive gear 8890 has a segment of drive gears 8894 thereon that are adapted for meshing engagement with a firing rack 8900 that is movably supported in the housing assembly 8800.

Various embodiments of the clutch assembly 8880 may further comprise a clutch plate 8910 that is slidably journaled on a clutch pin 8849 provided on the primary drive portion 8844 of the primary trigger 8840. The clutch pin 8849 may be movably received within a vertical slot 8912 in the clutch plate 8910. The clutch plate 8910 also has a distally-extending clutch arm 8914 that is adapted to actuatably engage a bevel plate 8889 formed on the clutch shaft 8882. In addition, a clutch spring 8920 is employed to bias the clutch shaft 8880 laterally such that the teeth 8888 on the clutch shaft 8882 are brought into meshing engagement with the teeth openings 8892 in the drive gear 8890.

As can be seen in FIGS. 92 and 96, the firing rack 8900 is coupled to a firing rod 8930 that is attached to the proximal end of the knife bar assembly 8970. In various embodiments, the knife bar assembly 8970 may comprise an upper bar segment 8971 and a lower bar segment 8972. Such arrangement may enable the knife bar assembly 8970 to flex as the end effector 8412 is articulated, while remaining sufficiently rigid to be driven distally through the shaft assembly 8500. In the depicted embodiment, the upper and lower knife bar segments 8971, 8972 are each attached to an "E-beam" cutting head 8973. In the depicted configuration, the E-beam cutting head 8973 includes a vertically oriented body portion 8974 that has an upper portion 8975 and a lower portion 8976. A bottom foot 8977 is formed on or attached to the lower portion 8976. In alternative embodiments, the bottom foot may essentially comprise laterally extending lower tabs that protrude laterally from the lower portion. Similarly, at least one upper tab 8977' is formed on or otherwise attached to the upper portion 8975 of the vertically oriented body portion 8974. In addition, as can be seen in FIG. 84, the vertically oriented body portion 8974 further includes at least one intermediate tab portion 8978 (only one is shown) as well as a tissue cutting edge 8979.

Referring to FIG. 84, the vertically oriented body portion 8974 extends through a longitudinally extending slot 8980 in the elongated channel 8414 and a longitudinally extending slot 8981 in the anvil 8420. When assembled, portions of the elongated channel 8414 are received between the bottom foot 8977 and the intermediate tab portions 8978. The, upper tab portion 8977' is arranged to be received within the anvil 8420 above portions 8982 of the anvil 8420 that define the anvil slot 8981. To facilitate ease of assembly, the anvil 8420 may be provided with a movable anvil cover 8983 and the elongated channel 8414 may be provided with a removable channel cover 8984. Once assembled, the anvil cover 8983 and the channel cover 8984 may be installed to prevent tissue, body fluids, etc. from entering the anvil 8420 and the elongated channel 8414, respectively which may hamper operation of the cutting head 8973.

In various arrangements, each staple cartridge 8430 includes a cartridge body 8431 that has a sled assembly 8985 operably supported therein. The sled assembly 8985 may have a mounting portion 8986 that is configured to extend into a sled slot 8987 formed in the vertically oriented body portion 8974 of the cutting head 8973. See FIGS. 84 and 86. The sled assembly 8985 may be configured with wedges 8988 that are arranged to contact staple drivers 8989 that are operably supported within the staple cartridge 8430. The staple drivers 8989 may support one or more staples 8990 thereon in a known manner. As the sled assembly 8985 is driven in the distal direction DD through the staple cartridge 8430, the wedges 8988 drive the drivers 8989 upward within the cartridge 8430 in a known manner. The upwardly moving drivers 8989 drive the staples 8990 into forming contact with a staple forming undersurface of the anvil 8420. The undersurface may, for example, include staple-forming pockets that correspond to each staple.

The end effector 8412 may also employ a cutting head lockout system, generally designated as 8991 that serves to prevent distal advancement of the cutting head 8973 when a new staple cartridge 8430 is not present within the elongated channel 8414. In at least one arrangement, for example, the cutting head lockout system 8991 may comprise a lockout spring 8992 that is mounted to the bottom of elongated channel 8414. The lockout spring 8992 may be configured to contact the bottom foot 8977 of the cutting head assembly 8973 when the cutting head assembly 8974 is in the starting position. See FIGS. 86, 88 and 91. An opening 8993 may be provided through the bottom of the elongated channel 8414 such that when in that position, the lockout spring 8992 biases the bottom foot 8977 such that it interferes with the bottom of the elongated channel 8414. Thus, when the bottom foot 8977 is in that position, if the clinician were to try advance the cutting head 8973 distally through the elongated channel 8414, the bottom foot portion 8977 will contact a portion of the elongated channel 8414 to prevent such advancement of the cutting head 8973. When a cartridge 8430 has been properly installed with the elongated channel 8414, the mounting portion 8986 of the sled assembly 8985 extends into the sled slot 8987 and serves to move the cutting head assembly 8973 into a position whereby the foot portion 8977 is moved out of interfering contact with the bottom of the elongated channel 8414. When in that position, the cutting head assembly 8973 is free to be advanced distally through the elongated channel 8414. Such arrangement serves to prevent the clinician from inadvertently firing the end effector when a new cartridge is not present which could otherwise result in the tissue being cut but not stapled. As the cutting head 8973 is advanced distally, the bottom foot 8977, the intermediate tab portions 8978 and the upper tab 8977' cooperate to orient the anvil 8420 relative to the staple cartridge deck at a desired spaced relationship relative to each other. A distally presented tissue-cutting edge 8979, which is between the upper tab 8977' and intermediate tab portions 8978, severs clamped tissue while causing the staples 8990 within the staple cartridge 8430 to be formed into the tissue clamped within the end effector 8412.

As can be seen in FIG. 84, the upper firing bar 8971 is attached to the upper end portion 8975 and the lower firing bar 8972 is spaced from the upper firing bar 8971 and is attached to the lower end portion 8976 of the vertically-extending 8974 of the cutting head 8973. Such arrangement serves to transmit the firing motions to the upper and lower portions of the cutting head 8973 in an equivalent manner to facilitate aligned movement of the cutting head through the anvil 8420, the surgical staple cartridge 8430 and the elongated channel 8414. In various arrangements, for example, the upper firing bar 8971 may be attached to the upper end portion directly behind the upper tabs(s) 8977' such that the upper firing bar 8971 is essentially axially aligned with point(s) from which the upper tab(s) 8977' protrude laterally from the upper end portion 8975. Similarly, the lower firing bar 8972 may be attached to the bottom end portion 8976 directly behind the bottom foot 8977 or the point(s) from which the laterally protruding bottom tabs protrude laterally from the bottom end portion 8976 such that the lower firing bar 8972 is axially aligned therewith. The upper and lower firing bars 8971, 8972 may be welded to the vertical extending portion 8974 in those locations. For example, the welds may be applied to the firing bars from one side or from both lateral sides of the firing bars. In at least one implementation, the upper and lower firing bars 8971, 8972 are not directly attached to each other. The portions of the upper and lower firing bars 8971, 8972 that extend through the elongated shaft assembly 8500 to be coupled to a distal end portion 8932 of the firing rod 8930 are supported in a contiguous orientation relative to each other. The proximal ends of the upper and lower firing bars 8971, 8972 may be attached to the distal end portion 8932 of the firing rod 8930 by a coupler member 8994. See FIG. 92. As will be discussed in further detail below, the firing rod 8930 facilitates the application of firing and retraction motions to the knife bar assembly 600 by the actuation system 8810. In at least one implementation, the anvil mounting portion 8422 has a wedge-like formation 8427 thereon that serves to separate the upper firing bar 8971 and lower firing bar 8972 as the knife bar assembly 8970 is driven in the distal direction "DD". See, for example, FIG. 91.

In various arrangements, the firing rod 8930 extends through a closure bushing 8940 that is mounted within the housing assembly 8800. In at least one form, a pair of mounting studs 8807 protrude from the handle casings 8802, 8804 and extend through corresponding slots in the closure carriage 8820 to be received in a retaining slot in the bushing 8840. A closure spring 8950 that is attached to a retainer clip 8952 is journaled on the closure bushing 8940. The closure spring 8950 extends between the nozzle body 8652 and an internal wall 8825 in the closure carriage 8820. Thus, the closure spring 8950 serves to bias the closure carriage 8820 in the proximal direction "PD".

Various embodiments may also include a releasable closure locking assembly 8960 that interfaces with the closure carriage 8820 to selectively retain the closure carriage 8820 in its distal-most closed or clamped position. In at least one form, the closure locking assembly 8960 includes a locking button 8962 that is pivotally supported in the housing assembly 8800. The locking button 8862 has a latch arm 8964 that is configured to abut a locking ledge 8826 formed on the closure carriage 8820 when the button 8962 is in the locked position. In addition, the latch arm 8964 has a catch 8966 formed thereon that is configured to releasably latch with a locking latch 8902 on the proximal end of the firing rack 8900. A locking spring 8968 serves to bias the locking button 8962 into the locked position.

Operation of the surgical instrument 8410 will now be described. FIGS. 89-91 illustrate the jaws 8413 and 8415 of the end effector 8412 in an open position. When the end effector 8412 is in the open position, the latch arm 8964 is located on top of the locking ledge 8826 formed on the closure carriage 8820 such that the catch 8966 of the latch arm 894 is in retaining engagement with the locking latch 8902 on the firing rack 8900. Thus, when in this initial starting position, the knife bar assembly 8790 cannot be inadvertently actuated. The clutch plate 8910, as well as the closure carriage, are each in their proximal-most unactuated positions. When in those positions, the clutch drive bevel 8889 on the clutch shaft 8882 is in contact with a portion of the closure carriage 8820, which prevents the clutch shaft 8882 from laterally moving into meshing engagement with the drive gear 8890 under the bias of the clutch spring 8920.

To initiate the closure process, a first stroke is applied to the trigger assembly 8830. That is, the trigger assembly 8830 is initially pivoted toward the pistol grip 8806. Such pivoting action serves to drive the closure carriage 8820 in the distal direction "DD" by virtue of the meshing engagement between the closure gear segment 8866 on the secondary trigger 8860 and the carriage rack 8823 formed on the underside of the closure carriage 8820. Such distal movement of the closure carriage 8820 also axially advances the proximal outer shaft segment 8700 and the distal closure tube segment 8590 in the distal direction "DD". As the distal closure tube segment 8590 moves distally, the pin 8419 which extends through the slots 8423 in the anvil mounting portion 8422, travels from the position illustrated in FIGS. 90 and 91 to the position illustrated in FIGS. 86-88 to pivot the anvil 8420 to the closed position. If the surgeon desires to simply grasp and manipulate tissue prior to clamping it between the anvil 8420 and the surgical staple cartridge 8430, the trigger assembly 8830 may be pivoted to open and close the anvil 8420 without fully pivoting the trigger assembly 8830 to the fully closed position.

Those of ordinary skill in the art will understand that, as the trigger assembly 8830 is pivoted toward the pistol grip 8806, the actuation bar 8870 will necessarily also be driven distally by virtue of the meshing engagement between the primary gear segment 8846 on the primary trigger 8840 and the first actuation rack 8872 on the actuation bar 8870. The distal movement of the actuation bar 8870 will also result in the an application of a rotary actuation motion to the clutch shaft 8882 by virtue of the meshing engagement between the clutch teeth 484 on the clutch shaft 8882 and the second actuation rack 8874 on the actuation bar 8870. However, such rotary motion is not applied to the drive gear 8890 because the clutch arm 8914 of the clutch plate 8910, in contact with the clutch drive bevel 8889 on the clutch shaft 8882, prevents the axial movement of the clutch shaft 8882 into meshing engagement with the drive gear 8890. Thus, the clutch shaft 8882 freely rotates relative to the drive gear 8890. Accordingly, the clutch assembly 8880 automatically prevents the activation of the firing rack 8900 during the initial actuation of the trigger assembly 8830.

Once the trigger assembly 8830 has been initially fully compressed into the closed position, the anvil 8420 will be retained in the locked or clamped position by the closure locking assembly 8960 which prevents the proximal movement of the closure carriage 8820. To drive the knife bar assembly 8970 distally through the tissue clamped in the end effector 8412, the surgeon again pivots the primary trigger 8840 toward the pistol grip 8806 of the housing assembly 8800. As the primary trigger 8840 is pivoted, the firing rack 8900, the firing rod 8930, and the knife bar assembly 600 are driven in the distal direction "DD". After the knife bar assembly 8970 has been driven through the tissue clamped in the end effector 8412, the surgeon then releases the primary trigger 8840 to thereby permit the primary trigger 8840 to pivot to its unactuated position under the bias of the firing spring 8832. As the primary trigger 8840 pivots back to the starting position, the firing rack 8900, firing rod 8930, and knife bar assembly 8970 are drawn proximally back to their respective starting positions. The end effector 12 remains in its clamped position as shown in FIG. 88. As can also be seen in that Figure, the sled assembly 8985 remains in the distal end of the cartridge 8430 while the knife bar assembly 8970 is returned to the starting position.

To unlock the closure carriage 8820 and the secondary trigger 8860, the surgeon depresses the locking button 8962. As the locking button 8962 is depressed, the locking arm 8964 is pivoted out of abutting engagement with the locking ledge 8826 on the closure carriage 8820. Further details regarding the operation of the firing and closure systems may be found in U.S. Patent Application Publication No. US 2012/0074200 which has been herein incorporated by reference in its entirety. As the closure carriage 8820 moves proximally, the proximal outer shaft segment 8700, the flexible neck assembly 8510, and the distal closure tube segment 8590 are drawn proximally. As the distal closure tube segment 8590 moves proximally, the shaft 8419 travels proximally within the slot 8423 in the anvil mounting portion 8422 to move the anvil 8420 to an open position.

As can be appreciated from the foregoing, the various surgical instruments disclosed herein afford the clinician with improved maneuverability and various other advantages that are not available when using prior surgical instruments that are configured to cut and fasten tissue. For example, in various implementations disclosed herein, the end effector is selectively articulatable in the same directions in which the jaws are movable relative to each other. Stated another way, the jaws of the surgical end effector are constrained to move in one plane. In various implementations disclosed herein, the end effector is also capable of moving in that same plane. Prior end effectors are commonly constrained to move in planes that differ from the plane in which the jaws move.

Another advantage provided by many of the present implementations is the use of a firing bar that comprises at least an upper firing bar and at least a lower firing bar that form a laminated structure. The upper and lower bars may at some point be attached to each other or they may be unattached and just be contiguous with each other. In either arrangement, the upper bar is attached to an upper end of the cutting head and the lower bar may be attached to the lower head such that they are spaced from each other at their points of attachment to the cutting head. Such arrangement serves to provide for a more stable cutting head arrangement that may be less likely to twist and/or buckle during actuation. In addition, the cutting head may be equipped with laterally protruding upper tab(s) that engage a portion of the anvil and lower tab(s) that engage the elongated channel. The upper firing bar may be attached directly behind the point where the upper tabs are attached such that it is axially aligned therewith. Likewise the lower firing bar may be attached to the bottom portion directly behind the points where the bottom tab(s) are attached such that it is axially aligned therewith. Such axial alignment facilitates transfer of the driving or actuation motions to the cutting head at the points where the cutting head engages the anvil and the elongated channel which may further prevent and buckling and/or twisting of the cutting head during actuation.

The various surgical instruments arrangements disclosed herein that employ tissue cutting and staple firing systems, jaw opening and closing systems and end effector articulation systems that essentially employ components that are axially reciprocated during actuation may be actuated by manually generated actuation motions, For example, the firing systems may be housed in a handle that includes trigger arrangements that are configured to generate actuation motions when the clinician manipulate the triggers. It will be appreciated, however, that such actuation motions may likewise be generated by motors that are supported in a handle or are supported or comprise a portion of a robotic system. Thus, the various surgical instruments disclosed herein should not be limited to use solely in connection with hand-held housings and manually generated actuation motions.

Figure 97:
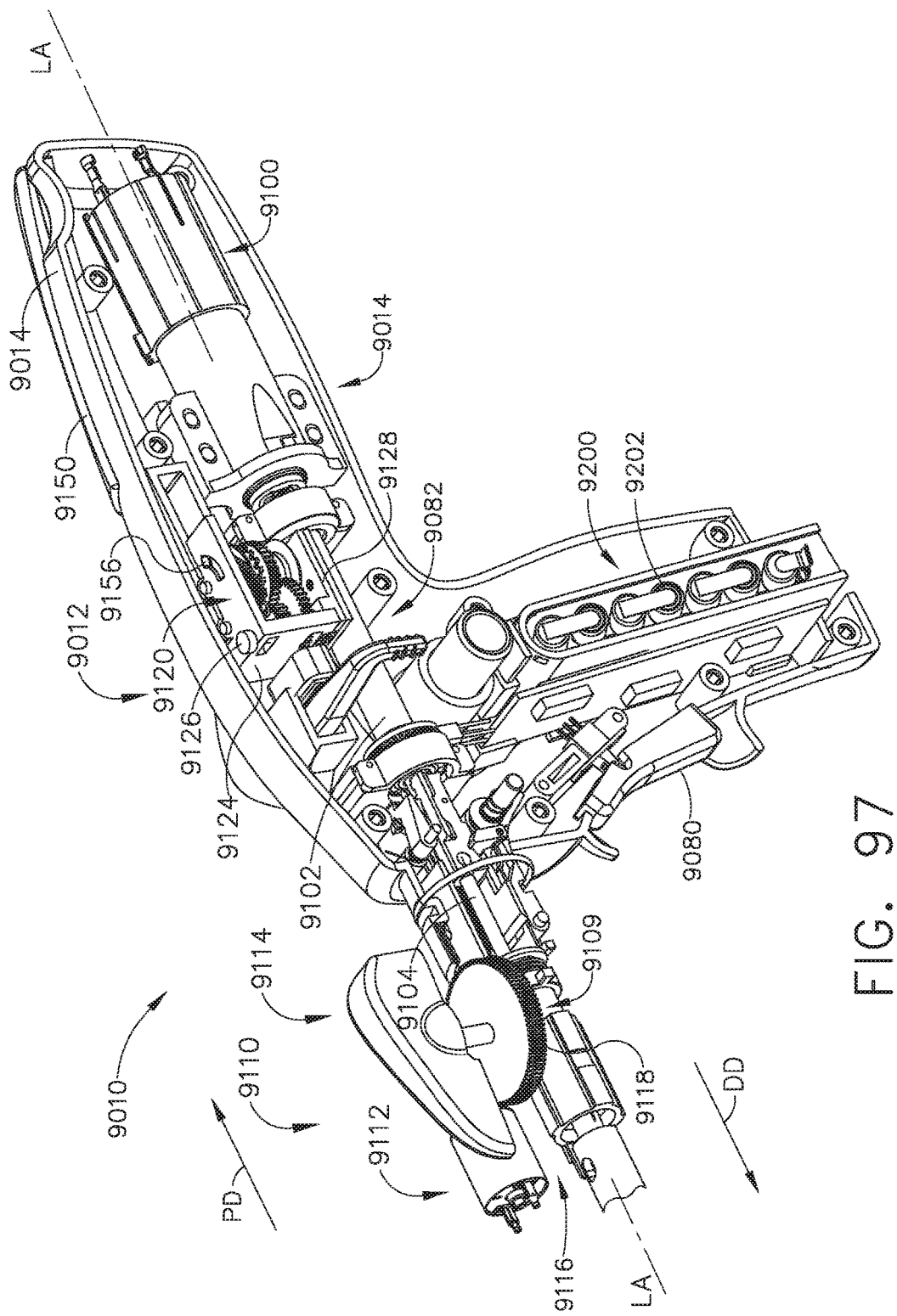
FIG. 97 is a perspective view of a surgical instrument arrangement of the present invention.
Figure 98:
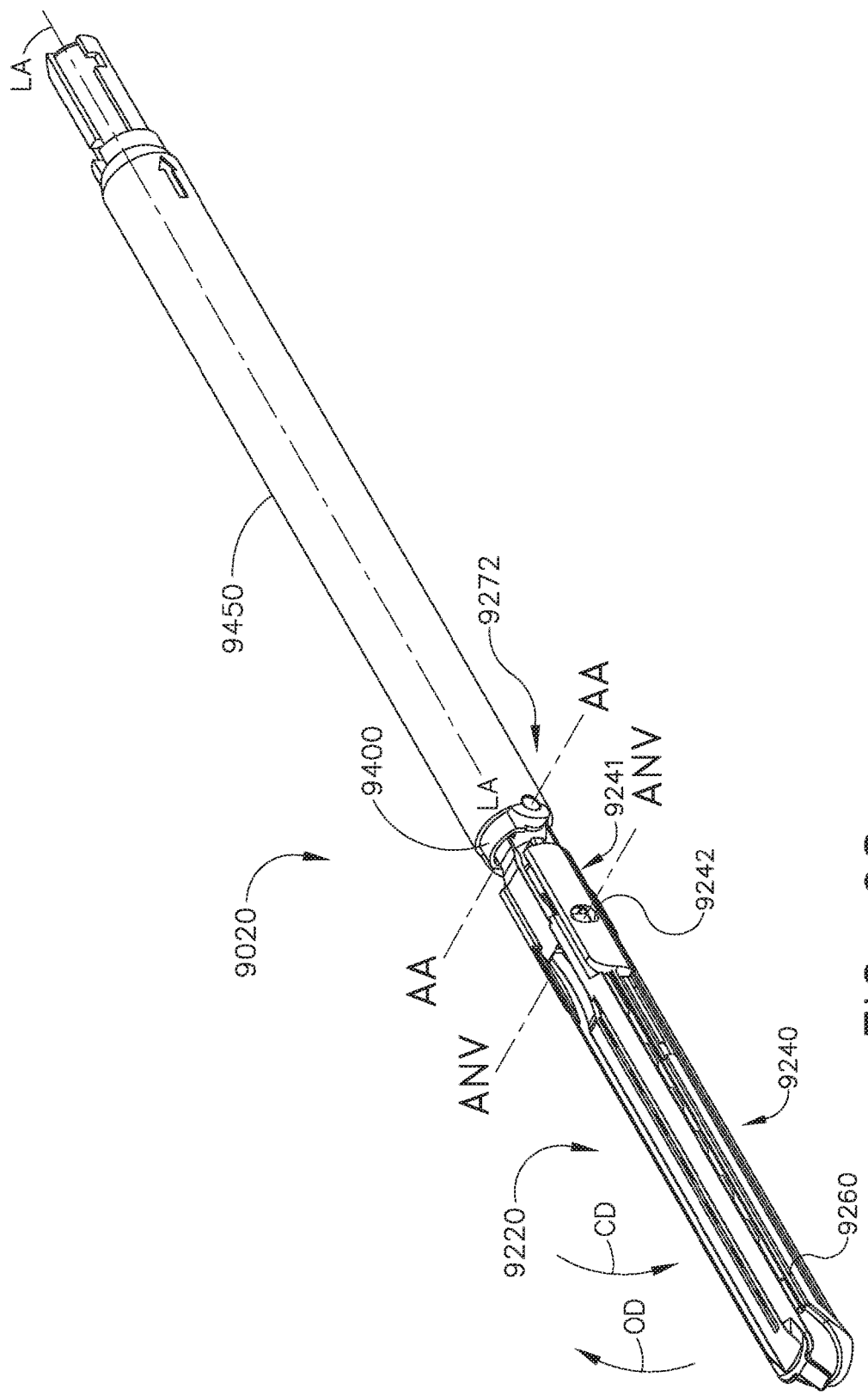
FIG. 98 is a perspective view of an exemplary loading unit that may be employed in connection with various surgical instruments disclosed herein.
Figure 99:
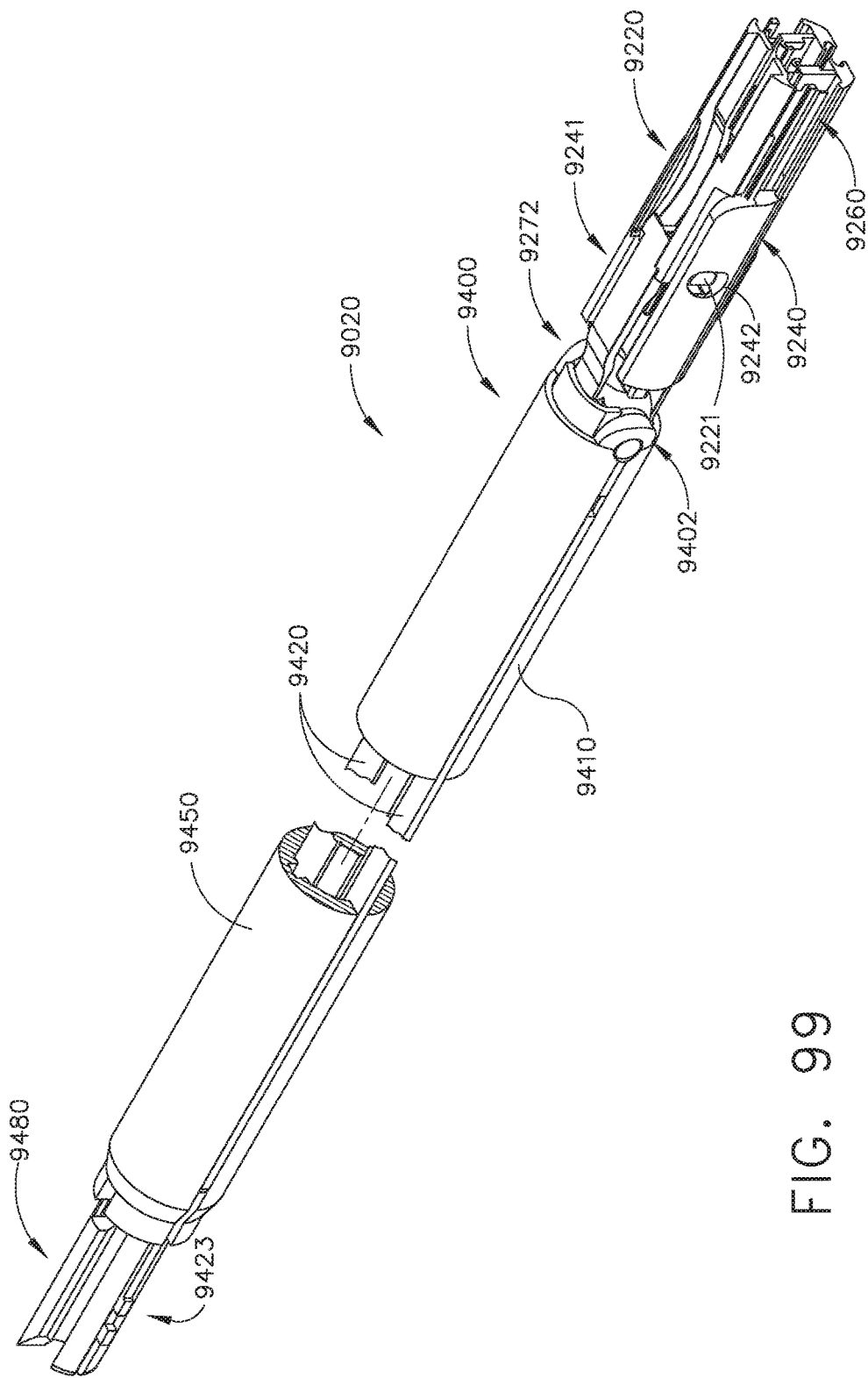
FIG. 99 is another partial cross-sectional view of a portion of the loading unit depicted in FIG. 98.

Powered surgical instruments are disclosed in U.S. Patent Application Publication No. 2009/0090763, entitled POWERED SURGICAL STAPLING DEVICE to Zemlok et al. (hereinafter "Zemlok '763"), the entire disclosure of which is hereby incorporated by reference herein. Powered surgical instruments are also disclosed in U.S. Patent Application Publication No. 2011/0278344, entitled POWERED SURGICAL INSTRUMENT to Zemlok et al. (hereinafter "Zemlok '344"), now U.S. Pat. No. 8,201,721, the entire disclosure of which is hereby incorporated by reference herein. FIG. 97 illustrates a powered surgical instrument 9010 that, in many ways, may be similar to those surgical instruments (including various features, components and subcomponents thereof) disclosed in, for example, Zemlok '763 and/or Zemlok '344, which have each been incorporated by reference herein in their respective entireties. Likewise, the surgical instrument 9010 may be similar to those instruments disclosed in U.S. patent application Ser. No. 13/974,205, filed Aug. 23, 2013, now U.S. Patent Application Publication No. 2015/0053740, entitled ATTACHMENT PORTIONS FOR SURGICAL INSTRUMENT ASSEMBLIES to Shelton et al. the entire disclosure of which is hereby incorporated by reference herein. The surgical instrument 9010 depicted in FIG. 97 includes a housing 9012 that has a handle portion 9014 for facilitating manual manipulation and operation of the instrument. Thus, the term "housing" as used herein may encompass a handheld or otherwise hand-manipulatable arrangement. However, the term "housing" may also encompass portions of an automated surgical instrument system such as a robotically-controlled system that is not intended to be handheld but is otherwise manipulated and actuatable by various components, portions, and/or actuators of the system. For example, various implementations of the surgical instrument described herein may be used in connection with those robotic systems and arrangements disclosed in U.S. patent application Ser. No. 13/536,323, entitled ROBOTICALLY-POWERED SURGICAL DEVICE WITH MANUALLY ACTUATABLE REVERSING SYSTEM, filed Jun. 28, 2012, now U.S. Pat. No. 9,408,606, the entire disclosure of which is incorporated by reference herein. Furthermore, the coupling arrangements and end effector arrangement disclosed herein may also be effectively employed with non-powered hand held surgical instruments. Thus, the end effector arrangements and coupling arrangements disclosed herein should not be limited to use in connection with powered instruments, whether they be hand-held or otherwise automated.

An elongated shaft assembly 9116 in the form of an endoscopic portion protrudes from the housing 9012 and is configured for operable attachment to a surgical end effector that is constructed to perform at least one surgical procedure in response to applications of firing motions thereto. The surgical end effector may comprise a device configured to cut and staple tissue such as a "loading unit" 9020 as shown in FIGS. 98-105. Surgical end effectors, such as loading unit 9020, for example, can be releasably attached to the elongated shaft assembly 9116 of the powered surgical instrument 9010, as described in greater detail herein.

Figure 100:
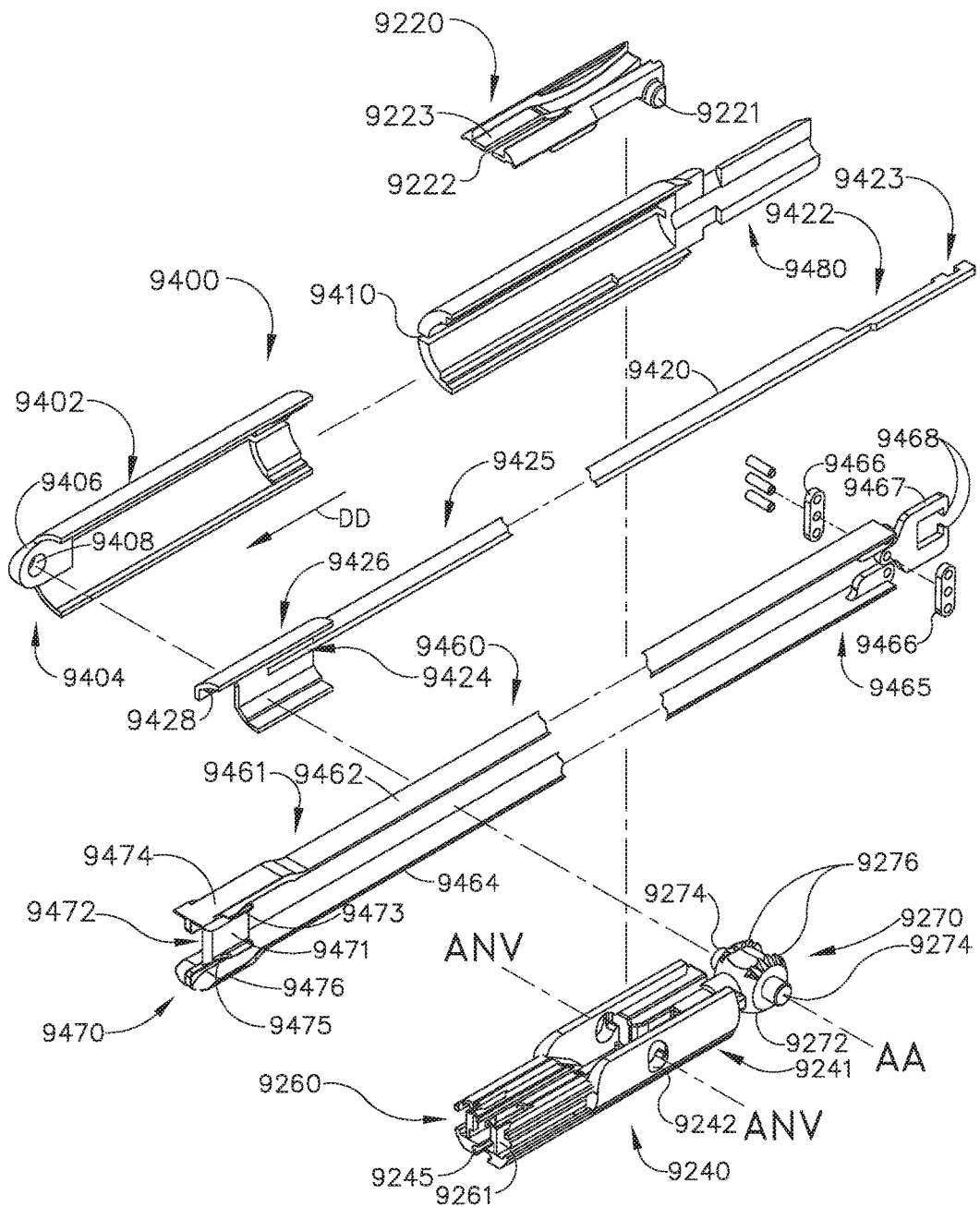
FIG. 100 is a an exploded perspective view of the loading unit of FIGS. 98 and 99.
Figure 101:
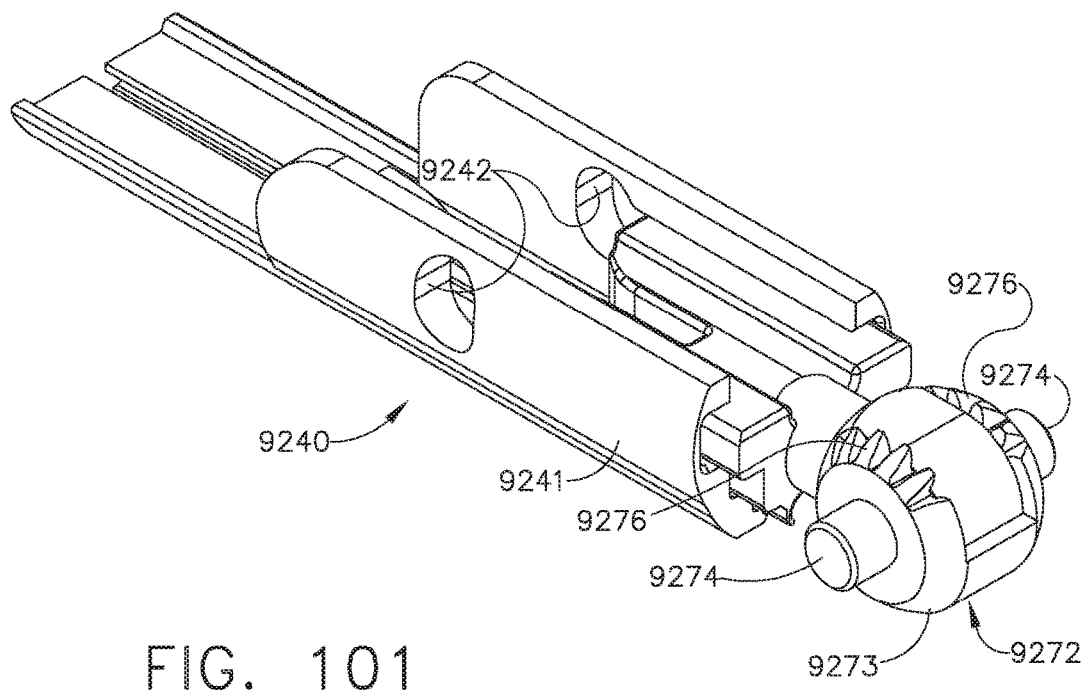
FIG. 101 is a partial perspective view of a portion of a carrier and an articulation ball assembly embodiment.

FIGS. 98-105 illustrate one exemplary form of end effector or loading unit 9020 that may be employed with the surgical instrument 9010. As can be seen in FIG. 100, the loading unit 9020 includes an anvil assembly 9220 that is supported for pivotal travel relative to a carrier 9240 that operably supports a staple cartridge 9260 therein. The staple cartridge 9260 may comprise a surgical staple cartridge that is designed to be "implanted" within the patient. For example, the implantable surgical staple cartridge 9260 may comprise any of the various surgical staple cartridge arrangements disclosed in U.S. Patent Application Publication No. US 2012-0080484, filed Sep. 30, 2010, entitled SURGICAL STAPLING INSTRUMENT WITH A VARIABLE STAPLE FORMING SYSTEM, now U.S. Pat. No. 9,113,862, the entire disclosure of which is hereby incorporated by reference herein. In at least one implementation for example, the staple cartridge 9260 includes a body portion 9261 that consists of a compressible hemostat material such as, for example, oxidized regenerated cellulose ("ORC") or a bio-absorbable foam in which lines of unformed metal staples are supported. In at least some embodiments, in order to prevent the staple from being affected and the hemostat material from being activated during the introduction and positioning process, the entire cartridge may be coated or wrapped in a biodegradable film such as a polydioxanon film sold under the trademark PDS® or with a Polyglycerol sebacate (PGS) film or other biodegradable films formed from PGA (Polyglycolic acid, marketed under the trademark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 9261 of staple cartridge 9260 is sized to be removably supported within the carrier 9240 as shown such that each staple therein is aligned with corresponding staple forming pockets in the anvil assembly 9220.

The anvil assembly 9220 has a pair of trunnions 9221 formed thereon that are adapted to be pivotally received within trunnion slots 9242 in a proximal end 9241 of the carrier 9240 such that the anvil assembly 9220 may move or pivot between an open position and a closed position relative to the carrier 9240 about an anvil pivot axis ANV-ANV. The anvil pivot axis ANV-ANV is transverse to a longitudinally extending tool axis LA-LA defined by the elongated shaft assembly 9116. When the anvil assembly 9220 is pivoted from an open position to a closed position, the anvil assembly 9220 is moving in a closing direction "CD" about anvil pivot axis ANV-ANV. Conversely, when the anvil assembly 9220 is moving from a closed position to an open position, the anvil assembly 9220 is moving in an opening direction "OD" about anvil pivot axis ANV-ANV.

The loading unit 9020 employs a unique and novel articulation joint 9270 that facilitates articulation of the carrier 9240 and anvil assembly 9220 to pivot about an articulation axis "AA-AA" that is transverse to a longitudinal tool axis "LA-LA". For example, the loading unit 9020 may include an end effector housing 9400 that is configured to be received within an outer casing 9450. The distal end 9402 of the end effector housing 9400 may have a clevis 9404 formed thereon by two distally protruding tabs 9406. Each tab 9406 has a pivot hole 9408 formed therein that is adapted to receive therein a corresponding pivot pin 9274 formed on an articulation ball assembly 9272. See FIG. 100. The articulation ball assembly 9272 may be rigidly affixed to the proximal end 9241 of the carrier 9240 by, for example, welding or other suitable fastening arrangement. As will be discussed in further detail below, when assembled together, the carrier 9240 and anvil assembly 9220 can selectively articulate as a unit about the articulation axis AA-AA in a first direction "FD" which is the same direction as the anvil closing direction "CD" and in a second direction "SD" which is the same as the anvil opening direction "OD". See FIG. 105.

Figure 102:
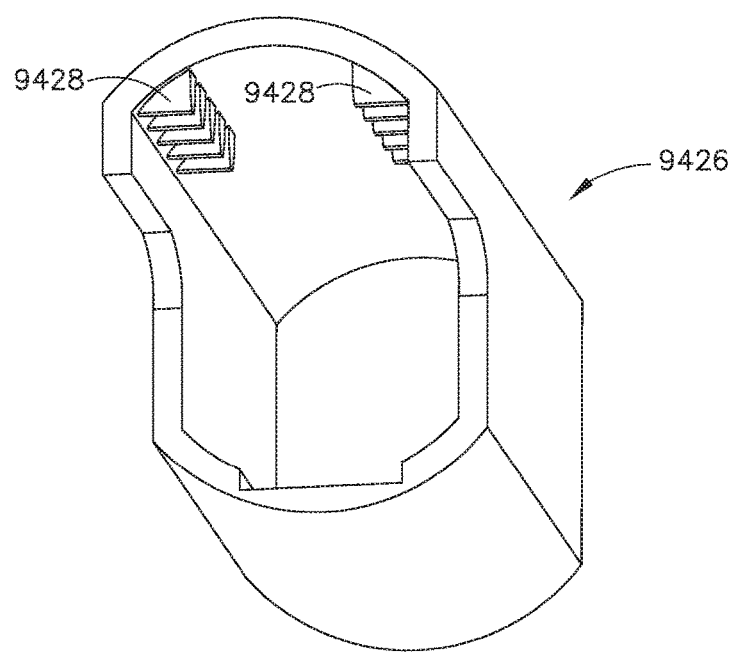
FIG. 102 is a perspective view of an articulation tube embodiment.
Figure 103:
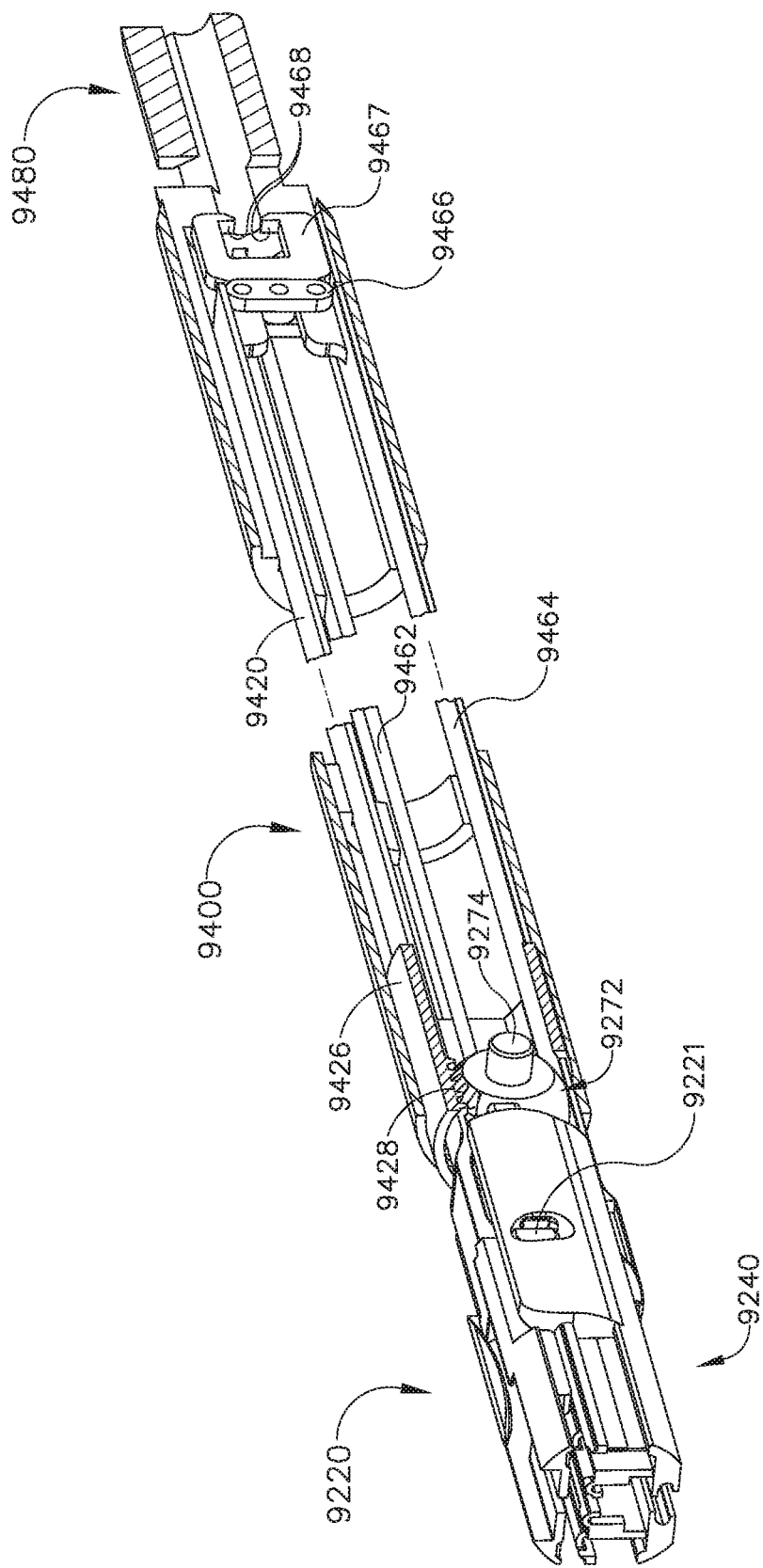
FIG. 103 is a partial cross-sectional view of a loading unit of FIGS. 98-100.

Still referring to FIG. 100, the end effector housing 9400 may be provided with a channel 9410 for slidably receiving an articulation link 9420 therein. The articulation link 9420 includes a proximal end portion 9422 and a distal end 9424. Fixedly attached to the distal end portion 9424 is an articulation tube 9426. The articulation tube 9426 may comprise a hollow tube and be attached to the distal end 9424 by, for example, welding or other suitable means. As can be seen in FIG. 102, the articulation tube 9426 may have a series of articulation teeth 9428 formed therein that are configured to meshingly engage sets of distal articulation teeth 9276 formed on the articulation ball 9272. Thus, movement of the articulation link 9420 in the distal direction "DD" will cause the carrier 9240 and anvil assembly 9220 to pivot in the first direction "FD" about the articulation axis AA-AA. Conversely, movement of the articulation link 420 in the proximal direction "PD" will cause the carrier 9240 and anvil assembly 9220 to pivot as a unit in the second direction "SD" about the articulation axis AA-AA. The articulation link 9420 and the articulation tube 9426 may be collectively referred to herein as the articulation link assembly 9425. See FIG. 100.

The loading unit 9020 may also be equipped with a drive assembly 9460 that is configured to axially move through the end effector housing 9400. In at least one implementation, the drive assembly 9460 includes a drive beam assembly 9461 that includes an upper drive beam 9462 and a lower drive beam 9464 that are attached to a cutting head 9470. The cutting head 9470 may include a body portion 9471 that has a tissue cutting edge 9472 formed thereon. An upper portion 9473 of the body portion 9471 has an upper tab 9474 formed thereon. A bottom foot or tab 9476 is formed on a lower portion 9475 of the body portion 9471. The vertically oriented body portion 9471 extends through a longitudinally extending slot 9245 in the carrier 9240 and a longitudinally extending slot 9222 in the anvil assembly 9220. When assembled, the bottom foot 9476 is configured to slide along the bottom of the carrier 9240. The, upper tab portion 9474 is arranged to be slidably received within an elongated channel 9223 formed in the anvil assembly 9220.

As can be seen in FIG. 100, the upper firing bar 9462 is attached to the upper end portion 9473 and the lower firing bar 9464 is spaced from the upper firing bar 9462 and is attached to the lower end portion 9475 of the vertically-extending portion 9471 of the cutting head 9470. Such arrangement serves to transmit the firing motions to the upper and lower portions of the cutting head 9470 in an equivalent manner to facilitate aligned movement of the cutting head 9470 through the anvil assembly 9220, the surgical staple cartridge 9260 and the carrier 9240. In various arrangements, for example, the upper firing bar 9462 may be attached to the upper end portion 9473 directly behind the upper tabs(s) 9474 such that the upper firing bar 9462 is essentially axially aligned with point(s) from which the upper tab(s) 9474 protrude laterally from the upper end portion 9473. Similarly, the lower firing bar 9464 may be attached to the bottom end portion 9475 directly behind the bottom foot 9476 or the point(s) from which the laterally protruding bottom tabs 9476 protrude laterally from the bottom end portion 9475 such that the lower firing bar 9464 is axially aligned therewith. The upper and lower firing bars 9462, 9464 may be welded to the vertical extending portion 9471 in those locations. For example, the welds may be applied to the firing bars from one side or from both lateral sides of the firing bars. As the cutting head 9470 is driven distally in the distal direction "DD", the anvil assembly 9220 is pivoted closed between the upper tabs(s) 9474 and the lower tab(s) or foot 9476. Further advancement of the cutting head assembly 9470 causes the surgical staple cartridge 9260 to be crushed between the anvil assembly 9220 and the carrier 9240 thereby causing the surgical staples supported therein to be formed on both sides of the tissue cut line as they are brought into contact with the staple forming underside of the anvil assembly 9220. After the cutting head assembly 9470 has been advanced to the distal end of the carrier 9240, the user retracts the cutting head assembly 9470 to the starting position whereupon the anvil assembly 9220 may be opened to release the staple cartridge 9260 and stapled tissue. In one implementation, for example, the upper tab(s) 9474 are configured to interact with the upper surface of the anvil assembly 9220 to cam or pivot the anvil assembly 9220 back to the open position. In alternative arrangements, a spring or other biasing member (not shown) may be employed to bias the anvil assembly 9220 to the open position when the cutting head assembly 9470 is in a starting position.

The drive beam assembly 9460 may further include a proximal engagement member 9467 that includes a pair of engagement fingers 9468 that are configured to operably engage a distal end 9522 of a firing rod 9104 as will be discussed in further detail herein. As can be seen in FIG. 100, for example, the proximal engagement member 9467 is pivotally coupled to the upper and lower firing bars 9462, 9464 to facilitate articulation and flexing thereof during articulation of the carrier 9240 about the articulation axis AA-AA without binding the drive beam assembly 9461. In at least one implementation, for example, the proximal engagement member 9467 is pivotally coupled to the upper and lower firing bars 9462, 9464 by a pair of pivot links 9466. Such links 9466 enable the upper firing bar 9462 to pivot relative to the proximal engagement member 9467 independent form the lower firing bar 9464 and visa versa.

As can be seen in FIG. 97, the surgical instrument 9010 may include a motor 9100 that is configured to generate rotary actuation motions that may be employed, for example, to apply firing motions to the loading unit 9020 as will be discussed in further detail below. In at least one form, for example, the motor 9100 is configured to apply rotary actuation motions to a firing member assembly, generally designated as 9082. In one arrangement, for example, the firing member assembly 9082 includes a drive tube 9102 that is rotatably supported within the housing 9012 and has an internal thread (not shown) formed therein. A proximal threaded portion of a firing member or firing rod 9104 is supported in threaded engagement with the drive tube 9102 such that rotation of the drive tube 9102 results in the axial movement of the firing rod 9104. The firing rod 9104 may interface with the interior of the drive assembly 9460 in the loading unit 9020. As discussed in further detail in the aforementioned incorporated Zemlok '763 and Zemlok '344, rotation of drive tube 9102 in a first direction (e.g., counter-clockwise) causes the firing rod 9104 to advance the drive assembly 9460 in the distal direction.

As can be further seen in FIG. 97, the surgical instrument 9010 may include an articulation system generally designated as 9109. However, surgical instrument 9010 may include various other articulation system arrangements disclosed in detail herein. In at least one form, the articulation system 9109 may include an articulation mechanism 9110 that includes an articulation motor 9112 and a manual articulation knob 9114. The articulation motor 9112 may be actuated by a powered articulation switch 9116 or by pivoting the manual articulation knob 9114. Actuation of the articulation motor 9112 serves to rotate an articulation gear 9118 of the articulation mechanism 9110. Actuation of articulation mechanism 9110 may cause the end effector (e.g., the cartridge/anvil portion of the loading unit 9020) to move from its first position, wherein its axis is substantially aligned with longitudinal tool axis "LA-LA" of the elongated shaft assembly 9116 to a position in which the axis of the end effector is disposed at an angle relative to the longitudinal tool axis "LA-LA" of the elongated shaft assembly about, for example, articulation axis "AA-AA". Further discussion regarding various aspects of the articulation mechanism 9110 may be found in Zemlok '763 which was previously incorporated by reference herein in its entirety. In addition, U.S. Pat. No. 7,431,188 entitled SURGICAL STAPLING APPARATUS WITH POWERED ARTICULATION, the entire disclosure of which is hereby incorporated by reference herein, discloses motor-powered articulatable end effectors which may be employed in connection with surgical instrument 9010. Those of ordinary skill in the art will understand, however, that the unique and novel coupling and end effector arrangements disclosed herein may also be effectively employed with manually-operated (i.e., non-powered) articulation systems that are known in the art.

In various embodiments, the surgical instrument can include at least one motor, which can apply firing motions to the loading unit 9020 and/or articulation motions to the articulation system 9109, as described elsewhere in greater detail. The motor 9100 may, for example, be powered by a power source 9200 of the type described in further detail in Zemlok '763. For example, the power source 9200 may comprise a rechargeable battery (e.g., lead-based, nickel-based, lithium-ion based, etc.). It is also envisioned that the power source 9200 may include at least one disposable battery. The disposable battery may, for example, be between about 9 volts and about 30 volts. However, other power sources may be employed. FIG. 97 illustrates one example wherein the power source 9200 includes a plurality of battery cells 9202. The number of battery cells 9202 employed may depend upon the current load requirements of the instrument 9010.

Referring to FIG. 97, a power source such as, for example, the power source 9200 can supply power for operation of the surgical instrument 9010. For example, the power source 9200 can supply power for a motor such as, for example, motor 9100 to cause rotation of the drive tube 9102 in a first direction and ultimately the axial advancement of the firing rod 9104 which drives the drive assembly 9460 distally through the loading unit 9020. Alternatively, the power source 9200 can supply power for the motor 9100 to cause rotation of the drive tube 9102 in a second direction opposite the first direction and ultimately the axial retraction of the firing rod 104 which can move the drive beam 9060 proximally to its starting and/or default position.

Figure 107:
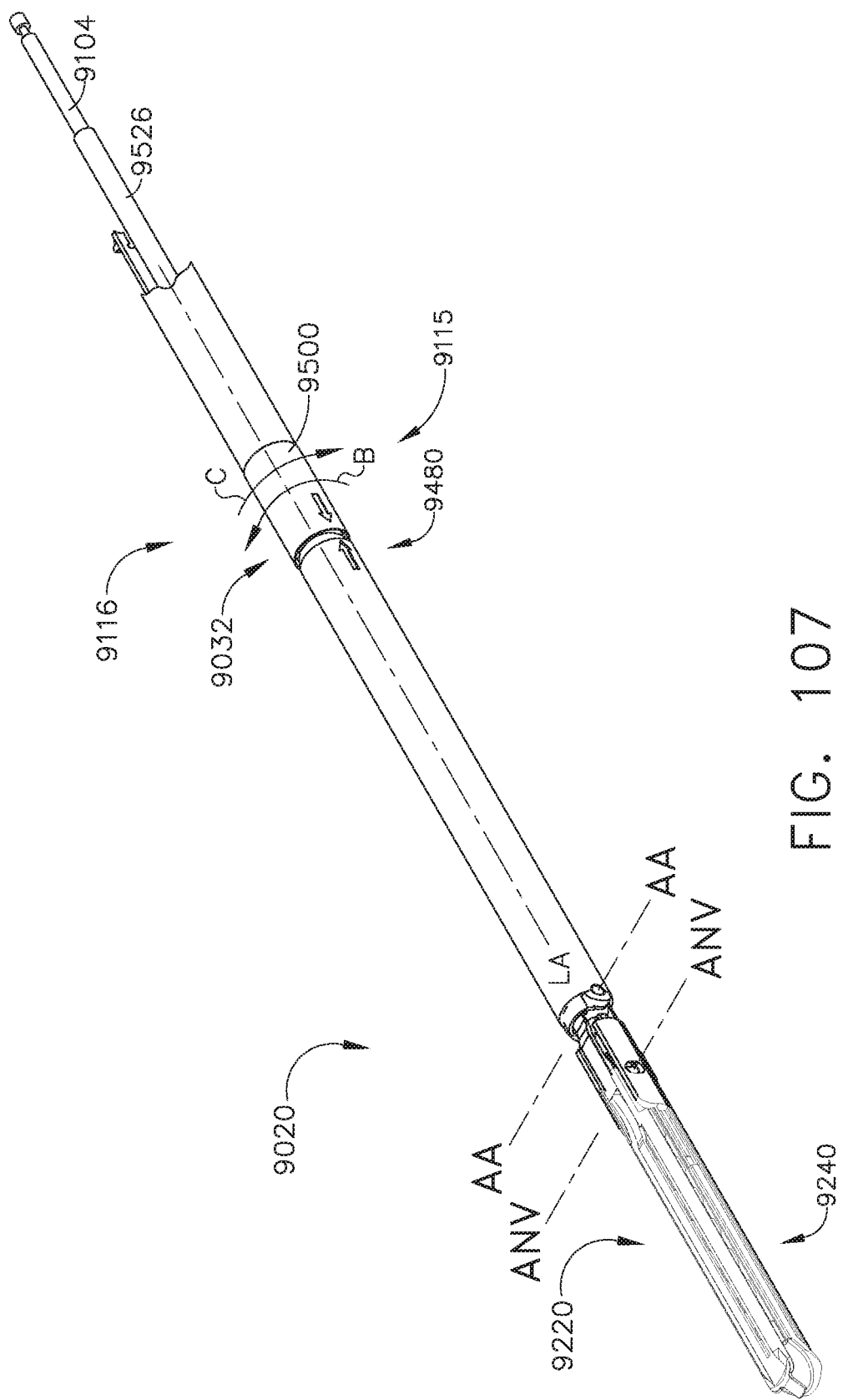
FIG. 107 is another perspective view of portions of the loading unit and elongated shaft assembly of FIG. 106 after being coupled together.

Surgical end effectors, such as a disposable loading unit 9020, for example, can be operably coupled to the elongated shaft assembly 9116 of the powered surgical instrument 10 (FIG. 1). In various embodiments, the surgical instrument 9010 can include an elongated shaft assembly 9116, which can engage the loading unit 9020, for example. In various embodiments, a coupling assembly 9115 that includes a rotatable coupling collar 9500, for example, can releasably lock the loading unit 9020 relative to the elongated shaft assembly 9116. Furthermore, in various embodiments, rotation of the coupling collar 9500 can facilitate attachment and/or alignment of a firing assembly and/or an articulation assembly, as described herein. In various embodiments, the loading unit 9020 can include a distal attachment portion 9480 and the elongated shaft assembly 9116 can include an outer tube 9030 and a distal attachment portion 9032. The distal attachment portion 9480 of the loading unit 9020 can receive the distal attachment portion 9032 of the shaft assembly 9116 when the loading unit 9020 is secured to the elongated shaft assembly 9116 (FIG. 107). Furthermore, the rotatable coupling collar 9500 can be positioned around the distal attachment portion 9032 of the shaft assembly 9116, such that the distal attachment portion 9480 of the loading unit 9020 can also be positioned within the rotatable coupling collar 9500. The rotatable coupling collar 9500 can be secured to the elongated shaft assembly 9116 and/or the proximal attachment portion 9480, and, in certain embodiments, can be rotatably fixed to the distal attachment portion 9032 of the shaft assembly 9116, for example. In certain embodiments, a proximal attachment portion of the shaft assembly 9116 can receive a distal attachment portion 9480 of the loading unit 9020 when the loading unit 9020 is secured to the shaft assembly 9116. Furthermore, in certain embodiments, a coupling collar 9500 can be rotatably fixed to the loading unit 9020.

Figure 106:
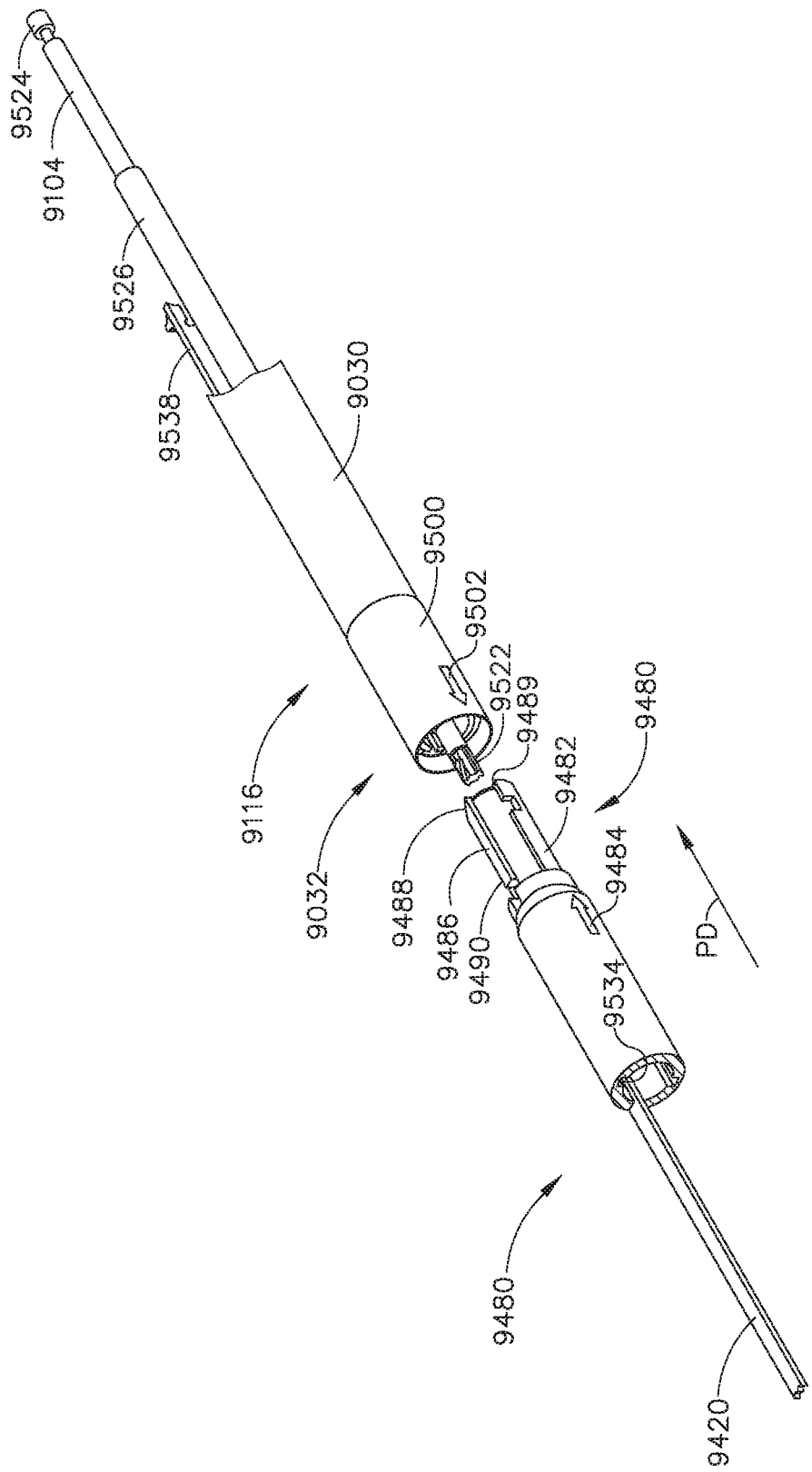
FIG. 106 is a partial perspective view of a loading unit and a portion of an elongated shaft assembly prior to commencing a coupling operation between the loading unit and a distal end of the elongated shaft assembly.
Figure 110:
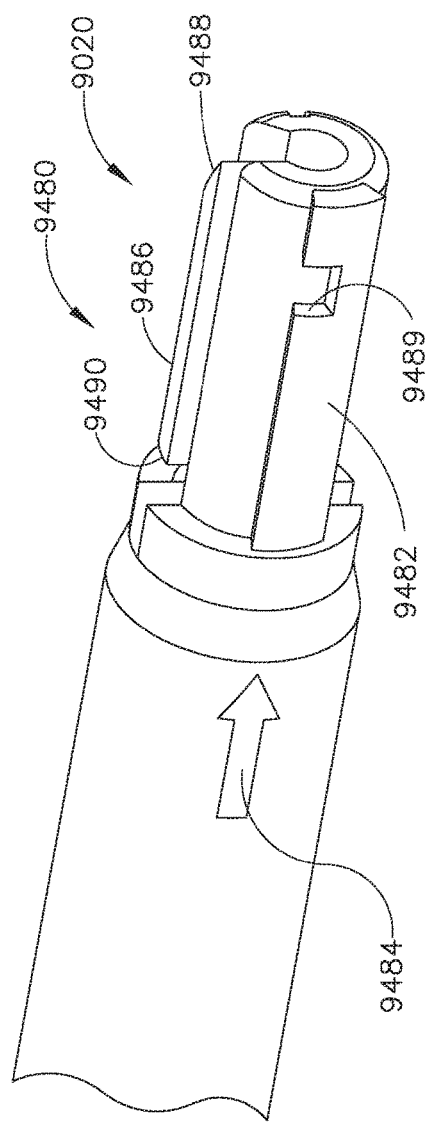
FIG. 110 is a perspective view of a distal attachment portion of the loading unit of FIG. 106.

Referring to FIGS. 106 and 107, as the loading unit 9020 moves between a non-attached position and an attached position relative to the elongated shaft assembly 9116 of the surgical instrument 9010, the loading unit 9020 can translate along a longitudinal tool axis LA-LA as defined by the elongated shaft assembly 9116. The distal attachment portion 9480 of the loading unit 9020 can be inserted into the distal attachment portion 9032 of the elongated shaft assembly 9116 as the loading unit 9020 moves from the non-attached position to the attached position. For example, the loading unit 9020 can translate in proximal direction "PD" (FIG. 107) when the loading unit 9020 is moved between the non-attached position and the attached position. In certain embodiments, a groove-and-slot engagement between the distal attachment portion 9480 and the distal attachment portion 9032 can guide the loading unit 20 along the longitudinal tool axis LA-LA defined by the elongated shaft assembly 9116. Referring primarily to FIG. 110, the distal attachment portion 9480 can include a guide rail 9482. Furthermore, referring primarily to FIG. 112, the distal attachment portion 9032 can include a guide slot 9034. The guide slot 9034 can be dimensioned and structured to receive and guide the guide rail 9482 as the proximal attachment portion 9480 of the loading unit 9020 is inserted into the distal attachment portion 9032 of the elongated shaft assembly 9116. For example, the guide slot 9034 can comprise a longitudinal slot, and the guide rail 9482 can comprise a longitudinal ridge, for example. In certain embodiments, the guide slot 9034 and guide rail 9482 can prevent twisting and/or rotating of the loading unit 9020 relative to the longitudinal tool axis LA-LA.

Referring primarily to FIG. 106, the distal attachment portion 9480 can include a first alignment indicia 9484, such as a first arrow, for example, and the elongated shaft assembly 9116 and/or the coupling collar 9500 can include a second alignment indicia 9502, such as a second arrow, for example. Alignment of the first and second alignment indicia 9484, 9502 can align the guide rail 9482 and the guide slot 9034, which can facilitate attachment of the distal attachment portion 9480 to the distal attachment portion 9032. As described herein, translation of the loading unit 9020 along a longitudinal path toward the elongated shaft assembly 9116 can releasably lock the loading unit 9020 relative to the elongated shaft assembly 9116. In such embodiments, rotation of the loading unit 9020 relative to the elongated shaft assembly 9116 may not be required to attach the loading unit 9020 relative to the elongated shaft assembly 9116. In fact, rotation of the loading unit 9020 relative to the elongated shaft assembly 9116 can be restrained and/or prevented by a groove-and-slot engagement between the distal attachment portion 9032 and the distal attachment portion 9480, as described herein. In various embodiments, the coupling collar 9500 can rotate relative to the loading unit 9020 and/or the elongated shaft assembly 9116 to releasably lock the loading unit 9020 to the elongated shaft assembly 9116. For example, as described herein, the coupling collar 9500 can rotate from an initial orientation (FIG. 120) toward a secondary orientation (FIG. 121) and then return toward the initial orientation (FIG. 124) to lock the loading unit 9020 to the elongated shaft assembly 9116.

Figure 111:
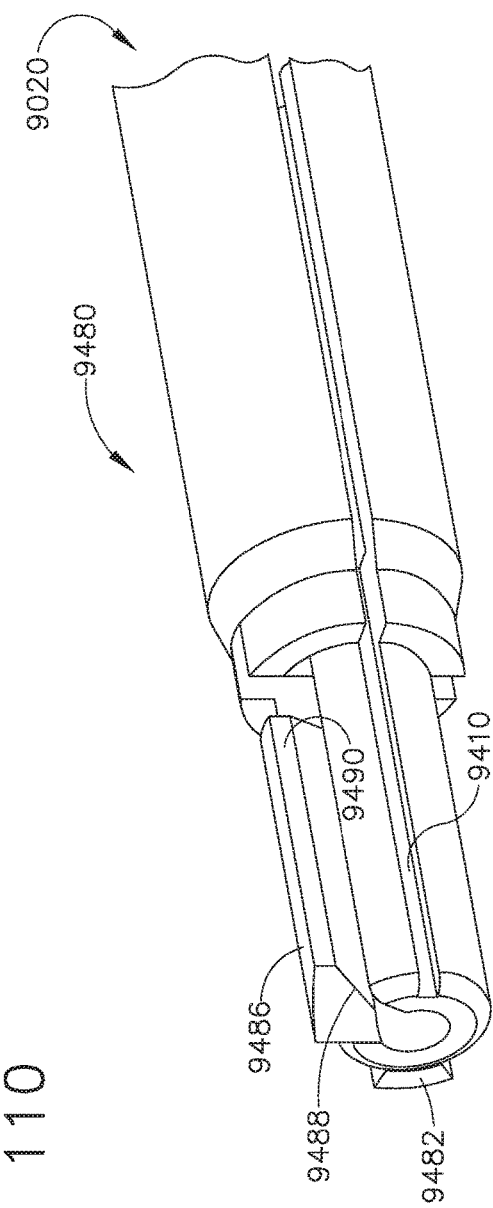
FIG. 111 is another perspective view of the distal attachment portion of the loading unit of FIG. 106.

Referring primarily to FIGS. 110 and 111, the proximal portion 9480 of the loading unit 9020 can include a rotation key or rib 9486. As the loading unit 9020 is moved in the proximal direction "PD" (FIG. 106) between a non-attached position (FIG. 106) and an attached position (FIG. 107), the rotation key 9486 can affect rotation of the coupling collar 9500. For example, the rotation key 9486 can rotate and/or bias the coupling collar 9500 in direction B (FIG. 107) from the initial orientation to the secondary orientation. The distal attachment portion 9480 can be inserted into the distal attachment portion 9032 when the coupling collar 9500 is biased into the secondary orientation. Furthermore, when the distal attachment portion 9480 is fully inserted into the distal attachment portion 9032, the rotation key 9486 can permit the coupling collar 9500 to rotate in direction C (FIG. 107) from the secondary orientation toward the initial orientation. As used herein the term "fully inserted" as used with respect to the coupling of the loading unit 9020 to the elongated shaft assembly 9116 means that the distal attachment portion 9480 of the loading unit 9020 has been fully inserted in mating or operational engagement with the distal attachment portion 9032 of the elongated shaft assembly 9116. Direction C can be opposite to direction B, for example. As described herein, when the coupling collar 9500 returns to the initial orientation, the coupling collar 9500 can lock the distal attachment portion 9480 relative to the distal attachment portion 9032. Referring to FIGS. 110 and 111, the rotation key 9486 can include a rotation ramp 9488 at the proximal end thereof. The rotation ramp 9488 can engage an element of the shaft assembly 9116 to effect rotation of the rotation coupling collar 9500, for example.

In various embodiments, the rotation ramp 9488 can affect rotation of a firing shaft 9104 positioned within the elongated shaft assembly 9116. For example, referring primarily to FIGS. 115-118, the firing shaft 9104 can include a firing shaft rotator 9600 which can extend radially outward from the firing shaft 9104. The rotation ramp 9488 of the rotation key 486 can engage the firing shaft rotator 9600 when the loading unit 9020 is inserted into the elongated shaft assembly 9116. In various embodiments, the rotation ramp 9448 can rotate the firing shaft rotator 9600, which can rotate the firing shaft 9104. For example, the firing shaft 104 and the firing shaft rotator 9600 can rotate in direction B between a first orientation (FIG. 121) and a second orientation (FIG. 122). Referring still to FIGS. 115-118, the firing shaft 9104 can be engaged with the rotatable coupling collar 9500. For example, the rotatable coupling collar 9500 can include a rotator groove 9502, which can be structured and dimensioned to receive and/or hold the firing shaft rotator 9600. The firing shaft rotator 9600 can be held by the rotator groove 9600, such that the rotation of the firing shaft rotator 9600 rotates the rotatable coupling collar 9500. In such embodiments, insertion of the loading unit 9020 into the elongated shaft assembly 9116, can affect rotation of the rotatable coupling collar 9500 in direction B (FIG. 122) via rotation of the firing shaft rotator 9600 in direction B, for example.

Referring primarily to FIGS. 112 and 113, the distal attachment portion 9032 can include a rotation key slot 9510, which can receive the rotation key 9486 when the distal attachment portion 9480 is inserted into the distal attachment portion 9032. In various embodiments, the rotation key slot 9510 can include a clearance notch 9512 for receiving the firing shaft rotator 9600. For example, the rotation ramp 9488 at the proximal end of the rotation key 9486 can rotate the firing shaft rotator 9600 to the second orientation and into the clearance notch 9512 (FIG. 122). The rotation key 9486 can continue to move along the rotation key slot 9510 as the loading unit 9020 is inserted into the elongated shaft assembly 9116. Furthermore, when the distal end 9490 of the rotation key 9486 moves past the firing shaft rotator 9600, the firing shaft rotator 9600 can rotate back toward the first orientation (FIG. 126), which can corresponding rotate the rotatable coupling collar 9500 back toward the initial orientation thereof.

In various embodiments, the rotatable coupling collar 9500 can be biased into the initial orientation relative to the elongated shaft assembly 9116 and/or the distal attachment portion 9032. For example, a spring 9514 can bias the coupling collar 9500 into the initial orientation. The spring 9514 can include a proximal end 9516 that can be secured relative to the elongated shaft assembly 9116, and a distal end 9550 that can be secured relative to the coupling collar 9500. For example, the proximal end 9516 of the spring 9514 can be retained in a proximal spring slot 9556 (FIG. 119) of the shaft assembly 9116, and the distal end 9550 of the spring 9514 can be retained in a distal spring slot 9552 (FIG. 114) of the rotatable coupling collar 9500, for example. In such embodiments, rotation of the coupling collar 9500 can displace the distal end 9550 of the spring 9514 relative to the proximal end 9516 of the spring 9514, which can generate a torsional force. Accordingly, the coupling collar 9500 can resist rotation from the initial orientation to the secondary orientation, and, when the coupling collar is rotated to the secondary orientation, the spring 9514 can bias the coupling collar 9500 back toward the initial orientation. Because the firing shaft rotator 9600 is engaged with the coupling collar 9500, the spring 9514 can also bias the firing shaft 9104 toward the first orientation thereof.

Figure 114:
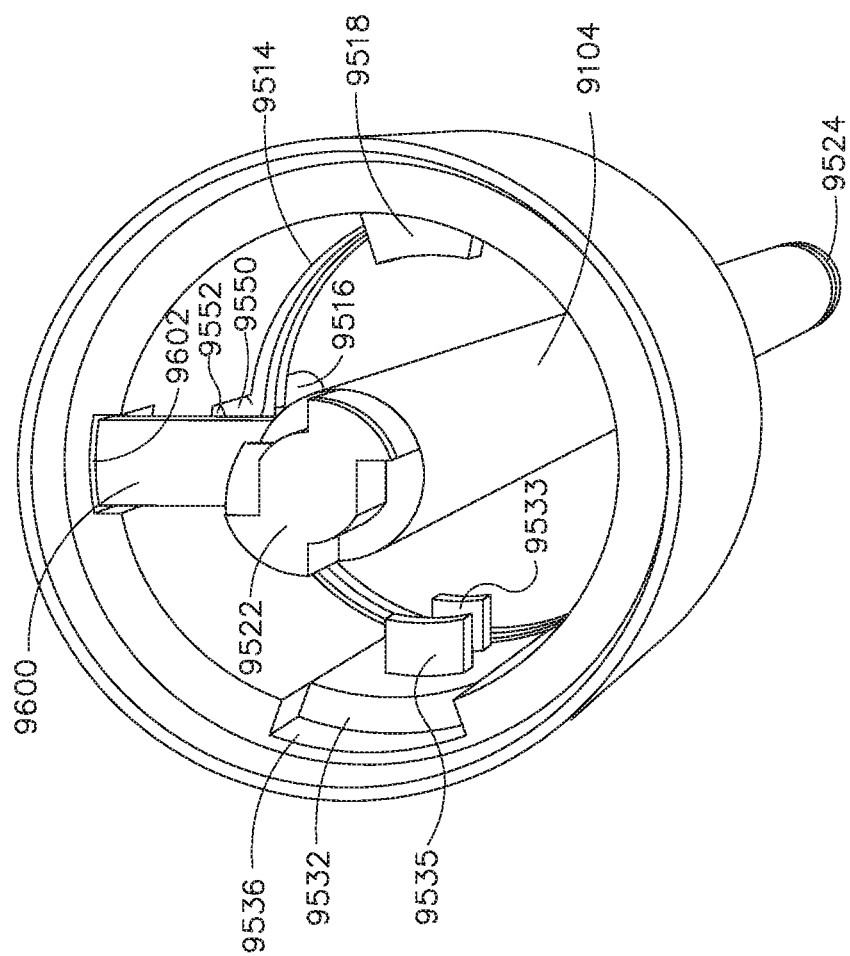
Figure 115:
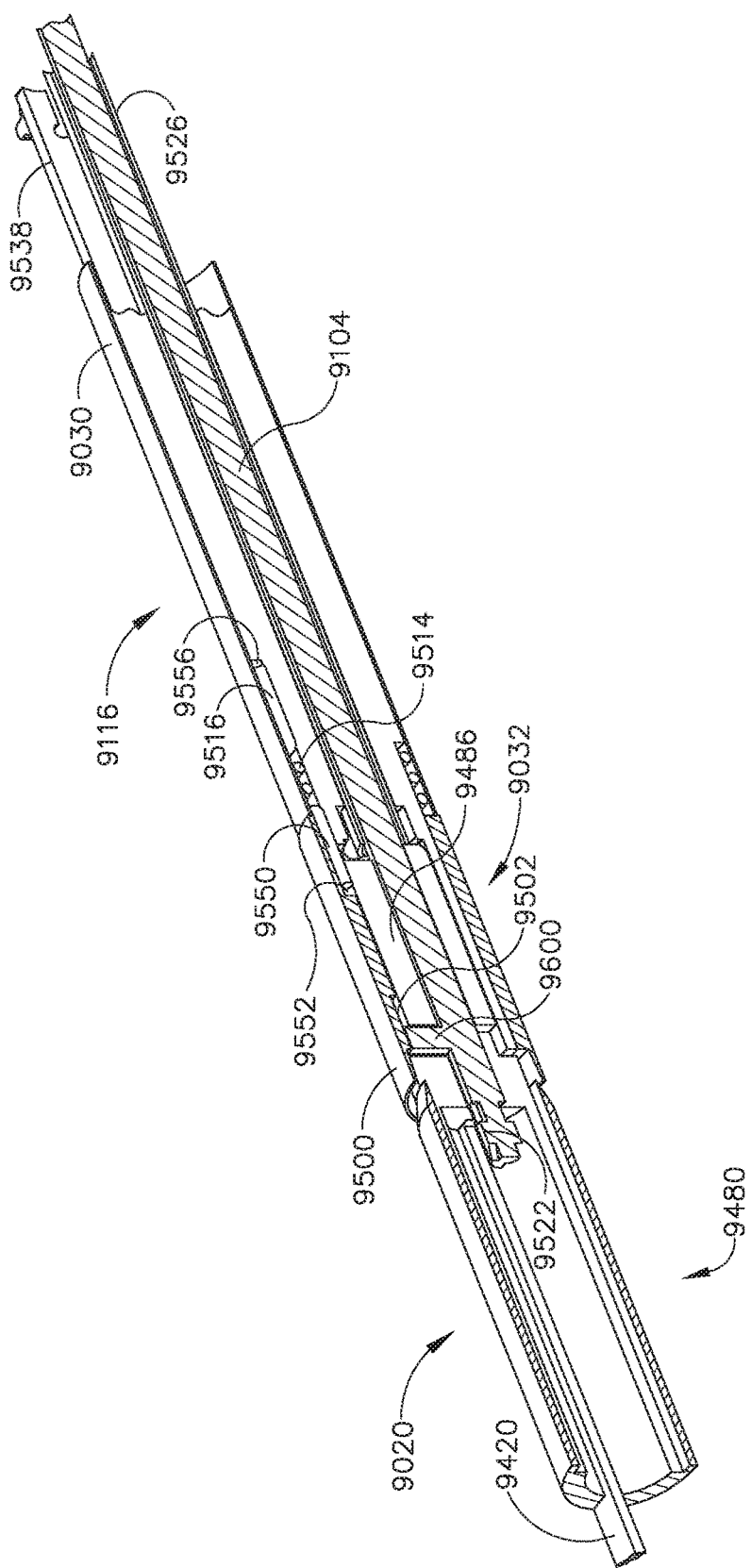
Figure 116:
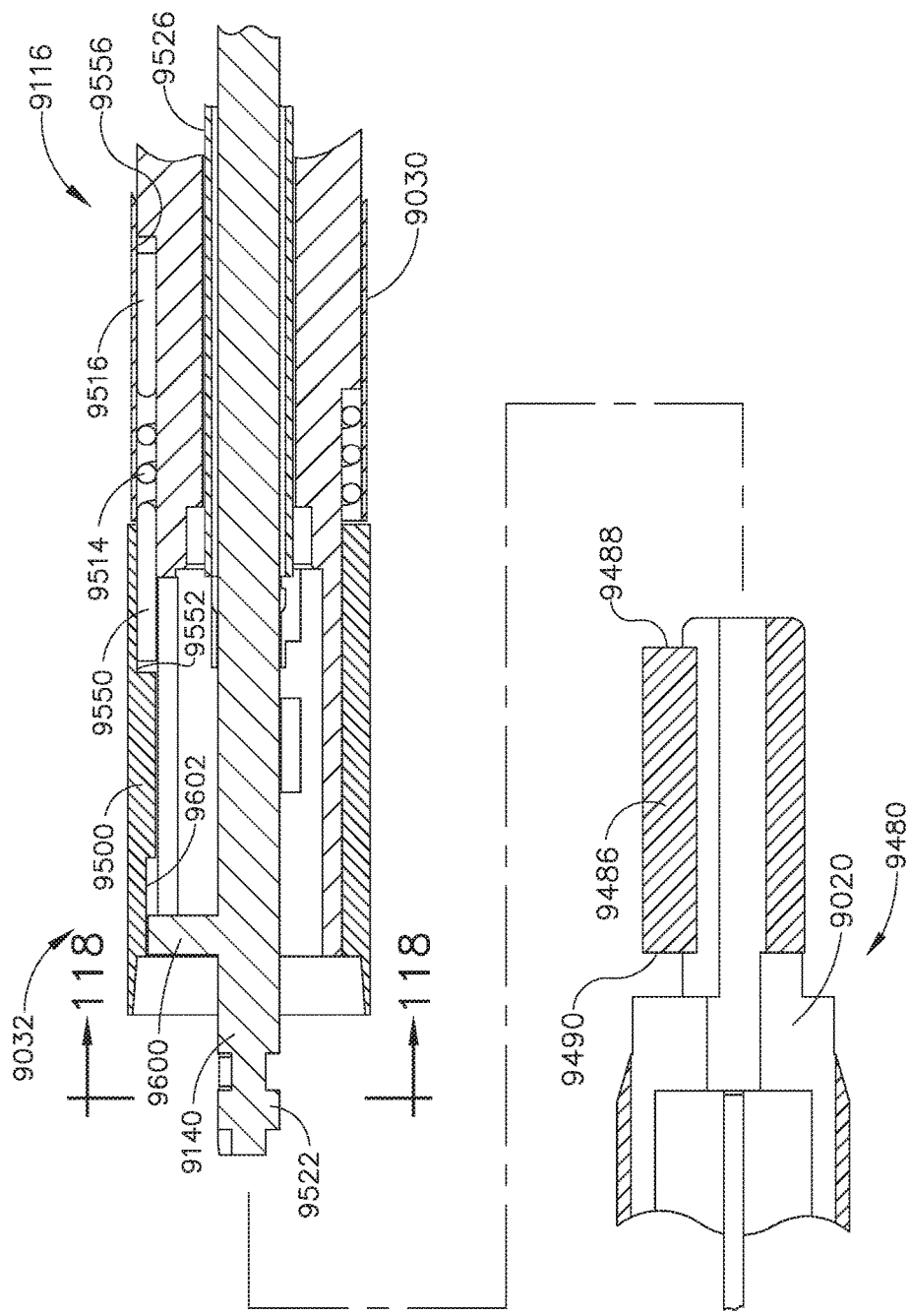
Figure 117:
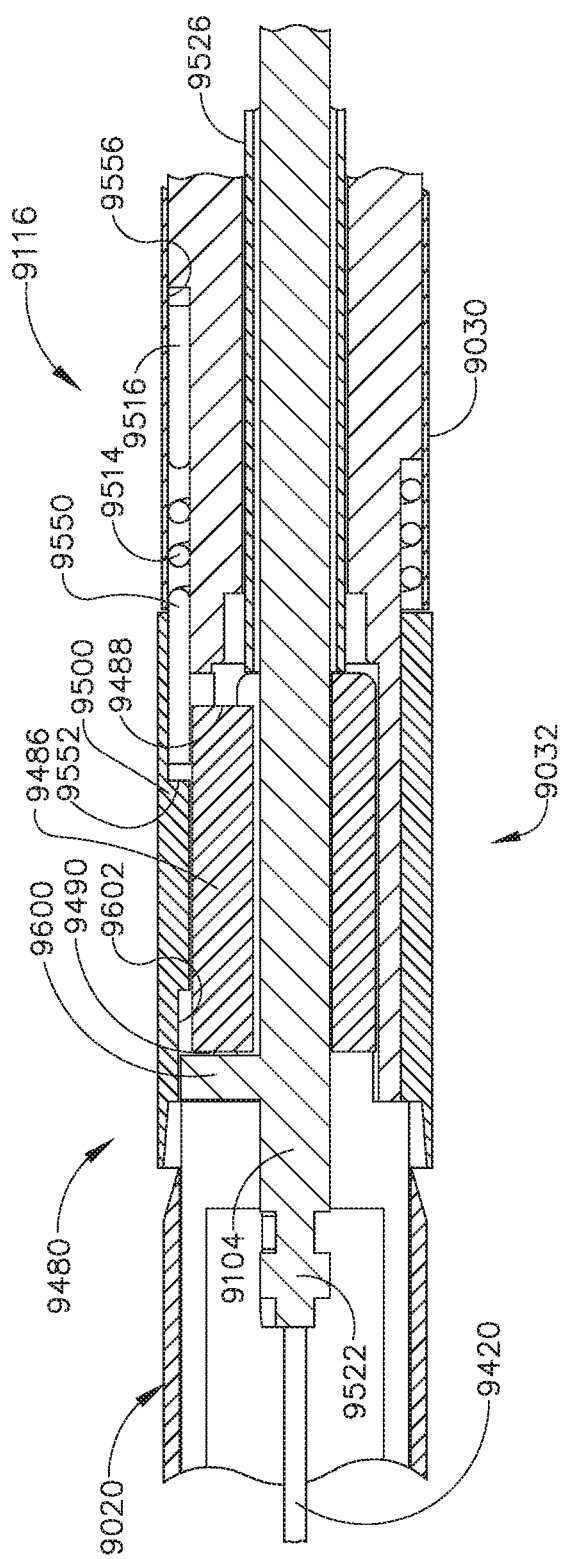
Figure 118:
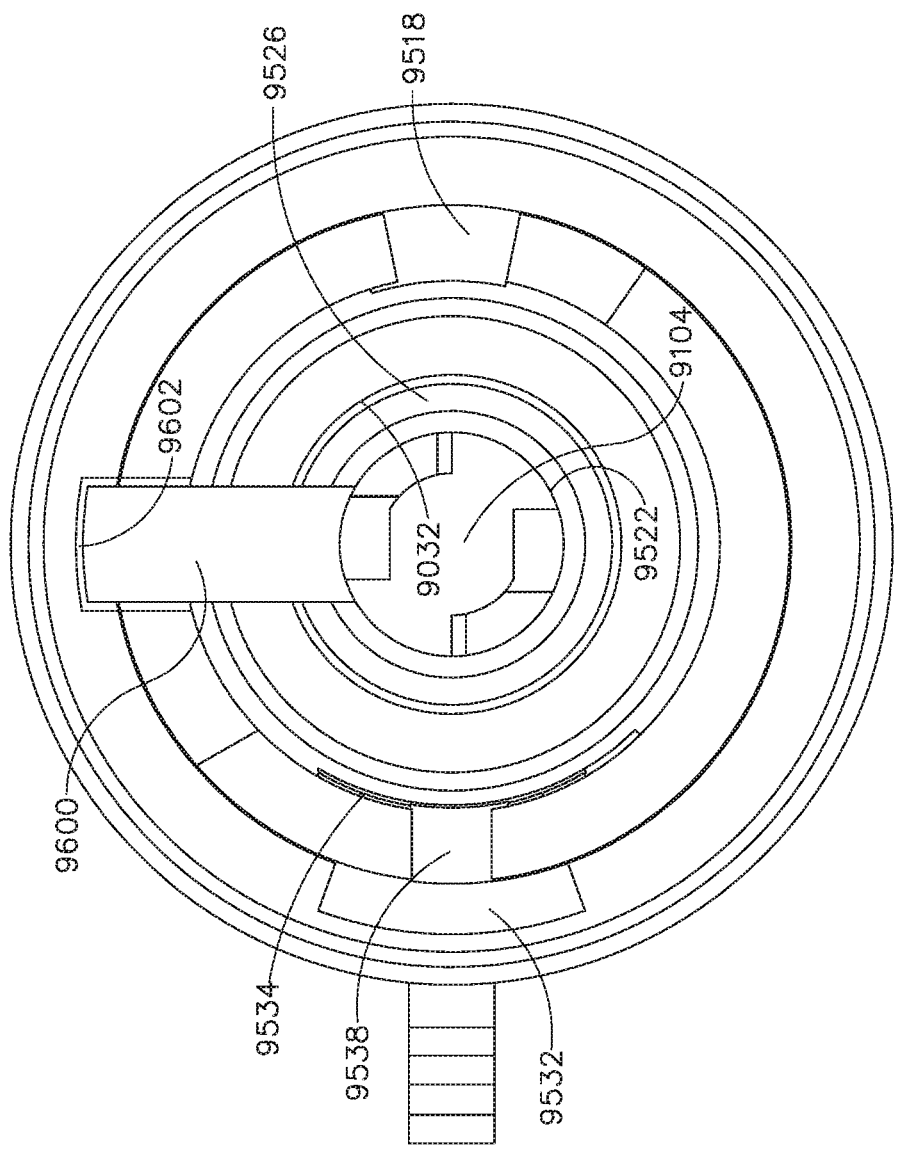

In various embodiments, the rotatable coupling collar 9500 can include a locking detent 9518 that releasably locks the loading unit 9020 to the elongated shaft assembly 9116. Referring primarily to FIG. 114, the locking detent 9518 can extend radially inward from the inner perimeter of the rotatable coupling collar 9500. In various embodiments, the locking detent 9518 can extend into a detent slot 9520 (FIG. 112) in the distal attachment portion 9032. Referring primarily to FIG. 112, the detent slot 9520 can form a notch in the guide slot 9034. In various embodiments, the detent slot 9520 can extend from the guide slot 9034, and can be perpendicular or substantially perpendicular to the guide slot 9034, for example. Further, the locking detent 9518 can move along the detent slot 9520 when the rotatable coupling collar 9500 rotates between the initial orientation and the secondary orientation relative to the elongated shaft assembly 9116.

In various embodiments, the locking detent 9518 can engage the distal attachment portion 9480 of the loading unit 9020 to lock the loading unit 9020 relative to the elongated shaft assembly 9116. For example, referring again to FIG. 110, the distal attachment portion 9480 can include the guide rail 9482, which can have a lock notch 9489 defined therein. The lock notch 9489 can be structured and dimensioned to receive the locking detent 9518 of the rotatable coupling collar 9500 when the loading unit 9020 is fully inserted into the distal attachment portion 9032. For example, when the distal attachment portion 9480 is fully inserted into the distal attachment portion 9032, the lock notch 9489 of the distal attachment portion 9480 can be aligned with the detent slot 9520 of the distal attachment portion 9032. Accordingly, the locking detent 9518 can slide along the detent slot 9520 in the distal attachment portion 9032 and into the lock notch 9489 in the distal attachment portion. Furthermore, the locking detent 9518 can be biased toward engagement with the lock notch 9489 by the torsion spring 9514. For example, after the firing shaft rotator 9600 clears the distal end 9490 of the rotation key 9486, the firing shaft 9104 can be biased back toward the first orientation and the rotatable coupling collar 9500 can be biased back toward the initial orientation by the torsion spring 9514. Furthermore, when the coupling collar 9500 is rotated from the secondary orientation back to the initial orientation, the locking detent 9518 thereof can be aligned and engaged with the lock notch 9489 in the guide rail 9482.

Figure 108:
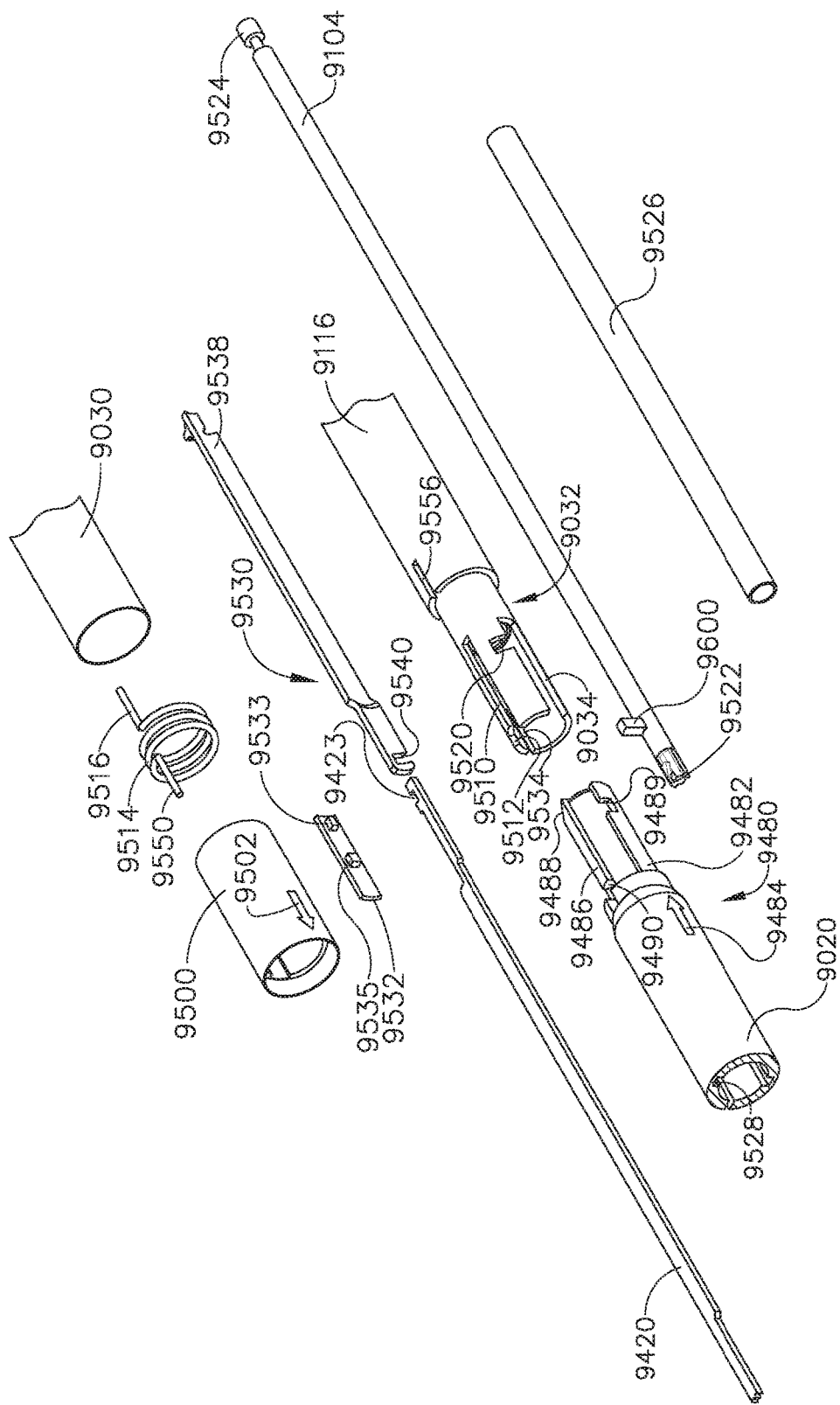
FIG. 108 is a partial exploded perspective view of portions of the elongated shaft assembly, a coupling assembly and the loading unit of FIG. 106.

In various embodiments, rotation of the coupling collar 9500 can facilitate attachment and/or alignment of a firing assembly. For example, the firing shaft 9104 can extend between a proximal end 9524 and a distal end 9522. The proximal end 9524 can have a rotation joint, which can permit rotation of the firing shaft 9104 between the first configuration and the second configuration. Furthermore, the distal end 9522 can have a coupler for attaching the proximal engagement member 9467 of the drive beam assembly 9461 to the firing shaft 104. Rotation of the firing shaft 9104 can facilitate attachment of the proximal engagement member 9467. For example, as the coupler at the distal end 9522 of the firing shaft 9104 rotates, the distal end 9522 is operably coupled to the proximal engagement member 9467. In certain embodiments, the coupler can include a bayonet mount, which can engage a corresponding bayonet receiver of the cutting element in the loading unit 9020. Referring primarily to FIGS. 108 and 109, the firing assembly can further include a sleeve 9526 positioned around the firing shaft 9104 between the proximal end 9524 and the distal end 9522, for example.

In various embodiments, when the firing shaft 9104 rotates within the elongated shaft assembly 9116, the firing shaft 9104 can rotate into alignment with a firing shaft slot 528 in the loading unit 9020. For example, the firing shaft rotator 9600 can be aligned with the firing shaft slot 9528 when the loading unit 9020 is fully inserted and attached to the elongated shaft assembly 9116. However, in various embodiments, when the loading unit 9020 is only partially inserted into the elongated shaft assembly 9116, the firing shaft rotator 9600 can be rotated, via the rotation key 9486, out of alignment with the firing shaft slot 9528. In other words, the firing shaft rotator 9600 can be aligned with the firing shaft slot 9482 when the firing shaft 9104 is in the first orientation, and can be misaligned with the firing shaft slot 9482 when the firing shaft 9104 rotates toward the second orientation. In such embodiments, when the loading unit is only partially inserted into the elongated shaft assembly 9116 and/or before the loading unit 9020 is releasably locked to the elongated shaft assembly 9116 by the rotatable coupling collar 9500, the firing path of the firing shaft rotator 9600 can be blocked by the distal attachment portion 9480. Integration of the firing shaft 9104 and the coupling collar 9500 can ensure the loading unit 9020 is securely attached to the elongated shaft assembly 9116 before the firing shaft 9104 can fire and/or advance. For example, the surgical instrument may be unable to fire until the cutting element in the loading unit 9020 is coupled to the firing shaft 9104, and/or until the firing shaft 9104 is properly aligned within the elongated shaft assembly 9116, for example.

In certain embodiments, rotation of the coupling collar 9500 can facilitate attachment and/or alignment of an articulation assembly 9530. Referring primarily to FIGS. 108 and 109, the articulation assembly 9530 can include a proximal articulation bar 9538, a distal articulation bar 9420, and an articulation connector 9532. Furthermore, the shaft assembly 9116 can include a proximal articulation bar slot 9534, and the loading unit 9020 can include a distal articulation bar slot 9410, for example. In certain embodiments, the proximal articulation bar 9538 can be aligned with the proximal articulation bar slot 9534, and the distal articulation bar 9420 can be aligned with the distal articulation bar slot 410. Referring now to FIG. 114, the articulation connector 9532 can be housed in the rotatable coupling collar 9500. For example, the rotatable coupling collar 9500 can include an articulation connector slot 9536, and the articulation connector 9532 can be moveably positioned therein.

In various embodiments, referring again to FIGS. 108 and 109, the proximal articulation bar 9538 can have a proximal notch 9540, and the distal articulation bar 9420 can have a distal notch 9423. Furthermore, the articulation connector 9532 can include a proximal articulation lug 9533 and a distal articulation lug 9540. The proximal articulation lug 9533 can be retained in the proximal notch 9540 of the proximal articulation bar 9538. In certain embodiments, the distal articulation lug 9535 can operably engage the distal notch 9423 of the distal articulation bar 9420. As described herein, the rotatable coupling collar 9500 can rotate between the initial configuration and the secondary configuration. As the coupling collar 9500 rotates, the articulation connector 9532 housed therein can also rotate relative to the longitudinal axis defined by the shaft assembly 9116. In various embodiments, the proximal articulation lug 9533 of the articulation connector 9532 can remain positioned in the proximal notch 9540 of the proximal articulation bar 9538 as the articulation connector 9532 rotates. Furthermore, the distal articulation lug 9535 of the articulation connector 9532 can move into engagement with the distal notch 9423 of the distal articulation bar 9420 as the articulation connector 9532 rotates with the coupling collar 9500 from the secondary orientation toward the initial orientation. For example, when the loading unit 9020 is fully inserted into the shaft 9488, the distal notch 9423 of the distal articulation bar 9420 can be aligned with the distal articulation lug 9533 of the articulation connector 9532. In such embodiments, when the rotatable collar 9500 rotates back to the initial configuration, the distal articulation lug 9533 can slide into the distal notch 9423 of the distal articulation bar 9420. When the distal articulation lug 9533 is positioned in the distal notch 9423, the articulation assembly 9530 can be fully assembled.

Referring primarily to FIG. 113, in various embodiments, the proximal articulation bar slot 9534 can include a first clearance 9542 and a second clearance 9544. The proximal and distal articulation lugs 9533, 9535 of the articulation connector 9532 can extend into the first and second clearances 942, 9544, respectively. In certain embodiments, the first and second clearances 9542, 9544 can provide a space for the proximal and distal articulation lugs 9533, 9535 to move as the collar 9500 rotates and/or as the articulation assembly 9530 articulates, for example.

Figure 119:
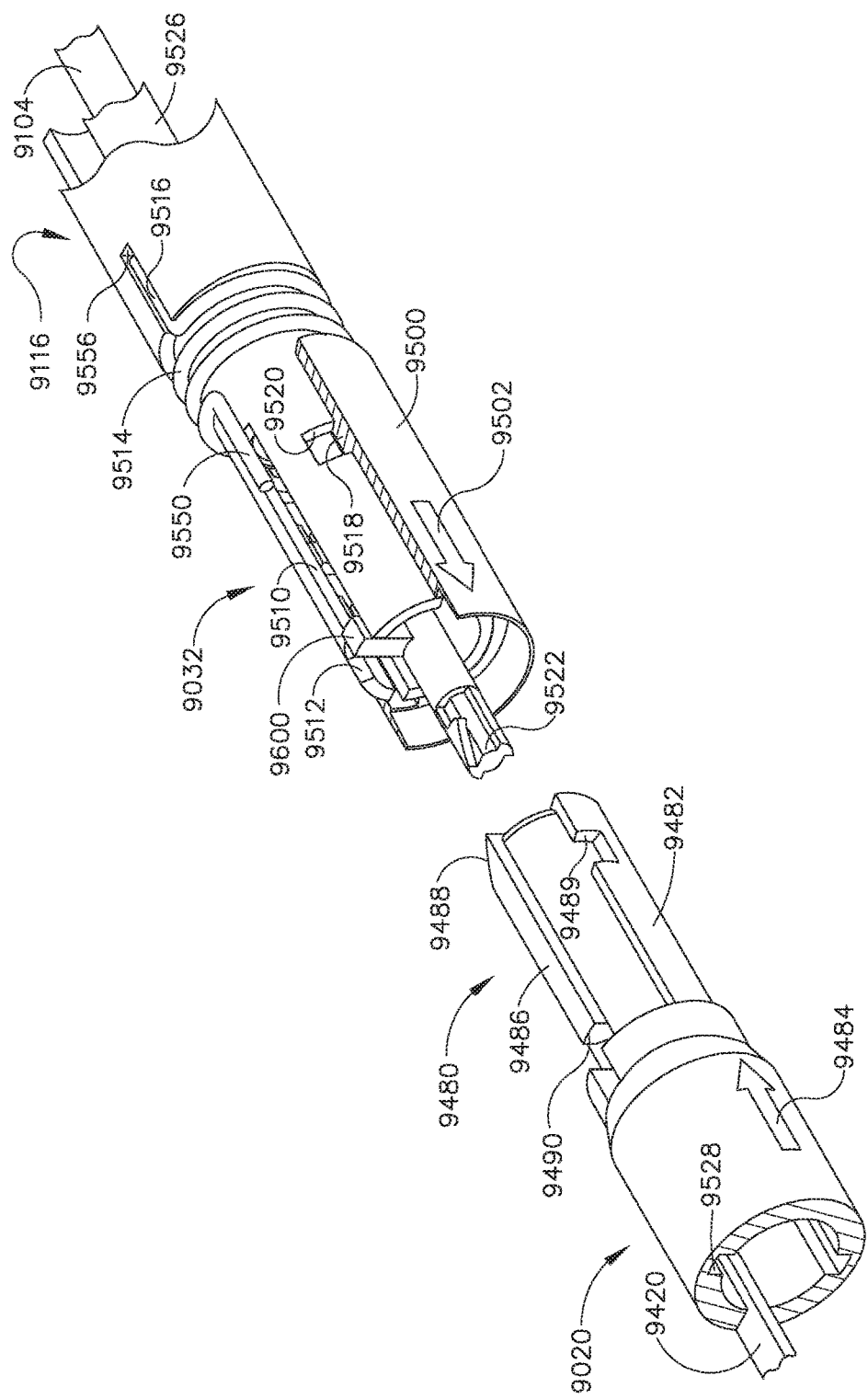
Figure 120:
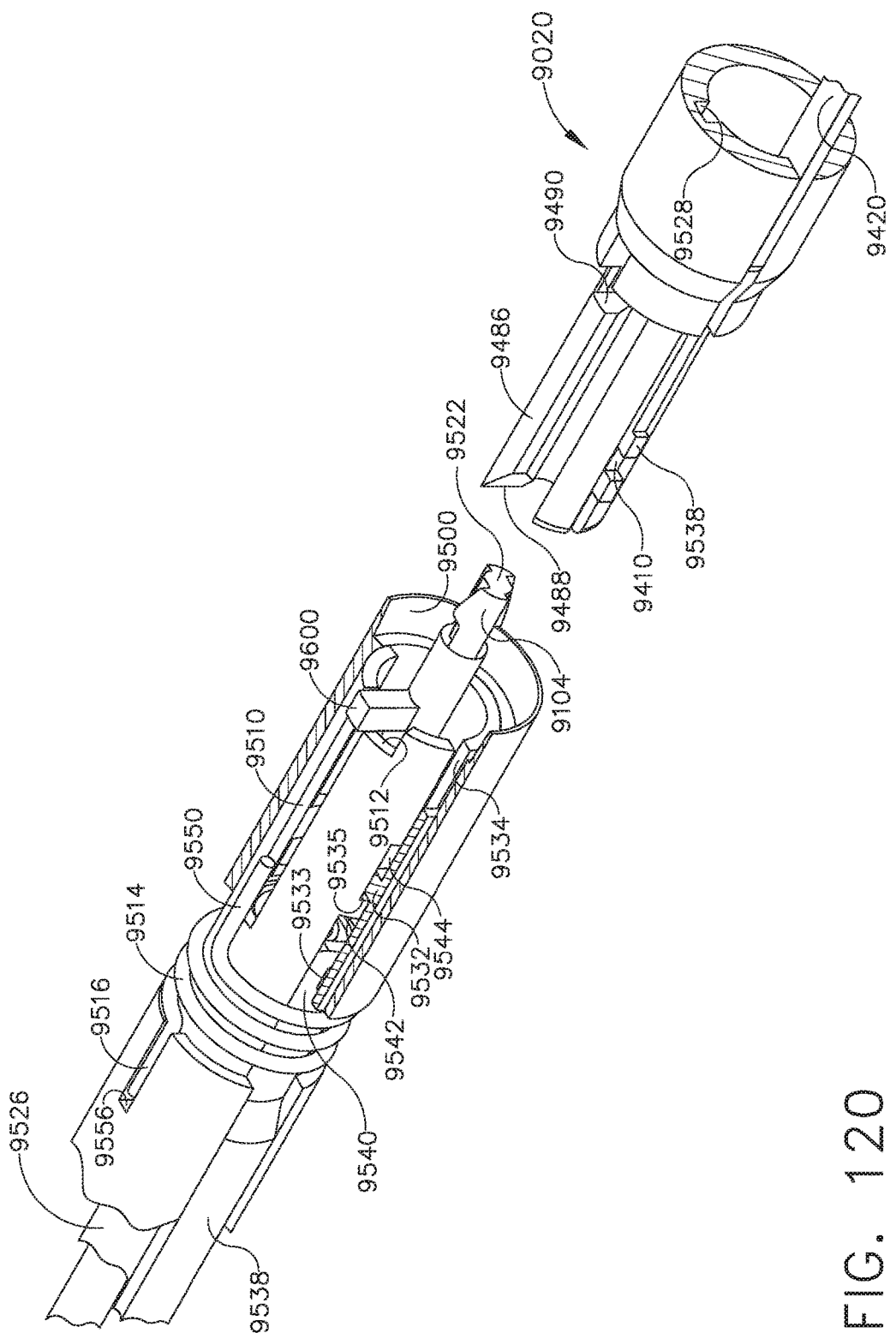
Figure 121:
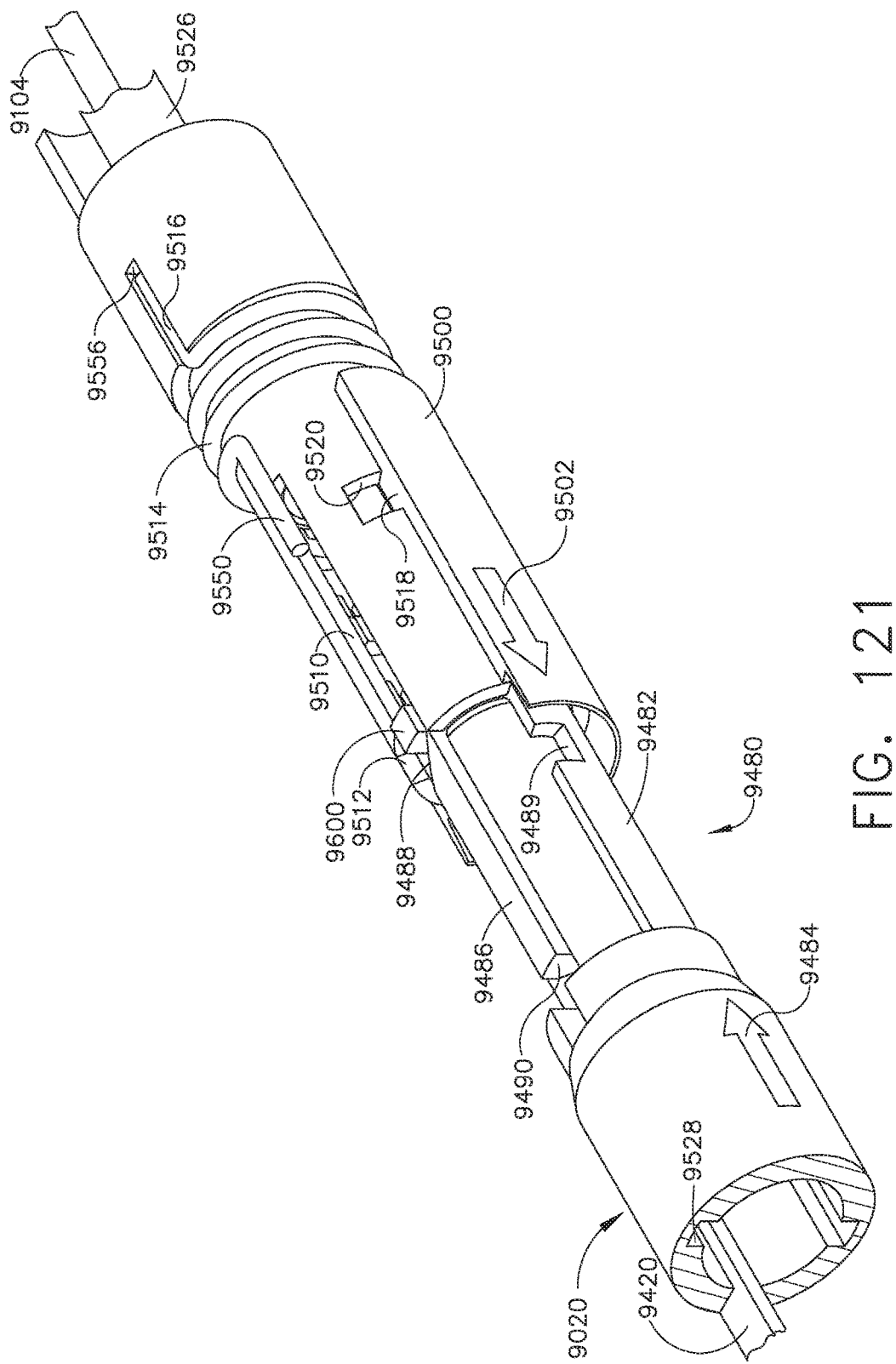
Figure 122:
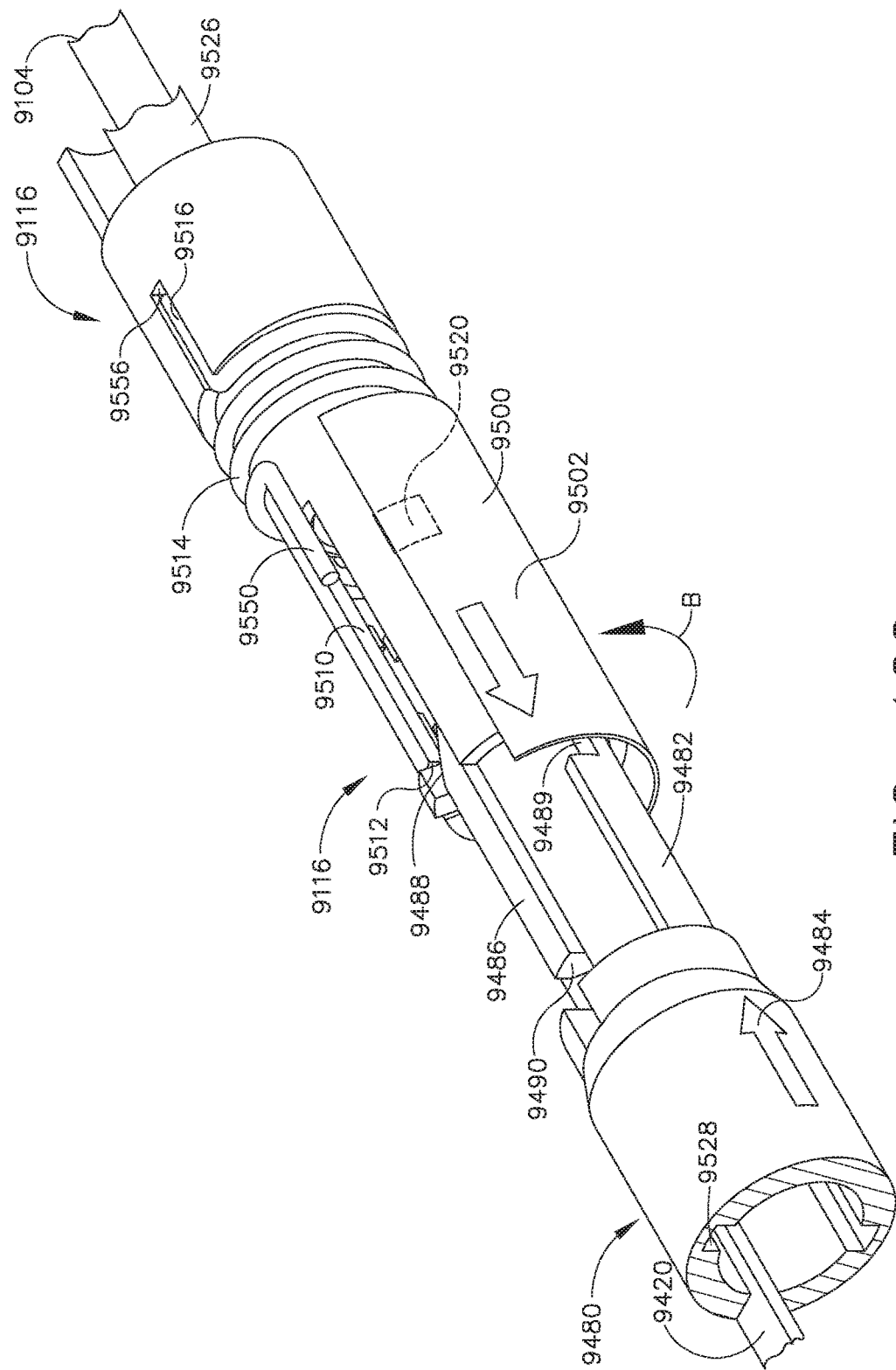

Referring now to FIGS. 119-126, to connect the loading unit to the elongated shaft assembly 9116 of the surgical instrument, a user can align the alignment indicia 9484 of the loading unit 9020 with the alignment indicia 9502 of the elongated shaft assembly 9116 and/or the coupling collar 9500 (FIG. 119). While maintaining alignment of the alignment indicia 9484, 9502, the user can move the loading unit 9020 relative to the elongated shaft assembly 9116 along the longitudinal axis LA-LA. The user can move the loading unit 9020 along a straight or substantially straight path, and, in various embodiments, need not rotate the loading unit 9020 relative to the elongated shaft assembly 9116, for example. Referring primarily to FIG. 121, the loading unit 9020 can continue to translate relative to the elongated shaft assembly 9116, and the guide rail 9482 of the distal attachment portion 9480 can fit into the guide slot 9034 (FIG. 112) in the distal attachment portion 9032 of the elongated shaft assembly 9116. As the distal attachment portion 9480 moves into the distal attachment portion 9032, the guide slot 9034 can guide the guide rail 9482, and can maintain alignment of the alignment indicia 9484, 9502, for example. In other words, the guide slot 9034 and the guide rail 9482 can prevent rotation of the loading unit 9020 relative to the longitudinal axis of the elongated shaft assembly 9116. Referring primarily to FIG. 120, the proximal articulation lug 9533 of the articulation connector 9032 can extend into the first clearance 9542 and can be positioned in the proximal notch 9540 of the proximal articulation bar 9420, and the distal articulation lug 9535 of the articulation connector 9032 can extend through the second clearance 9544, for example.

Referring primarily to FIG. 122, as the distal attachment portion 9480 is inserted into the distal attachment portion 9032, the rotation key ramp 9488 of the rotation key 9486 can abut the firing shaft rotator 9600. The rotation key ramp 9488 can guide and/or direct the firing shaft rotator 9600 into the clearance notch 9512 extending from the rotation key slot 9510. Furthermore, as the firing shaft rotator 9600 moves into the clearance notch 9512, the firing shaft 9104 can rotate in the direction B. The firing shaft 9104 can rotate from the first orientation to the second orientation. Such rotation of the firing shaft 9104 can facilitate attachment of the distal end 9522 of the firing shaft 9104 with the proximal engagement member 9467 that is pivotally coupled to the drive beam assembly 9461. Furthermore, rotation of the firing shaft rotator 9600 can rotate the coupling collar 9500 in the direction B via the engagement between the firing shaft rotator 9600 and the firing shaft rotator groove 9600 in the coupling collar 9500. The coupling collar 9500 can rotate from the initial orientation to the secondary orientation, for example. Additionally, the locking detent 9518 can move along the detent slot 9520 in the shaft assembly 9116 as the coupling collar 9500 rotates. Additionally, rotation of the coupling collar 9500 can rotate the distal end 9550 of the spring 9514 because the distal end 9550 of the spring 9514 can be retained in the distal spring slot 9552 (FIG. 114) in the coupling collar 9500. Displacement of the distal end 9550 relative to the proximal end 9516 can generate a torsional springback force, which can bias the coupling collar 9500 from the secondary orientation toward the initial orientation, for example, and can bias the firing shaft 9104 from the second orientation toward the first orientation, for example.

Figure 123:
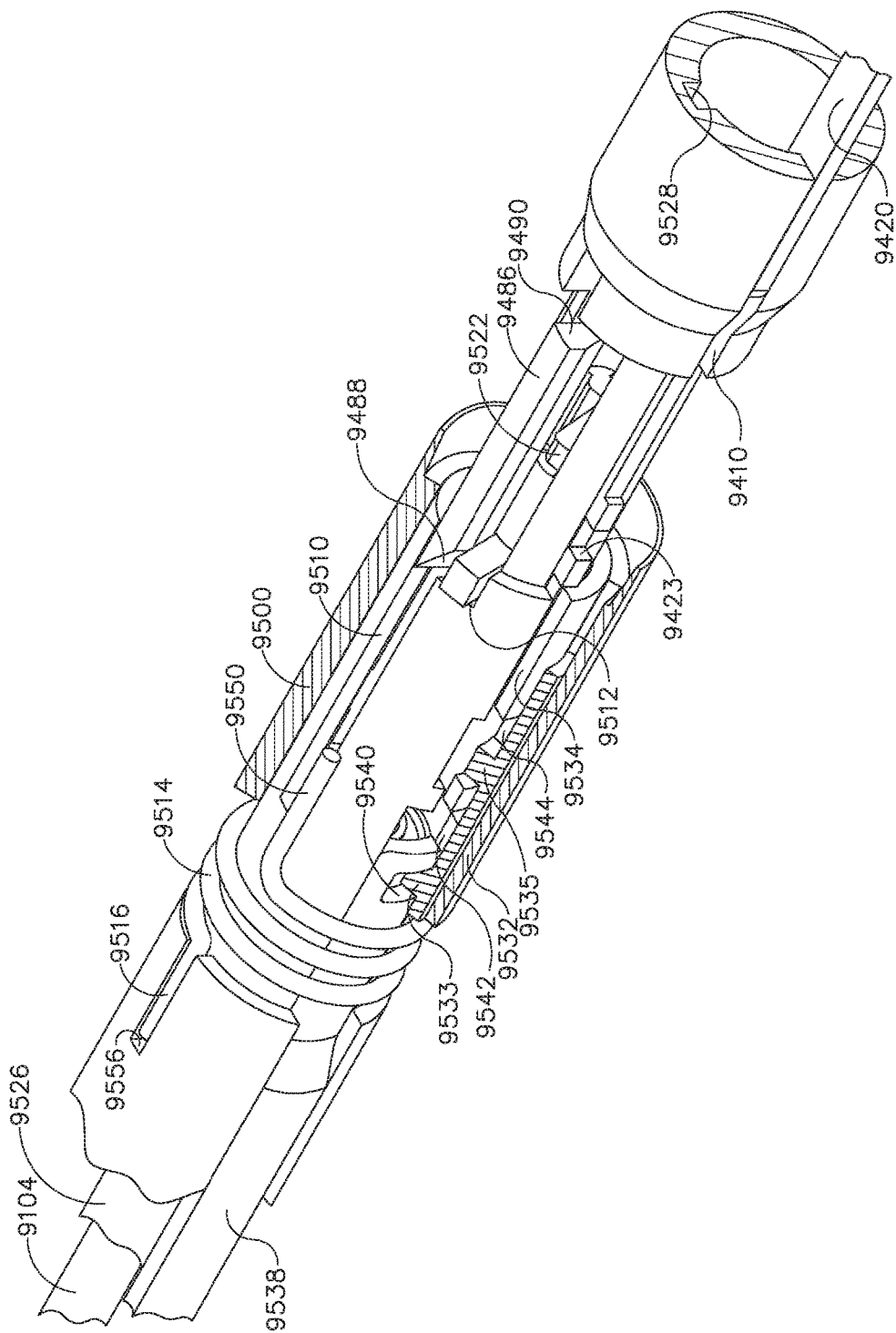
Figure 124:
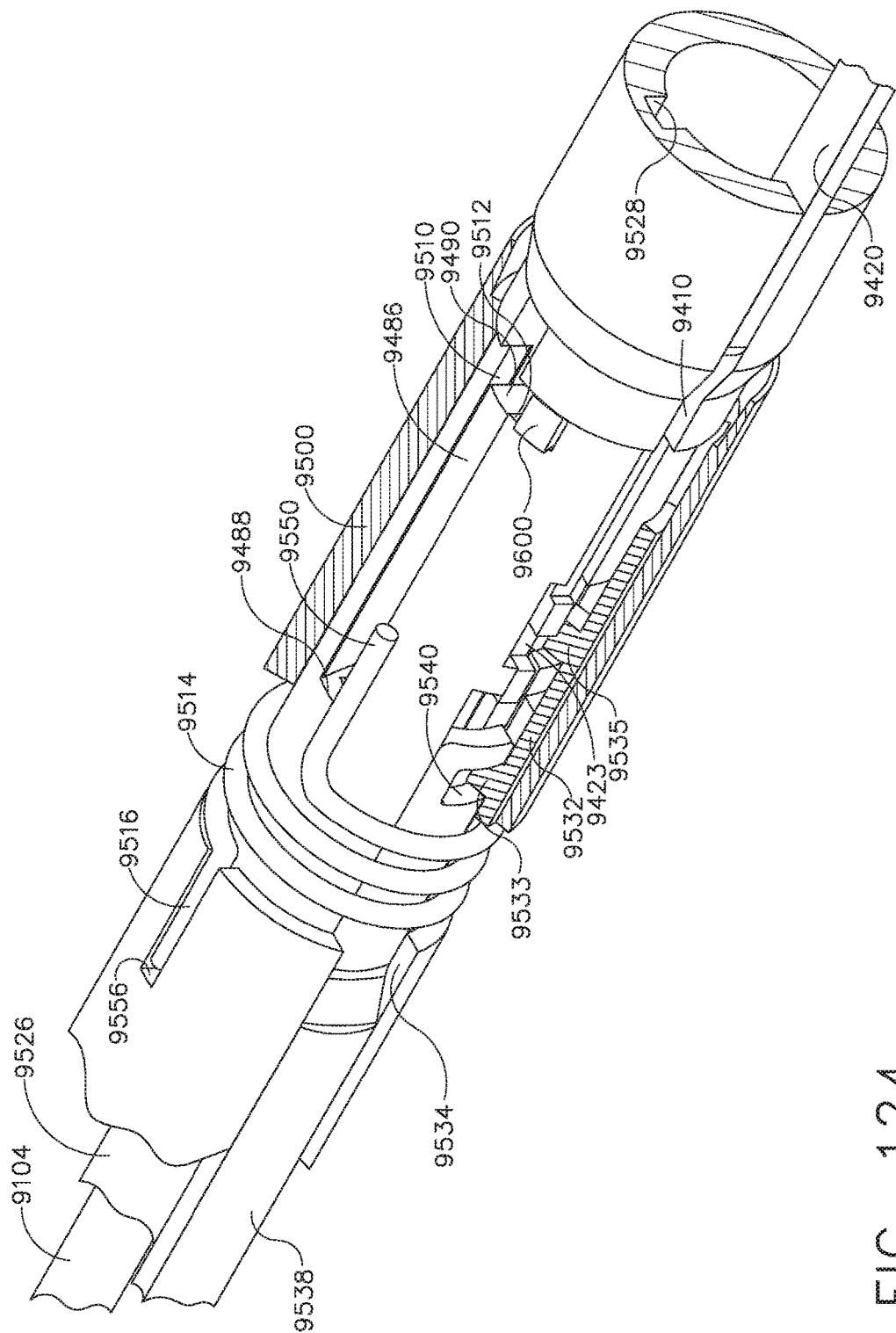

Referring primarily to FIG. 123, as the coupling collar 9500 rotates toward the secondary orientation, the proximal articulation lug 9533 can remain engaged with the proximal notch 9540 in the proximal articulation bar 9538. Furthermore, the distal articulation lug 9535 can rotate such that the distal articulation lug 9535 provides a clearance for the distal articulation bar 9420 of the loading unit 9020. Referring to FIG. 124, the loading unit 9020 can be fully inserted into the elongated shaft assembly 9116 when the coupling collar 9500 and the articulation connector 9532 positioned therein are rotated to the secondary orientation. In various embodiments, the distal articulation bar 9420 can clear the distal articulation lug 9535 of the articulation connector 9532 when the articulation connector 9532 is rotated to the secondary orientation. Furthermore, the distal articulation lug 9535 can be rotatably aligned with the distal notch 9423 in the articulation connector 9532. Referring still to FIG. 124, when the loading unit 9020 is fully inserted into the elongated shaft assembly 9116, the firing rod rotator 9600 can clear the distal end 9490 of the rotation key 9486.

Referring now to the FIG. 125, the firing shaft rotator 9600 can rotate in the direction C when the distal end 9490 of the rotation key 9486 passes the firing shaft rotator 9600. For example, the firing shaft rotator 9600 can rotate in direction C from the second orientation toward the first orientation. Furthermore, rotation of the firing shaft rotator 9600 can affect rotation of the coupling collar 9500 in the direction C from the secondary orientation toward the initial orientation. In various embodiments, the spring 9514 can bias the firing rod 9104 toward the first orientation thereof and the collar 9500 toward the initial orientation thereof. For example, the firing shaft rotator 9600 can be positioned in the firing shaft rotator groove 9602 (FIG. 114) in the coupling collar 9500 such that rotation of the firing shaft rotator 9600 rotates the coupling collar 9500. Due to the alignment of the distal articulation lug 9535 of the articulation connector 9532 and the distal notch 9423 of the distal articulation bar 9420, the articulation connector 9532 can rotate as the coupling collar 9500 rotates, and the distal articulation lug 9535 can rotate into engagement with the distal notch 9423. The articulation assembly 9530 can be assembled when the distal articulation lug 9535 engages the distal notch 9423. Furthermore, as the firing shaft rotator 9600 rotates in direction C, the distal end 9522 of the firing shaft 9104 can rotate in direction C, which can facilitate attachment of a the proximal engagement member 9467 of the drive beam assembly 9461 to the distal end 9522 of the firing shaft 9104.

Referring now to FIG. 126, rotation of the coupling collar 9500 can also rotate the locking detent 9518 of the collar 9500 into the lock notch 9489 in the guide rail 9482 of the distal attachment portion 9480. For example, when the loading unit 9020 is fully inserted into the elongated shaft assembly 9116, the lock notch 9489 can be aligned with the detent slot 9520 such that the locking detent 9518 can rotate through the detent slot 9520 and into the lock notch 9489. As described herein, the spring 9514 can bias the coupling collar 9500 to rotate in the direction C (FIG. 125) after the firing shaft rotator 9600 clears the distal end 9490 of the rotation key 9486. Referring still to FIG. 126, when the firing shaft rotator 9600 rotates in direction C, the firing shaft rotator 9600 can move into alignment with the firing shaft slot 9528 in the loading unit 9020. Alignment of the firing shaft rotator 9600 with the firing shaft slot 9528 can permit the firing shaft 9104 to be advanced distally to fire the loading unit 9020, for example.

As described herein, the rotatable coupling collar 9500 can releasably lock the loading unit 9020 relative to the elongated shaft assembly 9116. Furthermore, rotation of the coupling collar 9500 can facilitate simultaneous attachment and/or alignment of the articulation assembly 9530, as well as attachment and/or alignment of the firing shaft 9104 with a cutting head assembly in the loading unit 9020, for example. Furthermore, rotation of the coupling collar 9500 can also simultaneously unlock the loading unit 9020 from the elongated shaft assembly 9116, disconnect the articulation assembly 9530, and/or disconnect the firing shaft 104 from the cutting element in the loading unit 9020. For example, when the coupling collar 9500 is again rotated from the initial orientation toward the secondary orientation, the locking detent 9518 can disengage the lock notch 9489 in the distal attachment portion 9480. Accordingly, the distal attachment portion 9480 can be withdrawn from the distal attachment portion 9032 along the longitudinal axis defined by the elongated shaft assembly 9116, for example. In various embodiments, the loading unit 9020 can be unattached from the elongated shaft assembly 9116 without rotating the loading unit 9020 relative to the elongated shaft assembly 9116. However, the coupling collar 9500 can rotate relative to the elongated shaft assembly 9116, which can disconnect the distal articulation bar 9420 from the articulation connector 9532 in the coupling collar 9500, and can disconnect the firing shaft 9104 from the cutting element or drive beam assembly in the loading unit 9020, for example.

Thus, as can be appreciated from the foregoing, at least one surgical instrument embodiment of the present invention includes a surgical end effector that comprises a lower jaw and an upper jaw. In one implementation, the upper jaw comprises a proximal upper jaw portion that is pivotally coupled to the lower jaw for selective pivotal travel relative thereto about a pivot axis between open and closed positions upon application of closing and opening motions to the proximal upper jaw portion. A distal upper jaw portion may be movably coupled to the proximal upper jaw portion and is supported for parallel movement toward and away from the lower jaw when the proximal upper jaw portion is in the closed position. A firing member may be operably supported for operable travel within the surgical end effector relative to the upper and lower jaws when the proximal upper jaw portion is in the closed position and firing motions are applied to the firing member.

In at least one implementation, the surgical instrument may employ a lockout system that is configured to not only prevent actuation of the firing system or stated another way, advancement of the cutting head through the elongated channel when a cartridge is not present, but also to prevent such firing system actuation unless a new cartridge has been properly supported within the elongated channel. In such implementations, each new cartridge has a sled assembly supported in a starting position. When a cartridge has been properly installed within the elongated channel, the sled assembly interfaces with the lockout system to thereby enable the cutting head to be advanced distally through the cartridge. If, however, a spent cartridge has been inadvertently installed in the elongated channel, the lockout system will prevent actuation of the cutting head, because the sled assembly will be located in the distal end of the cartridge and thereby unable to interface with the lockout system. Such system will prevent re-actuation of the firing system, should the clinician fail to replace a spent cartridge and attempt to actuate the firing system.

In at least one other implementation, there is provided a surgical instrument that comprises an elongated shaft assembly and a surgical end effector that includes an elongated channel that is coupled to the elongated shaft assembly. A surgical staple cartridge may be operably supported in the elongated channel. The end effector may further comprise an anvil assembly that includes a proximal anvil portion that is pivotally coupled to the elongated channel about a pivot axis. The proximal anvil portion is selectively movable between open and closed positions upon application of closing and opening motions thereto. The anvil assembly may further comprise a distal anvil portion that is slidably coupled to the proximal anvil portion such that when the proximal anvil portion is in the closed position, the distal anvil portion is movable relative thereto while remaining parallel to the elongated channel. A firing member may be operably supported for operable movement within the surgical end effector upon application of firing and retraction motions thereto. A firing system may be configured to selectively apply the firing and retraction motions to the firing member. The instrument may further include a closure system for applying the opening and closing motions to the proximal anvil portion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In connection with another implementation, there is provided a surgical instrument that includes an elongated shaft assembly that defines a longitudinal tool axis. The instrument further includes a surgical end effector that has an elongated channel that is movably coupled to the elongated shaft assembly for selective pivotal travel about a pivot axis that is transverse to the longitudinal tool axis upon application of articulation motions thereto. The elongated channel may be configured to operably support a surgical staple cartridge. An anvil assembly is pivotally coupled to the elongated channel for selective pivotal travel relative thereto between open and closed positions about the pivot axis upon application of closing and opening motions thereto.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical cutting and stapling instrument, comprising:
   a surgical end effector, comprising:
      an elongated channel configured to operably support a surgical staple cartridge therein;
      an anvil movably supported relative to the elongated channel such that the anvil and elongated channel may move toward and away from each other; and
      a firing member operably supported for selective operable travel through the surgical staple cartridge upon application of firing motions to the firing member and wherein the surgical cutting and stapling instrument further comprises:
   a first jaw closure system operably interfacing with the elongated channel and configured to selectively move the elongated channel relative to the anvil;

a second jaw closure system independently operable from the first jaw closure system, wherein the second jaw closure system operably interfacing interfaces with the anvil and is configured to selectively move the anvil relative to the elongated channel; and a firing system operably interfacing with the firing member and configured to apply the firing motions to the firing member to move the firing member within the surgical staple cartridge.

2. The surgical cutting and stapling instrument of claim 1 wherein the first jaw closure system is configured to move a portion of the elongated channel toward and away from a corresponding portion of the anvil.

3. The surgical cutting and stapling instrument of claim 2 wherein the second jaw closure system is configured to move the corresponding portion of the anvil toward and away from the portion of the elongated channel.

4. The surgical cutting and stapling instrument of claim 1 wherein the elongated channel is pivotally coupled to an elongated shaft assembly about a pivot axis and wherein the anvil is pivotally supported relative to the elongated channel for selective pivotal travel relative to the elongated channel about the pivot axis.

5. The surgical cutting and stapling instrument of claim 4 further comprising a handle operably supporting portions of each of the first jaw closure system, the second jaw closure system, and the firing system therein, wherein the elongated shaft assembly is operably coupled to the surgical end effector for transferring first jaw control motions from the first jaw closure system to the elongated channel, second jaw control motions from the second jaw closure system to the anvil, and the firing motions from the firing system to the firing member.

6. The surgical cutting and stapling instrument of claim 4 further comprising a housing operably supporting portions of each of the first jaw closure system, the second jaw closure system, and the firing system therein, and wherein the elongated shaft assembly is operably coupled to the surgical end effector for transferring first jaw control motions from the first jaw closure system to the elongated channel, second jaw control motions from the second jaw closure system to the anvil, and the firing motions from the firing system to the firing member.

7. The surgical cutting and stapling instrument of claim 1 wherein the firing member comprises a tissue cutting head configured for axial travel through the surgical staple cartridge such that upon application of one of the firing motions thereto, the firing member moves the anvil towards the elongated channel and severs tissue clamped between the surgical staple cartridge supported in the elongated channel and the anvil.

8. The surgical cutting and stapling instrument of claim 7 wherein the surgical staple cartridge comprises a bio-absorbable cartridge body operably supporting a plurality of surgical staples therein.

9. The surgical cutting and stapling instrument of claim 8 wherein said firing member comprises a tissue cutting head configured for axial travel through the surgical staple cartridge such that upon application of one of the firing motions to the tissue cutting head, the tissue cutting head moves the anvil into crushing engagement with the bio-absorbable cartridge body to form the surgical staples supported therein and severs the tissue clamped between the anvil and the surgical staple cartridge.

10. A surgical cutting and stapling instrument, comprising:
a surgical end effector, comprising:
an elongated channel configured to operably support a surgical staple cartridge therein;
an anvil movably supported relative to the elongated channel such that the anvil and elongated channel may move toward and away from each other; and
a firing member operably supported for selective operable travel through the surgical staple cartridge upon application of firing motions to the firing member, wherein the surgical cutting and stapling instrument further comprises:
a first jaw closure system operably interfacing with the elongated channel and configured to selectively move the elongated channel relative to the anvil;
a second jaw closure system operably interfacing with the anvil and configured to selectively move the anvil relative to the elongated channel;
a firing system operably interfacing with the firing member and configured to apply the firing motions to the firing member to move the firing member within the surgical staple cartridge; and
a handle operably supporting portions of each of the first jaw closure system, the second jaw closure system and the firing system therein, wherein the elongated channel is pivotally coupled to an elongated shaft assembly about a pivot axis, wherein the anvil is pivotally supported relative to the elongated channel for selective pivotal travel relative to the elongated channel about the pivot axis, wherein the first jaw closure system comprises a first jaw actuator bar movably supported by the elongated shaft assembly for selective axial travel in response to actuation of the first jaw closure system, wherein the first jaw actuator bar operably interfaces with the elongated channel, wherein the second jaw closure system comprises a second jaw actuator bar movably supported by the elongated shaft assembly for selective axial travel relative to the first jaw actuator bar in response to actuation of the second jaw closure system, and wherein the second jaw actuator bar operably interfaces with the anvil.

11. A surgical cutting and fastening instrument comprising:
a housing;
an elongated shaft assembly operably coupled to the housing;
a surgical end effector, comprising:
an elongated channel configured to support a surgical staple fastener cartridge therein, the elongated channel movably coupled to a distal end of the elongated shaft assembly;
an anvil movably coupled to the distal end of the elongated shaft assembly, the anvil and elongated channel being supported for movable travel toward and away from each other; and
a firing member operably supported for selective operable travel within the surgical end effector and wherein the surgical cutting and fastening instrument further comprises:
a first jaw closure system operably supported by the housing;
a first jaw actuator bar operably supported by the elongated shaft assembly and operably interfacing with the elongated channel and the first jaw closure system such that actuation of the first jaw closure system causes the elongated channel to move in a desired direction relative to the anvil;

a second jaw closure system operably supported by the housing;

a second jaw actuator bar operably supported by the elongated shaft assembly and operably interfacing with the anvil and the second jaw closure system such that actuation of the second jaw closure system causes the anvil to move relative to the elongated channel; and a firing system operably supported by the housing and operably interfacing with the firing member such that actuation of the firing system causes the firing member to move axially relative to the elongated channel and the anvil.

12. The surgical cutting and fastening instrument of claim 11 wherein the elongated channel and the anvil are pivotally coupled to the elongated shaft assembly for pivotal travel relative thereto about a common axis.

13. The surgical cutting and fastening instrument of claim 11 wherein the housing comprises a handle.

14. The surgical cutting and fastening instrument of claim 11 wherein the first jaw closure system is configured to move a portion of the elongated channel toward and away from a corresponding portion of the anvil.

15. The surgical cutting and fastening instrument of claim 14 wherein the second jaw closure system is configured to move the corresponding portion of the anvil toward and away from the portion of the elongated channel.

16. The surgical cutting and fastening instrument of claim 15 wherein the firing member comprises a tissue cutting head configured for axial travel through the surgical end effector such that upon application of firing motions thereto, the firing member moves the anvil towards the elongated channel and severs tissue clamped between the surgical fastener cartridge supported in the elongated channel.

17. The surgical cutting and fastening instrument of claim 16 wherein the surgical fastener cartridge comprises a bioabsorbable cartridge body operably supporting a plurality of surgical fasteners therein.

18. A surgical cutting and fastening instrument, comprising:

a surgical end effector comprising:
an elongated channel configured to operably support a surgical fastener cartridge therein;
an anvil supported relative to the elongated channel such that the anvil and elongated channel may selectively move toward and away from each other; and
a firing member operably supported for selective axial travel through the surgical fastener cartridge and wherein the surgical cutting and fastening instrument further comprises:
means for selectively moving the elongated channel relative to the anvil;
means for selectively moving the anvil relative to and independently of the elongated channel; and
means for applying firing motions to the firing member to move the firing member within the surgical fastener cartridge.

19. The surgical cutting and fastening instrument of claim 18 wherein the elongated channel is configured to be pivotally coupled to an elongated shaft assembly about a pivot axis and wherein the anvil is pivotally supported relative to the elongated channel for selective pivotal travel relative to the elongated channel about the pivot axis.

20. The surgical cutting and fastening instrument of claim 18 wherein the firing member comprises a tissue cutting head configured for axial travel through the surgical fastener cartridge such that upon application of one of the firing motions thereto, the firing member moves the anvil into crushing engagement with the surgical fastener cartridge to form surgical fasteners therein.

* * * * *